(12) United States Patent
Palermo et al.

(10) Patent No.: US 8,398,656 B2
(45) Date of Patent: Mar. 19, 2013

(54) CLIP APPLIER AND METHODS OF USE

(75) Inventors: Thomas J. Palermo, San Jose, CA (US);
William M. Belef, San Jose, CA (US);
Michael T. Carley, San Jose, CA (US);
Richard S. Ginn, Gilroy, CA (US);
Anthony J. Pantages, San Jose, CA (US); Ronald J. Jabba, Redwood City, CA (US); Brian A. Ellingwood, Sunnyvale, CA (US); Laveille Kao Voss, Belmont, CA (US); Kelly J. McCrystle, Menlo Park, CA (US); T. Daniel Gross, Los Gatos, CA (US); Arkady Kokish, Los Gatos, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 10 days.

(21) Appl. No.: 13/039,087

(22) Filed: Mar. 2, 2011

(65) Prior Publication Data
US 2011/0230897 A1 Sep. 22, 2011

Related U.S. Application Data

(60) Continuation-in-part of application No. 12/973,204, filed on Dec. 20, 2010, now Pat. No. 8,202,294, which is a division of application No. 11/048,503, filed on Feb. 1, 2005, now Pat. No. 7,857,828, which is a continuation-in-part of application No.

(Continued)

(51) Int. Cl.
*A61B 17/08* (2006.01)
*A61B 17/10* (2006.01)

(52) U.S. Cl. ...................................... 606/142; 606/213

(58) Field of Classification Search .................. 606/142, 606/151, 153, 213, 232
See application file for complete search history.

(56) References Cited

U.S. PATENT DOCUMENTS

| 287,046 A | 10/1883 | Norton |
|---|---|---|
| 438,400 A | 10/1890 | Brennen |
| 1,088,393 A | 2/1914 | Backus |
| 1,331,401 A | 2/1920 | Summers |

(Continued)

FOREIGN PATENT DOCUMENTS

| AU | 2003297432 | 7/2004 |
|---|---|---|
| CA | 2 339 060 | 2/2000 |

(Continued)

OTHER PUBLICATIONS

U.S. Appl. No. 10/667,144, Oct. 28, 2011, Notice of Allowance.

(Continued)

*Primary Examiner* — Julian Woo
(74) *Attorney, Agent, or Firm* — Workman Nydegger; Randy Shen

(57) ABSTRACT

An apparatus for delivering a closure element can include a splittable carrier tube and a splitter to split the tube. The carrier tube can have an outer surface retaining a closure element in a tubular configuration and can be split into radially-expandable flaps. A closure element can have a shape-memory body having a relaxed configuration with a planar-annular body defining a lumen with tines directed inwardly from the body. The clip can be held in a retaining configuration having a substantially asymmetrically-elongated tubular shape with a trapezoidal longitudinal cross-sectional profile and a proximal end having the tines being longitudinally directed with a first tine being more distally oriented compared to a substantially opposite second tine being more proximal, and retracting to a deploying configuration having a tubular shape with a rectangular longitudinal cross-sectional profile with the first tine being even with the second tine when being delivered.

18 Claims, 90 Drawing Sheets

Related U.S. Application Data

10/638,115, filed on Aug. 8, 2003, now Pat. No. 7,867,249, which is a continuation-in-part of application No. 10/356,214, filed on Jan. 30, 2003, now Pat. No. 7,905,900, application No. 13/039,087, which is a continuation-in-part of application No. 11/852,190, filed on Sep. 7, 2007, and a continuation-in-part of application No. 12/143,020, filed on Jun. 20, 2008, now Pat. No. 8,202,293, and a continuation-in-part of application No. 11/048,503, filed on Feb. 1, 2005, now Pat. No. 7,857,828, which is a continuation-in-part of application No. 10/638,115, which is a continuation-in-part of application No. 10/356,214, application No. 13/039,087, which is a continuation-in-part of application No. 12/393,877, filed on Feb. 26, 2009, and a continuation-in-part of application No. 12/961,331, filed on Dec. 6, 2010.

(60) Provisional application No. 60/843,325, filed on Sep. 8, 2005, provisional application No. 60/946,030, filed on Jun. 25, 2007, provisional application No. 60/946,042, filed on Jun. 25, 2007.

(56) References Cited

U.S. PATENT DOCUMENTS

| | | | |
|---|---|---|---|
| 1,596,004 | A | 8/1926 | De Bengoa |
| 1,647,958 | A | 11/1927 | Ciarlante |
| 1,880,569 | A | 10/1932 | Weis |
| 2,087,074 | A | 7/1937 | Tucker |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | James |
| 2,583,625 | A | 1/1952 | Bergan |
| 2,684,070 | A | 7/1954 | Kelsey |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,015,403 | A | 1/1962 | Fuller |
| 3,113,379 | A | 12/1963 | Frank |
| 3,120,230 | A | 2/1964 | Skold |
| 3,142,878 | A | 8/1964 | Santora |
| 3,209,754 | A | 10/1965 | Brown |
| 3,482,428 | A | 12/1969 | Kapitanov et al. |
| 3,494,533 | A | 2/1970 | Green et al. |
| 3,510,923 | A | 5/1970 | Blake |
| 3,523,351 | A | 8/1970 | Filia |
| 3,586,002 | A | 6/1971 | Wood et al. |
| 3,604,425 | A | 9/1971 | Le Roy |
| 3,618,447 | A | 11/1971 | Goins |
| 3,677,243 | A | 7/1972 | Nerz |
| 3,757,629 | A | 9/1973 | Schneider |
| 3,805,337 | A | 4/1974 | Branstetter |
| 3,823,719 | A | 7/1974 | Cummings |
| 3,828,791 | A | 8/1974 | Santos |
| 3,856,016 | A | 12/1974 | Davis |
| 3,874,388 | A | 4/1975 | King et al. |
| 3,908,662 | A | 9/1975 | Razgulov et al. |
| 3,926,194 | A | 12/1975 | Greenberg et al. |
| 3,939,820 | A | 2/1976 | Grayzel |
| 3,944,114 | A | 3/1976 | Coppens |
| 3,960,147 | A | 6/1976 | Murray |
| 3,985,138 | A | 10/1976 | Jarvik |
| 4,007,743 | A | 2/1977 | Blake |
| 4,014,492 | A | 3/1977 | Rothfuss |
| 4,018,228 | A | 4/1977 | Goosen |
| 4,047,533 | A | 9/1977 | Perciaccante et al. |
| 4,064,881 | A | 12/1977 | Meredith |
| 4,112,944 | A | 9/1978 | Williams |
| 4,153,321 | A | 5/1979 | Pombrol |
| 4,162,673 | A | 7/1979 | Patel |
| 4,169,476 | A | 10/1979 | Hiltebrandt |
| 4,192,315 | A | 3/1980 | Hilzinger et al. |
| 4,201,215 | A | 5/1980 | Crossett et al. |
| 4,204,541 | A | 5/1980 | Kapitanov |
| 4,207,870 | A | 6/1980 | Eldridge |
| 4,214,587 | A | 7/1980 | Sakura, Jr. |
| 4,215,699 | A | 8/1980 | Patel |
| 4,217,902 | A | 8/1980 | March |
| 4,273,129 | A | 6/1981 | Boebel |
| 4,274,415 | A | 6/1981 | Kanamoto et al. |
| 4,278,091 | A | 7/1981 | Borzone |
| 4,317,445 | A | 3/1982 | Robinson |
| 4,317,451 | A | 3/1982 | Cerwin et al. |
| 4,318,401 | A | 3/1982 | Zimmerman |
| 4,327,485 | A | 5/1982 | Rix |
| 4,345,606 | A | 8/1982 | Littleford |
| 4,368,736 | A | 1/1983 | Kaster |
| 4,396,139 | A | 8/1983 | Hall et al. |
| 4,411,654 | A | 10/1983 | Boarini et al. |
| 4,412,832 | A | 11/1983 | Kling et al. |
| 4,428,376 | A | 1/1984 | Mericle |
| 4,440,170 | A | 4/1984 | Golden et al. |
| 4,449,531 | A | 5/1984 | Cerwin et al. |
| 4,475,544 | A | 10/1984 | Reis |
| 4,480,356 | A | 11/1984 | Martin |
| 4,485,816 | A | 12/1984 | Krumme |
| RE31,855 | E | 3/1985 | Osborne |
| 4,505,273 | A | 3/1985 | Braun et al. |
| 4,505,274 | A | 3/1985 | Speelman |
| 4,523,591 | A | 6/1985 | Kaplan et al. |
| 4,523,695 | A | 6/1985 | Braun et al. |
| 4,525,157 | A | 6/1985 | Valaincourt |
| 4,526,174 | A | 7/1985 | Froehlich |
| 4,586,503 | A | 5/1986 | Kirsch et al. |
| 4,592,498 | A | 6/1986 | Braun et al. |
| 4,596,559 | A | 6/1986 | Fleischhacker |
| 4,607,638 | A | 8/1986 | Crainich |
| 4,610,251 | A | 9/1986 | Kumar |
| 4,610,252 | A | 9/1986 | Catalano |
| 4,635,634 | A | 1/1987 | Santos |
| 4,651,737 | A | 3/1987 | Deniega |
| 4,664,305 | A | 5/1987 | Blake, III et al. |
| 4,665,906 | A | 5/1987 | Jervis |
| 4,687,469 | A | 8/1987 | Osypka |
| 4,693,249 | A | 9/1987 | Schenck et al. |
| 4,719,917 | A | 1/1988 | Barrows et al. |
| 4,724,840 | A | 2/1988 | McVay et al. |
| 4,738,658 | A | 4/1988 | Magro et al. |
| 4,744,364 | A | 5/1988 | Kensey |
| 4,747,407 | A | 5/1988 | Liu et al. |
| 4,759,364 | A | 7/1988 | Boebel |
| 4,771,782 | A | 9/1988 | Millar |
| 4,772,266 | A | 9/1988 | Groshong |
| 4,777,950 | A | 10/1988 | Kees, Jr. |
| 4,789,090 | A | 12/1988 | Blake, III |
| 4,832,688 | A | 5/1989 | Sagae et al. |
| 4,836,204 | A | 6/1989 | Landymore et al. |
| 4,852,568 | A | 8/1989 | Kensey |
| 4,860,746 | A | 8/1989 | Yoon |
| 4,865,026 | A | 9/1989 | Barrett |
| 4,874,122 | A | 10/1989 | Froelich et al. |
| 4,878,915 | A | 11/1989 | Brantigan |
| 4,885,003 | A | 12/1989 | Hillstead |
| 4,886,067 | A | 12/1989 | Palermo |
| 4,887,601 | A | 12/1989 | Richards |
| 4,890,612 | A | 1/1990 | Kensey |
| 4,902,508 | A | 2/1990 | Badylak et al. |
| 4,917,087 | A | 4/1990 | Walsh et al. |
| 4,917,089 | A | 4/1990 | Sideris |
| 4,929,240 | A | 5/1990 | Kirsch et al. |
| 4,934,364 | A | 6/1990 | Green |
| 4,950,258 | A | 8/1990 | Kawai et al. |
| 4,957,499 | A | 9/1990 | Lipatov et al. |
| 4,961,729 | A | 10/1990 | Vaillancourt |
| 4,976,721 | A | 12/1990 | Blasnik et al. |
| 4,983,176 | A | 1/1991 | Cushman et al. |
| 4,997,436 | A | 3/1991 | Oberlander |
| 4,997,439 | A | 3/1991 | Chen |
| 5,002,562 | A | 3/1991 | Oberlander |
| 5,007,921 | A | 4/1991 | Brown |

| | | | | | |
|---|---|---|---|---|---|
| 5,015,247 A | 5/1991 | Michelson | 5,366,458 A | 11/1994 | Korthoff et al. |
| 5,021,059 A | 6/1991 | Kensey et al. | 5,366,479 A | 11/1994 | McGarry et al. |
| 5,026,390 A | 6/1991 | Brown | 5,383,896 A | 1/1995 | Gershony et al. |
| 5,030,226 A | 7/1991 | Green et al. | RE34,866 E | 2/1995 | Kensey et al. |
| 5,032,127 A | 7/1991 | Frazee et al. | 5,392,978 A | 2/1995 | Valez et al. |
| 5,047,047 A | 9/1991 | Yoon | 5,395,030 A | 3/1995 | Kuramoto et al. |
| 5,053,008 A | 10/1991 | Bajaj | 5,411,520 A | 5/1995 | Nash et al. |
| 5,059,201 A | 10/1991 | Asnis | 5,413,571 A | 5/1995 | Katsaros et al. |
| 5,061,274 A | 10/1991 | Kensey | 5,413,584 A | 5/1995 | Schulze |
| 5,078,731 A | 1/1992 | Hayhurst | 5,416,584 A | 5/1995 | Kay |
| 5,092,941 A | 3/1992 | Miura | 5,417,699 A | 5/1995 | Klein et al. |
| 5,100,418 A | 3/1992 | Yoon et al. | 5,419,777 A | 5/1995 | Hofling |
| 5,100,422 A | 3/1992 | Berguer et al. | 5,421,832 A | 6/1995 | Lefebvre |
| 5,108,420 A | 4/1992 | Marks | 5,423,857 A | 6/1995 | Rosenman et al. |
| 5,108,421 A | 4/1992 | Fowler | 5,425,489 A | 6/1995 | Shichman et al. |
| 5,114,032 A | 5/1992 | Laidlaw | 5,425,740 A | 6/1995 | Hutchinson, Jr. |
| 5,114,065 A | 5/1992 | Storace | 5,431,639 A | 7/1995 | Shaw |
| 5,116,349 A | 5/1992 | Aranyi | 5,431,667 A | 7/1995 | Thompson et al. |
| 5,122,122 A | 6/1992 | Allgood | 5,433,721 A | 7/1995 | Hooven et al. |
| 5,122,156 A | 6/1992 | Granger et al. | 5,437,631 A | 8/1995 | Janzen |
| 5,131,379 A | 7/1992 | Sewell, Jr. | 5,439,479 A | 8/1995 | Shichman et al. |
| 5,141,520 A | 8/1992 | Goble et al. | 5,443,477 A | 8/1995 | Marin et al. |
| 5,147,381 A | 9/1992 | Heimerl et al. | 5,443,481 A | 8/1995 | Lee |
| 5,156,609 A | 10/1992 | Nakao et al. | 5,445,167 A | 8/1995 | Yoon et al. |
| 5,167,634 A | 12/1992 | Corrigan, Jr. et al. | 5,449,359 A | 9/1995 | Groiso |
| 5,167,643 A | 12/1992 | Lynn | 5,451,235 A | 9/1995 | Lock et al. |
| 5,171,249 A | 12/1992 | Stefanchik et al. | 5,456,400 A | 10/1995 | Shichman et al. |
| 5,171,250 A | 12/1992 | Yoon | 5,462,561 A | 10/1995 | Voda |
| 5,176,648 A | 1/1993 | Holmes et al. | 5,464,413 A | 11/1995 | Siska, Jr. et al. |
| 5,192,288 A | 3/1993 | Thompson et al. | 5,466,241 A | 11/1995 | Leroy et al. |
| 5,192,300 A | 3/1993 | Fowler | 5,470,010 A | 11/1995 | Rothfuss et al. |
| 5,192,301 A | 3/1993 | Kamiya et al. | 5,471,982 A | 12/1995 | Edwards et al. |
| 5,192,302 A | 3/1993 | Kensey et al. | 5,474,557 A | 12/1995 | Mai |
| 5,192,602 A | 3/1993 | Spencer et al. | 5,474,569 A | 12/1995 | Zinreich et al. |
| 5,193,533 A | 3/1993 | Body et al. | 5,476,505 A | 12/1995 | Limon |
| 5,197,971 A | 3/1993 | Bonutti | 5,478,352 A | 12/1995 | Fowler |
| 5,209,756 A | 5/1993 | Seedhorm et al. | 5,478,353 A | 12/1995 | Yoon |
| 5,217,024 A | 6/1993 | Dorsey et al. | 5,478,354 A | 12/1995 | Tovey et al. |
| 5,222,974 A | 6/1993 | Kensey et al. | 5,486,195 A | 1/1996 | Myers et al. |
| 5,226,908 A | 7/1993 | Yoon | 5,497,933 A | 3/1996 | DeFonzo et al. |
| 5,236,435 A | 8/1993 | Sewell, Jr. | 5,507,744 A | 4/1996 | Tay et al. |
| 5,242,456 A | 9/1993 | Nash et al. | 5,507,755 A | 4/1996 | Gresl et al. |
| 5,242,457 A | 9/1993 | Akopov et al. | 5,522,840 A | 6/1996 | Krajicek |
| 5,242,459 A | 9/1993 | Buelna | 5,527,322 A | 6/1996 | Klein et al. |
| 5,243,857 A | 9/1993 | Velez | 5,536,251 A | 7/1996 | Evard et al. |
| 5,246,156 A | 9/1993 | Rothfuss et al. | 5,540,712 A | 7/1996 | Kleshinski et al. |
| 5,246,443 A | 9/1993 | Mai | 5,540,716 A | 7/1996 | Hlavacek |
| 5,250,058 A | 10/1993 | Miller et al. | 5,544,802 A | 8/1996 | Crainich |
| 5,254,105 A | 10/1993 | Haaga | 5,547,474 A | 8/1996 | Kloeckl et al. |
| 5,255,679 A | 10/1993 | Imran | 5,560,532 A | 10/1996 | DeFonzo et al. |
| 5,269,792 A | 12/1993 | Kovac et al. | 5,571,120 A | 11/1996 | Yoon |
| 5,275,616 A | 1/1994 | Fowler | 5,573,784 A | 11/1996 | Badylak et al. |
| 5,281,422 A | 1/1994 | Badylak et al. | 5,575,771 A | 11/1996 | Walinsky |
| 5,282,808 A | 2/1994 | Kovac et al. | 5,584,879 A | 12/1996 | Reimold et al. |
| 5,282,827 A | 2/1994 | Kensey et al. | 5,591,205 A | 1/1997 | Fowler |
| 5,289,963 A | 3/1994 | McGarry et al. | 5,593,412 A | 1/1997 | Martinez et al. |
| 5,290,243 A | 3/1994 | Chodorow et al. | 5,601,602 A | 2/1997 | Fowler |
| 5,290,310 A | 3/1994 | Makower et al. | 5,609,597 A | 3/1997 | Lehrer |
| 5,292,309 A | 3/1994 | Van Tassel et al. | 5,613,974 A | 3/1997 | Andreas et al. |
| 5,292,332 A | 3/1994 | Lee | 5,618,291 A | 4/1997 | Thompson et al. |
| 5,304,183 A | 4/1994 | Gourlay et al. | 5,620,452 A | 4/1997 | Yoon |
| 5,304,184 A | 4/1994 | Hathaway et al. | 5,620,461 A | 4/1997 | Muijs et al. |
| 5,304,204 A | 4/1994 | Bregen | 5,634,936 A | 6/1997 | Linden et al. |
| 5,306,254 A | 4/1994 | Nash et al. | 5,643,318 A | 7/1997 | Tsukernik et al. |
| 5,309,927 A | 5/1994 | Welch | 5,645,565 A | 7/1997 | Rudd et al. |
| 5,318,542 A | 6/1994 | Hirsch et al. | 5,645,566 A | 7/1997 | Brenneman et al. |
| 5,320,639 A | 6/1994 | Rudnick | 5,645,567 A | 7/1997 | Crainich |
| 5,327,908 A | 7/1994 | Gerry | 5,649,959 A | 7/1997 | Hannam et al. |
| 5,330,445 A | 7/1994 | Haaga | D383,539 S | 9/1997 | Croley |
| 5,334,216 A | 8/1994 | Vidal et al. | 5,674,231 A | 10/1997 | Green et al. |
| 5,334,217 A | 8/1994 | Das | 5,676,689 A | 10/1997 | Kensey et al. |
| 5,335,680 A | 8/1994 | Moore | 5,676,974 A | 10/1997 | Valdes et al. |
| 5,340,360 A | 8/1994 | Stefanchik | 5,681,280 A | 10/1997 | Rusk et al. |
| 5,342,393 A | 8/1994 | Stack | 5,681,334 A | 10/1997 | Evans et al. |
| 5,344,439 A | 9/1994 | Otten | 5,683,405 A | 11/1997 | Yacoubian et al. |
| 5,350,399 A | 9/1994 | Erlebacher et al. | 5,690,674 A | 11/1997 | Diaz |
| 5,352,229 A | 10/1994 | Goble et al. | 5,695,504 A | 12/1997 | Gifford, III et al. |
| 5,364,406 A | 11/1994 | Sewell, Jr. | 5,695,505 A | 12/1997 | Yoon |
| 5,364,408 A | 11/1994 | Gordon | 5,695,524 A | 12/1997 | Kelley et al. |

| Patent No. | Date | Inventor |
|---|---|---|
| 5,700,273 A | 12/1997 | Buelna et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,976,161 A | 11/1999 | Kirsch et al. |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,102,271 A | 8/2000 | Longo et al. |
| 6,110,184 A | 8/2000 | Weadock |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,102 B1 | 4/2001 | Baker et al. |
| 6,231,561 B1 | 5/2001 | Frazier et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |

| Patent | Date | Inventor |
|---|---|---|
| 6,287,322 B1 | 9/2001 | Zhu et al. |
| 6,296,657 B1 | 10/2001 | Brucker |
| 6,302,898 B1 | 10/2001 | Edwards et al. |
| 6,305,891 B1 | 10/2001 | Burlingame |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,261,716 B2 | 8/2007 | Strobel et al. |
| 7,311,720 B2 | 12/2007 | Mueller et al. |
| 7,316,704 B2 | 1/2008 | Bagaoisan et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| D611,144 S | 3/2010 | Reynolds |
| 7,780,696 B2 | 8/2010 | Daniel et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |

| Patent/Publication | Date | Name |
|---|---|---|
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 | 2/2011 | Carley et al. |
| 7,887,555 B2 | 2/2011 | Carley et al. |
| 7,887,563 B2 | 2/2011 | Cummins et al. |
| 7,901,428 B2 | 3/2011 | Ginn et al. |
| 7,905,900 B2 | 3/2011 | Palermo |
| 7,918,873 B2 | 4/2011 | Cummins et al. |
| 7,931,669 B2 | 4/2011 | Ginn et al. |
| 7,931,671 B2 | 4/2011 | Tenerz |
| 7,967,842 B2 | 6/2011 | Bakos |
| 8,103,327 B2 | 1/2012 | Harley et al. |
| 8,105,352 B2 | 1/2012 | Egnelöv |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026215 A1 | 2/2002 | Redmond et al. |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0183786 A1 | 12/2002 | Girton |
| 2002/0183787 A1 | 12/2002 | Wahr et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0023248 A1 | 1/2003 | Parodi |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0167484 A1 | 7/2006 | Carley et al. |
| 2006/0190014 A1 | 8/2006 | Ginn et al. |
| 2006/0190037 A1 | 8/2006 | Carley et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0021778 A1 | 1/2007 | Carly |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0083230 A1 | 4/2007 | Javois |
| 2007/0112304 A1 | 5/2007 | Voss |
| 2007/0112365 A1 | 5/2007 | Hilal et al. |
| 2007/0123816 A1 | 5/2007 | Zhu et al. |
| 2007/0123817 A1 | 5/2007 | Khosravi et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |

| Pub. No. | Date | Name | Country | Number | Date |
|---|---|---|---|---|---|
| 2008/0065152 A1 | 3/2008 | Carley | IE | S2002/0452 | 12/2002 |
| 2008/0086075 A1 | 4/2008 | Isik et al. | IE | S2002/0664 | 2/2003 |
| 2008/0093414 A1 | 4/2008 | Bender et al. | IE | S2002/0665 | 2/2003 |
| 2008/0114378 A1 | 5/2008 | Matsushita | IE | S2002/0451 | 7/2003 |
| 2008/0114395 A1 | 5/2008 | Mathisen et al. | IE | S2002/0552 | 7/2003 |
| 2008/0177288 A1 | 7/2008 | Carlson | IE | S2003/0424 | 12/2003 |
| 2008/0210737 A1 | 9/2008 | Ginn et al. | IE | S2003/0490 | 1/2004 |
| 2008/0221616 A1 | 9/2008 | Ginn et al. | IE | S2004/0368 | 11/2005 |
| 2008/0243148 A1 | 10/2008 | Mikkaichi et al. | IE | S2005/0342 | 11/2005 |
| 2008/0243182 A1 | 10/2008 | Bates et al. | JP | 58-181006 | 12/1983 |
| 2008/0269801 A1 | 10/2008 | Coleman et al. | JP | 12 74750 | 11/1989 |
| 2008/0269802 A1 | 10/2008 | Coleman et al. | JP | 2000102546 | 4/2000 |
| 2008/0272173 A1 | 11/2008 | Coleman et al. | NL | 9302140 | 7/1995 |
| 2008/0300628 A1 | 12/2008 | Ellingwood | PL | 171425 | 4/1997 |
| 2008/0312666 A1 | 12/2008 | Ellingwood et al. | RU | 2086192 | 8/1997 |
| 2008/0312686 A1 | 12/2008 | Ellingwood | SU | 495067 | 12/1975 |
| 2008/0312740 A1 | 12/2008 | Wachter et al. | SU | 912155 | 3/1982 |
| 2008/0319475 A1 | 12/2008 | Clark | SU | 1243708 | 7/1986 |
| 2009/0054912 A1 | 2/2009 | Heanue et al. | SU | 1324650 | 7/1987 |
| 2009/0112306 A1 | 4/2009 | Bonsignore et al. | SU | 1405828 | 6/1988 |
| 2009/0137900 A1 | 5/2009 | Bonner et al. | SU | 1456109 | 2/1989 |
| 2009/0157101 A1 | 6/2009 | Reyes et al. | SU | 1560133 | 4/1990 |
| 2009/0157102 A1 | 6/2009 | Reynolds et al. | WO | WO 96/24291 | 8/1996 |
| 2009/0171388 A1 | 7/2009 | Dave et al. | WO | WO 97/07741 | 3/1997 |
| 2009/0177212 A1 | 7/2009 | Carley et al. | WO | WO 97/20505 | 6/1997 |
| 2009/0187215 A1 | 7/2009 | Mackiewicz et al. | WO | WO 97/27897 | 8/1997 |
| 2009/0216267 A1 | 8/2009 | Willard et al. | WO | WO 98/06346 | 2/1998 |
| 2009/0227938 A1 | 9/2009 | Fasching et al. | WO | WO 98/06448 | 2/1998 |
| 2009/0230168 A1 | 9/2009 | Coleman et al. | WO | WO 98/16161 | 4/1998 |
| 2009/0254119 A1 | 10/2009 | Sibbitt, Jr. et al. | WO | WO 98/17179 | 4/1998 |
| 2009/0287244 A1 | 11/2009 | Kokish | WO | WO 98/18389 | 5/1998 |
| 2009/0312789 A1 | 12/2009 | Kassab et al. | WO | WO 98/24374 | 6/1998 |
| 2010/0114156 A1 | 5/2010 | Mehl | WO | WO 98/25508 | 6/1998 |
| 2010/0114159 A1 | 5/2010 | Roorda et al. | WO | WO 98/58591 | 12/1998 |
| 2010/0160958 A1 | 6/2010 | Clark | WO | WO 99/21491 | 5/1999 |
| 2010/0168790 A1 | 7/2010 | Clark | WO | WO 99/40849 | 8/1999 |
| 2010/0179567 A1 | 7/2010 | Voss et al. | WO | WO 99/60941 | 12/1999 |
| 2010/0179571 A1 | 7/2010 | Voss | WO | WO 99/62408 | 12/1999 |
| 2010/0179572 A1 | 7/2010 | Voss et al. | WO | WO 99/62415 | 12/1999 |
| 2010/0179589 A1 | 7/2010 | Roorda et al. | WO | WO 00/06029 | 2/2000 |
| 2010/0179590 A1 | 7/2010 | Fortson et al. | WO | WO 00/07505 | 2/2000 |
| 2010/0185234 A1 | 7/2010 | Fortson et al. | WO | WO 00/07640 | 2/2000 |
| 2010/0217132 A1 | 8/2010 | Ellingwood et al. | WO | WO 00/27311 | 5/2000 |
| 2011/0054492 A1 | 3/2011 | Clark | WO | WO 00/27313 | 5/2000 |
| 2011/0060355 A1 | 3/2011 | Carley et al. | WO | WO 00/56223 | 9/2000 |
| 2011/0066164 A1 | 3/2011 | Walberg et al. | WO | WO 00/56227 | 9/2000 |
| 2011/0071565 A1 | 3/2011 | Ginn | WO | WO 00/56228 | 9/2000 |
| 2011/0106148 A1 | 5/2011 | Ginn et al. | WO | WO 00/71032 | 11/2000 |
| 2011/0178548 A1 | 7/2011 | Tenerz | WO | WO 01/21058 | 3/2001 |
| 2012/0035630 A1 | 2/2012 | Roorda | WO | WO 01/35832 | 5/2001 |
| 2012/0245626 A1 | 9/2012 | Ellingwood et al. | WO | WO 01/47594 | 7/2001 |
| 2012/0255655 A1 | 10/2012 | Carley et al. | WO | WO 01/49186 | 7/2001 |
| FOREIGN PATENT DOCUMENTS | | | WO | WO 01/91628 | 12/2001 |
| DE | 197 11 288 | 10/1998 | WO | WO 02/19915 | 3/2002 |
| DE | 29723736 U1 | 4/1999 | WO | WO 02/19920 | 3/2002 |
| DE | 19859952 | 2/2000 | WO | WO 02/19922 | 3/2002 |
| DE | 102006056283 | 6/2008 | WO | WO 02/19924 | 3/2002 |
| EP | 0 386 361 | 9/1990 | WO | WO 02/28286 | 4/2002 |
| EP | 0 534 696 | 3/1993 | WO | WO 02/38055 | 5/2002 |
| EP | 0 621 032 | 10/1994 | WO | WO 02/45593 | 6/2002 |
| EP | 0 756 851 | 2/1997 | WO | WO 02/45594 | 6/2002 |
| EP | 0 774 237 | 5/1997 | WO | WO 02/062234 | 8/2002 |
| EP | 0 858 776 | 8/1998 | WO | WO 02/098302 | 12/2002 |
| EP | 0 941 697 | 9/1999 | WO | WO 03/013363 | 2/2003 |
| EP | 1 867 287 | 12/2007 | WO | WO 03/013364 | 2/2003 |
| FR | 2 443 238 | 7/1980 | WO | WO 03/047434 | 6/2003 |
| FR | 2 715 290 | 7/1995 | WO | WO 03/071955 | 9/2003 |
| FR | 2 722 975 | 2/1996 | WO | WO 03/071956 | 9/2003 |
| FR | 2 768 324 | 3/1999 | WO | WO 03/071957 | 9/2003 |
| GB | 1 358 466 | 7/1974 | WO | WO 03/094748 | 11/2003 |
| GB | 2 075 144 | 11/1981 | WO | WO 03/101310 | 12/2003 |
| GB | 2 397 240 | 7/2004 | WO | WO 2004/004578 | 1/2004 |
| IE | S2000/0722 | 10/2001 | WO | WO 2004/012602 | 2/2004 |
| IE | S2000/0724 | 10/2001 | WO | WO 2004/060169 | 7/2004 |
| IE | S2001/0547 | 7/2002 | WO | WO 2004/069054 | 8/2004 |
| IE | S2001/0815 | 7/2002 | WO | WO 2005/000126 | 1/2005 |
| IE | S2001/0748 | 8/2002 | WO | WO 2005/006990 | 1/2005 |
| IE | S2001/0749 | 8/2002 | WO | WO 2005/041782 | 5/2005 |
| | | | WO | WO 2005/063129 | 7/2005 |

| | | |
|---|---|---|
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 11/675,462, Dec. 22, 2011, Notice of Allowance.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Restriction Requirement.
U.S. Appl. No. 12/684,470, Dec. 20, 2011, Restriction Requirement.
U.S. Appl. No. 12/684,562, Dec. 28, 2011, Restriction Requirement.
U.S. Appl. No. 12/684,569, Dec. 20, 2011, Restriction Requirement.
U.S. Appl. No. 12/897,358, Jan. 12, 2012, Notice of Allowance.
U.S. Appl. No. 12/941,809, Dec. 13, 2011, Restriction Requirement.
U.S. Appl. No. 12/945,646, Oct. 26, 2011, Office Action.
U.S. Appl. No. 12/955,859, Dec. 15, 2011, Office Action.
U.S. Appl. No. 12/338,977, Jan. 19, 2012, Office Action.
U.S. Appl. No. 12/684,569, Jan. 27, 2012, Office Action.
U.S. Appl. No. 11/767,818, Feb. 3, 2012, Notice of Allowance.
U.S. Appl. No. 12/684,542, Jan. 30, 2012, Restriction Requirement.
U.S. Appl. No. 12/941,809, Jan. 30, 2012, Office Action.
U.S. Appl. No. 12/966,923, Feb. 3, 2012, Notice of Allowance.
U.S. Appl. No. 12/114,031, Mar. 6, 2012, Office Action.
U.S. Appl. No. 12/135,858, Feb. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/608,769, Feb. 10, 2012, Office Action.
U.S. Appl. No. 12/642,319, Feb. 27, 2012, Office Action.
U.S. Appl. No. 12/684,400, Feb. 13, 2012, Office Action.
U.S. Appl. No. 12/684,562, Feb. 16, 2012, Office Action.
U.S. Appl. No. 12/724,304, Feb. 10, 2012, Office Action.
U.S. Appl. No. 12/897,358, Mar. 5, 2012, Notice of Allowance.
U.S. Appl. No. 12/945,646, Feb. 21, 2012, Notice of Allowance.
U.S. Appl. No. 12/973,204, Mar. 7, 2012, Notice of Allowance.
U.S. Appl. No. 12/113,851, Mar. 29, 2012, Office Action.
U.S. Appl. No. 12/114,091, Apr. 5, 2012, Office Action.
U.S. Appl. No. 12/403,277, Apr. 3, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/987,792, Mar. 13, 2012, Office Action.
U.S. Appl. No. 13/308,227, filed Nov. 30, 2011, Yibarren.
U.S. Appl. No. 11/390,586, May 3, 2012, Notice of Allowance.
U.S. Appl. No. 12/684,542, Apr. 16, 2012, Office Action.
U.S. Appl. No. 12/688,065, Apr. 26, 2012, Office Action.
U.S. Appl. No. 12/897,358, May 2, 2012, Issue Notification.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/724,304, filed Mar. 15, 2010, Fortson.
U.S. Appl. No. 12/848,642, filed Aug. 2, 2010, Fortson et al.
U.S. Appl. No. 12/897,358, filed Oct. 4, 2010, Carley.
U.S. Appl. No. 12/961,331, filed Dec. 6, 2010, Voss.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 13/017,636, filed Jan. 31, 2011, Carley et al.
U.S. Appl. No. 13/026,989, filed Feb. 14, 2011, Cummins.
U.S. Appl. No. 13/028,041, filed Feb. 15, 2011, Von Oepen.
U.S. Appl. No. 13/030,922, filed Feb. 18, 2011, Cummins.
U.S. Appl. No. 13/112,618, filed May 20, 2011, Gianotti et al.
U.S. Appl. No. 13/112,631, May 20, 2011, Voss.
U.S. Appl. No. 13/153,594, filed Jun. 6, 2011, Reyes et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 11/427,297, Jun. 26, 2012, NOA.
U.S. Appl. No. 11/744,089, Aug. 8, 2012, OA.
U.S. Appl. No. 12/338,977, Jul. 11, 2012, OA.
U.S. Appl. No. 12/402,398, Sep. 20, 2012, OA.
U.S. Appl. No. 12/481,377, Aug. 10, 2012, NOA.
U.S. Appl. No. 12/548,274, Sep. 10, 2012, OA.
U.S. Appl. No. 12/608,769, Aug. 22, 2012, OA.
U.S. Appl. No. 12/608,733, Jul. 20, 2012, OA.
U.S. Appl. No. 12/642,319, Aug. 28, 2012, OA.
U.S. Appl. No. 12/684,400, Oct. 16, 2012, OA.
U.S. Appl. No. 12/684,470, Aug. 30, 2012, OA.
U.S. Appl. No. 12/684,542, Sep. 13, 2012, OA.
U.S. Appl. No. 12/684,562, Aug. 21, 2012, OA.
U.S. Appl. No. 12/684,569, Jul. 30, 2012, OA.
U.S. Appl. No. 12/688,065, Oct. 12, 2012, OA.
U.S. Appl. No. 12/848,642, Sep. 20, 2012, RR.
U.S. Appl. No. 12/850,242, Aug. 6, 2012, RR.
U.S. Appl. No. 12/955,859, Aug. 6, 2012, OA.
U.S. Appl. No. 12/987,792, Sep. 17, 2012, OA.
"Hand tool for forming telephone connections—comprises pliers with reciprocably driven ram crimping clip around conductors against anvil".
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.

Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.

J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.

Jeremy L Gilbert Phd, Wound Closure Biomaterials and Devices, Shock., Mar. 1999, p. 226, vol. 11—No. 3, Institution Northwestern University (editorial review).

Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.

K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.

Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, Phd, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,81, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.

U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.
U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, R312.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006 Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/638,115, Dec. 22, 2010, Issue Notification.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/667,144, Jun. 6, 2011, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/682,459, Apr. 1, 2011, Notice of Allowance.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.

U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/113,549, Jan. 4, 2011, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No. 11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/396,731, Mar. 22, 2011, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,297, Mar. 21, 2011, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/767,818, Feb. 16, 2011, Office Action.
U.S. Appl. No. 11/852,190, Jun. 24, 2010, Office Action.
U.S. Appl. No. 11/852,190, Nov. 1, 2010, Office Action.
U.S. Appl. No. 11/852,190, Mar. 2, 2011, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,281, Mar. 10, 2011, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/113,851, Dec. 16, 2010, Office Action.
U.S. Appl. No. 12/113,851, Apr. 27, 2011, Office Action.
U.S. Appl. No. 12/114,031, Oct. 5, 2010, Office Action.
U.S. Appl. No. 12/114,031, Nov. 22, 2010, Office Action.
U.S. Appl. No. 12/114,031, May 11, 2011, Office Action.
U.S. Appl. No. 12/114,091, Oct. 27, 2010, Office Action.
U.S. Appl. No. 12/114,091, Dec. 17, 2010, Office Action.
U.S. Appl. No. 12/122,603, Mar. 3, 2011, Office Action.
U.S. Appl. No. 12/122,603, Apr. 22, 2011, Office Action.
U.S. Appl. No. 12/143,020, May 11, 2011, Office Action.
U.S. Appl. No. 12/402,398, Mar. 9, 2010, Office Action.
U.S. Appl. No. 12/402,398, May 20, 2010, Office Action.
U.S. Appl. No. 12/402,398, Jan. 24, 2011, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,277, Jul. 8, 2010, Office Action.
U.S. Appl. No. 12/403,277, Oct. 12, 2010, Office Action.
U.S. Appl. No. 12/403,277, Mar. 31, 2011, Office Action.
U.S. Appl. No. 12/481,377, Apr. 28, 2011, Office Action.
U.S. Appl. No. 12/945,646, Jan. 20, 2011, Office Action.
U.S. Appl. No. 12/955,859, May 26, 2011, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 12/143,020, May 30, 2012, Issue Notification.
U.S. Appl. No. 12/393,877, May 21, 2012, Office Action.
U.S. Appl. No. 12/608,773, Jun. 7, 2012, Office Action.
U.S. Appl. No. 12/684,400, May 9, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.

U.S. Appl. No. 13/026,989, Jun. 8, 2012, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 13/026,989, Sep. 16, 2011, Office Action.
U.S. Appl. No. 12/122,603, Sep. 23, 2011, Office Action.
U.S. Appl. No. 12/393,877, Sep. 29, 2011, Office Action.
U.S. Appl. No. 11/427,297, filed Oct. 31, 2012, Issue Notification.
U.S. Appl. No. 12/114,091, filed Nov. 8, 2012, Office Action.
U.S. Appl. No. 12/403,277, filed Nov. 5, 2012, Office Action.
U.S. Appl. No. 12/481,377, filed Nov. 14, 2012, Issue Notification.
U.S. Appl. No. 12/608,769, filed Nov. 5, 2012, Notice of Allowance.
U.S. Appl. No. 12/848,642, filed Nov. 9, 2012, Office Action.
U.S. Appl. No. 12/850,242, filed Oct. 17, 2012, Office Action.
U.S. Appl. No. 12/338,977, filed Nov. 28, 2012, Office Action.
U.S. Appl. No. 12/961,331, filed Dec. 4, 2012, Office Action.
U.S. Appl. No. 13/030,922, filed Dec. 18, 2012, Office Action.
U.S. Appl. No. 12/608,773, filed Jan. 7, 2013, Office Action.
U.S. Appl. No. 13/490,143, filed Jan. 4, 2013, Office Action.
U.S. Appl. No. 11/344,891, filed Jan. 22, 2013, Notice of Allowance.
U.S. Appl. No. 13/615,547, filed Jan. 18, 2013, Office Action.

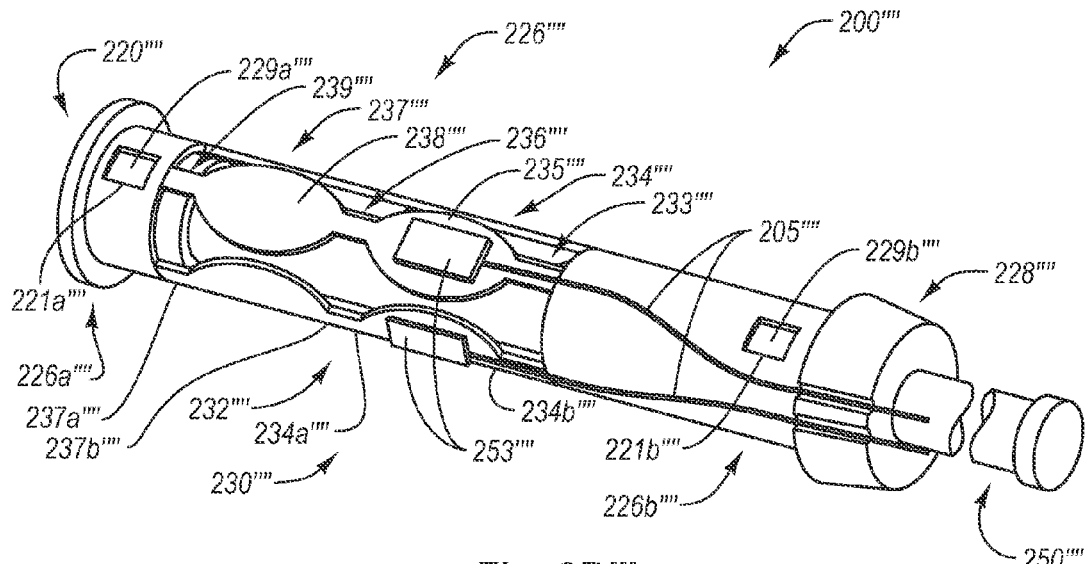
Fig. 2B''''
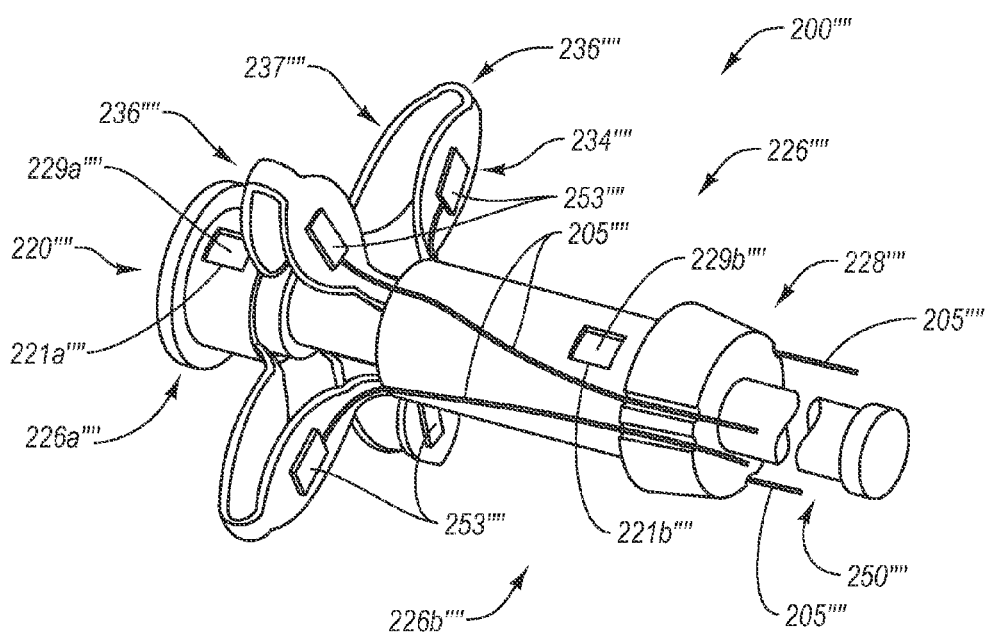
Fig. 2C''''

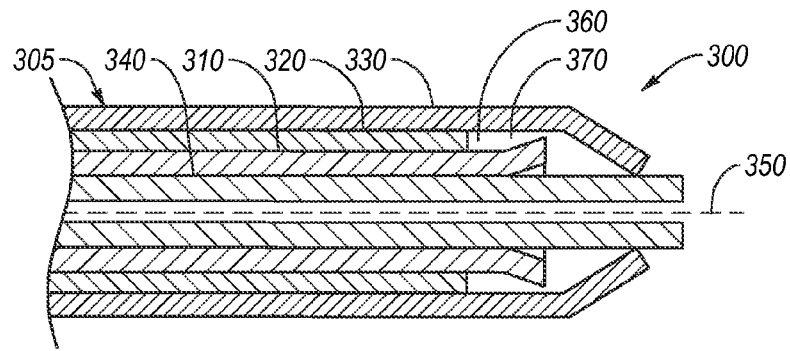
Fig. 3A
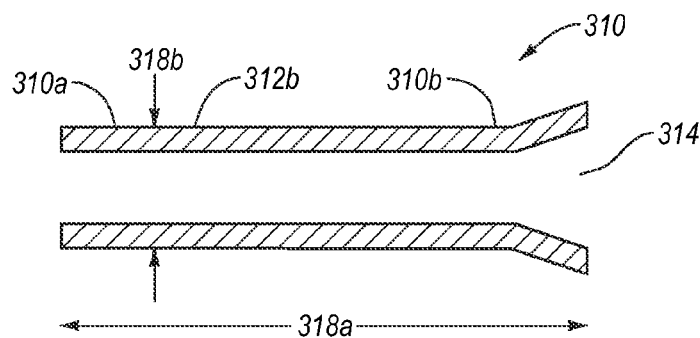
Fig. 3B
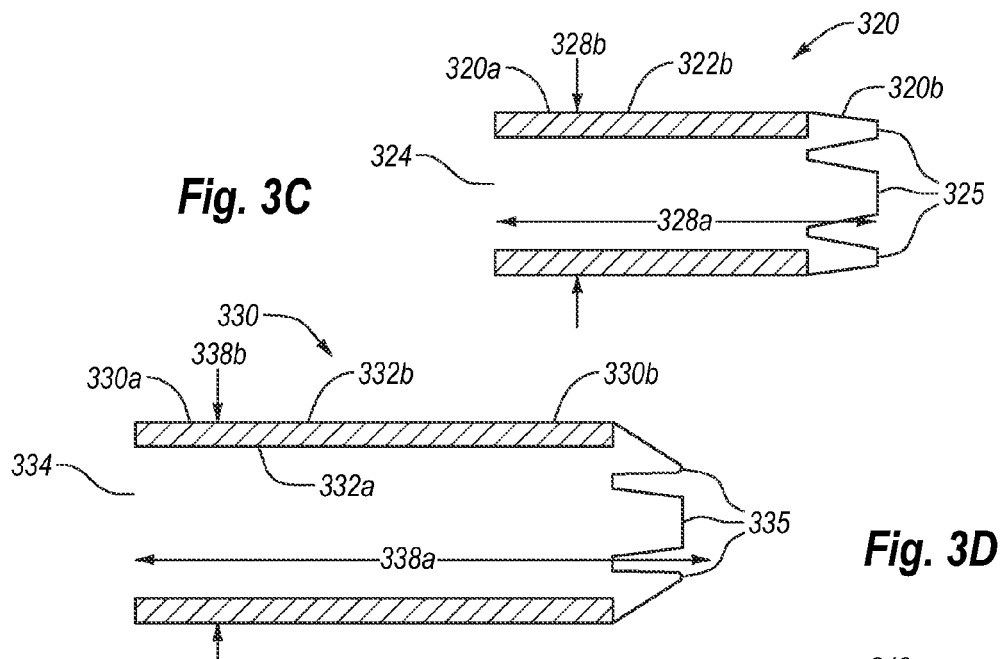
Fig. 3C
Fig. 3D
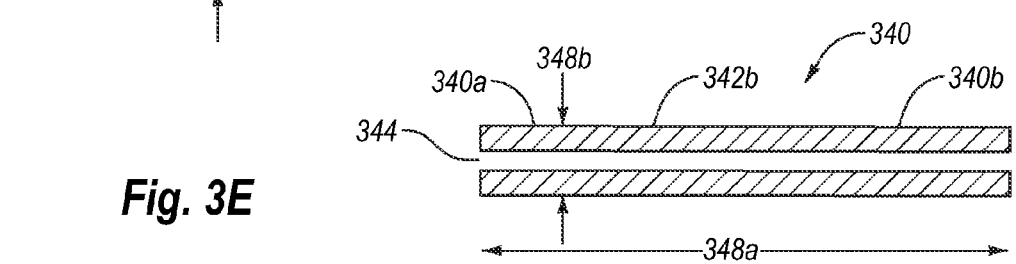
Fig. 3E

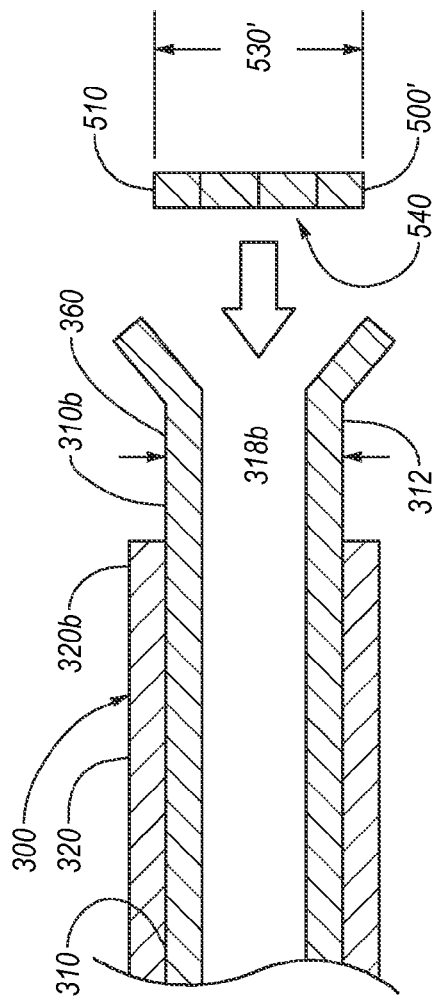
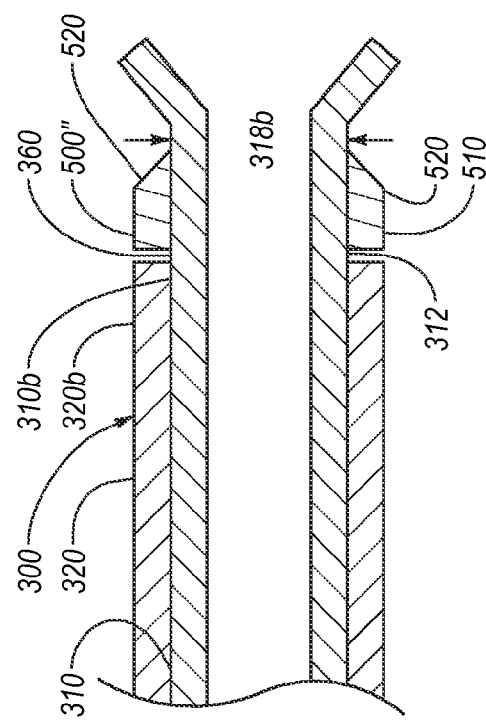
Fig. 7A
Fig. 7B

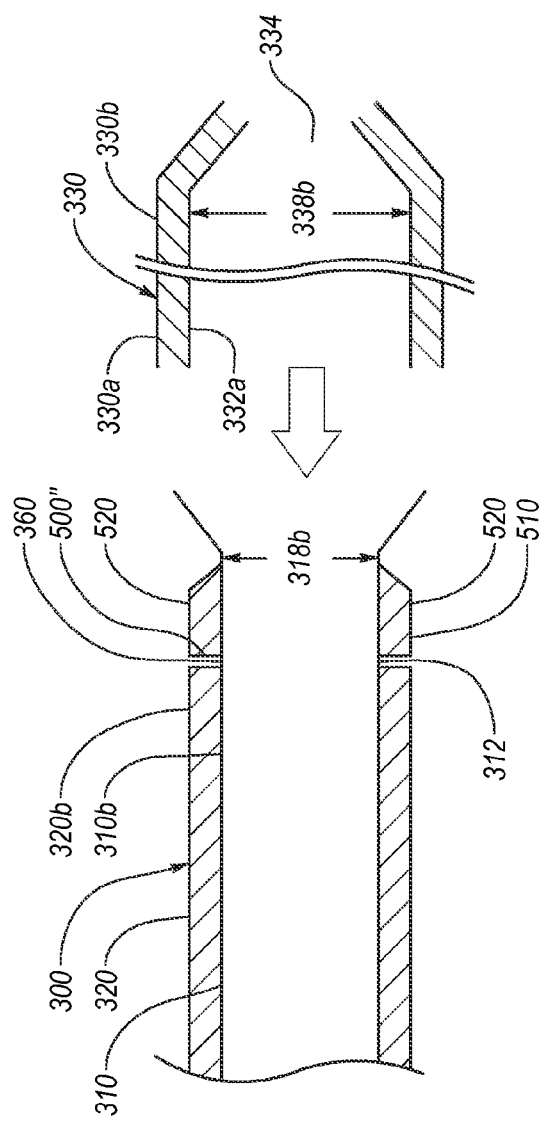
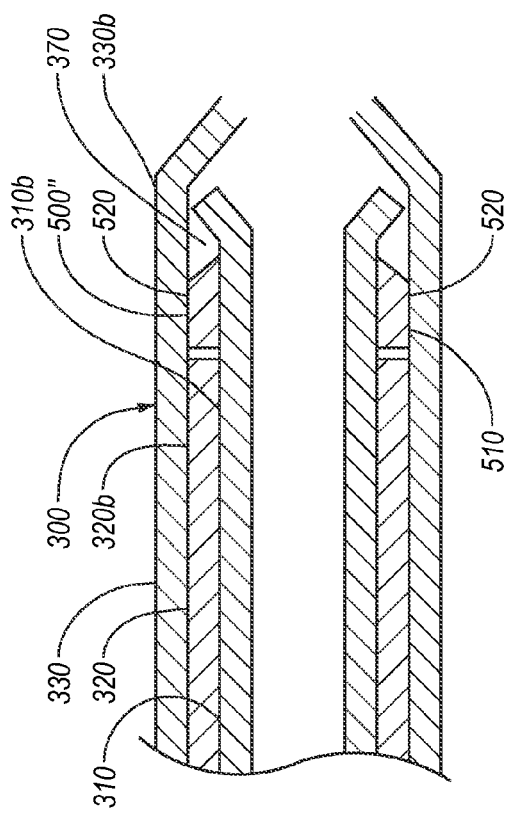
Fig. 7C
Fig. 7D

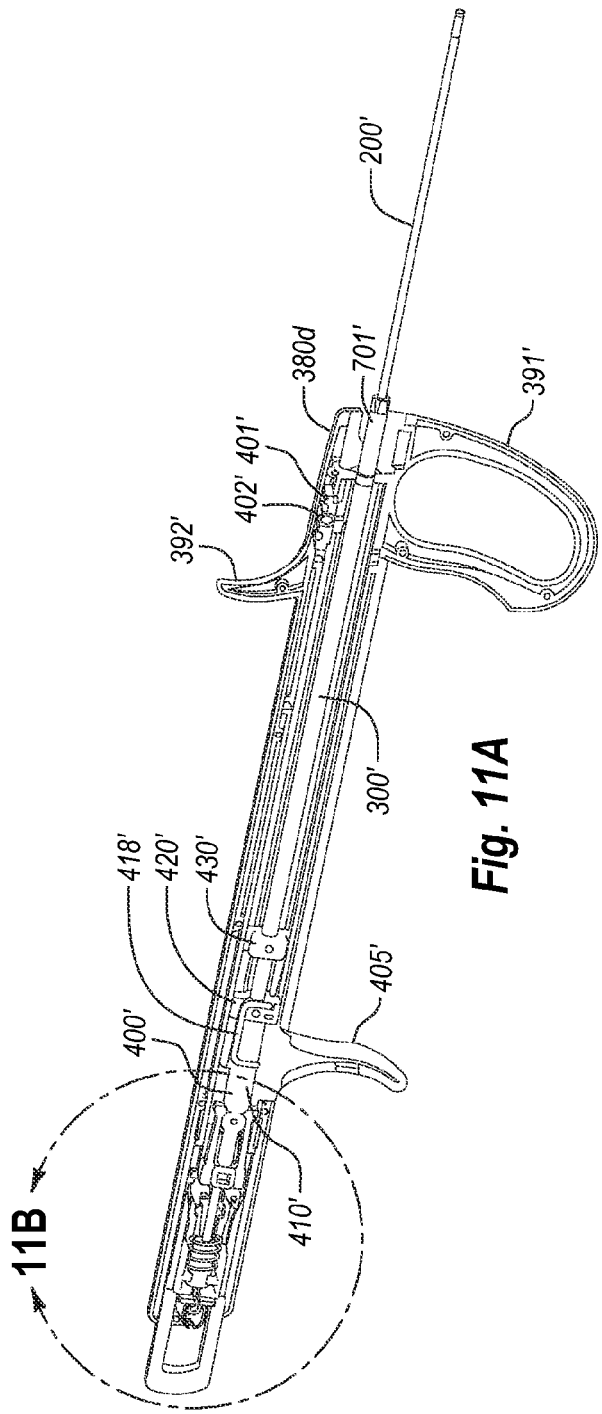
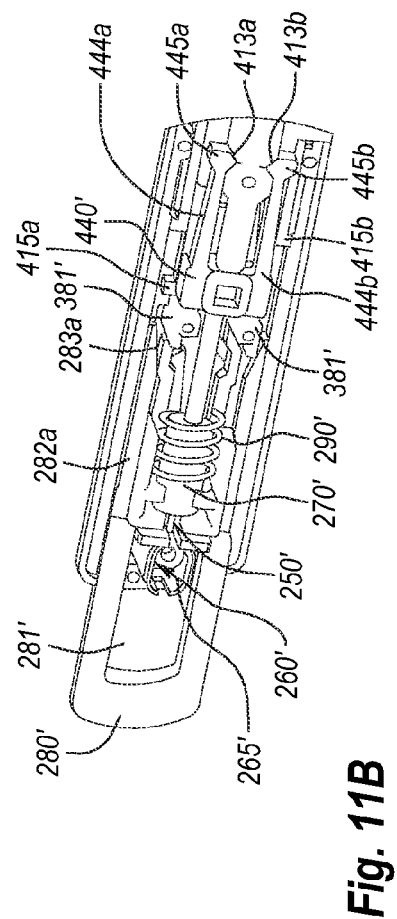
Fig. 11A
Fig. 11B

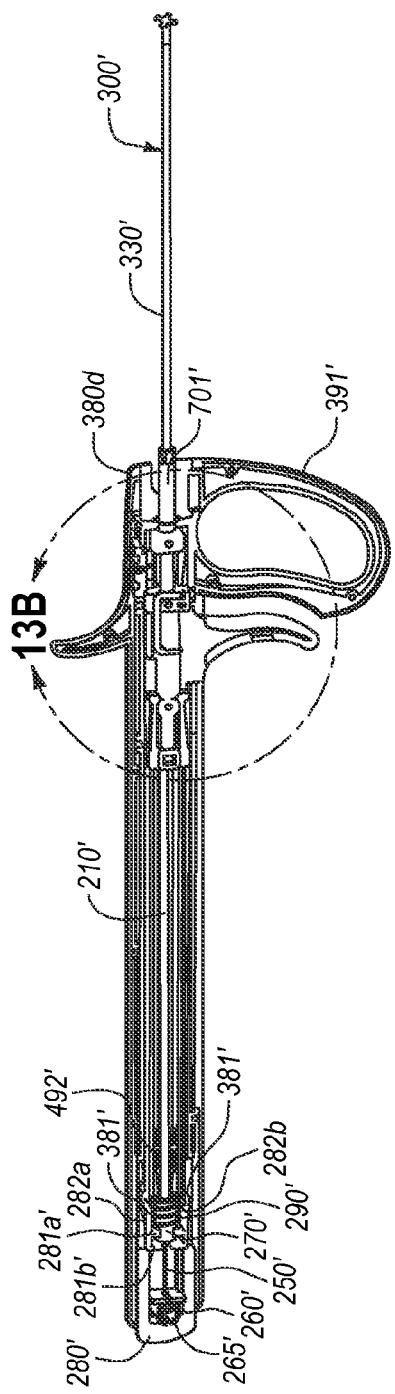
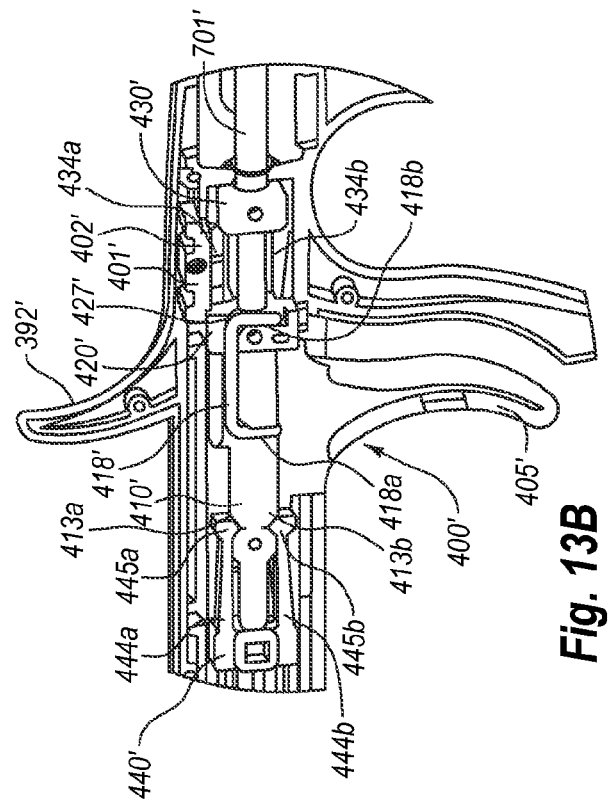
Fig. 13A
Fig. 13B

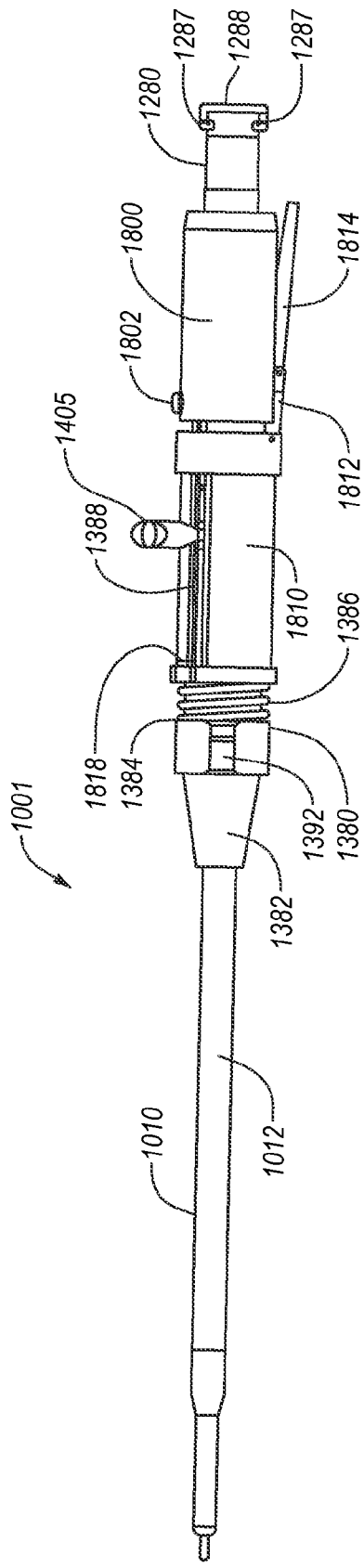
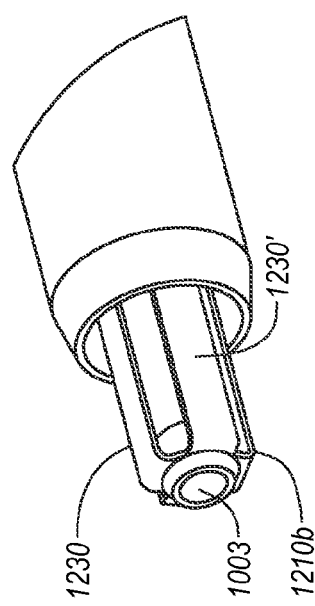
Fig. 16
Fig. 16A

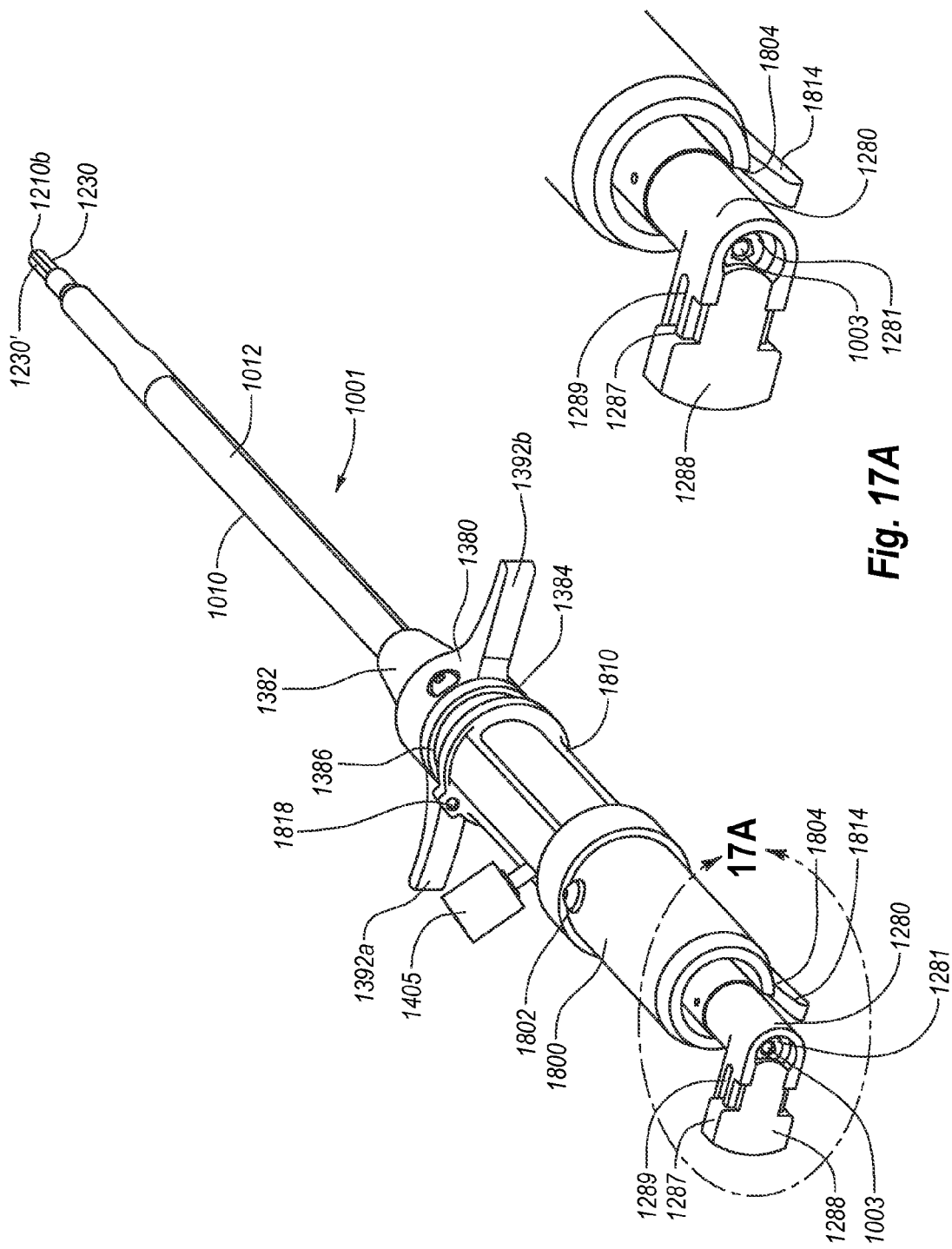

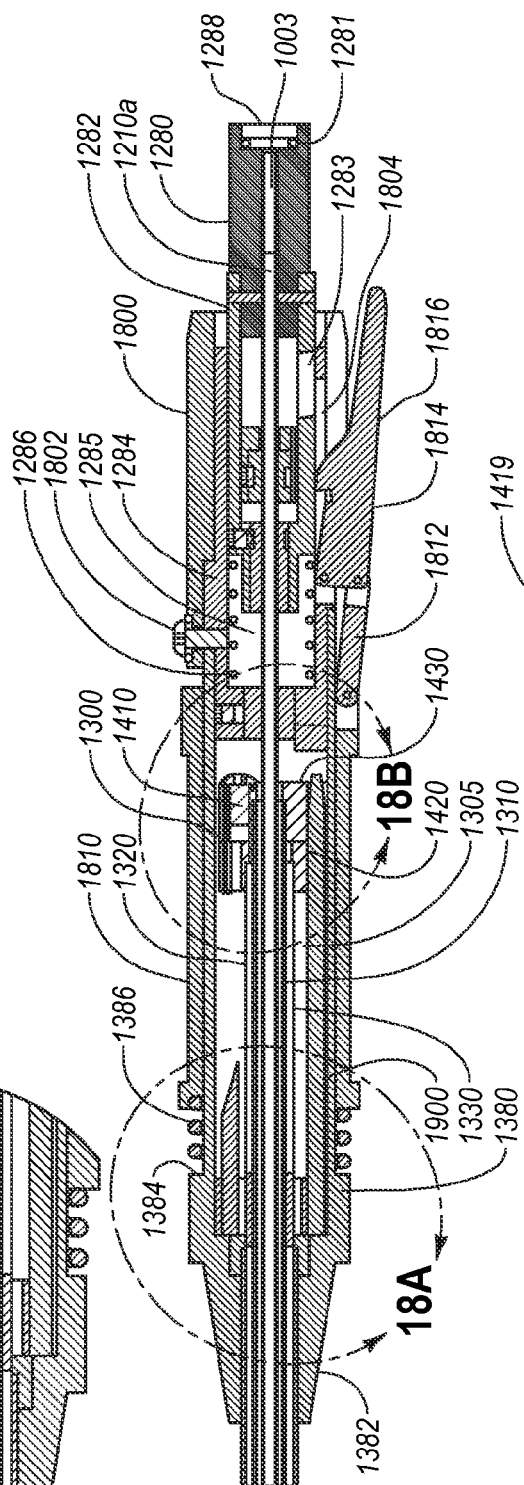
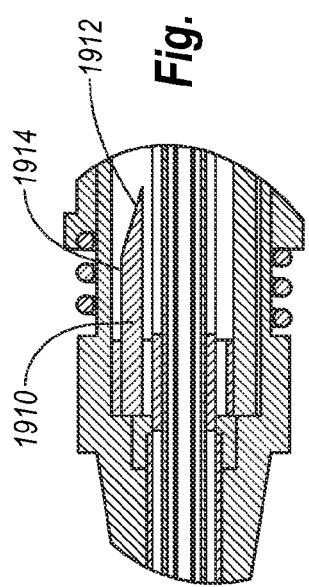
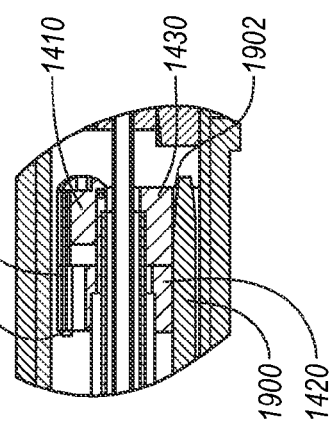
Fig. 18
Fig. 18A
Fig. 18B

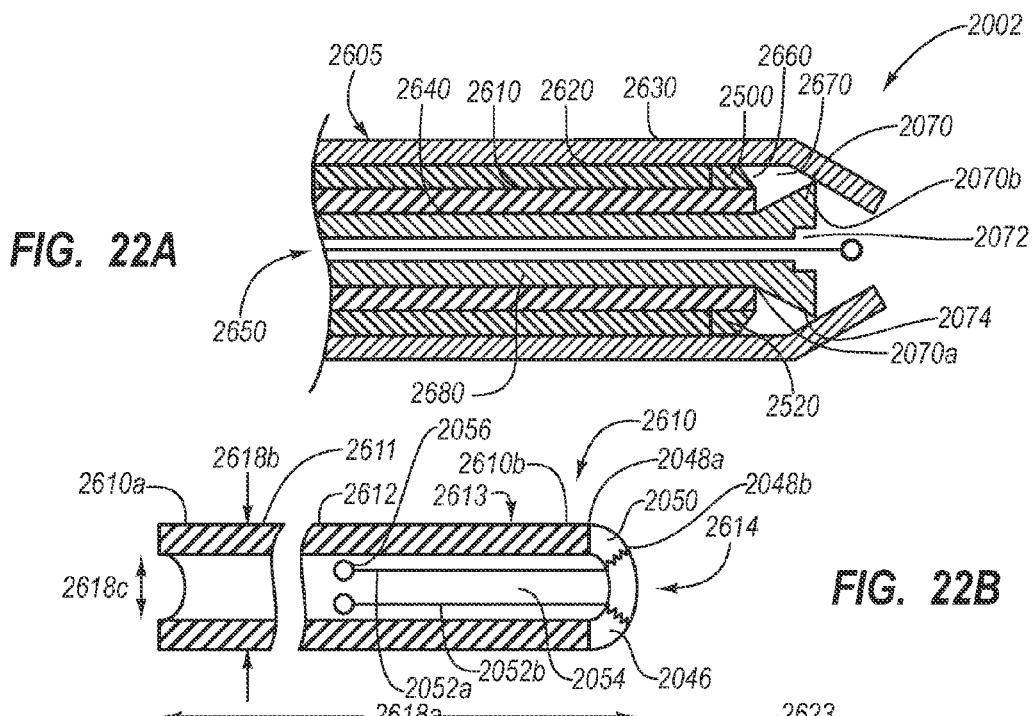
FIG. 22A
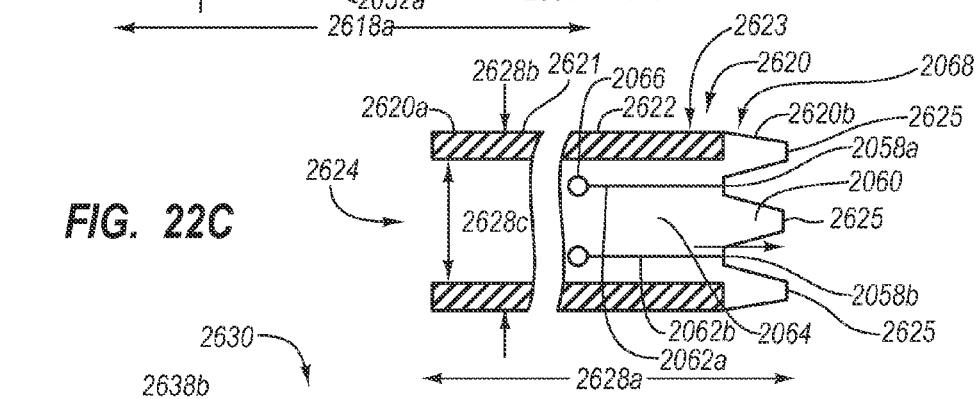
FIG. 22B
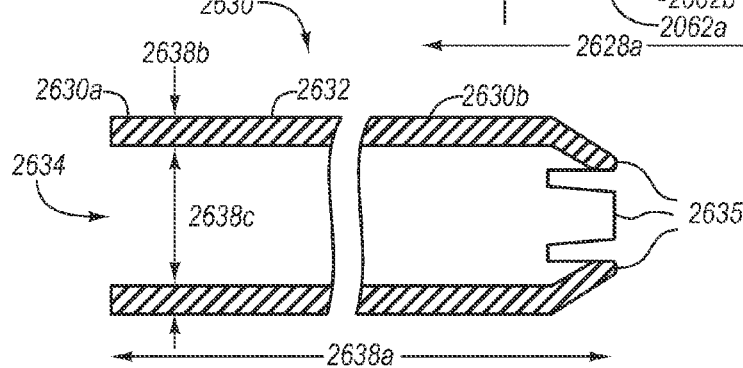
FIG. 22C
FIG. 22D
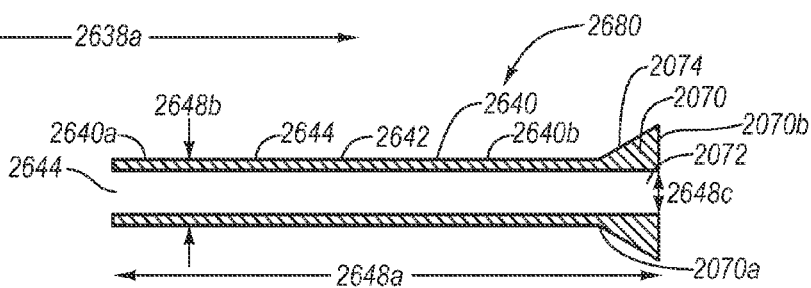
FIG. 22E

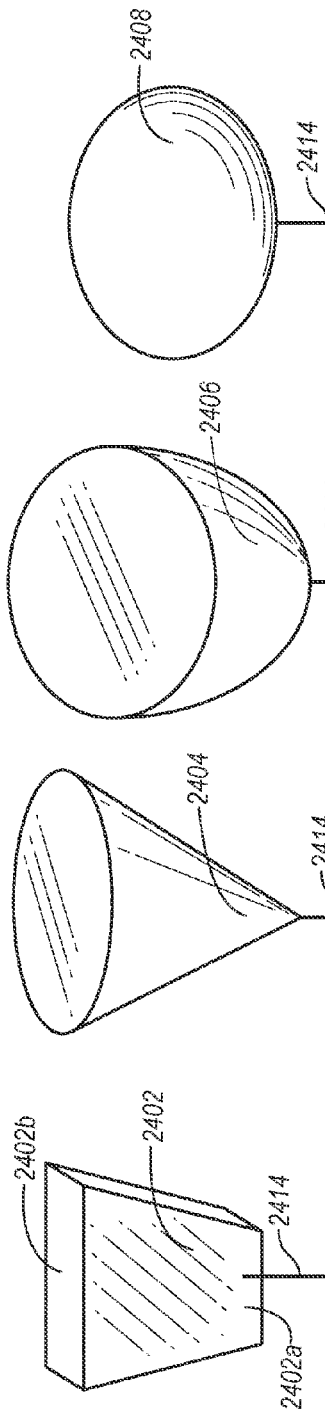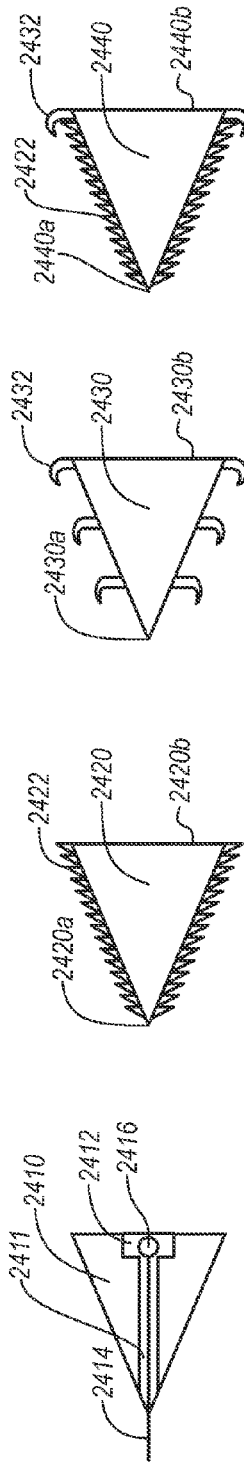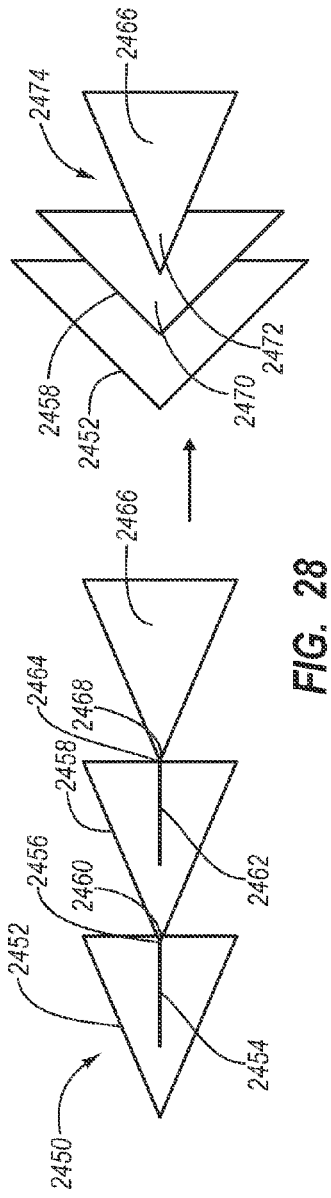

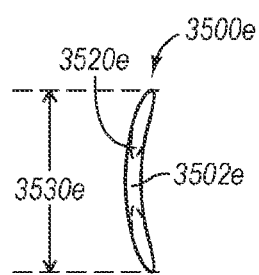
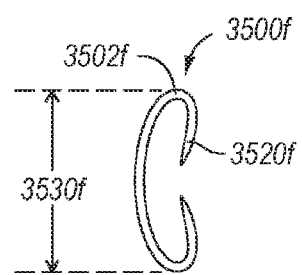
FIG. 37A   FIG. 37B
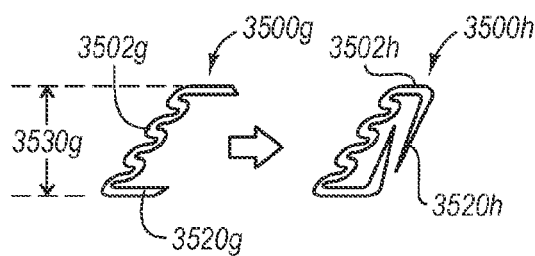
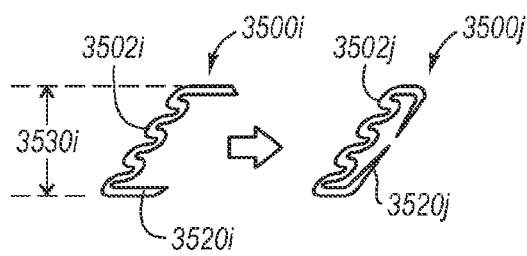
FIG. 37C   FIG. 37D

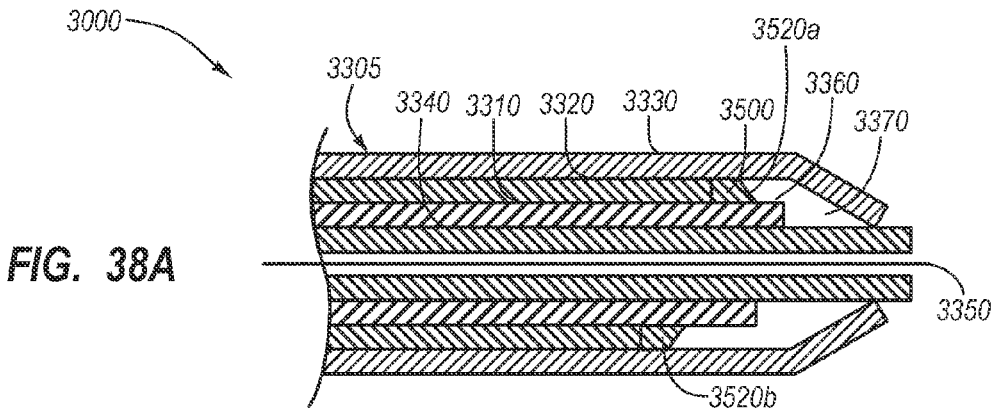
FIG. 38A
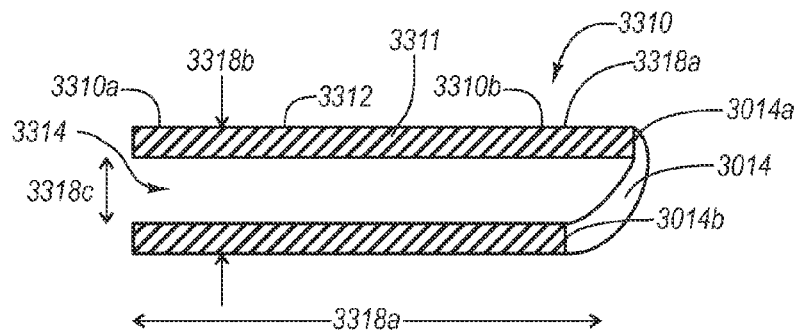
FIG. 38B
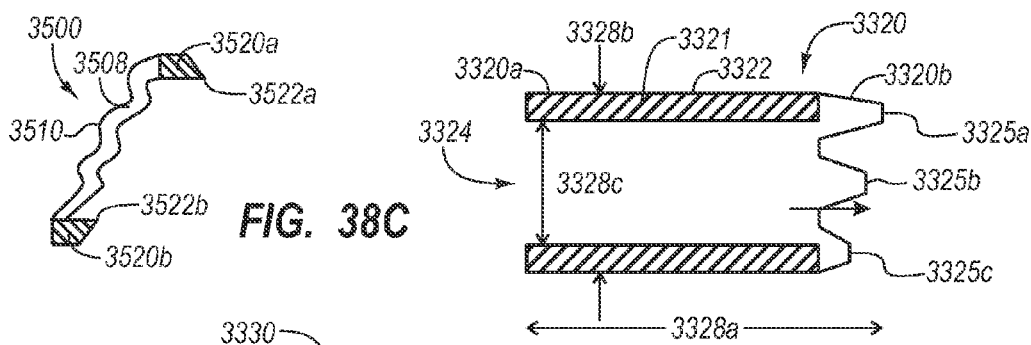
FIG. 38C
FIG. 38D
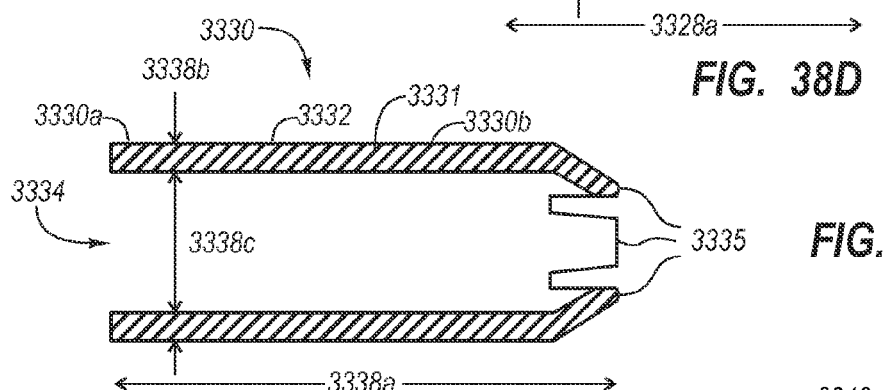
FIG. 38E
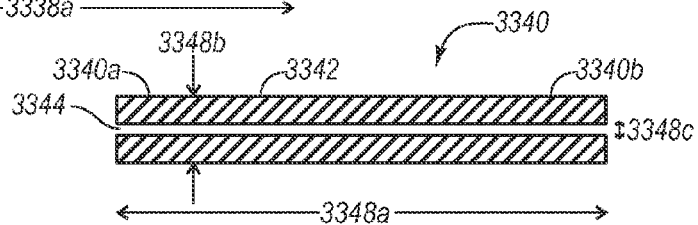
FIG. 38F

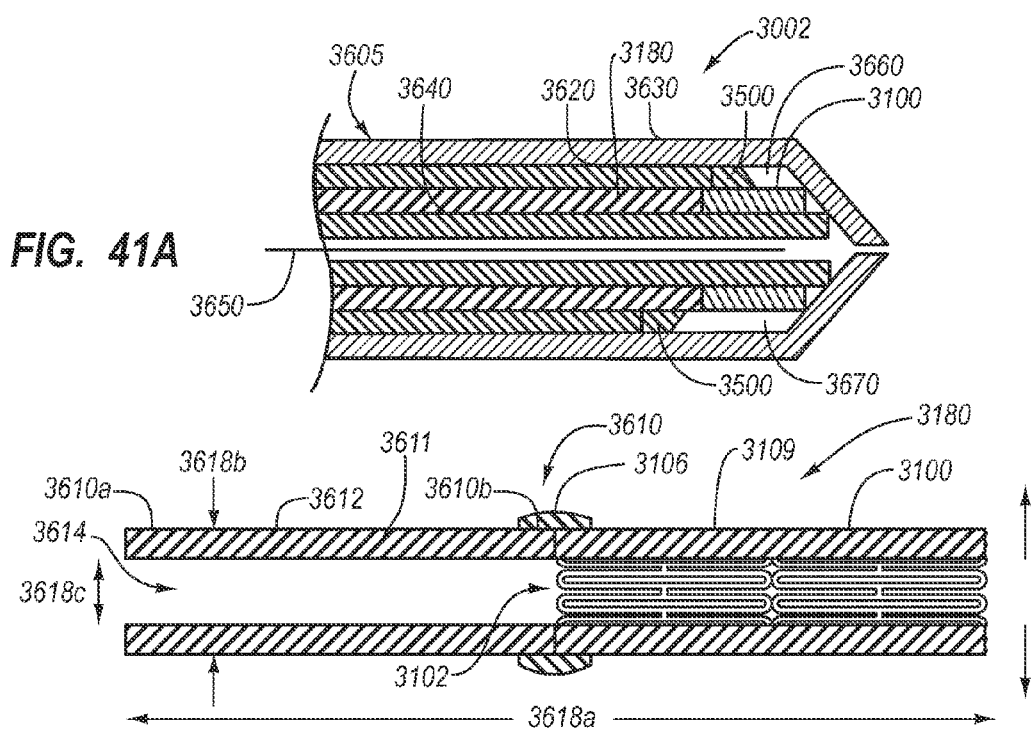
FIG. 41A
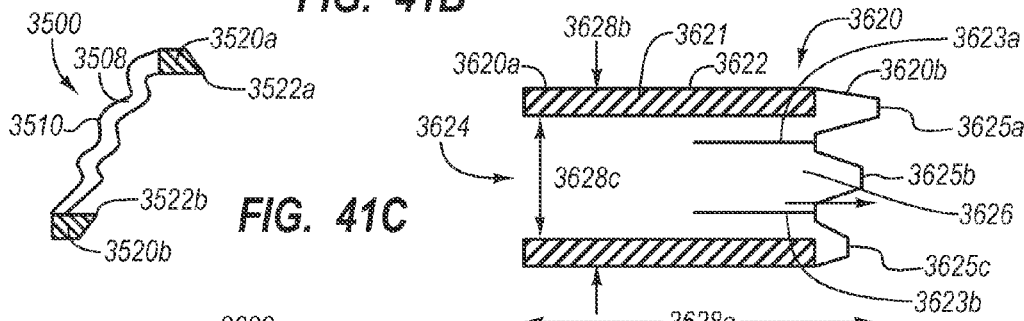
FIG. 41B
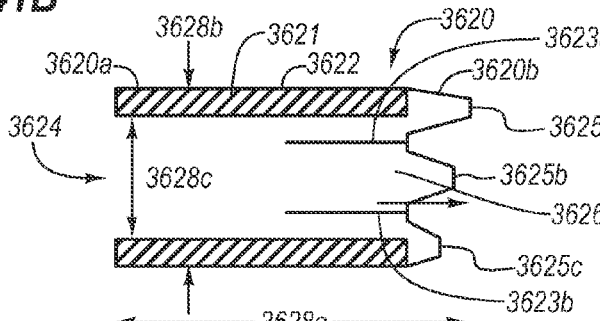
FIG. 41C
FIG. 41D
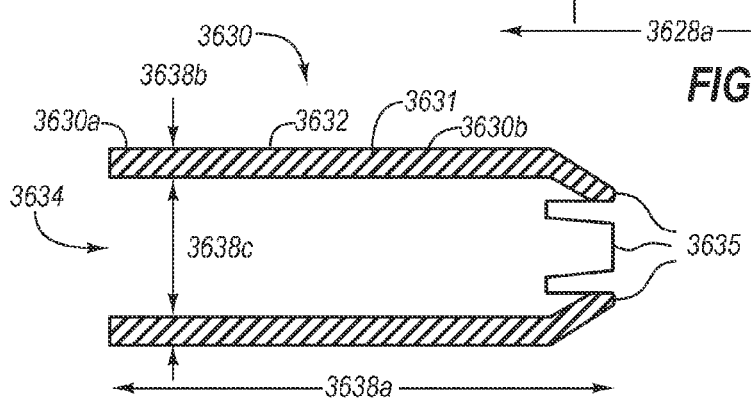
FIG. 41E
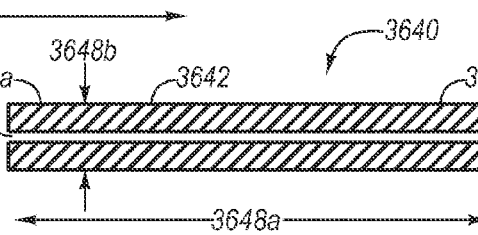
FIG. 41F

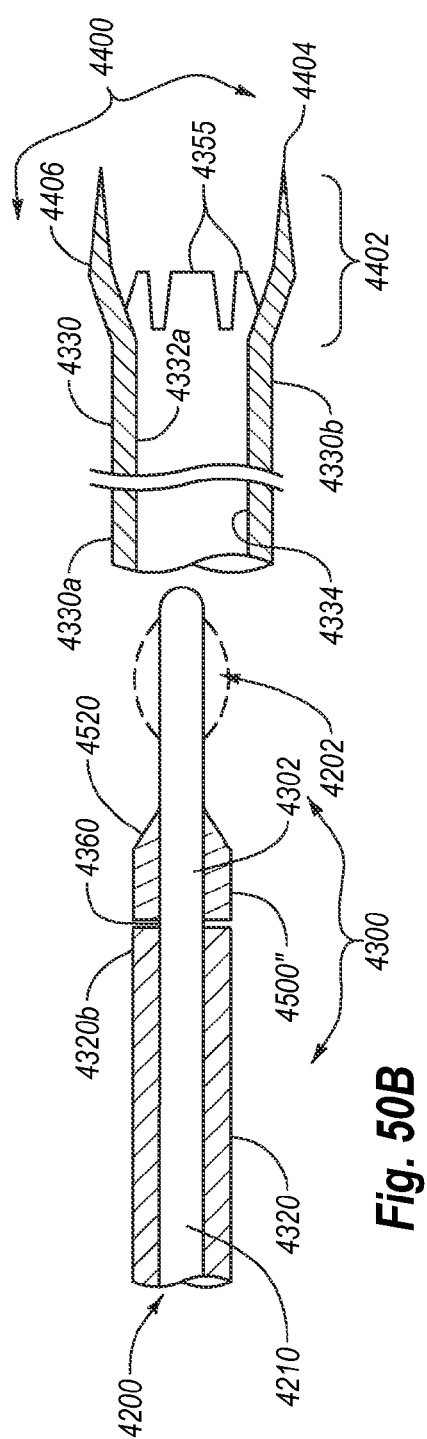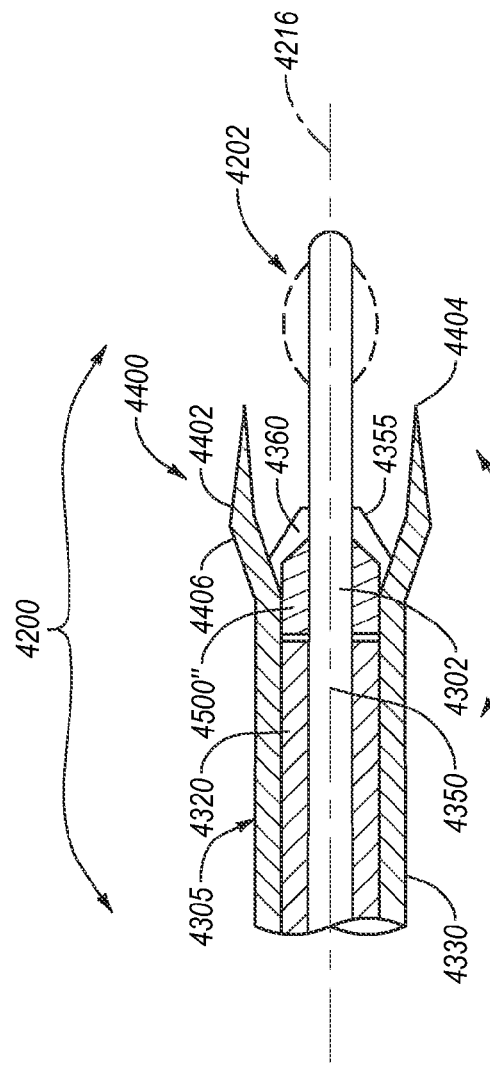
Fig. 50B
Fig. 50C

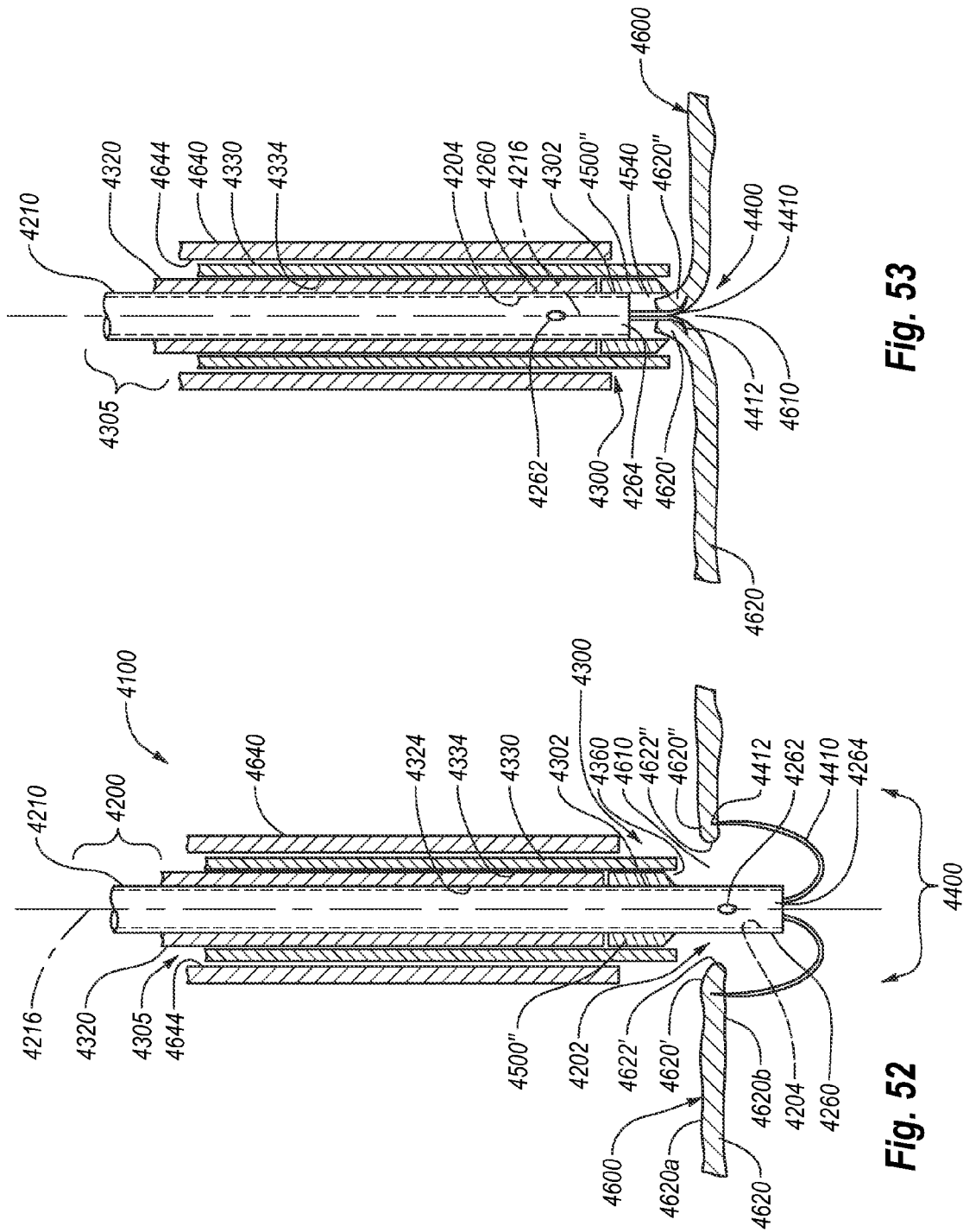

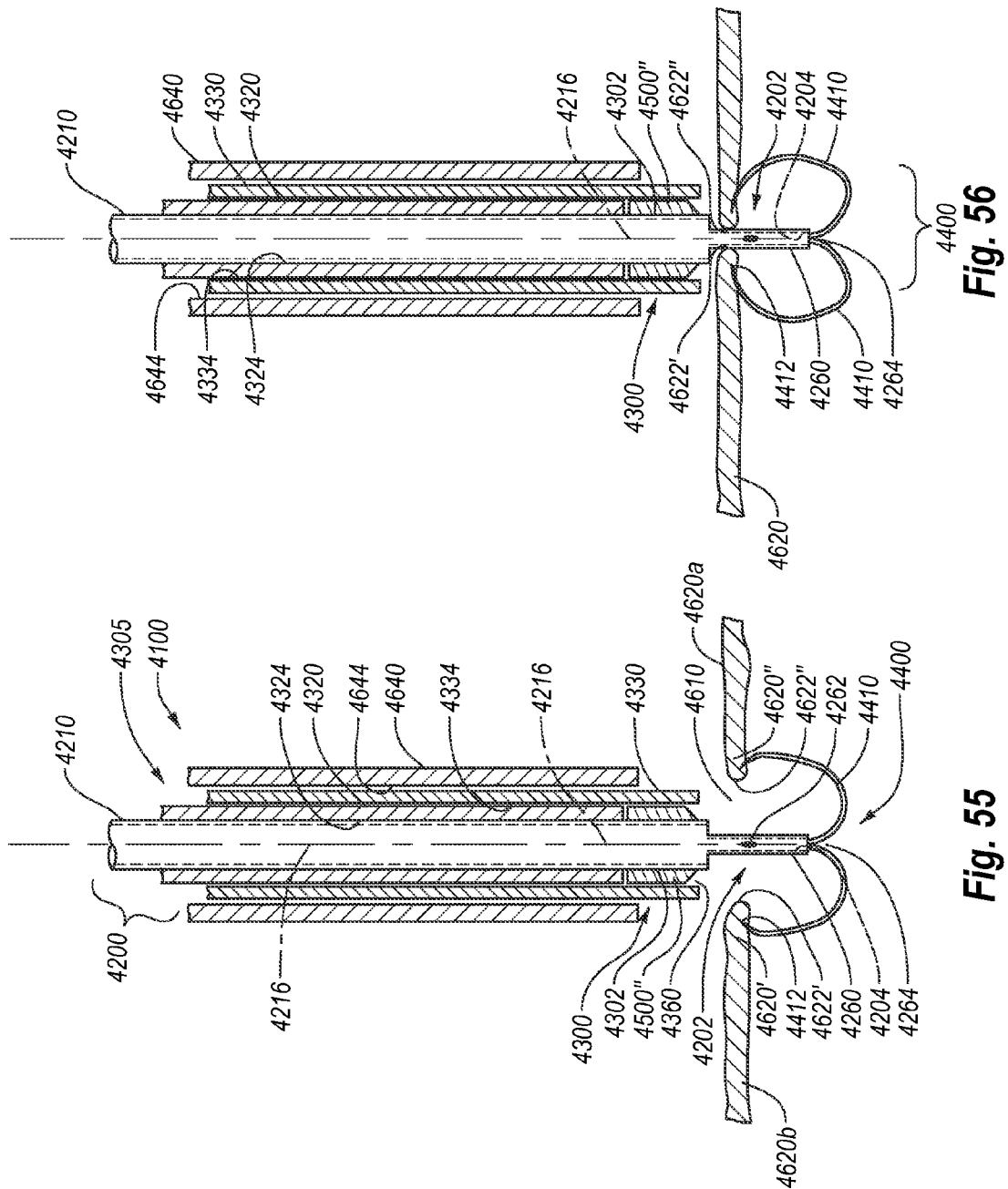

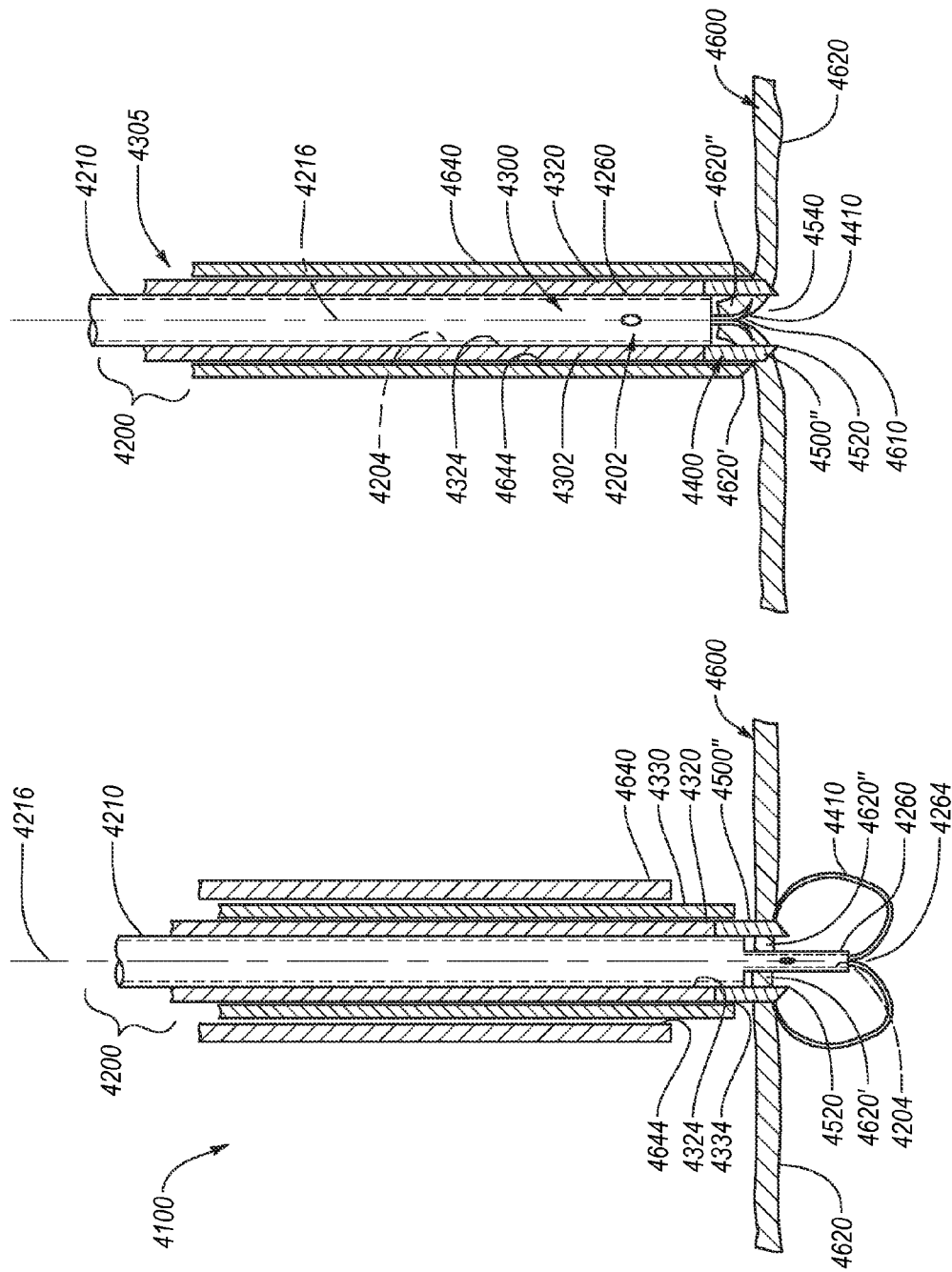

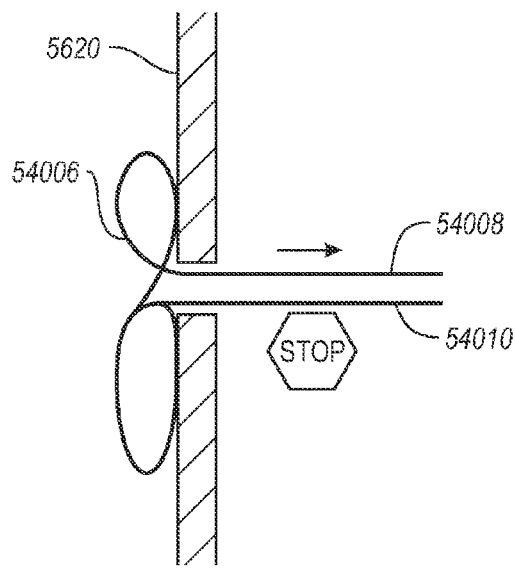
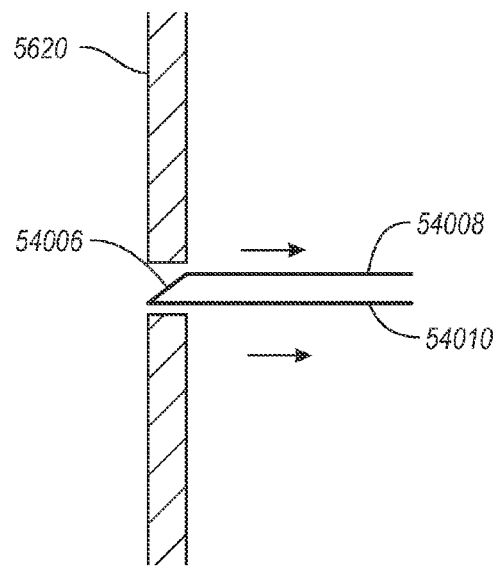
Fig. 64A       Fig. 64B
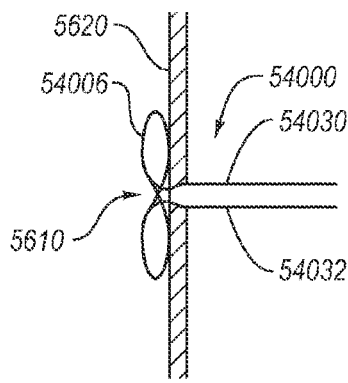
Fig. 65A
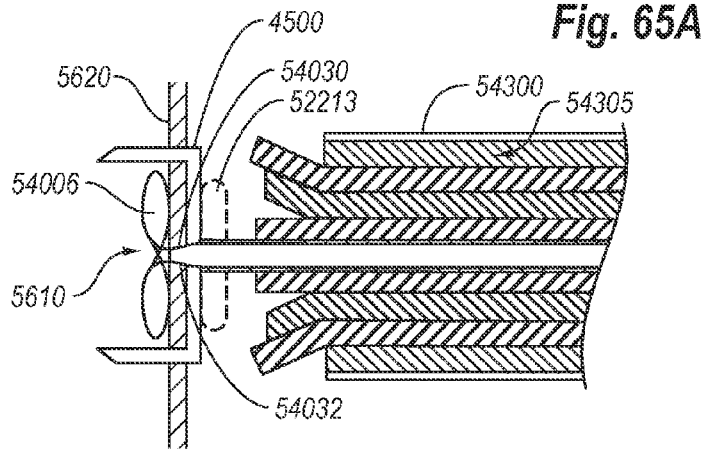
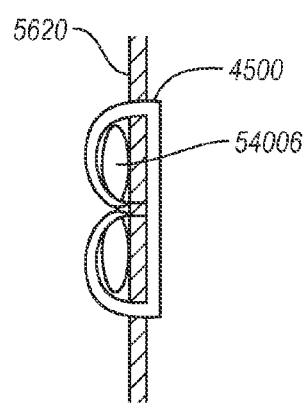
Fig. 65B       Fig. 65C

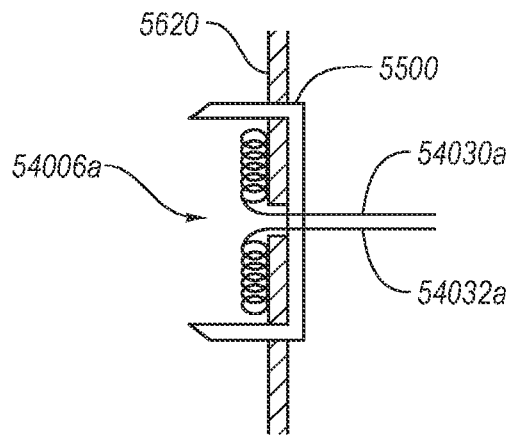
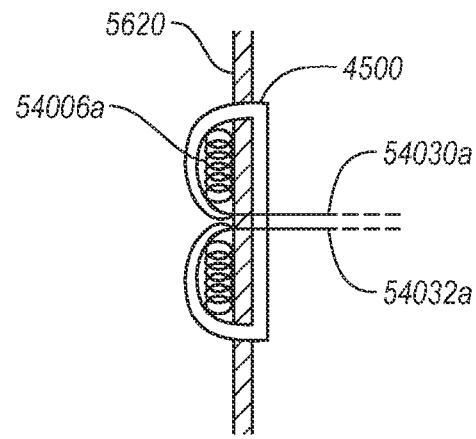
Fig. 66A  Fig. 66B
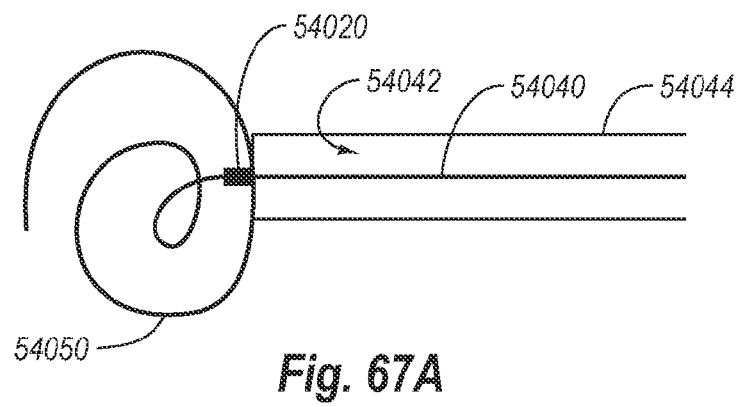
Fig. 67A
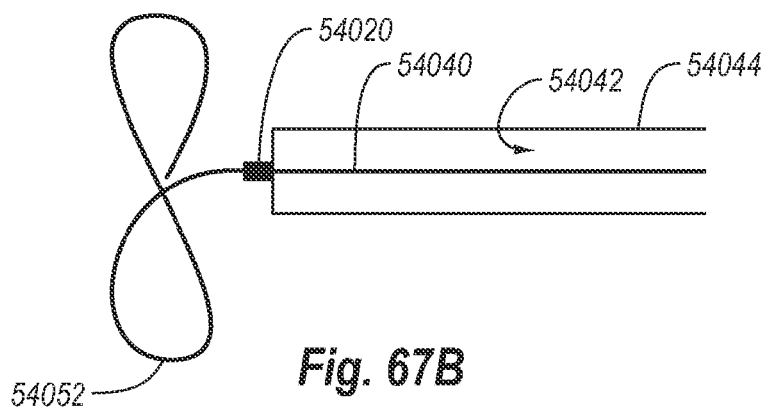
Fig. 67B

CLIP APPLIER AND METHODS OF USE

CROSS-REFERENCE TO RELATED APPLICATIONS

This application is a continuation-in-part of U.S. patent application Ser. No. 12/973,204, filed Dec. 20, 2010, now U.S. Pat. No. 8,202,294, which is a divisional of U.S. patent application Ser. No. 11/048,503, filed Feb. 1, 2005, now U.S. Pat. No. 7,857,828, which is a continuation-in-part of U.S. patent application Serial No. 10/638,115, filed Aug. 8, 2003, now U.S. Pat. No. 7,867,249, which is a continuation-in-part of U.S. patent application Ser. No. 10/356,214, filed Jan. 30, 2003, now U.S. Pat. No. 7,905,900, each of which are incorporated herein by specific reference in its entirety. This application is also a continuation-in-part of U.S. patent application Ser. No. 11/852,190, filed on Sep. 7, 2007, which claims benefit of U.S. Provisional Application Ser. No. 60/843,325, filed Sep. 8, 2006, each of which are incorporated herein by specific reference in its entirety. This application is also a continuation-in-part of U.S. patent application Ser. No. 12/143,020, filed Jun. 20, 2008, now U.S. Pat. No. 8,202,293, which claims priority to U.S. Provisional Application Ser. No. 60/946,030, filed June 25, 2007 and U.S. Provisional Application Ser. No. 60/946,042, filed Jun. 25, 2007, and is a continuation-in-part of U.S. patent application Ser. No. 11/048,503, filed Feb. 1, 2005 now U.S. Pat. No. 7,857,828, which is a continuation-in-part of U.S. patent application Ser. No. 10/638,115 filed Aug. 8, 2003 now U.S. Pat. No. 7,867, 249, which is a continuation-in-part of U.S. patent application Ser. No. 10/356,214, filed Jan. 30, 2003 now U.S. Pat. No. 7,905,900, each of which are incorporated herein by specific reference in its entirety. This application is also a continuation-in-part of U.S. patent application Ser. No. 12/393,877, filed Feb. 26, 2009. This application is also a continuation-in-part of U.S. patent application Ser. No. 12/961,331, filed Dec. 6, 2010, which is incorporated herein by specific reference in its entirety

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle then is removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al. To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. Accordingly, apparatus and methods for delivering a device for closing a vascular puncture site or other opening through tissue would be useful.

BRIEF SUMMARY

The present invention is directed toward an apparatus and method for delivering a closure element (e.g., clip) through tissue and into an opening formed in, or adjacent to, a wall of a blood vessel or other body lumen of any size.

Generally, an embodiment of such a clip applier apparatus can include a carrier tube carrying a closure element and a splitter configured to split the carrier tube. As such, the carrier tube can have an outer surface retaining the closure element in a substantially tubular configuration. Also, the carrier tube can be configured to split into radially-expandable or outwardly bendable carrier flaps. The splitter can be disposed distally from the carrier tube, and can be configured to move into a lumen of the carrier tube. Alternatively, the splitter can be disposed in a distal end of the lumen of the carrier tube. The splitter can split the carrier tube into the radially-expandable or outwardly bendable carrier flaps when moved through the lumen of the carrier tube. Also, the splitter can have a proximal end with a cross-sectional profile smaller than a cross-sectional profile of a distal end.

In another embodiment, a clip applier apparatus for delivering a closure element to an opening formed in a wall of a body lumen or body tissue can include a slidable splitter or an expandable splitter. As such, the carrier tube can have an outer surface retaining the closure element in a substantially tubular configuration. Also, the carrier tube can have a lumen and slits at a distal end of the carrier tube. The carrier tube can be configured to split at the slits so as to form outwardly bendable carrier flaps. Additionally, the splitter can be disposed adjacent to the slits so that the splitter can split the carrier tube at the distal end to form and outwardly bend the carrier flaps.

In one embodiment, the apparatus can include a splittable pusher tube that splits similarly as the carrier tube. The pusher tube can be configured to split into radially-expandable or outwardly bendable pusher flaps by the splitter when moved distally with respect to the carrier tube to deploy the closure element over the radially-expandable or outwardly bendable carrier flaps after expanding over the splitter. On the other hand, the expandable splitter can expand to split the pusher tube in order to form the pusher flaps.

In another embodiment, a clip applier apparatus for delivering a closure element to an opening formed in a wall of a body lumen or body tissue can include at least a partially splittable carrier tube and a splitter. Such a clip applier apparatus can include a partially splittable carrier tube having a length and slits extending at least partially along the length from a distal end toward a proximal end. The slits can be configured to separate at a distal portion of the carrier tube to form carrier flaps. Also, the carrier tube can have an outer surface retaining a closure element in a substantially tubular configuration at the splittable distal portion.

In one option, the splitter can be configured to move into a lumen of the carrier tube so as to split the distal portion of the carrier tube into the carrier flaps. The splitter can have a proximal end with a cross-sectional profile smaller than a cross-sectional profile of a distal end. Moreover, at least the distal end of the splitter can be larger than the lumen of the carrier tube.

In another option, the splitter can be an expandable splitter. As such, the entire splitter can selectively expand to split the carrier tube into the carrier flaps. Alternatively, the distal end of the splitter can selectively expand to split the carrier tube into the carrier flaps.

Additionally, the splitter can be coupled to a support tube so as to form a splitter tube. Alternatively, the splitter can be coupled to a wire disposed within the lumen of the carrier tube. The wire can extend through a passage in the splitter and have an end with an expanded diameter or retaining element disposed within a cavity in the splitter so that the end cannot pass through the passage.

A slidable splitter can be planar or volumetric, and can be shaped as at least one of a cone, wedge, sphere, hemisphere, trapezoid, combinations thereof, or other configurations that allow the splitter to perform the functions described herein. Also, the splitter can include a series of combinable splitters, wherein proximally disposed combinable splitters each have a recess for receiving a proximal portion of a distally-adjacent combinable splitter. Similarly, the splitter can include at least a proximal combinable splitter and a distal combinable splitter, wherein the proximal combinable splitter has a recess for receiving a proximal end of the distal combinable splitter. Furthermore, the splitter can be adapted to take hold of or grab a portion of tissue to the splitter. To aid with this functionality, the splitter can include teeth, barbs, or other structures that enable tissue to be selectively secured to a portion of the splitter.

In one embodiment, the present invention can use a clip applier having a carrier tube and a splitter in a method for closing an opening formed in a wall of a body lumen or body tissue. Such a method can include the following: positioning a carrier tube adjacent to the opening, the carrier tube having a distal end with an outer surface retaining a closure element in a substantially tubular configuration, the carrier tube having a lumen and being configured to split into flaps; splitting a distal end of the carrier tube with a splitter so as to form the flaps that deform outwardly over the splitter; and deploying the closure element from the outwardly deformed flaps of the carrier tube and over the splitter so that the closure element engages at least a portion of the wall of the body lumen or the body tissue whereby the opening is drawn substantially closed.

Accordingly, the carrier tube can be split with the splitter by at least one of the following: moving the splitter proximally with respect to the carrier tube; moving the carrier tube distally with respect to the splitter, or simultaneously moving the splitter proximally with respect to the carrier tube and moving the carrier tube distally with respect to the splitter; expanding the splitter; or selectively expanding a distal portion of the splitter.

In one embodiment, a tissue-grabbing splitter can be used in a method for closing an opening formed in a wall of a body lumen or body tissue. Such a method can include grabbing tissue around the opening with teeth and/or barbs on the splitter, and drawing the grabbed tissue toward the opening when the splitter is being pulled therethrough.

The present invention is also directed toward an apparatus and method for delivering a closure element through tissue and into an opening formed in, or adjacent to, a wall of a blood vessel or other body lumen of any size. It is further contemplated that the closure element and devices described herein can be utilized for other medical procedures not described herein, and it shall be further understood that the methods described herein should be considered exemplary and not limiting.

Generally, an embodiment of a closure element in accordance with the present can include a clip for closing an opening formed in a wall of a body lumen or body tissue. Such a clip can include a shape-memory clip having a relaxed configuration with a substantially planar-annular body defining a lumen with a plurality of tines directed inwardly from the body. Additionally, the clip can be oriented and held by a clip applier in a retaining configuration having a substantially asymmetrically-elongated tubular shape with a substantially trapezoidal longitudinal cross-sectional profile and a body portion having the plurality of tines being longitudinally and distally directed with a first tine of the plurality being more distally oriented compared to a substantially opposite second tine being more proximal. Also, the clip can be capable of retracting to a deploying configuration having a substantially symmetrical tubular shape with a substantially rectangular longitudinal cross-sectional profile with the first tine being substantially even with the second tine when the clip is being delivered from the clip applier to close the opening.

Additionally, the clip in the retaining configuration can have a lumen that has a smaller orthogonal cross-sectional profile (e.g., orthogonal to longitudinal direction) compared to the lumen in the deploying configuration. Alternatively, the clip in the retaining configuration can have a lumen that has a more oval orthogonal cross-sectional profile compared to the lumen in the deploying configuration having a more circular orthogonal cross-sectional profile. Also, the clip can automatically retract from the retaining configuration to the deploying configuration when being released from the clip applier. Further, the clip can automatically convert to the relaxed configuration from the deploying configuration after being released from the clip applier.

In another embodiment, the present invention can include a clip applier apparatus for delivering a clip to an opening formed in a wall of a body lumen or body tissue. Such a clip applier can include a shape-memory clip as described herein. Additionally, the clip applier can include a carrier tube having an outer surface configured for slidably retaining the clip in a retaining configuration and slidably delivering the clip in a deploying configuration, wherein the retaining configuration and deploying configuration are described herein.

In one embodiment, the clip applier can include a pusher tube that can push the clip from the retaining configuration to the deploying configuration. Also, the pusher tube can be configured to distally push the clip in the retaining configuration over the carrier tube toward a distal end of the carrier tube. Further, the pusher tube can be configured to distally push the clip over a distal end of the carrier tube so that the clip retracts from the retaining configuration to the deploying configuration.

Additionally, the carrier tube can be configured so that the outer surface corresponds in shape and size with the lumen of the clip in the retaining configuration. Accordingly, the outer surface of the carrier tube can be generally oval in shape. Also, the outer surface can have a smaller orthogonal cross-sectional profile compared to the size of the lumen of the clip in the deploying configuration.

In yet another embodiment, the clip applier can include a clip expander that is capable of expanding the clip during deployment. As such, the clip expander can be a selectively expandable shape-memory clip expander. Also, the clip expander can be disposed at a distal portion of the carrier tube.

In still another embodiment, the clip applier can include a cover tube that contains any of the carrier tube, pusher tube, clip, and/or clip expander. As such, the cover tube can define a lumen that retains the clip in the retaining configuration. Also, the lumen of the cover tube can retain the clip expander in a contracted orientation so that the clip expander can be capable of expanding when moved distally past a distal end of the cover tube.

Another embodiment of the present invention can include a method for closing an opening formed in a wall of a body lumen or body tissue. Such a method can include positioning a carrier tube adjacent to the opening, wherein the carrier tube has a distal portion with an outer surface retaining a shape-memory clip in a retaining configuration. The carrier tube, clip, and retaining configuration can be as described herein. Additionally, the method can include pushing the clip over a distal end of the carrier tube so that the clip retracts to a deploying configuration, wherein the deploying configuration is described herein. Further, the method can include ejecting the clip from the carrier tube so that at least a portion of the plurality of tines disposed on the body portion of the clip engages a portion of the wall of the body lumen or the body tissue whereby the opening is drawn substantially closed.

Additionally, the method can include pushing the clip toward the distal end of the carrier tube with a pusher tube being configured to distally push the clip in the retaining configuration. Also, the method can include flattening the clip, after being deployed from the carrier tube, to a relaxed configuration with a substantially planar-annular body defining a lumen with a plurality of tines directed inwardly from the body of the clip, wherein at least a portion of the tines have inwardly drawn a portion of the wall of the body lumen or the body tissue so as to substantially close the opening. Further, the method can include expanding the clip from the retaining configuration having a lumen with a smaller orthogonal cross-sectional profile to the deploying configuration so that the lumen has a larger orthogonal cross-sectional profile. Optionally, the clip can be expanded by a selectively expandable shape-memory clip expander. Furthermore, the method can include expanding the clip from the retaining configuration having a lumen with a more oval orthogonal cross-sectional profile to the deploying configuration so that the lumen has a more circular orthogonal cross-sectional profile.

An embodiment of an apparatus for locating a surface of a body lumen is disclosed. The apparatus includes a locator assembly that has a distal end region configured to extend into an opening of the body lumen and to selectably engage at least a portion of the body lumen adjacent to the opening. The distal end region includes at least one surface engaging element that is configured to engage the surface of the body lumen. The apparatus includes a measuring device that is in electrical communication with the surface engaging element. The measuring device is configured to determine changes in measurable characteristics of the surface engaging element.

An embodiment of a method for locating a surface of a body lumen is disclosed. The method includes inserting a locator assembly through an opening of the body lumen. The locator assembly includes a distal end region having a surface engaging element configured to selectively engage the surface of the body lumen. The locator assembly is positioned in close proximity to the opening of the body lumen. A measurable characteristic of the surface engaging element is measured within the body lumen. It is determined whether the measurable characteristic of the surface engaging element indicates that the surface engaging element has engaged the surface of the body lumen.

An embodiment of a surface engaging element is disclosed. The surface engaging element includes a proximal end portion that has at least one retaining portion. The surface engaging element includes a distal end portion that has at least one retaining portion. The surface engaging element includes at least one engaging member that extends toward the proximal end portion and extends toward the distal end portion. The at least one engaging member is configured to engage a surface of a body lumen.

In one embodiment, the present invention includes an apparatus for positioning a closure element to close an opening in a body lumen. Such an apparatus includes a carrier assembly and a distal tissue engaging device. The carrier assembly is configured to support a closure element in a substantially tubular configuration in a first diameter. The closure element is configured to substantially uniformly deform from a substantially tubular configuration to a natural, substantially planar configuration. The distal tissue engaging device is selectably axially displaceable relative to at least a portion of the carrier assembly. As such, the distal tissue engaging device moves between a tissue engaging condition and a tissue closing condition. The tissue engaging condition engages opposing portions of an arterial wall defining said body lumen adjacent to the opening. The tissue closing condition urges the engaged opposing portions of the arterial wall substantially together such that the closure element may be deployed from the delivery assembly to engage the opposed portions of the arterial wall and to return to the natural, substantially planar configuration.

In one embodiment, the distal tissue engaging device includes two or more opposed engaging tongs having respective end tips configured to open radially in directions extending beyond the first diameter to initially engage the opposing portions of the arterial wall, in the engaging condition.

In one embodiment, the carrier assembly further includes a cover member protecting at least the closure element which is contained therein.

In one embodiment, the distal tissue engaging device is integral with a distal end of the cover member.

In one embodiment, the carrier assembly is formed and dimensioned for sliding axial, reciprocating, receipt in a lumen of an introducer sheath extending through said tissue and terminating proximate the opening. The tissue engaging device is configured to cooperate with the introducer sheath to enable movement between the engaging condition and the closing condition.

In one embodiment, the present invention includes an apparatus for delivering and deploying a substantially resilient closure element through tissue to an opening in a body lumen perimeterically defined by opposing arterial walls. The closure element is configured to substantially uniformly deform from a natural, substantially resilient planar configuration to a substantially tubular configuration having a substantially natural transverse cross-sectional dimension. The apparatus includes a delivery assembly positionable through the tissue toward the opening in the body lumen. Also, the delivery assembly has a distal tissue engaging device and a carrier assembly configured to support the closure element in the substantially tubular configuration in a first diameter. The distal tissue engaging device is selectably axially displaceable relative to at least a portion of the carrier assembly between a tissue engaging condition and a tissue closing condition. The tissue engaging condition engages the opposing arterial walls of the body lumen adjacent to the opening. The tissue closing condition urges the engaged opposing arterial walls substantially transversely together such that the closure element may be deployed from the delivery assembly, while substantially maintained in the first diameter, into the opposing arterial walls. The closure element is oriented to engage the engaged opposing arterial walls when deployed and to return to the natural, substantially planar configuration and the natural, transverse cross-sectional dimension such that the engaged opposing arterial walls are drawn substantially closed.

In one embodiment, the apparatus includes a locator configured to position the carrier assembly and distal tissue engaging device adjacent to the opening in the body lumen. Also, the locator has a distal locator portion selectably controllable between an unexpanded state and an expanded state for engaging the opposing portions of the arterial wall of the body lumen.

In one embodiment, the apparatus includes a distal tissue locator portion contained on the delivery assembly. The distal tissue locator portion is configured to facilitate detection of the body lumen and includes one or more expansion elements configured to expand substantially transversely with respect to a longitudinal axis of the distal locator portion.

In one embodiment, the distal locator portion is selectably controllable between an unexpanded state and an expanded state for engaging said opposing arterial walls of said body lumen.

In one embodiment, while in the unexpanded state, the distal locator portion has a transverse cross-sectional dimension less than that of the opening. Also, while in the expanded state, the distal locator portion has a transverse cross-sectional dimension greater than or substantially equal to that of said opening.

In one embodiment, the present invention includes an apparatus for positioning a closure element to close an opening in a body lumen. Such an apparatus includes a carrier assembly and a distal tissue engaging device. The carrier assembly has a tubular body configured to receive a closure element in a substantially tubular configuration in a first diameter prior to deployment. Also, the tubular body has a distal port. The distal tissue engaging device is disposed within the tubular body and is selectably axially displaceable from the distal port. A portion of the distal tissue engaging device is biased to selectively radially extend outwardly from a longitudinal axis of the tubular body to intravascularly engage opposing arterial walls of the body lumen. A portion of the distal tissue engaging device urges the engaged opposing portions of the arterial wall substantially together as the distal tissue engaging device moves proximally. The closure element is then deployed to engage the opposed portions of the arterial wall.

In one embodiment, the carrier assembly includes a cover member defining a lumen configured for slidable receipt of the closure element therein.

In one embodiment, the carrier assembly includes a pusher member that slides for distally deploying the closure element.

In one embodiment, the pusher member and the tubular body are disposed as a nested, telescoping tube set with a common longitudinal axis.

In one embodiment, the tubular body includes a tissue locator portion. The tissue locator portion includes a bleed back shaft having a bleed back port distally disposed on a distal end of the tubular body.

In one embodiment, the present invention includes a closure system for closing an opening formed in a body lumen perimeterically defined by opposing arterial walls. Such a closure system includes a closure element, a delivery assembly, and a pusher member. The closure element is adapted to deform from a natural, substantially resilient planar configuration to a substantially tubular configuration that has a substantially natural transverse cross-sectional dimension. The delivery assembly is capable of being positioned through the tissue and into the opening in the body lumen.

Additionally, the delivery assembly has an elongated body, a carrier assembly and a distal tissue engaging device. The carrier assembly includes a carrier seat configured to carry and peripherally support the closure element in the substantially tubular configuration in a first diameter. The distal tissue engaging device is selectably, axially displaceable relative to the carrier seat between an engaging condition and a closing condition. The engaging condition engages the opposing arterial walls of the body lumen adjacent to the opening. The closing condition urges the engaged opposing arterial walls substantially transversely together such that the closure element may be deployed from the carrier assembly, while substantially maintained in the first diameter, into the opposing arterial walls.

The pusher member is slidably disposed about the elongated body for relative axial sliding displacement therebetween. The pusher member has a contact portion disposed proximally adjacent to the closure element in order to selectively distally deploy the closure element from the carrier assembly. The closure element is deployed in the substantially tubular configuration so as to engage the opposing arterial walls and to return to the natural, substantially planar configuration and the natural, transverse cross-sectional dimension such that the engaged opposing arterial walls are drawn substantially closed.

In one embodiment, the delivery assembly includes a tubular body supporting the carrier seat. Also, the tubular body defines a central receiving lumen extending longitudinally therethrough that is configured for sliding support of the tissue engaging device for axial movement between the engaging condition and the closing condition.

In one embodiment, the pusher member comprises one or more distally extending longitudinal extensions.

In one embodiment, the closure system includes a locator slidably receivable within the pusher member and the delivery assembly.

In one embodiment, the present invention includes a method for closing an opening defined by edges of arterial walls of a body lumen. Such a method includes the following: positioning a distal end region of a carrier assembly through tissue adjacent to an opening so that a distal tissue engaging device engages opposing portions of arterial walls, the distal end region of the carrier assembly includes a carrier seat configured to seat said closure element thereon in a substantially tubular configuration, having a first diameter; urging the engaged arterial walls radially inwardly and toward one another such that at least opposed edges of the arterial walls are drawn with the first diameter of the closure element; and distally deploying the closure element from the carrier assembly without further substantial radial expansion for the closure element, in the substantially tubular configuration, such that the closure element engages the arterial walls, and returns to the natural, planar configuration and the natural cross-section wherein the tissue is drawn substantially closed.

In one embodiment, the engagement of the arterial walls is performed by extravascularly engaging the arterial walls with the tissue engaging device.

In one embodiment, the engagement of the arterial walls is performed by intravascularly engaging the arterial walls with the tissue engaging device.

In one embodiment, the method includes placing a distal end region of a locator portion through tissue into the opening.

In one embodiment, the method includes engaging the arterial walls adjacent to the opening.

In one embodiment, the method includes orientating the carrier assembly proximal to the locator portion.

In one embodiment, the present invention is a medical device for delivering a closure element to an opening formed in a body lumen or body tissue with improved hemostasis. Such a medical device can include a locator assembly, a hemostasis assembly, and a carrier assembly. The locator assembly can have a distal end region configured to extend through tissue into the opening and to selectively engage an internal surface of said body lumen adjacent to the opening so as to provide a desired position of the medical device relative to the body lumen. The distal end region can include a locator that is implantable to improve hemostasis. Also, the locator can be a hemostatic locator with similar hemostatic characteristics as the hemostasis assembly. The hemostasis assembly can be associated with the locator assembly, whether or not the locator assembly includes an implantable locator or hemostatic locator. The hemostasis assembly can have a selectively expandable member on a distal end configured to extend into the opening so as to be disposed therein when the locator assembly is in contact with said internal surface of said body lumen. The expandable member can be configured to expand laterally when disposed in the opening so as to substantially plug the opening to provide hemostasis. Also, the hemostasis assembly can include a member, such as the selectively expandable member or other aspect of the distal end that includes a hemostatic agent coated thereon. The carrier assembly can be slidably coupled with the locator assembly and hemostasis assembly. The carrier assembly can have a carrier member supporting the closure element and a cover member retaining the closure element within the carrier assembly. The carrier assembly can be positioned through the tissue adjacent to the opening and can be configured to distally deploy the closure element such that the closure element substantially uniformly expands to a cross-section that is greater than a natural cross-section of the closure element. The closure element can be configured to engage the body lumen when deployed such that the lumen is drawn substantially closed.

In one embodiment, the expandable member of the hemostasis assembly can be selectively controlled between an unexpanded state and an expanded state for engaging a wall of said opening. The expandable member of the hemostasis assembly in the unexpanded state can have a cross-section that is less than a cross-section of the opening. The expandable member of the hemostasis assembly in the expanded state can have a cross-section that is greater than or substantially equal to a cross-section of the opening. Also, a hemostatic agent can be included with the expandable member or the expandable member can be configured to release some hemostatic agent when expanding or fully expanded.

In one embodiment, the expandable member of the hemostasis assembly can include one or more expansion elements configured to expand substantially transversely with respect to a longitudinal axis of the hemostasis assembly. The one or more expansion elements can be disposed within a flexible portion of the expandable member of the hemostasis assembly so that the expansion elements flex the flexible portion from the unexpanded state to the expanded state in order to plug the opening and provide hemostasis.

In one embodiment, the expandable member includes a substantially flexible and/or deformable member with a substantially fixed end region fixedly coupled with the hemostasis assembly, an intermediate region, and a movable end region movable coupled with the hemostasis assembly such that the intermediate region is configured to expand transversely outwardly when the movable end region is axially moved toward the substantially fixed end region.

In one embodiment, the hemostasis assembly can include a control system coupled to a proximal end region of the hemostasis assembly. The control system can be configured to selectively control the expandable member of the hemostasis assembly between the expanded state and the unexpanded state. The control system can expand the expandable member and maintain the expandable member in the expanded state for a desired duration when the control system is engaged. The control system can change the expandable member from the expanded state to the unexpanded state when the control system is disengaged.

In one embodiment, the expandable member can include an expandable bladder. The bladder can be coupled to a fluid source that can inflate the bladder. For example, an inflation tube can be coupled with the bladder such that fluid, such as air, can be passed through the inflation tube to expand the bladder. A pump or other device that can cause the bladder to inflate may also be associated with the bladder and inflation tube.

In one embodiment, the expandable member expands by longitudinally compressing the expandable member so as to laterally expand the expandable member.

In one embodiment, the hemostasis assembly can include an actuator member that is actuated so as to expand the expandable member.

In one embodiment, the present invention includes a medical system for closing an opening formed in a body lumen or body tissue with improved hemostasis. Such a system can include an introducer sheath, locator assembly, hemostasis assembly, closure element, and carrier assembly for the closure element. The introducer sheath can be configured to be deployed into the body lumen or body tissue. The introducer sheath can include a proximal end, a distal end, and a lumen extending from the proximal end to the distal end. The locator assembly can be configured so as to be capable of being disposed in the lumen of the introducer sheath. The locator assembly can have a locator member at a distal end region of the locator assembly configured to extend through tissue into the opening and to selectively engage an internal surface of the body lumen adjacent to the opening so as to provide a desired position of the medical device relative to the opening and body lumen. Optionally, the locator member can be implantable and either biostable or biodegradable. In another option, the locator member can be hemostatic. The hemostasis assembly can be associated with the locator assembly, and can be capable of being disposed in the lumen of the introducer sheath with the locator assembly. The hemostasis assembly can have a selectively expandable member on a distal end configured to extend into the opening so as to be disposed therein when the locator assembly is in contact with the internal surface of the body lumen. The expandable member can be configured to expand laterally when disposed in the opening so as to contact the wall of the opening and substantially plug the opening to provide hemostasis. The carrier assembly can be slidably coupled with the locator assembly and hemostasis assembly, and can be dimensioned so as to be capable of being disposed in the introducer sheath with the locator assembly and the hemostasis assembly. The carrier assembly can have a carrier member supporting the closure element and a cover member retaining the closure element within the carrier assembly. The carrier assembly can be positioned through the tissue adjacent to the opening, and can be configured to distally deploy the closure element such that the closure element substantially uniformly expands to a cross-section that is greater than a natural cross-section of the closure element. The closure element can be configured to engage the tissue when deployed such that the tissue is drawn substantially closed.

In one embodiment, the expandable member of the hemostasis assembly can be selectively controlled between an unexpanded state and an expanded state for engaging a wall of the opening. Also, the locator member of the locator assembly can be selectively controlled between an unexpanded state and an expanded state for engaging the body lumen. The expandable member of the hemostasis assembly and the locator member of the locator assembly both can be in the unexpanded state and can have a cross-section that is less than a cross-section of the opening. The expandable member of the hemostasis assembly and the locator member of the locator assembly both in the expanded state can each have a cross-section that is greater than or substantially equal to a cross-section of the opening. Optionally, the expandable member and locator member can be configured to cooperate in providing hemostasis. This can allow for the locator member to apply pressure to the inside wall of a blood vessel while the expandable member of the hemostasis assembly can apply pressure to the outside of the vessel and/or against the vessel walls surrounding the opening in the vessel.

In one embodiment, the expandable member of the hemostasis assembly can include one or more hemostasis expansion elements configured to expand substantially transversely with respect to a longitudinal axis of the hemostasis assembly. The locator member of the locator assembly can also include one or more locator expansion elements configured to expand substantially transversely with respect to a longitudinal axis of the locator assembly.

In one embodiment, the hemostasis expansion elements are disposed within a flexible portion of the expandable member of the hemostasis assembly so that the one or more hemostasis expansion elements flex the flexible portion from the unexpanded state to the expanded state in order to plug the opening and provide hemostasis. The locator expansion elements can be substantially equally distributed about an outer periphery of the locator member of the locator assembly.

In one embodiment, each of the locator expansion elements can include a substantially flexible member with a substantially fixed end region fixedly coupled with said distal end region of the locator assembly, an intermediate region, and a movable end region movable coupled with the distal end region of the locator assembly such that the intermediate regions are configured to expand transversely outwardly when the movable end regions are axially moved toward said substantially fixed end regions.

In one embodiment, the expandable member of the hemostasis assembly can include a substantially flexible member with a substantially fixed end region fixedly coupled with the hemostasis assembly, an intermediate region, and a movable end region movable coupled with the hemostasis assembly such that the intermediate region is configured to expand transversely outwardly when the movable end region is axially moved toward the substantially fixed end region.

In one embodiment, the hemostasis assembly can include a hemostasis control system coupled to a proximal end region of the hemostasis assembly. The hemostasis control system can be configured to selectively control the expandable member of the hemostasis assembly between the expanded state and the unexpanded state.

In one embodiment, the locator assembly can include a locator control system coupled to a proximal end region of the locator assembly. The locator control system can be configured to selectively control the locator member of the locator assembly between the expanded state and the unexpanded state. The locator control can also be configured to release the locator upon application of the closure element so that the locator is retained against the inner wall of the vessel in order to facilitate hemostasis. The hemostasis control system and locator control system can be integrated. Also, the hemostasis control system and locator control system can be included in the same control system.

Generally, an embodiment of a closure element in accordance with the present can include a clip for closing an opening formed in a wall of a body lumen or body tissue. Such a clip can include a shape-memory clip having a relaxed configuration with a substantially planar-annular body defining a lumen with a plurality of tines directed inwardly from the body. Additionally, the clip can be oriented and held by a clip applier in a retaining configuration having a substantially asymmetrically-elongated tubular shape with a substantially trapezoidal longitudinal cross-sectional profile and a proximal portion having the plurality of tines being longitudinally and distally directed with a first tine of the plurality being more distally oriented compared to a substantially opposite second tine being more proximal. Also, the clip can be capable of retracting to a deploying configuration having a substantially symmetrical tubular shape with a substantially rectangular longitudinal cross-sectional profile with the first tine being substantially even with the second tine when the clip is being delivered from the clip applier to close the opening.

Additionally, the clip in the retaining configuration can have a lumen that has a smaller orthogonal cross-sectional profile (e.g., orthogonal to longitudinal direction) compared to the lumen in the deploying configuration. Alternatively, the clip in the retaining configuration can have a lumen that has a more oval orthogonal cross-sectional profile compared to the lumen in the deploying configuration having a more circular orthogonal cross-sectional profile. Also, the clip can automatically retract from the retaining configuration to the deploying configuration when being released from the clip applier. Further, the clip can automatically convert to the relaxed configuration from the deploying configuration after being released from the clip applier. Such conversion to the relaxed configuration can allow for the tines of the clip to grab the locator during the relaxation process, and retain the locator against the blood vessel wall to facilitate hemostasis.

In another embodiment, the present invention can include a clip applier apparatus for delivering a clip to an opening formed in a wall of a body lumen or body tissue. Such a clip applier can include a shape-memory clip as described herein. Additionally, the clip applier can include a carrier tube having an outer surface configured for slidably retaining the clip in a retaining configuration and slidably delivering the clip in a deploying configuration, wherein the retaining configuration and deploying configuration are described herein.

In one embodiment, the clip applier can include a pusher tube that can push the clip from the retaining configuration to the deploying configuration. Also, the pusher tube can be configured to distally push the clip in the retaining configuration over the carrier tube toward a distal end of the carrier tube. Further, the pusher tube can be configured to distally push the clip over a distal end of the carrier tube so that the clip retracts from the retaining configuration to the deploying configuration.

Additionally, the carrier tube can be configured so that the outer surface corresponds in shape and size with the lumen of the clip in the retaining configuration. Accordingly, the outer surface of the carrier tube can be generally oval in shape. Also, the outer surface can have a smaller orthogonal cross-sectional profile compared to the size of the lumen of the clip in the deploying configuration.

In yet another embodiment, the clip applier can include a clip expander that is capable of expanding the clip during deployment. As such, the clip expander can be a selectively expandable shape-memory clip expander. Also, the clip expander can be disposed at a distal portion of the carrier tube.

In still another embodiment, the clip applier can include a cover tube that contains any of the carrier tube, pusher tube, clip, and/or clip expander. As such, the cover tube can define a lumen that retains the clip in the retaining configuration. Also, the lumen of the cover tube can retain the clip expander in a contracted orientation so that the clip expander can be capable of expanding when moved distally past a distal end of the cover tube.

Another embodiment of the present invention can include a method for closing an opening formed in a wall of a body lumen or body tissue. Such a method can include positioning a carrier tube adjacent to the opening, wherein the carrier tube has a distal portion with an outer surface retaining a shape-memory clip in a retaining configuration. The carrier tube, clip, and retaining configuration can be as described herein. Additionally, the method can include pushing the clip over a distal end of the carrier tube so that the clip retracts to a deploying configuration, wherein the deploying configuration is described herein. Further, the method can include ejecting the clip from the carrier tube so that at least a portion of the plurality of tines disposed on the proximal end of the clip engages a portion of the wall of the body lumen or the body tissue whereby the opening is drawn substantially closed.

Additionally, the method can include pushing the clip toward the distal end of the carrier tube with a pusher tube being configured to distally push the clip in the retaining configuration. Also, the method can include flattening the clip, after being deployed from the carrier tube, to a relaxed configuration with a substantially planar-annular body defining a lumen with a plurality of tines directed inwardly from the body of the clip, wherein at least a portion of the tines have inwardly drawn a portion of the wall of the body lumen or the body tissue so as to substantially close the opening. Further, the method can include expanding the clip from the retaining configuration having a lumen with a smaller orthogonal cross-sectional profile to the deploying configuration so that the lumen has a larger orthogonal cross-sectional profile. Optionally, the clip can be expanded by a selectively expandable shape-memory clip expander. Furthermore, the method can include expanding the clip from the retaining configuration having a lumen with a more oval orthogonal cross-sectional profile to the deploying configuration so that the lumen has a more circular orthogonal cross-sectional profile.

In one embodiment, a method of closing an opening in a body lumen of a subject can include use of a medical device having a locator assembly and hemostasis assembly as described herein. Such a method can include: locating the body lumen with the locator; expanding the expandable hemostasis member so as to provide hemostasis to the opening; and deploying the closure element into the body lumen so as to close the body lumen. The method can also include expanding the locator from an unexpanded state to an expanded state and pulling the locator against the internal surface of the body lumen. The locator can be configured to automatically expand when moved out from the tube of the locator assembly.

In one embodiment, the locator is configured to be implanted. As such, deployment of the closure element traps the implantable locator against and adjacent to the internal surface of the body lumen. Optionally, the locator assembly includes a suture coupled to the implantable locator, and the suture is cut after the opening of the body lumen is closed. The suture can be biodegradable and any portion of the suture remaining in the subject degrades. The locator can be biostable or biodegradable.

In one embodiment, the locator is configured to be withdrawn from the body lumen as the closure element is deployed to close the opening. The locator assembly can include at least a first wire and a second wire that are coupled to the locator such that pulling on both the first wire and second wire draws the locator against the internal surface of the body lumen, and pulling on one of the first wire or second wire unwinds the locator and withdraws the locator from the body lumen.

In one embodiment, a hemostasis assembly can have a hemostasis tube, and an expandable hemostasis member located at a distal end of the hemostasis tube, said expandable hemostasis member being configured to selectively expand at an opening in a body lumen so as to cover or plug the opening and provide hemostasis.

In one embodiment, an implantable body lumen locator can include: a biocompatible locator configured to be in an unexpanded state while being inserted through an opening in a body lumen and to be in an expanded state that is larger in diameter than the opening; and a locator assembly configured to deliver the biocompatible locator into the body lumen and selectively expand the locator assembly, and configured to release the biocompatible locator therefrom for implantation. The locator assembly can include one or more sutures coupled to the locator, the one or more sutures being configured to be cut.

In one embodiment, an implantable body lumen locator can include: a biocompatible locator configured to be in an unexpanded state while being inserted through an opening in a body lumen and to be in an expanded state that is larger in diameter than the opening; and a locator assembly configured to deliver the biocompatible locator into the body lumen and selectively expand the locator assembly, and configured to retract the biocompatible locator from the body lumen, said locator assembly having at least a first locator wire coupled with a first end of the locator and a second locator wire coupled to a second end of the locator such that pulling on both the first locator wire and second locator wire draws the locator against the internal surface of the body lumen, and pulling on one of the first wire or second wire unwinds the locator and withdraws the locator from the body lumen.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of embodiments of the present invention, a more particular description of embodiments of the present invention will be rendered by reference to the appended drawings. It is appreciated that these drawings depict only typical embodiments of the invention and are therefore not to be considered limiting of its scope. The invention will be described and explained with additional specificity and detail through the use of the accompanying drawings in which:

FIGS. 2B' and 2C' illustrate an alternative embodiment of a locator assembly for locating a surface of a body lumen, in accordance with the present invention.

FIGS. 2B'' and 2C'' illustrate a further embodiment of a locator assembly for locating a surface of a body lumen, in accordance with the present invention.

FIGS. 2B''' and 2C''' illustrate a still further embodiment of a locator assembly for locating a surface of a body lumen, in accordance with the present invention.

FIG. 3A illustrates one embodiment of a carrier assembly for the apparatus of FIG. 1.

FIG. 3B illustrates one embodiment of a carrier member for the carrier assembly of FIG. 3A.

FIG. 3C illustrates one embodiment of a pusher member for the carrier assembly of FIG. 3A.

FIG. 3D illustrates one embodiment of a cover member for the carrier assembly of FIG. 3A.

FIG. 3E illustrates one embodiment of a support member for the carrier assembly of FIG. 3A.

FIG. 7A illustrates the closure element of FIGS. 6A-G prior to being disposed upon the carrier member of FIG. 3B.

FIG. 7B illustrates the closure element of FIGS. 6A-G upon being disposed upon the carrier member of FIG. 3B.

FIG. 7C illustrates the closure element of FIGS. 6A-G as the cover member of FIG. 3D receives the carrier member of FIG. 3B.

FIG. 7D illustrates the closure element of FIGS. 6A-G being retained substantially within the carrier assembly of FIG. 3A when the carrier member of FIG. 3B is disposed substantially within the cover member of FIG. 3D.

FIG. 11A illustrates the assembled carrier assembly and triggering assembly of the alternative embodiment of the apparatus shown in FIG. 10A.

FIG. 11B illustrates a close-up view of the proximal end of the apparatus shown in FIG. 11A.

FIG. 13A illustrates the apparatus of FIG. 12 after distal advancement of the triggering system and carrier assembly.

FIG. 13B illustrates a close-up view of the distal end of the housing and internal components of the apparatus shown in FIG. 13A.

FIG. 16 illustrates a side view of another alternative embodiment of an apparatus for closing openings formed in blood vessel walls.

FIG. 16A illustrates a close-up view of the distal end of the device shown in FIG. 16.

FIG. 17 illustrates a perspective view of the proximal end of the device shown in FIG. 16.

FIG. 17A illustrates a close-up view of the proximal end of the device shown in FIG. 17.

FIG. 18 illustrates a cross-sectional view of the device shown in FIG. 16.

FIG. 18A illustrates a close-up cross-sectional view of a portion of the device shown in FIG. 18.

FIG. 18B illustrates a close-up cross-sectional view of a portion of the device shown in FIG. 18.

FIG. 22A illustrates one embodiment of a carrier assembly for delivering a closure element.

FIG. 22B illustrates one embodiment of a carrier member for the carrier assembly of FIG. 22A.

FIG. 22C illustrates one embodiment of a pusher member for the carrier assembly of FIG. 22A.

FIG. 22D illustrates one embodiment of a cover member for the carrier assembly of FIG. 22A.

FIG. 22E illustrates one embodiment of a support member having a splitter for the carrier assembly of FIG. 22A.

FIGS. 25A-25D illustrate embodiments of splitters for use with a carrier assembly.

FIG. 26 illustrates one embodiment of a splitter attached to a guide wire for use with a carrier assembly.

FIGS. 27A-27C illustrate embodiments of tissue-grabbing splitters for use with a carrier assembly.

FIG. 28 illustrates an embodiment of a series of splitters configured to combine and expand for use with a carrier assembly.

FIGS. 37A-37D illustrate other clip configurations according to the present invention.

FIG. 38A illustrates one embodiment of a carrier assembly having tubular members for retaining and delivering a closure element.

FIG. 38B illustrates one embodiment of an offset carrier member for the carrier assembly of FIG. 38A.

FIG. 38C illustrates one embodiment of a closure element in an offset retaining configuration when retained by the carrier assembly of FIG. 38A.

FIG. 38D illustrates one embodiment of an offset pusher member for the carrier assembly of FIG. 38A.

FIG. 38E illustrates one embodiment of a cover member for the carrier assembly of FIG. 38A.

FIG. 38F illustrates one embodiment of a support member for the carrier assembly of FIG. 38A.

FIG. 41A illustrates one embodiment of a carrier assembly having an expandable member for delivering a closure element.

FIG. 41B illustrates one embodiment of a selectively expandable carrier member for the carrier assembly of FIG. 41A.

FIG. 41C illustrates one embodiment of a closure element in an offset retaining configuration when held by the carrier assembly of FIG. 41A.

FIG. 41D illustrates one embodiment of an offset pusher member for the carrier assembly of FIG. 41A.

FIG. 41E illustrates one embodiment of a cover member for the carrier assembly of FIG. 41A.

FIG. 41F illustrates one embodiment of a support member for the carrier assembly of FIG. 41A.

FIG. 42A is a cross-sectional side view illustrating an opening formed in a vessel, wherein a guidewire is shown disposed within the opening.

FIG. 42B illustrates the guidewire being used to deploy a locator through the opening and locating the position of the vessel.

FIG. 42C illustrates an embodiment of a carrier assembly having offset tubular members for delivering a closure element in an offset retaining configuration so as to be capable of engaging tissue adjacent to the opening in the blood vessel wall.

FIG. 42D illustrates an embodiment of the closure element in a deploying configuration while being deployed from the carrier assembly.

FIG. 42E illustrates an embodiment of the closure element on a relaxed planar configuration after being deployed from the carrier assembly.

FIG. 43A is a cross-sectional side view illustrating a carrier assembly retaining a closure element in an offset retaining configuration and having a selectively expandable member in contracted orientation.

FIG. 43B is a cross-sectional side view illustrating a carrier assembly retaining a closure element in an offset retaining configuration and having a selectively expandable member in an expanded orientation and being positioned for deploying the closure element into tissue around an opening in the tissue.

FIG. 43C illustrates an embodiment of the closure element in a retaining configuration being deployed over the expanded expandable member.

FIG. 43D illustrates an embodiment of the closure element being deployed from the expanded expandable member so as to engage the tissue surrounding the opening.

Figure 44:
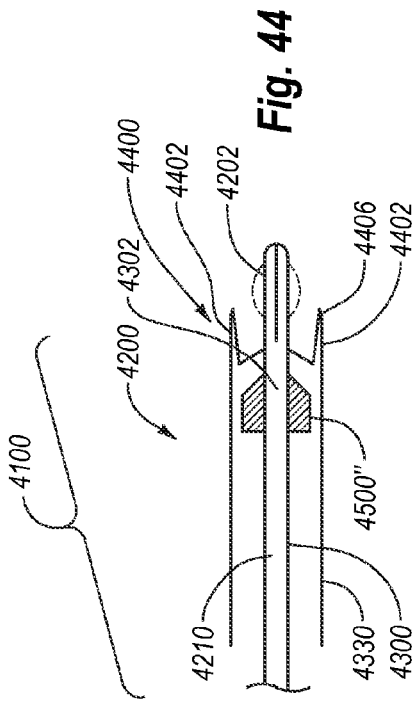

FIG. 44 provides a general illustration of an apparatus for closing openings formed in blood vessel walls constructed in accordance with the present invention.

Figure 45:
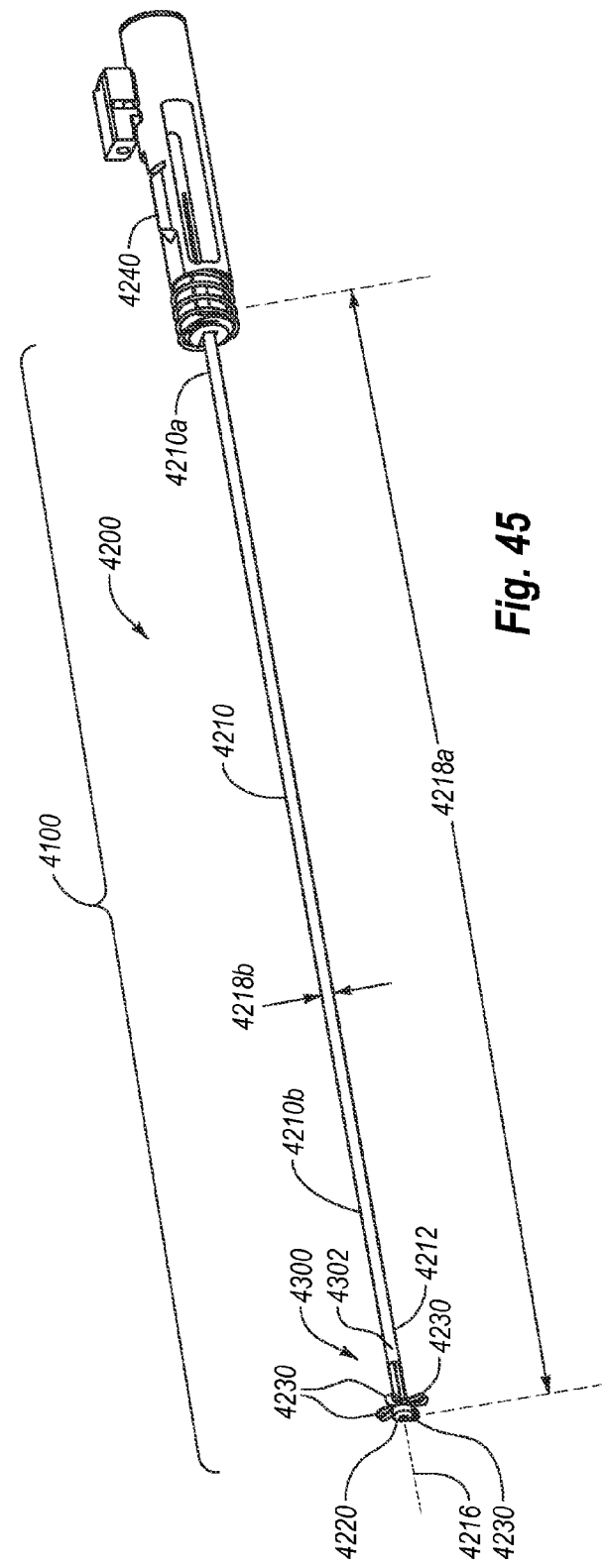

FIG. 45 illustrates one embodiment of a delivery assembly for the apparatus of FIG. 44.

Figure 46A:
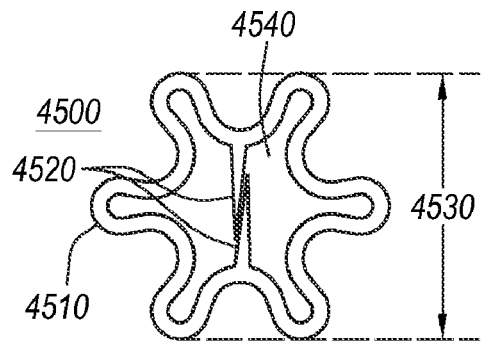

FIG. 46A illustrates a top view of one embodiment of a closure element in a natural, planar configuration and with a natural cross-section for use with the apparatus of FIG. 45, prior to curing.

Figure 46B:
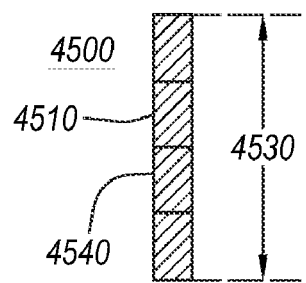

FIG. 46B illustrates a side view of the closure element of FIG. 46A.

Figure 46C:
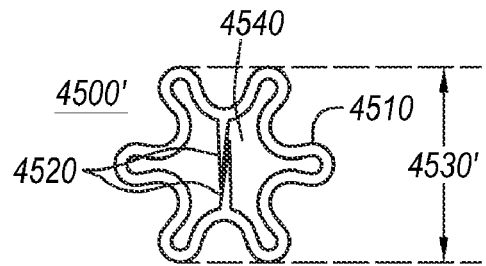

FIG. 46C illustrates a top view of the closure element of FIGS. 46A-46B after a natural cross-section of the closure element has been reduced, via a curing process.

Figure 46D:
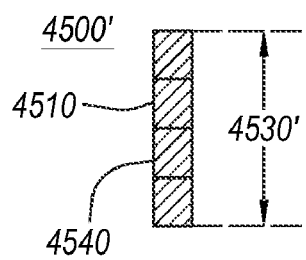

FIG. 46D illustrates a side view of the closure element of FIG. 46C.

Figure 46E:
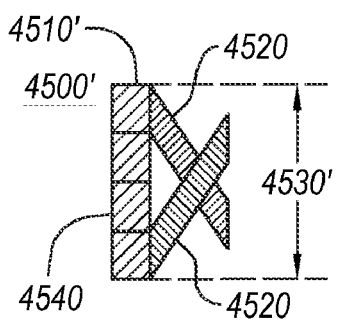

FIG. 46E illustrates a side view of the closure element of FIGS. 46C-46D as the closure element transitions from the natural, planar configuration to a tubular configuration.

Figure 46F:
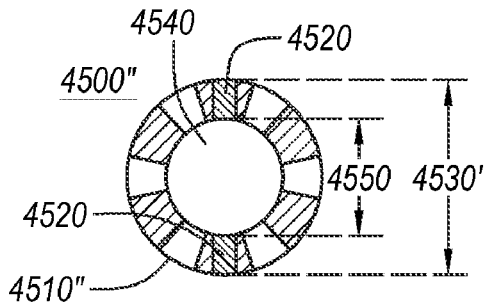

FIG. 46F illustrates a top view of the closure element of FIGS. 46C-46D upon completing the transition from the natural, planar configuration to a substantially tubular configuration, albeit a natural tubular configuration.

Figure 46G:
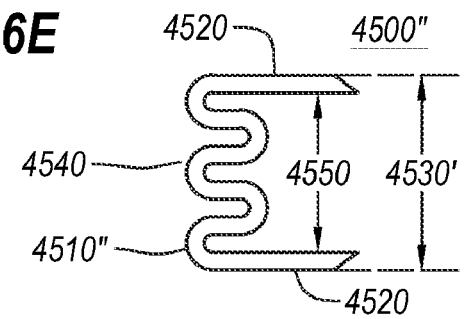

FIG. 46G illustrates a side view of the closure element of FIG. 46F.

Figure 47A:
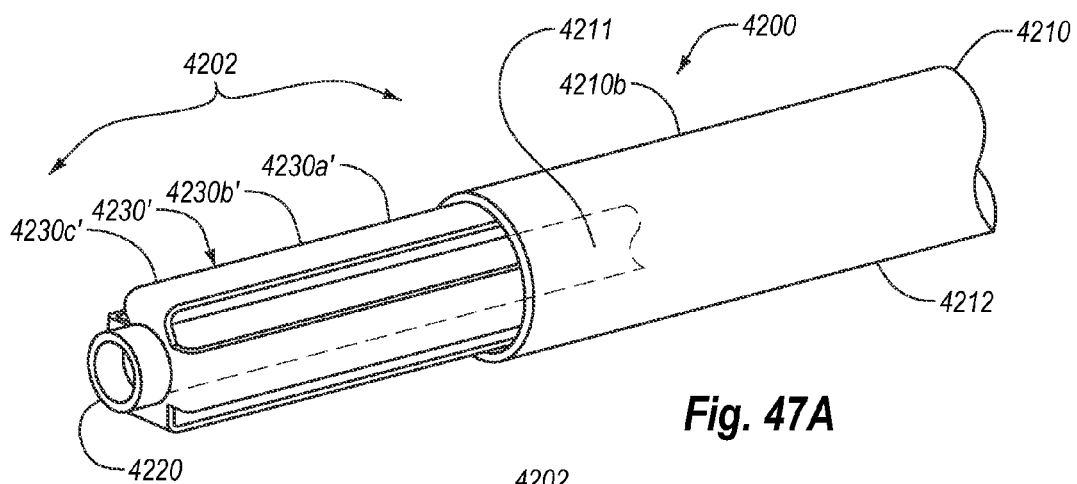

FIG. 47A illustrates one embodiment of a distal locator portion and a carrier seat of a carrier assembly of FIG. 44, both of which are illustrated in an unexpanded state.

Figure 47B:
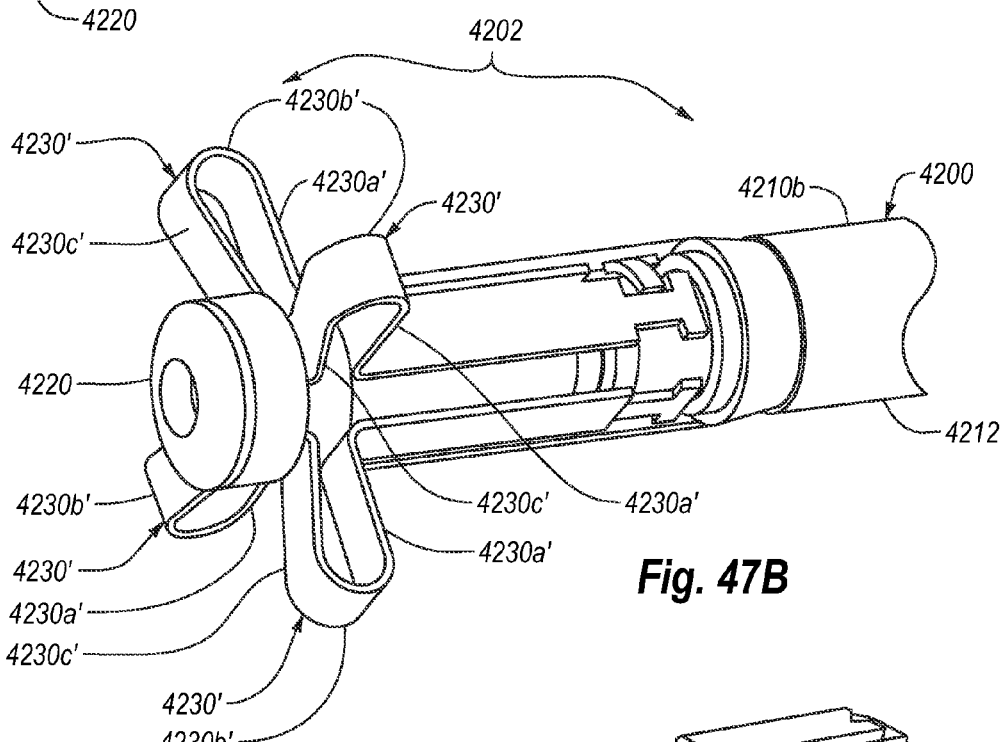

FIG. 47B illustrates the distal locator portion and the carrier seat of FIG. 47A, both of which are illustrated in an expanded state.

Figure 47C:
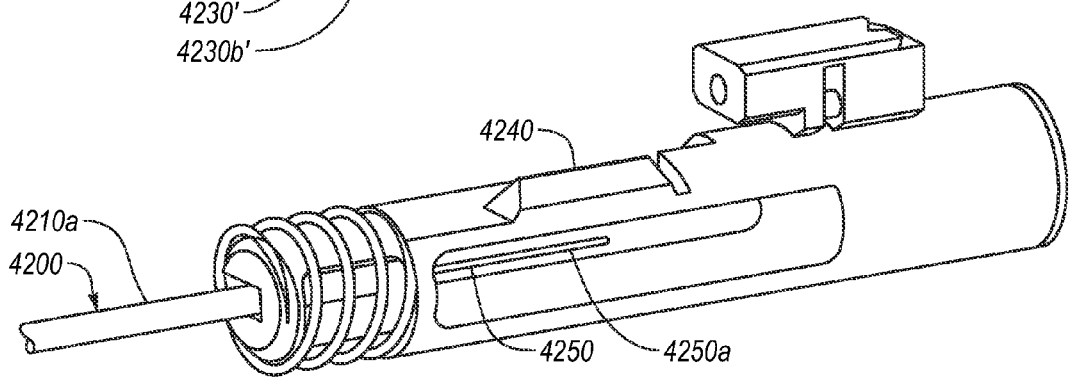

FIG. 47C illustrates one embodiment of a proximal end region of the delivery assembly of FIG. 44.

Figure 48A:
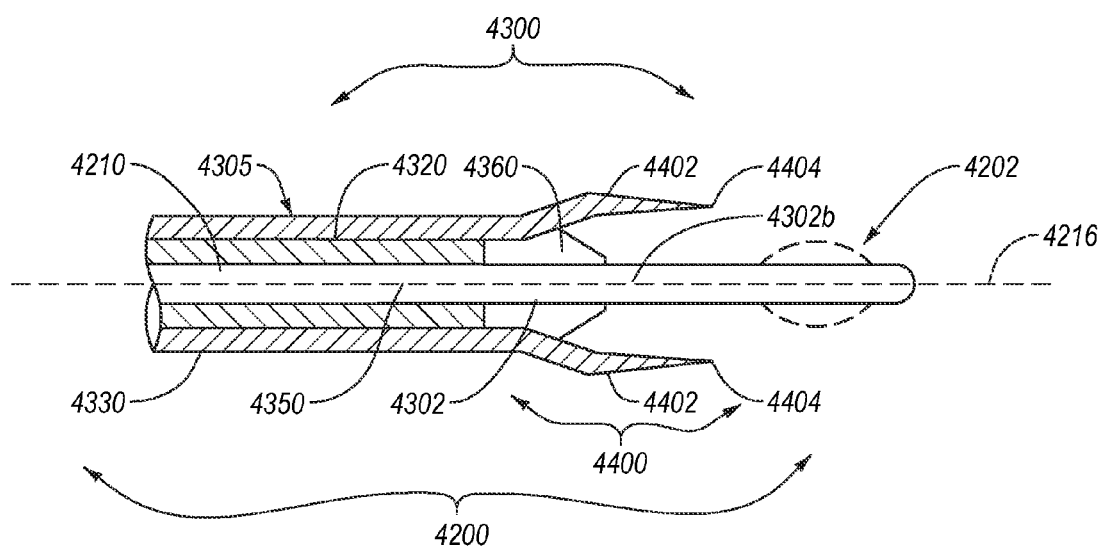

FIG. 48A illustrates one embodiment of a carrier assembly for the apparatus of FIG. 44.

Figure 48B:
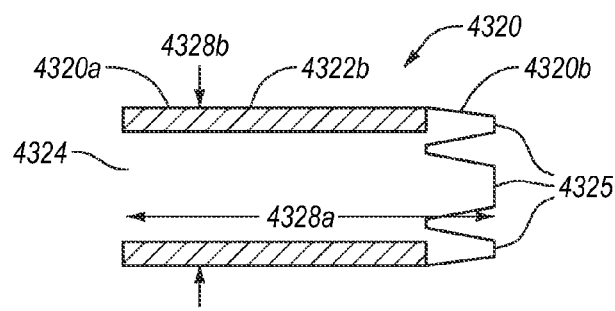

FIG. 48B illustrates one embodiment of a pusher member for the carrier assembly of FIG. 48A.

Figure 48C:
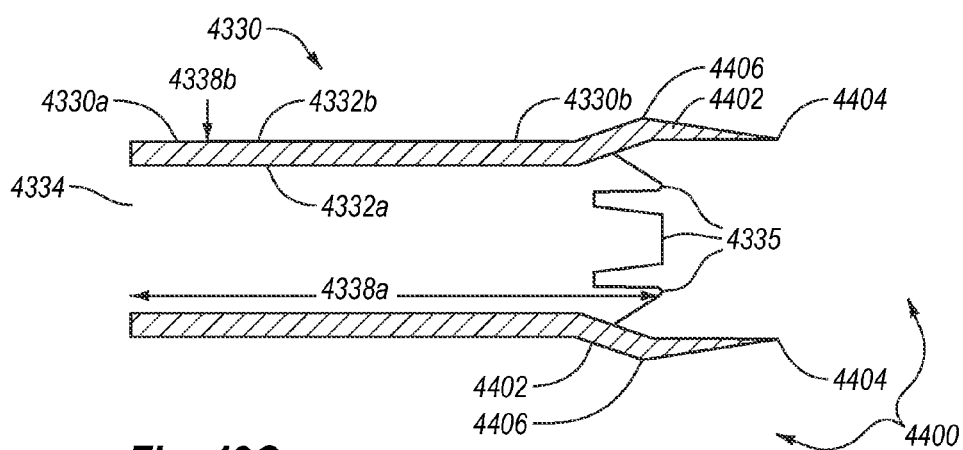

FIG. 48C illustrates one embodiment of a cover member for the carrier assembly of FIG. 48A.

Figure 49:
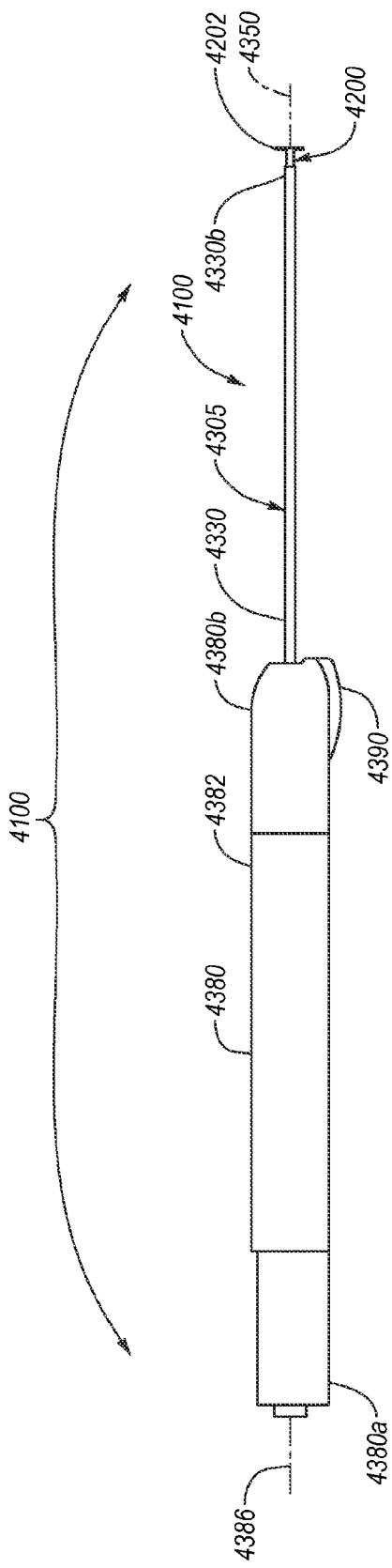

FIG. 49 illustrates a tube set and the delivery assembly of the apparatus of FIG. 44 mounted to a handle portion for operative manipulation thereof.

Figure 50A:
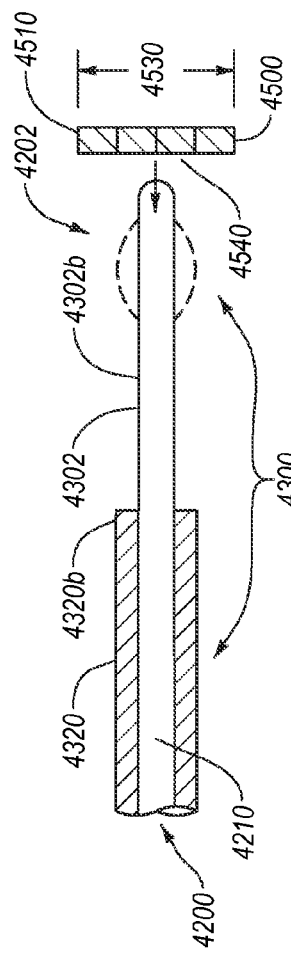

FIG. 50A illustrates the closure element of FIGS. 46A-46G prior to being disposed upon the carrier assembly of FIG. 48A.

FIG. 50B illustrates the closure element of FIGS. 46A-46G upon being disposed upon the carrier assembly of FIG. 48A, and further as the cover member of FIG. 48C receives the carrier assembly.

FIG. 50C illustrates the closure element of FIGS. 46A-46G being retained substantially within the carrier assembly of FIG. 48A when the carrier assembly is disposed substantially within the cover member of FIG. 48C.

Figure 51A:
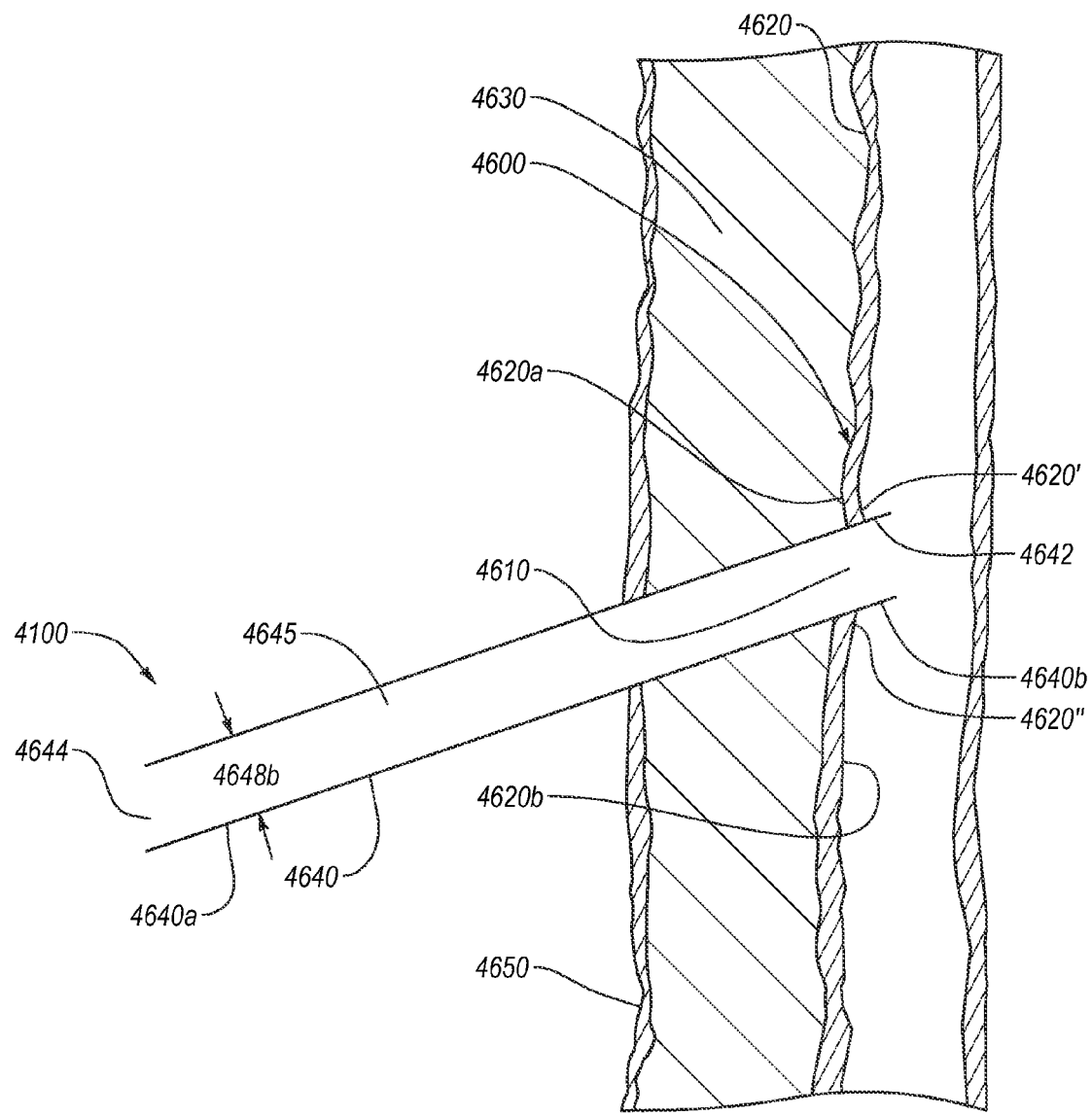

FIG. 51A illustrates a sheath that is positioned through tissue and into an opening formed in a wall of a blood vessel, in one embodiment of the present invention.

Figure 51B:
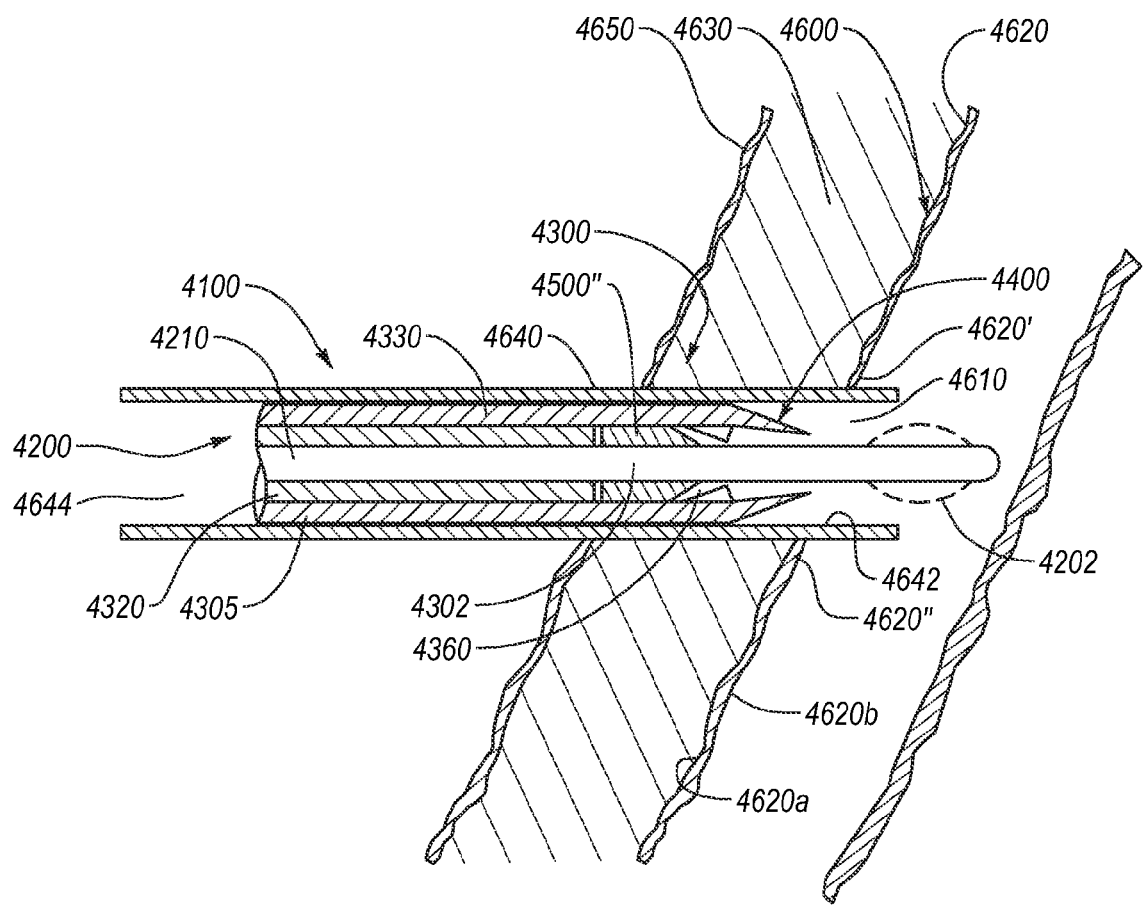

FIG. 51B illustrates the locator portion and the carrier assembly of the delivery assembly of the apparatus being advanced distally into the blood vessel.

Figure 51C:
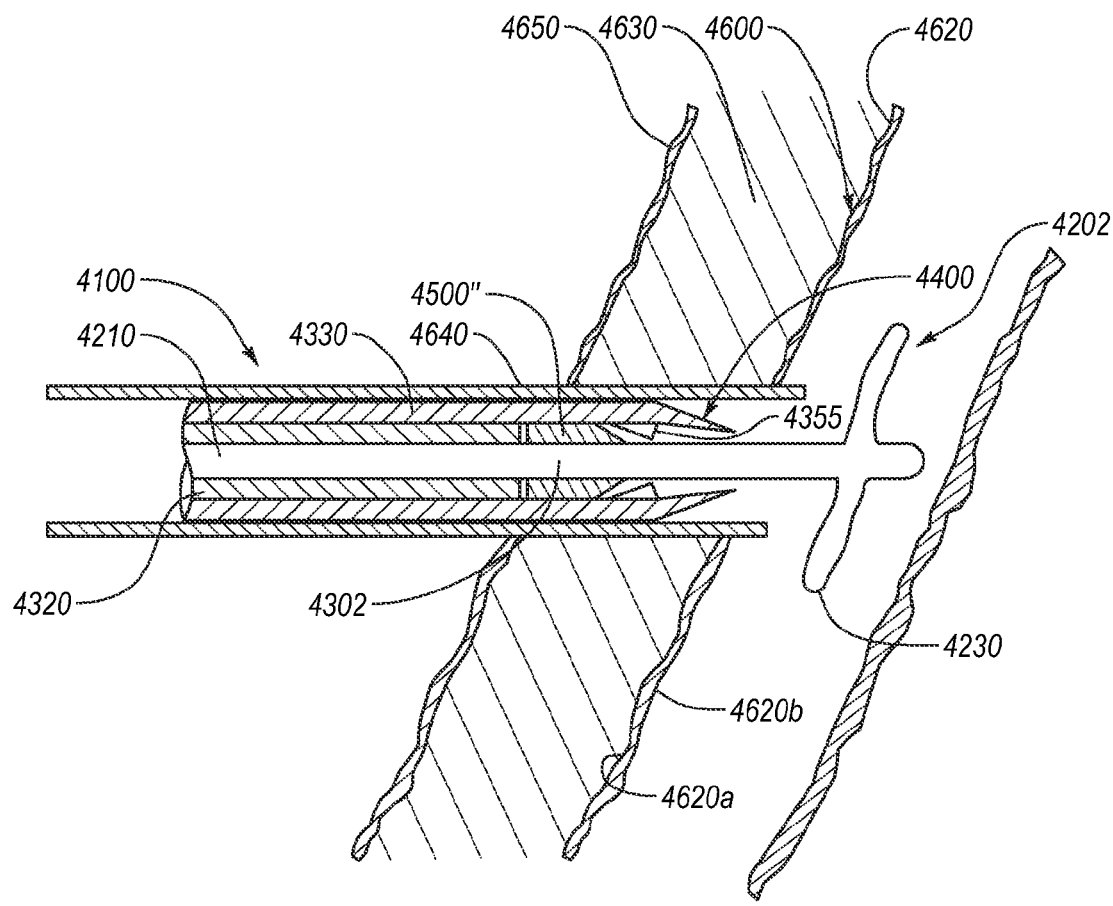

FIG. 51C illustrates a distal end region of the locator portion of FIG. 51B extending into the blood vessel and being transitioned into an expanded state.

Figure 51D:
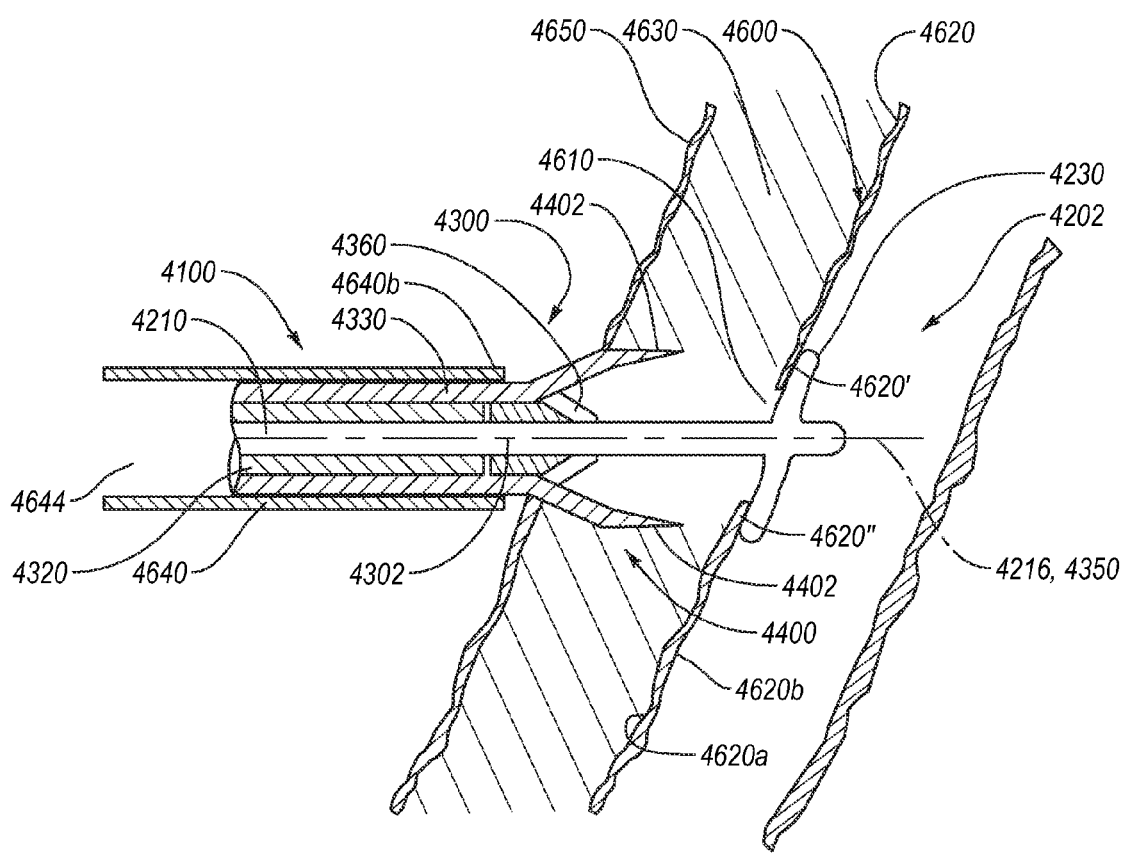

FIG. 51D illustrates the distal end region of the locator portion of FIG. 51C being retracted proximally to engage an inner surface of the blood vessel wall, and the retraction of the sheath to expose the tissue engaging device, in a tissue engaging condition.

Figure 51E:
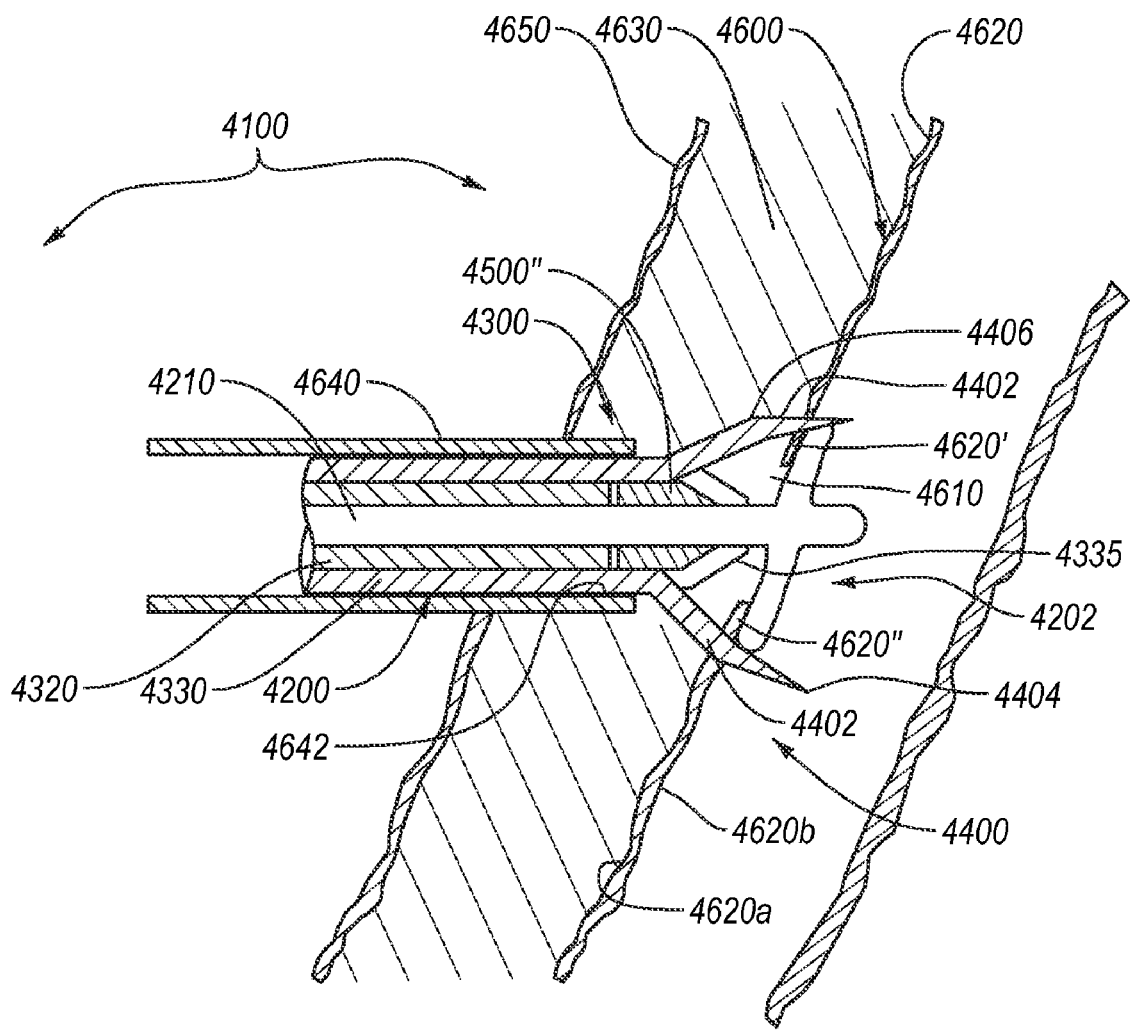

FIG. 51E illustrates engagement of the tissue engaging device of the apparatus of FIG. 51D with the blood vessel wall.

Figure 51F:
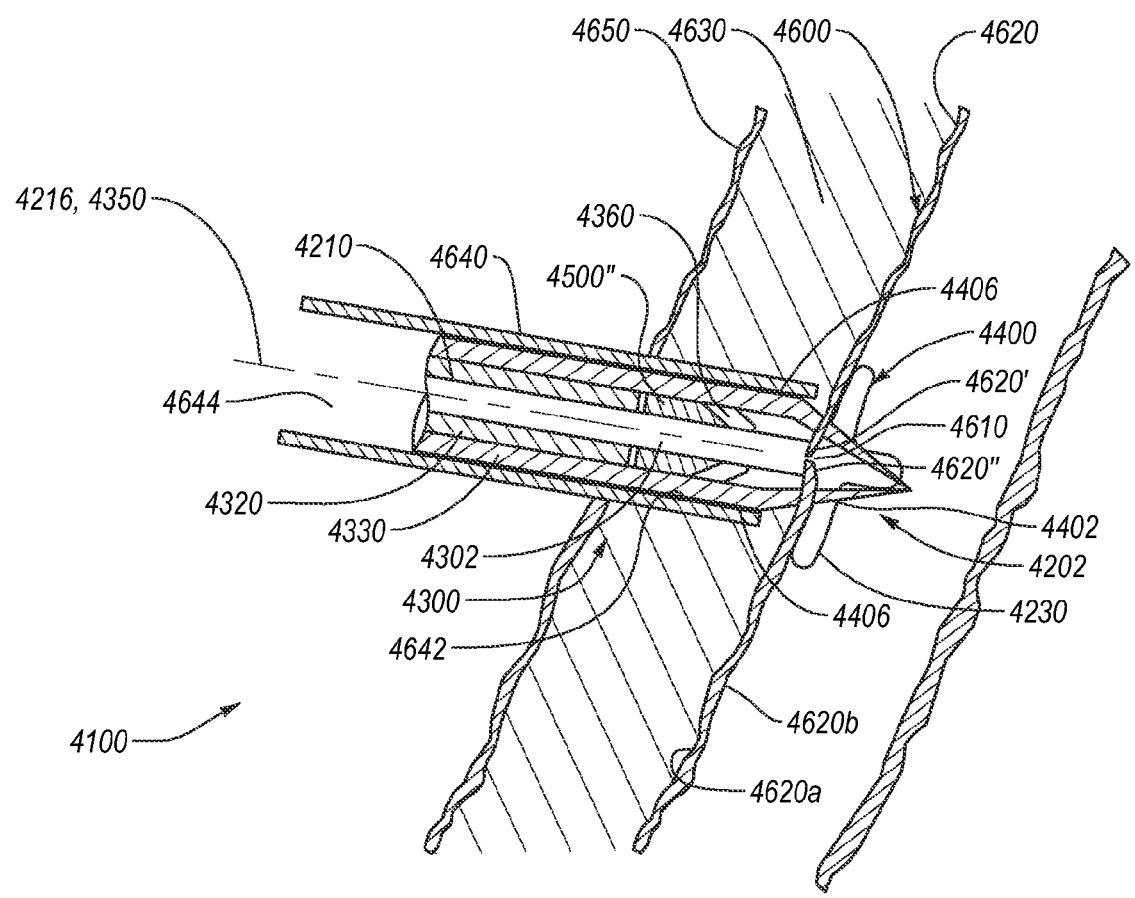

FIG. 51F illustrates movement of the tissue engaging device from the tissue engaging condition to a closing condition.

Figure 51G:
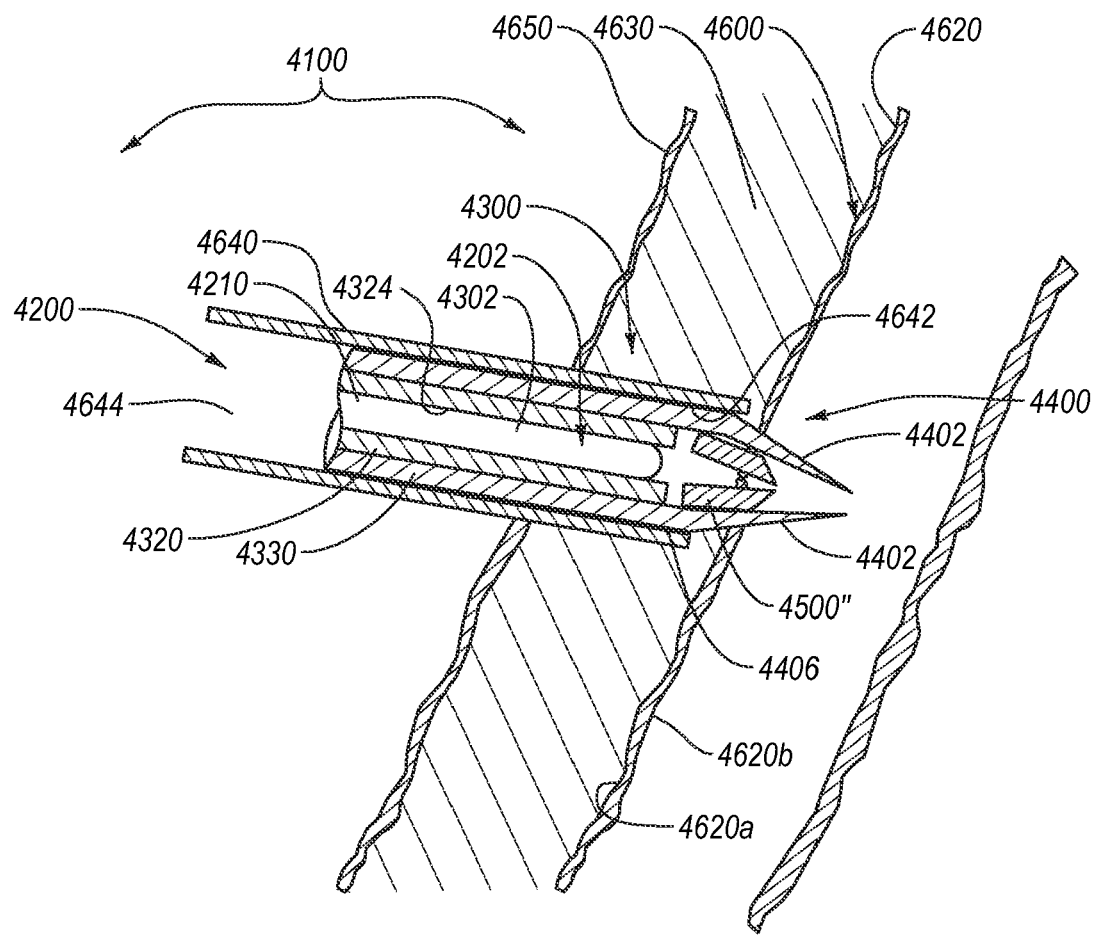

FIG. 51G illustrates the closure element being deployed and engaging tissue adjacent to the opening in the blood vessel wall.

Figure 51H:
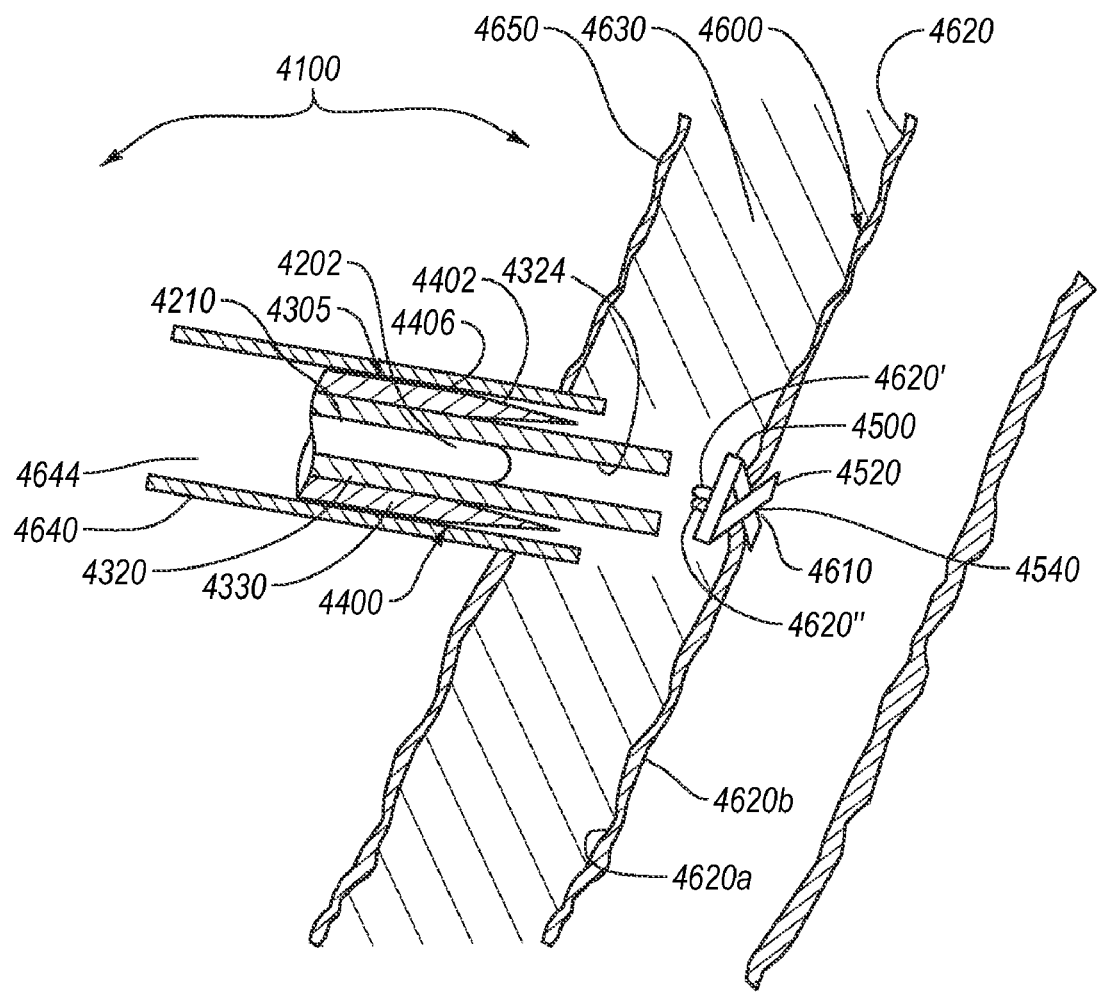

FIG. 51H illustrates the closure element of FIG. 51G transitioning from the substantially tubular configuration to the natural, planar configuration while engaging the engaged tissue.

FIG. 52 is a side elevation view, in cross-section, of another embodiment of the clip applier apparatus having a tissue engaging device deployed from a central lumen of the tubular body, in a tissue engaging condition.

FIG. 53 is a side elevation view, in cross-section, of the clip applier apparatus of FIG. 52, illustrating the tissue engaging device in a closing condition.

Figure 54:
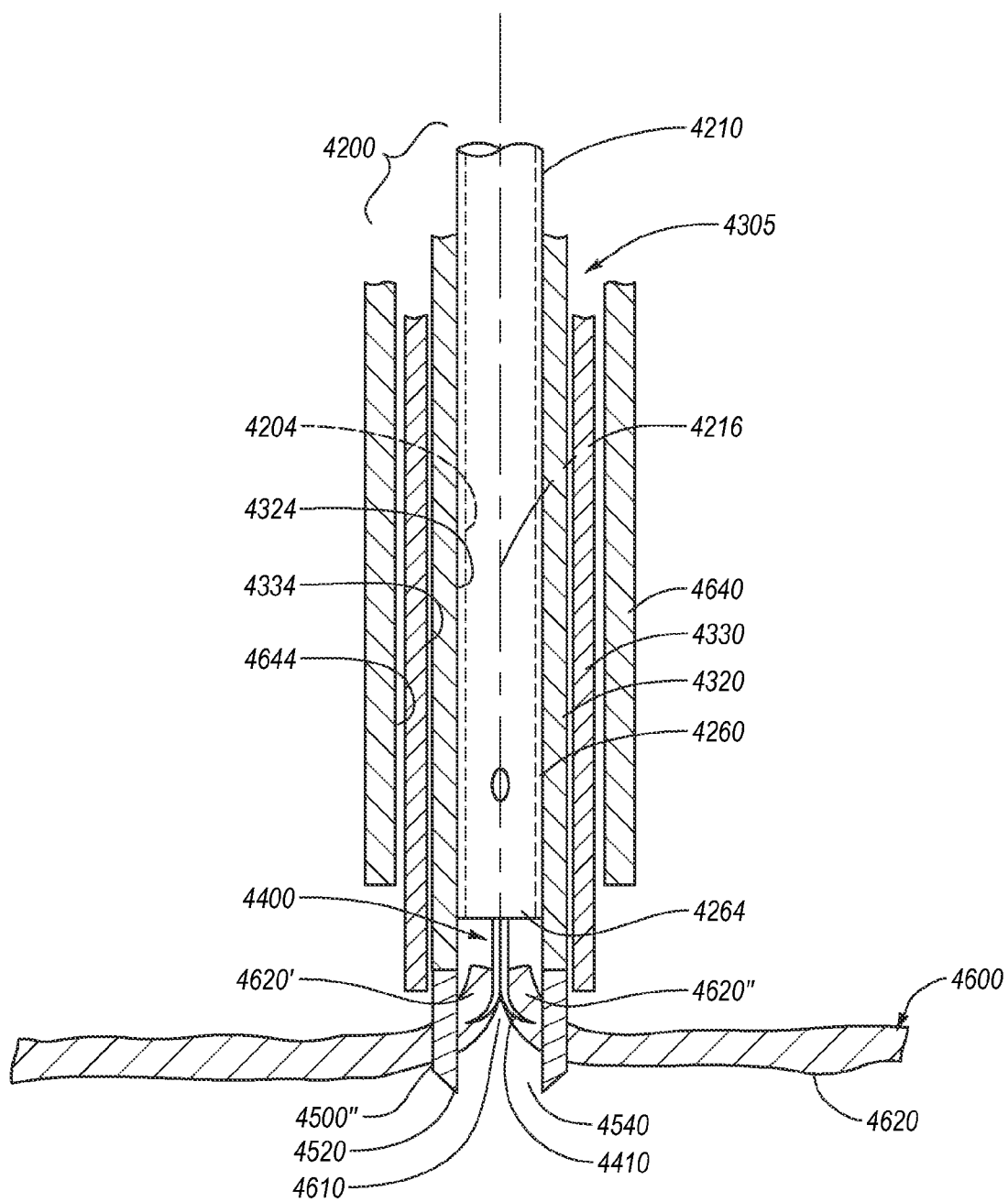

FIG. 54 is a side elevation view, in cross-section, of the clip applier apparatus of FIG. 52, illustrating deployment of the closure element.

FIG. 55 is a side elevation view, in cross-section, of yet another embodiment of the clip applier apparatus also having a tissue engaging device deployed from a central lumen of a tubular body, in a tissue engaging condition.

FIG. 56 is a side elevation view, in cross-section, of the clip applier apparatus of FIG. 55, illustrating the tissue engaging device in a closing condition.

FIG. 57 is a side elevation view, in cross-section, of the clip applier apparatus of FIG. 55, illustrating deployment of the closure element.

FIG. 58 is a side elevation view, in cross-section, of another embodiment of the clip applier apparatus also having a tissue engaging device deployed from a central lumen of a tubular body, in a tissue closing condition.

FIGS. 59A-59E are partial cross-sectional views illustrating the luminal placement of a medical device for closing openings formed in blood vessel walls with improved hemostasis.

Figure 60A:
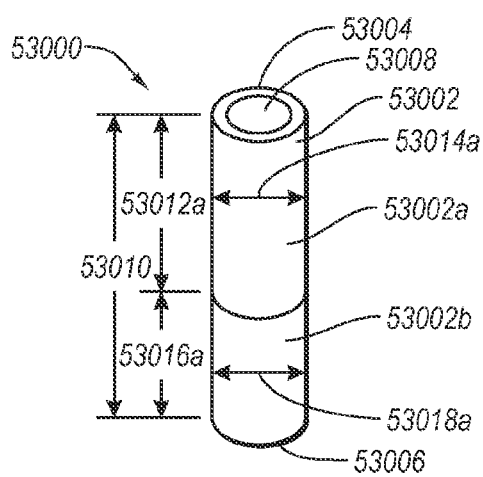
Figure 60B:
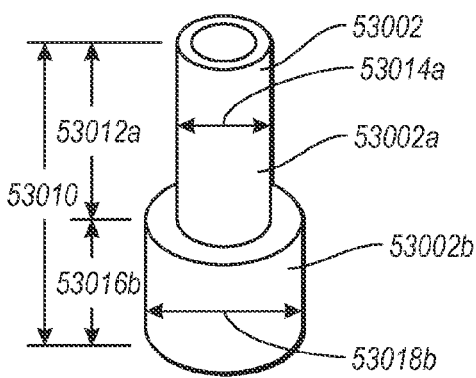

FIGS. 60A-60B are side views illustrating an embodiment of an expanding member for improving hemostasis during delivery of a closure device.

FIGS. 61A-61F are side views illustrating different embodiments of expanding members for improving hemostasis during delivery of a closure device.

Figure 62A:
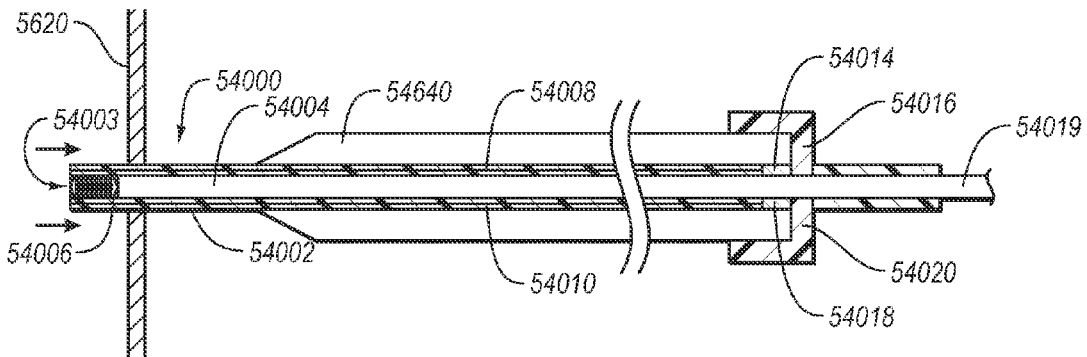
Figure 62B:
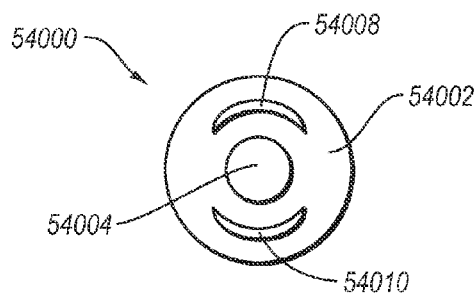

FIGS. 62A-62B illustrate an anchor system in a collapsed configuration, and which can function as a locator.

Figure 63:
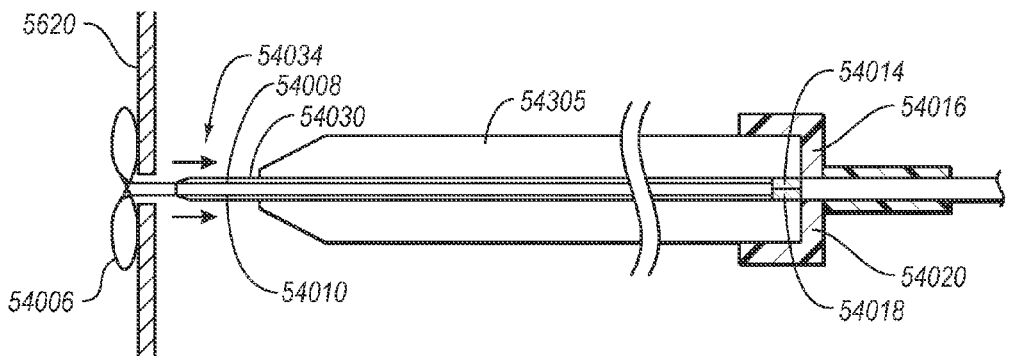

FIG. 63 illustrates an anchor system being deployed and expanded within a vessel.

FIGS. 64A-64B show an anchor being collapsed and withdrawn.

FIGS. 65A-65C show an implantable "looped" anchor system being used with a carrier assembly and tube set that deploys a blood vessel closure element.

FIGS. 66A-66B show an implantable coil anchor system being implanted with a closure element.

FIGS. 67A-67B show examples of removable or implantable anchors, which can be used as locators.

Figure 68A:
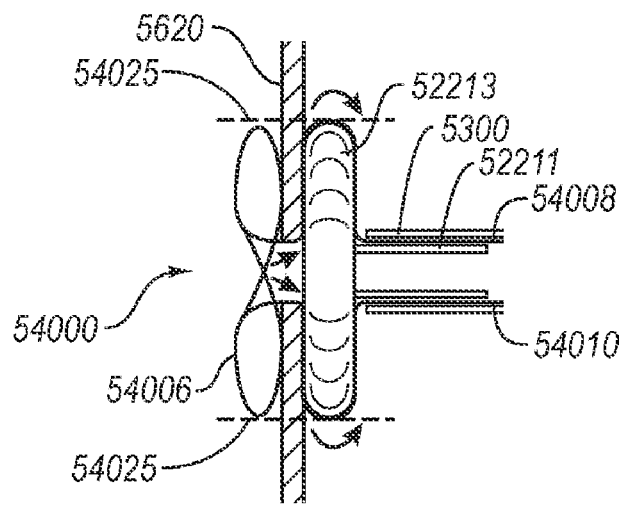

FIG. 68A shows an expanded hemostasis member and an implantable anchor cooperating to provide hemostasis.

Figure 68B:
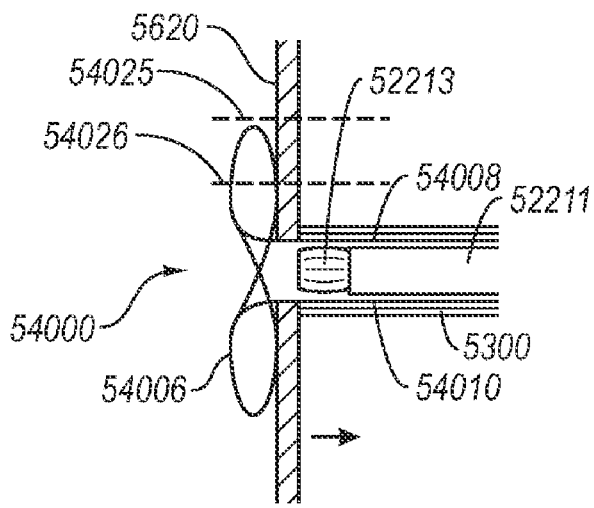

FIG. 68B shows the unexpanded hemostasis member and an implantable anchor as a closure element is about to be deployed.

It should be noted that the figures are not drawn to scale and that elements of similar structures or functions are generally represented by like reference numerals for illustrative purposes throughout the figures. It also should be noted that the figures are only intended to facilitate the description of the preferred embodiments of the present invention. The figures do not describe every aspect of the present invention and do not limit the scope of the invention.

DETAILED DESCRIPTION

The embodiments described herein extend to methods, systems, and apparatus for managing access through tissue. Some of the apparatuses of the present invention are configured to deliver a device for managing access through tissue into an opening formed in and/or adjacent to tissue. Embodiments are additionally directed to an apparatus and method for delivering a closure element through tissue and into an opening formed in, or adjacent to, a wall of a blood vessel or other body lumen of any size.

The apparatus can be configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus can be configured to substantially uniformly expand the closure element beyond a natural cross-section of the closure element such that the closure element, when deployed, is configured to engage a significant amount of the blood vessel wall and/or tissue. Engaging the blood vessel wall and/or tissue, the closure element can be further configured to return to the natural cross-section. Thereby, the engaged blood vessel wall and/or tissue are drawn substantially closed and/or sealed, such that, for example, hemostasis within the opening is enhanced.

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved by employing a clip applier and associated methods of use in accordance with the present invention.

Medical devices may be used in a variety of spaces. It may be desirable to generally reduce the size of medical devices. For example, stents may be inserted into smaller and smaller vasculature, thus making it generally desirable to reduce the pre-deployment size of a stent. In another example, a closure device may be used to close tissue in, for example, a body lumen. In order to reach the desired body lumen, typically a delivery device may be used to reach an access point in the body lumen. To minimize the effects of a procedure on a patient, the reduction in size of the access point may be desirable.

When engaging tissue and/or closing openings in tissue, it may be desirable to use a locator assembly to selectably contact a portion of the tissue. In some cases, the locator assembly may not contact a portion of the desired tissue. For example, the locator assembly may be positioned within a body lumen but away from an inside surface of the body lumen. In these instances, engagement of a portion of the desired tissue may be less likely and/or favorable. It may be desirable to verify contact with a portion of the desired tissue during a medical procedure.

In one embodiment, a locator assembly may include engagement members configured to engage a portion of the desired tissue. The locator assembly may include a device to take measurements of a desired measurable characteristic. The measurable characteristic may include, for example, impedance. Measurements may be taken when a portion of the locator assembly is within a body lumen and when the locator assembly is believed to be in contact with tissue. Comparing the measurements taken when within the body lumen and when the locator assembly is believed to be in contact with tissue may indicate that the locator assembly has contacted a portion of the desired tissue. For example, an impedance measurement taken when within the body lumen may be higher than an impedance measurement taken when the locator assembly is in contact with tissue.

In a further embodiment, a surface engaging element can be provided. The surface engaging element may include a flexible body that may actuate between an expanded and relaxed configuration.

In some embodiments, an engagement portion of the surface engaging element may include substantially uniform dimensions. In other embodiments, the engagement portion of the surface engaging element may include at least one non-uniform dimension. For example, the engagement portion may have a dimension that is larger than a support portion of the surface engaging element.

In further embodiments, the surface engaging element may be assembled using a retaining portion. For example, an engagement portion may be connected to a proximal, distal, and/or other portion of the surface engaging element by a retaining portion, such as a detent.

These results, whether individually or collectively, can be achieved, according to one embodiment of the present invention, by employing methods, systems, and/or apparatus as shown in the figures and described in detail below.

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved, according to one embodiment of the present invention, by employing an apparatus 100 as shown in FIG. 1.

Figure 1:
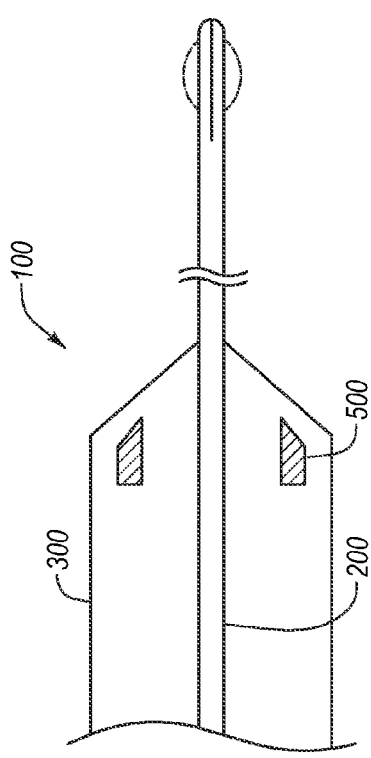
FIG. 1 provides a general illustration of an apparatus for closing openings formed in blood vessel walls in accordance with the present invention.
Figure 6A:
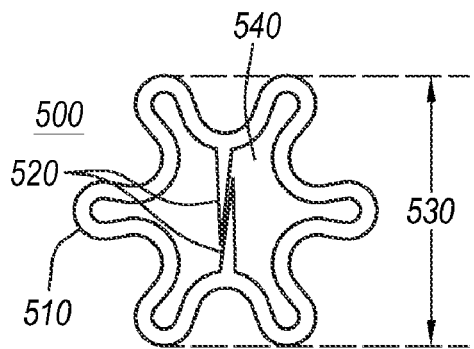
FIG. 6A illustrates a top view of one embodiment of a closure element in a natural, planar configuration and with a natural cross-section for use with the apparatus of FIG. 1.
Figure 6B:
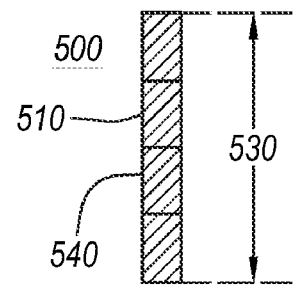
FIG. 6B illustrates a side view of the closure element of FIG. 6A.
Figure 6C:
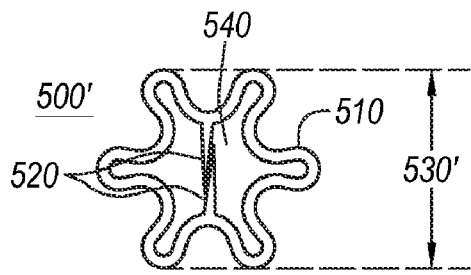
FIG. 6C illustrates a top view of the closure element of FIGS. 6A-B after a natural cross-section of the closure element has been reduced.
Figure 6D:
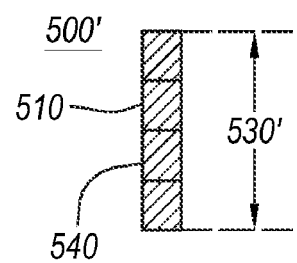
FIG. 6D illustrates a side view of the reduced closure element of FIG. 6C.
Figure 6E:
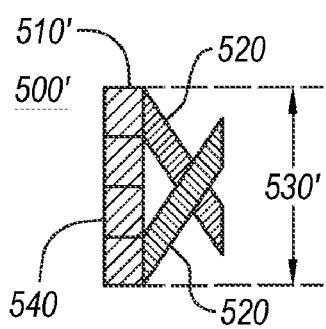
FIG. 6E illustrates a side view of the reduced closure element of FIGS. 6C-D as the reduced closure element transitions from the natural, planar configuration to a tubular configuration.
Figure 6F:
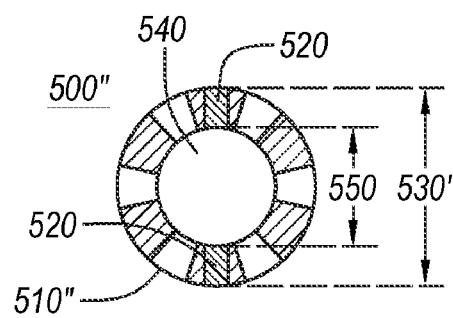
FIG. 6F illustrates a top view of the closure element of FIGS. 6C-D upon completing the transition from the natural, planar configuration to a substantially tubular configuration.

FIG. 1 illustrates a clip applier apparatus 100 in accordance with the present invention. As will be discussed in more detail below, the apparatus 100 can deliver a closure element 500 (shown in FIGS. 6A-6B) through tissue 630 (shown in FIG. 8A) and into an opening 610 (shown in FIG. 8A) formed in and/or adjacent to a wall 620 (shown in FIG. 8A) of a blood vessel 600 (shown in FIG. 8A) or other body lumen. The closure element (also referred to herein as a "clip") 500 can have a generally annular-shapes body 510 (shown in FIGS. 6A-6B) defining a channel 540 and one or more barbs and/or tines 520 (shown in FIGS. 6A-6B) for receiving and engaging the blood vessel wall 620 and/or the tissue 630 around the opening 610. Although the closure element 500 has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 6A-6B. The natural cross-section 530 of the closure element 500 can be reduced to form a reduced closure element 500' that has a natural, planar configuration with opposing tines 520 and a reduced cross-section 530' as shown in FIGS. 6C-6D. By rotating the opposing tines 520 axially as shown in FIG. 6E, the reduced closure element 500' can be further deformed to form a substantially tubular closure element 500" (shown in FIG. 6F) having the reduced cross-section 530' as well as being in a substantially tubular configuration with the tines 520 in an axial configuration.

Being configured to draw the blood vessel wall 620 and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof. Additionally, it is contemplated that the closure element may be coated with a beneficial agent or be constructed as a composite, wherein one component of the composite would be a beneficial agent. As desired, the closure element 500 may further include radiopaque markers (not shown) or may be wholly or partially formed from a radiopaque material to facilitate observation of the closure element 500 using fluoroscopy or other imaging systems. Exemplary embodiments of a closure element are disclosed in U.S. Pat. Nos. 6,197,042, and 6,623,510, and in co-pending application Ser. Nos. 09/546,998, 09/610,238, and 10/081,726. The disclosures of these references and any others cited therein are expressly incorporated herein by reference.

The apparatus 100 can be configured to receive and retain the closure element 500 such that the closure element 500 is disposed substantially within the apparatus 100. Thereby, if the apparatus 100 is introduced via an introducer sheath 640 (shown in FIG. 8A), for example, the closure element 500 can be disposed within, and delivered by way of, a lumen 644 (shown in FIG. 8A) of the introducer sheath 640. The apparatus 100 also can be configured to engage the blood vessel wall 620 adjacent to the opening 610. Being disposed substantially within the apparatus 100, the closure element 500 can deeply penetrate, without inadvertently contacting, tissue 630 adjacent to the opening 610 such that the apparatus 100 can position the closure element 500 substantially adjacent to an outer surface 620a (shown in FIG. 8A) of the blood vessel wall 620 adjacent to the opening 610.

When properly positioned, the apparatus 100 can be activated to deploy the closure element 500. The apparatus 100 can be configured to substantially uniformly expand the closure element 500 beyond the natural cross-section 530 of the closure element 500 during deployment, the apparatus 100, as desired, and/or can deploy the closure element 500 without expanding the closure element 500. The closure element 500, when deployed, can be configured to engage a significant amount of the blood vessel wall 620 and/or tissue 630 adjacent to the opening 610. Engaging the blood vessel wall 620 and/or tissue 630, the closure element 500 is further configured to return to the natural cross-section 530. Thus, the engaged blood vessel wall 620 and/or tissue 630 can be drawn substantially closed and/or sealed, such that, for example, hemostasis within the opening 610 is enhanced.

The apparatus 100 can be provided as one or more integrated components and/or discrete components. As shown in FIG. 1, for example, the apparatus 100 can include a locator (or obturator) assembly 200 and a carrier assembly 300. For purposes of illustration, the locator assembly 200 and the carrier assembly 300 are shown in FIG. 1 as including substantially separate assemblies. As desired, however, the locator assembly 200 and the carrier assembly 300 each can be provided, in whole or in part, as one or more integrated assemblies.

Figure 2A:
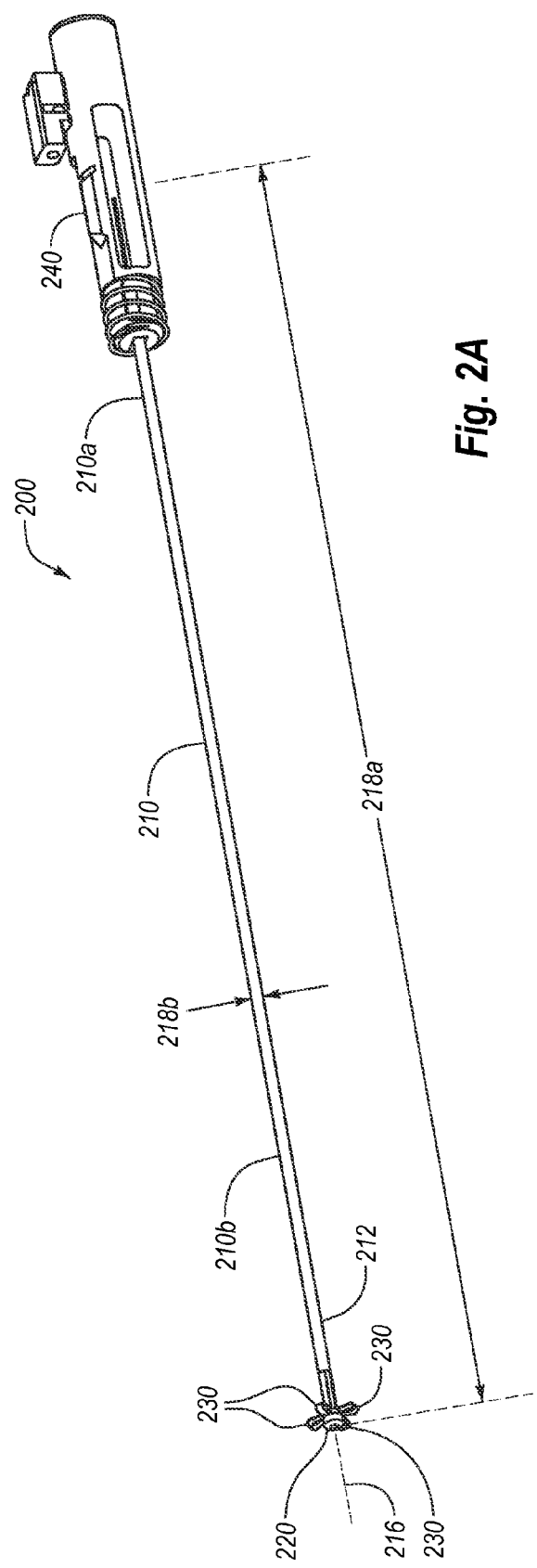
FIG. 2A illustrates one embodiment of a locator assembly for the apparatus of FIG. 1.

Being configured to extend into the opening 610, the locator assembly 200 can selectably contact the inner surface 620b of the blood vessel wall 620 adjacent the opening 610. Whereby, the locator assembly 200 can be configured to draw the blood vessel wall 620 taut and maintain the proper position of the apparatus 100 in relation to the opening 610 as the blood vessel 600 pulsates. The locator assembly 200 can be provided in the manner disclosed in co-pending application Ser. Nos. 09/732,835 and 10/081,723, the disclosures of which are expressly incorporated herein by reference. The locator assembly 200 can include a flexible or semi-rigid tubular body 210. As illustrated in FIG. 2A, the tubular body 210 has a proximal end region 210a and a distal end region 210b and includes a predetermined length 218a and a predetermined outer cross-section 218b, both of which can be of any suitable dimension. The distal end region 210b of the locator assembly 200 can include a substantially rounded, soft, and/or flexible distal end or tip 220 to facilitate atraumatic advancement and/or refraction of the distal end region 210b into the blood vessel 600. As desired, a pigtail (not shown) may be provided on the distal end 220 to further aid atraumatic advancement of the distal end region 210b.

The distal end region 210b of the locator assembly 200 further can be selectably controllable between an unexpanded state and an expanded state. In the unexpanded state, the distal end region 210b has an unexpanded size; whereas, the distal end region 210b in the expanded state has an expanded size, which is greater than the unexpanded size of the distal end region 210b in the unexpanded state. The distal end region 210b can be configured to expand from the unexpanded size to the expanded size and/or to contract from the expanded size to the unexpanded size, and the expansion and contraction of the distal end region 210b can be substantially uniform about a longitudinal axis of the locator assembly 200. For example, one or more expansion elements 230 can be provided on the distal end region 210b and can be configured to expand substantially transversely with respect to a longitudinal axis of the locator assembly 200. The expansion elements 230 can be substantially equally distributed about an outer periphery 212 of the distal end region 210b. Optionally, the expansion elements 230 may include radiopaque markers (not shown) or may be wholly or partially formed from a radiopaque material to facilitate observation of the expansion elements 230 and/or the distal end region 210b using fluoroscopy or other imaging systems.

Figure 2B:
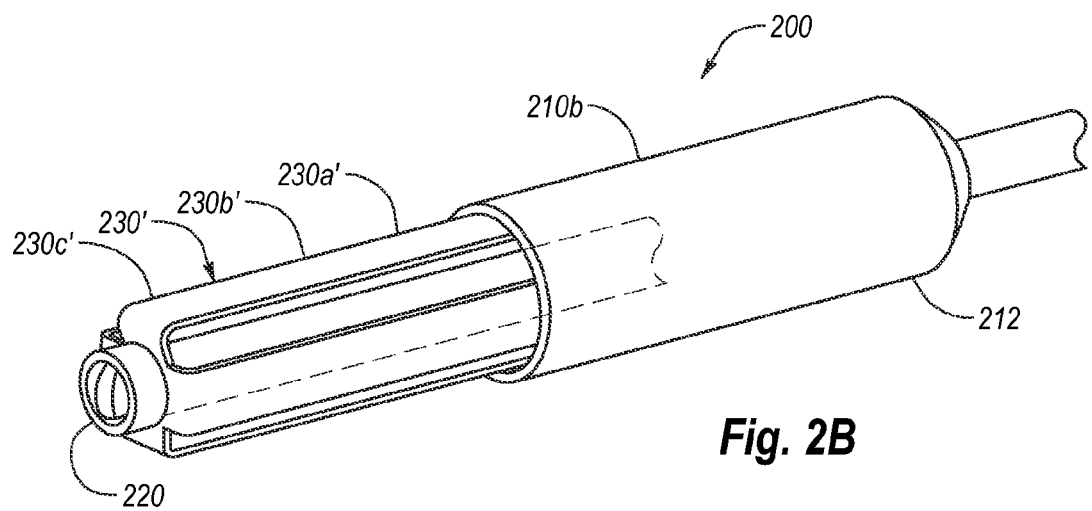
FIG. 2B illustrates one embodiment of a distal end region of the locator assembly of FIG. 2A when the distal end region is in an unexpanded state.
Figure 2C:
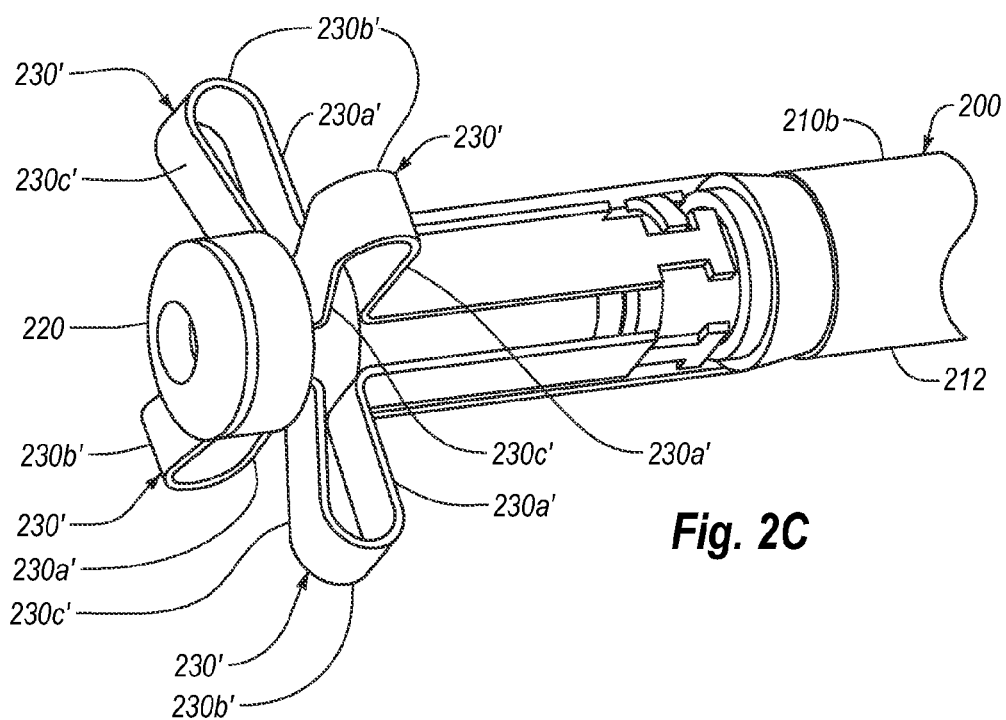
FIG. 2C illustrates the distal end region of the locator assembly of FIG. 2B when the distal end region is in an expanded state.
Figure 2B:
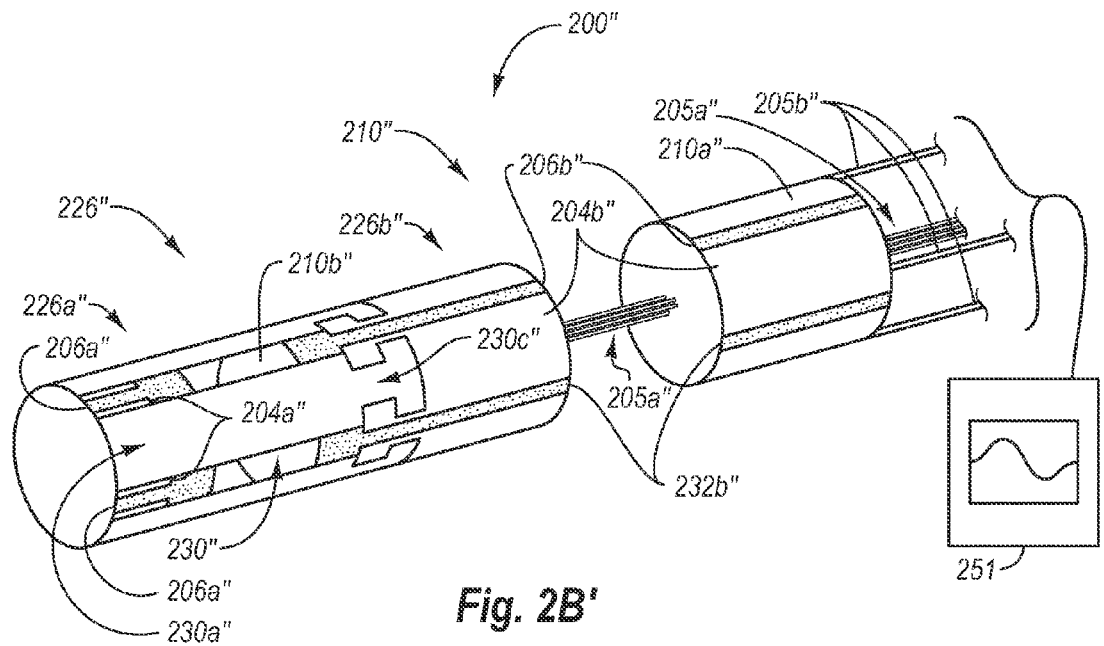
Figure 2C:
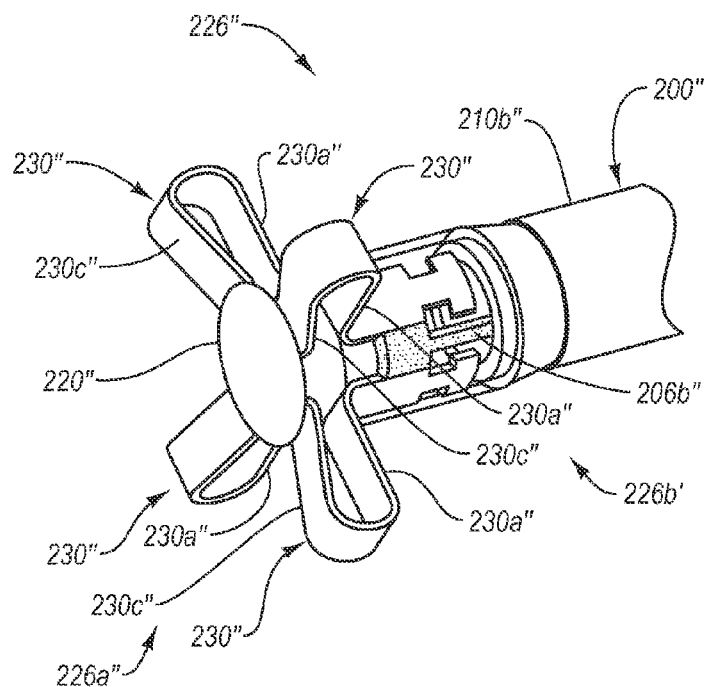
Figure 2B:
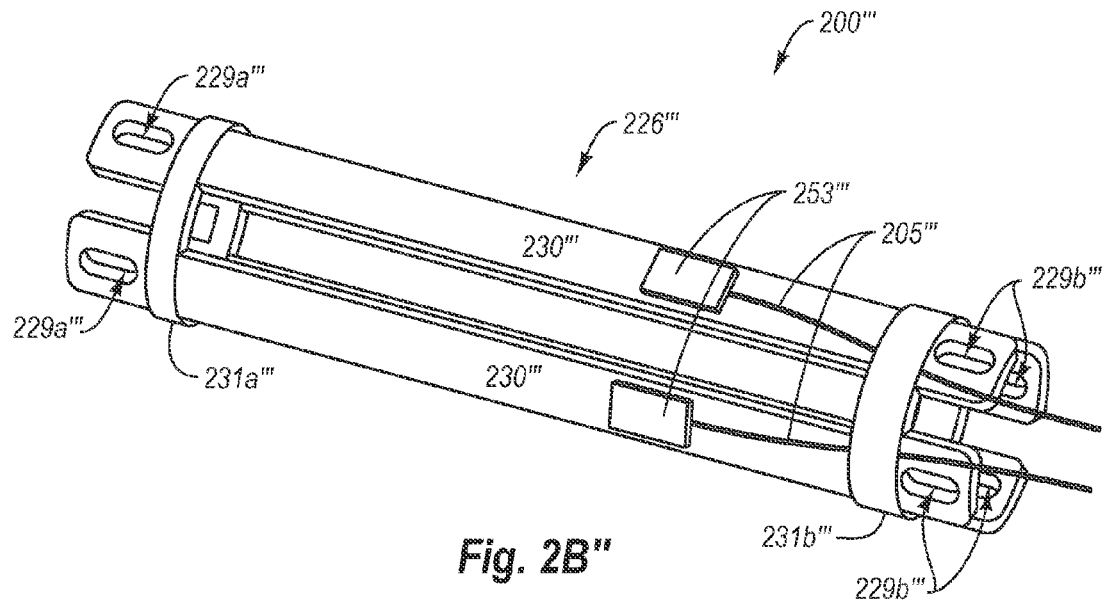
Figure 2C:
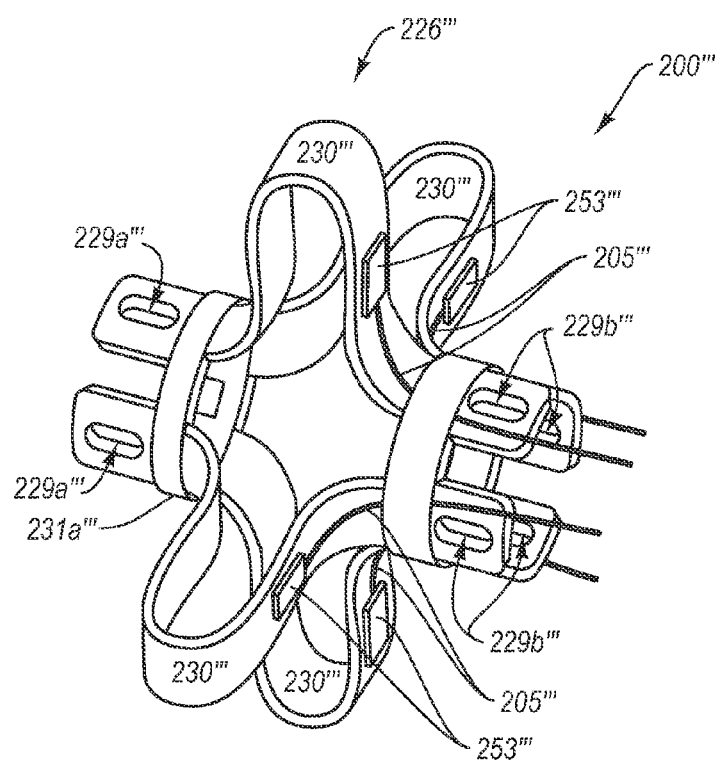

At least one (and, at least in some cases, all) of the expansion elements 230 can include a substantially flexible member 230' with a substantially fixed end region 230a', an intermediate region 230b', and a movable end region 230c' as shown in FIGS. 2B-2C. For each substantially flexible member 230', the fixed end region 230a' can be fixedly coupled with the distal end region 210b; whereas, the movable end region 230c' can be movably coupled with the distal end region 210b and configured to be axially movable relative to the fixed end region 230a'. When each movable end region 230c' can be axially moved toward the relevant fixed end region 230a', the intermediate regions 230b' buckle and/or expand transversely outwardly, thereby transitioning the distal end region 210b of the locator assembly 200 from the unexpanded state to the expanded state. In contrast, the distal end region 210b transitions from the expanded state to the unexpanded state as each of the movable end regions 230c' are axially moved away from the relevant fixed end region 230a'. Although the expansion elements 230 are shown as including the flexible members 230' in FIGS. 2B-2C for purposes of illustration, it is understood that the expansion elements 230 can include any type of expansion elements and are not limited to the illustrated embodiments. It is further contemplated that the expansion elements 230 may further include geometric features that allow/enhance the ability of the expansion elements to bend or fold from a retracted position to an expanded position. The expansion elements may be constructed of a material such as steel, spring steel, plastics or composites. In one embodiment, the expansion elements are constructed of Nitinol®.

FIGS. 2B' and 2C' illustrate an alternative embodiment of a locator assembly 200" for locating a surface of a body lumen, in accordance with the present invention. The locator assembly 200" of this embodiment may be functionally similar to that of the locator assembly 200 previously described above and shown in FIGS. 2B and 2C in most respects, wherein certain features will not be described in relation to this embodiment wherein those components may function in the manner as described above and are hereby incorporated into this alternative embodiment described below. Like structures and/or components are given like reference numerals.

The locator assembly 200" may be located proximal to a distal end 210b" of a tubular member 210" and/or an apparatus (such as apparatus 100 shown in FIG. 1). The locator assembly 200" may include a surface engagement assembly 226". The surface engagement assembly 226" may include a distal end portion 226a", a proximal end portion 226b", and/or at least one surface engagement element 230". The surface engagement elements 230" may be configured to transition from a relaxed state to an expanded state, similar to the substantially flexible member 230' described above. For example, the surface engagement elements 230" may be moveably connected to and/or fixedly connected to a distal end region 210b" of the locator assembly 200". In this example, a distal end 230a" of the surface engagement elements 230" may be moveably connected to a proximal end 230c" of the surface engagement elements 230" may be fixedly connected to the distal end region 210b". In other examples, other types of connections may be contemplated.

The locator assembly 200" may include two, three, four, and/or other numbers of surface engaging elements 230". At least one of the surface engaging elements 230" may be configured to conduct a measurable characteristic of the surface engaging elements 230" to the locator assembly 200". For instance, the locator assembly 200" may be in communication with a measuring device 251. An example of a measuring device 251 may include an impedance measuring device, a volt meter, an amp meter, a pressure transducer, piezoelectric crystals, other measuring devices, or combinations thereof. The measuring device 251 may determine changes in measurable characteristics of the locator assembly 200". For instance, the measuring device 251 may measure changes in the impedance of the locator assembly 200". In another example, the measuring device 251 may determine changes in pressure. Changes in pressure may be determined by a pressure transducer or other pressure measuring device. In a further example, the measuring device 251 may retrieve ultrasonic data in and/or around the body lumen. Ultrasonic data may be retrieved by piezoelectric crystal or other ultrasonic data gathering device. Other measurable characteristics may include electrical characteristics such as voltage, current, other electrical characteristics, and/or other measurable characteristics.

In embodiments where the measurable characteristic is an electrical characteristic, the locator assembly 200" may be in electrical communication with at least one of the surface engaging elements 230". In the present embodiment, the locator assembly 200" may include at least one distal conductive portion 204a" and/or at least one proximal conductive portion 204b" with which at least one surface engaging element 230" may be in electrical communication. At least one of surface engaging elements 230" may be formed at least partially from an electrically conductive material. In the present embodiment, at least one of surface engaging elements 230" may be formed at least partially from Nitinol®.

The distal conductive portions 204a" and/or the proximal conductive portions 204b" may be in electrical communication with the measuring device 251. For example, the at least one distal conductive portion 204a" may be in electrical communication with the measuring device 251 through at least one distal conductor connector 205a" and/or the at least one proximal conductive portion 204b" may be in electrical communication with the measuring device 251 through at least one proximal conductor connector 205b". The distal and/or proximal conductor connectors 205a", 205b" may extend toward the distal end 210b" and/or toward a proximal end 210a" of the tubular member 210" through at least one lumen (not shown).

In the present embodiment, each of the surface engaging elements 230" may be in electrical communication with a different distal conductive portion 204a" and/or proximal conductive portion 204b". Alternatively, more than one surface engaging element 230" may be in electrical communication with the same distal conductive portion 204a" and/or proximal conductive portion 204b". Other combinations are also contemplated.

The surface engaging elements 230" may be in electrical communication with each other. For instance, two or more surface engaging elements 230" may be may be formed from the same piece of material. In the present embodiment, each of the surface engaging elements 230" may be selectively electrically isolated from each other. Isolation of the surface engaging elements 230" may be accomplished by insulators 206a", 206b". The insulators 206a", 206b" may include materials such as ceramics, polyethylene, and/or other insulating materials.

FIGS. 2B''' and 2C''' illustrate a further embodiment of a locator assembly 200''' for locating a surface of a body lumen, in accordance with the present invention. The locator assembly 200''' of this embodiment may be functionally similar to that of the locator assemblies 200, 200" previously described above and shown in FIGS. 2B-2C and 2B'-2C' in most respects, wherein certain features will not be described in relation to this embodiment wherein those components may function in the manner as described above and are hereby incorporated into this alternative embodiment described below. Like structures and/or components are given like reference numerals. For example, the locator assembly 200''' may be configured to facilitate the determination of changes in measurable characteristics of the locator assembly.

The locator assembly 200' may be located proximal to a distal end of a tubular member (such as 210b, 210b" shown in FIGS. 2A, 2B, 2A', and 2B') and/or an apparatus (such as apparatus 100 shown in FIG. 1). The locator assembly 200''' may include a surface engagement assembly 226'''.

The surface engagement assembly 226''' may include a distal end portion 226a''', a proximal end portion 226b''', and/or at least one surface engagement element 230'''. In the present embodiment, the surface engagement assembly 226''' may include four surface engagement elements 230''' that may be separated by a distal and/or proximal engagement element support 231a''', 231b'''. The distal and/or proximal engagement element supports 231a''', 231b''' may electrically insulate the surface engagement elements 230'''. In an alternative embodiment, the distal engagement element supports 231a''', proximal engagement element supports 231b''', and/or surface engagement elements 230''' may be formed as a unitary piece and/or from the same material. For example, the distal engagement element supports 231a''', proximal engagement element supports 231b''', and/or surface engagement elements 230''' may be laser cut from a Nitinol® tube.

The surface engagement elements 230''' may include a distal and/or proximal retaining portion 229a''', 229b'''. The distal and/or proximal retaining portions 229a''', 229b''' may include an aperture and/or other retaining mechanism that may receive, for example, a detent and/or other retaining mechanism. For instance, a cover member (such as the cover member 220 shown in FIG. 2C) may include a retaining mechanism (not shown) to limit motion between the cover member and the surface engagement elements 230'''. The cover member may be connected to a control member (such as control member 250 shown in FIG. 2D) that is configured to transition the surface engagement elements 230''' from a relaxed state to an expanded state, similar to the substantially flexible member 230' described above.

The surface engaging elements 230''' may include a measuring component 253'''. The measuring component 253''' may facilitate the determination of changes in measurable characteristics of the locator assembly 200'''. For instance, the measuring component 253''' may facilitate the determination of changes in impedance, pressure, ultrasonic data, or other measurable characteristics. The measuring component 253''' may be in electrical communication with a connector 205'''. The connector 205''' may be in electrical communication with a measuring device (shown as 251 in FIG. 2B').

FIGS. 2B'''' and 2C'''' illustrate a further embodiment of a locator assembly 200'''' for locating a surface of a body lumen, in accordance with the present invention. The locator assembly 200'''' of this embodiment may be functionally similar to that of the locator assemblies 200, 200', 200", 200''' previously described above and shown in FIGS. 2B-2C, 2B'-2C', and 2B"-2C" in most respects, wherein certain features will not be described in relation to this embodiment wherein those components may function in the manner as described above and are hereby incorporated into this alternative embodiment described below. Like structures and/or components are given like reference numerals.

The locator assembly 200'''' may be located proximal to a distal end of a tubular member (such as 210b, 210b" shown in FIGS. 2A, 2B, 2A', and 2B') and/or an apparatus (such as apparatus 100 shown in FIG. 1). The locator assembly 200'''' may include a surface engagement assembly 226'''', a cover member 220'''', and/or a proximal end portion 226b''''.

The cover member 220'''' and/or proximal end portion 226b'''' may include a distal retaining portion 221a'''' and/or a proximal retaining portion 221b'''', respectively. The surface engagement assembly 226'''' may include at least one surface engagement element 230''''. The surface engagement elements 230'''' may include a distal and/or proximal retaining portion 229a'''', 229b''''. The distal and/or proximal retaining portions 221a'''', 221b'''' on the cover member 220'''' and/or proximal end portion 226b'''' may include an aperture and/or other retaining mechanism that may cooperate with corresponding distal and/or proximal retaining portions 229a'''', 229b'''', such as a detent and/or other retaining mechanism, on the surface engagement elements 230'''' to limit motion between the cover member 220'''', the proximal end portion 226b'''', and/or the surface engagement elements 230''''. The distal and/or proximal retaining portions 229a'''', 229b'''' may be located near a distal and/or proximal end 230a'''', 230b'''' of the surface engagement element 230'''', respectively.

A control member 250'''' may be inserted through the proximal end portion 226b'''' and/or may be connected to the cover member 220''''. The control member 250'''' may be used to transition the surface engagement elements 230'''' from a relaxed state to an expanded state, similar to the substantially flexible member 230' described above.

In the present embodiment, the control member 250'''' may be a single piece, which may be elongate from the cover member 220'''' toward a proximal end (such as proximal end 210a'' shown in FIG. 2B') of the locator assembly 200''''. Alternatively, the control member 250'''' may be in one or more pieces that may be connected together using various mechanisms, similar to the retaining portions 221a'''', 221b'''', 229a'''', 229b'''' described above.

The proximal end portion 226b'''' may include a tubular member retaining portion 228''''. The tubular member retaining portion 228'''' may be configured to engage a distal end (such as distal end 210b, 210b'' shown in FIGS. 2B and 2B'). The tubular member retaining portion 228'''', in the present embodiment, may include a ramp and/or other retaining mechanism to limit the motion of the tubular member in at least one direction.

The surface engagement elements 230'''' may include an engagement member 232''''. The engagement member 232'''' may include an engagement portion 234'''' and/or an engagement support portion 237''''.

The engagement portion 234'''' may be configured to contact and/or engage tissue. The engagement portion 234'''', in the present embodiment, may be enlarged in an intermediate portion 235'''' in comparison to distal and/or proximal end 234a'''', 234b'''' of the engagement portion 234''''. An enlarged intermediate portion 235'''' may facilitate contact and/or engagement with tissue.

The engagement support portion 237'''' may support the engagement portion 234'''' during, for example, transitioning from a relaxed state to an expanded state. The engagement support portion 237'''' may include an enlarged intermediate portion 238'''', similar to the enlarged intermediate portion 235'''' of the engagement portion 234''''. Having an enlarged intermediate portion 238'''' on the engagement support portion 237'''' may add stability to the engagement portion 234'''' while in the expanded state.

The intermediate portions 235'''', 238'''' of the engagement portions 234' and/or the engagement support portions 237'''' may be oval shaped. Alternatively, the intermediate portions 235'''', 238'''' may have the same shape, have differing shapes, and/or have other combinations of shapes.

In the present embodiment, the proximal end 234b'''' of the engagement portion 234'''' may be connected to a proximal support portion 233''''. The proximal support portion 233'''' may be connected to the proximal end portion 226b'''' and may separate the engagement portion 234'''' from the proximal end portion 226b''''. The distal end 234a'''' of the engagement portion 234'''' may be connected to an intermediate support portion 236''''. The intermediate support portion 236'''' may be connected to the proximal end 237b'''' of the engagement support portion 237'''' and may separate the engagement portion 234'''' from the engagement support portion 237''''. The distal end 237a'''' of the engagement support portion 237'''' may be connected to a distal support portion 239''''. The distal support portion 239'''' may be connected to the distal end (not shown) of the surface engagement element 230'''' and may separate the engagement support portion 237'''' from the distal end portion 226a''''.

The surface engaging elements 230'''' may include a measuring component 253''''. The measuring component 253'''' may facilitate the determination of changes in measurable characteristics of the locator assembly 200''''. For instance, the measuring component 253'''' may facilitate the determination of changes in impedance, pressure, ultrasonic data, or other measurable characteristics. The measuring component 253'''' may be in electrical communication with a connector 205''''. The connector 205'''' may be in electrical communication with a measuring device (shown as 251 in FIG. 2B').

Figure 2D:
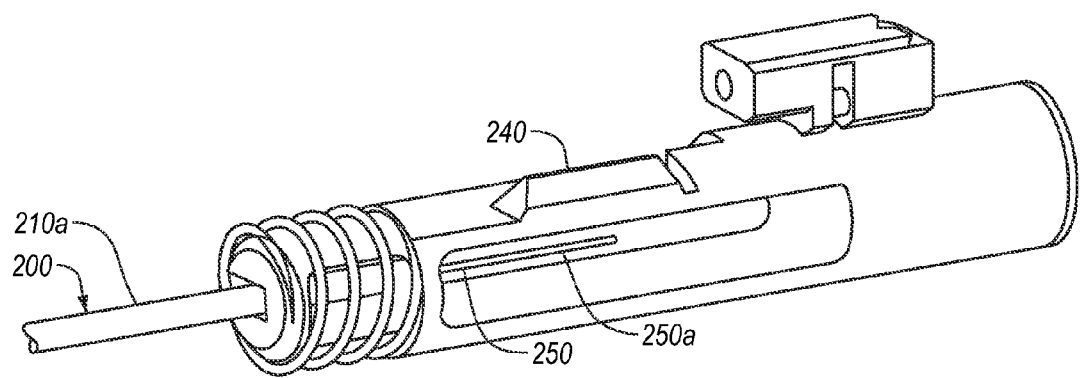
FIG. 2D illustrates one embodiment of a proximal end region of the locator assembly of FIG. 2A.

Referring now to FIG. 2D, the locator assembly 200 may further include a locator control system associated with the locator assembly. As shown in FIG. 2D, the locator control system 240 can be associated with the proximal end region 210a of the locator assembly 200 and can be configured to selectively control the distal end region 210b of the locator assembly 200 between the unexpanded and expanded states. The locator control system 240 can selectively control the distal end region 210b between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210a and the distal end region 210b. The control member 250 has a proximal end region 250a that is coupled with the locator control system 240, which can be via a control block 260 (shown in FIG. 4D), and a distal end region (not shown) that is coupled with the distal end region 210b of the locator assembly 200, the expansion elements 230, and/or the movable end regions 230c' of the substantially flexible members 230'. The locator control system 240 can selectively transition the distal end region 210b, the expansion elements 230, and/or the substantially flexible members 230' between the unexpanded and expanded states by moving the control member 250 axially relative to the tubular body 210.

The locator control system 240 further includes a locator release system 490 for maintaining the unexpanded state and/or the expanded state of the distal end region 210b, the expansion elements 230, and/or the substantially flexible members 230'. The locator release system 490 can be configured to maintain the expanded state of the distal end region 210b, and can include any type of locking system and can be engaged, for instance, by activating the switching system. For example, once the substantially flexible members 230' have entered the expanded state, the locator release system 490 can secure the control member 250 to prevent axial movement relative to the tubular body 210, thereby maintaining the substantially flexible members 230' in the expanded state.

In the manner described in more detail below, the locator control system 240 also can be configured to disengage the locator release system 490, such that the distal end region 210b, the expansion elements 230, and/or the substantially flexible members 230' can transition between the expanded and unexpanded states. The locator release system 490 can be disengaged, for example, by activating an emergency release system (not shown). As desired, the locator control system 240 may further include a biasing system (not shown), such as one or more springs or other resilient members, to bias the distal end region 210*b*, the expansion elements 230, and/or the substantially flexible members 230' to enter and/or maintain the unexpanded state when the locator release system 490 is disengaged.

Returning to FIG. 1, the carrier assembly 300 can be coupled with, and slidable relative to, the locator assembly 200. The carrier assembly 300 is configured to receive and retain the closure element 500 (shown in FIGS. 6A-6B), which can be disposed substantially within the carrier assembly 300. When the locator assembly 200 engages the inner surface 620*b* (shown in FIG. 8A) of the blood vessel wall 620 (shown in FIG. 8A), the carrier assembly 300 can be further configured to position the closure element 500 substantially adjacent to the opening 610 (shown in FIG. 8A) and to deploy the closure element 500. Upon being deployed, the closure element 500 can maintain the reduced cross-section 530' (shown in FIGS. 6C-6D), and can temporarily and substantially uniformly expand beyond the natural cross-section 530 (shown in FIGS. 6A-6B) of the closure element 500. In either case, the closure element 500, when deployed, can engage a significant amount of the blood vessel wall 620 and/or tissue 630 adjacent to the opening 610. Thereafter, the closure element 500 can be configured to return to the natural cross-section 530 such that the blood vessel wall 620 and/or tissue 630 is drawn substantially closed and/or sealed.

Figure 6G:
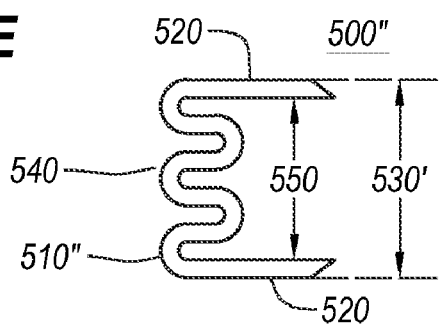
FIG. 6G illustrates a side view of the closure element of FIG. 6F.

Turning to FIGS. 3A-3D, the carrier assembly 300 can include a tube set 305, including a carrier member 310, a pusher member 320, a support tube 340, and a cover member 330. The carrier member 310, the pusher member 320, the support tube 340, and the cover member 330 can be provided as a plurality of nested, telescoping members with a common longitudinal axis 350 as illustrated in FIG. 3A. The carrier member 310 can be configured to receive and support the closure element 500. While being disposed on the carrier member 310, the closure element 500 can be deformed from the natural, planar configuration to form the substantially tubular closure element 500" (shown in FIGS. 6F-6G) as will be discussed in more detail below. Being disposed substantially about, and supported by, an outer periphery 312*b* of the carrier member 310, the substantially tubular closure element 500" can be substantially in axial alignment with the carrier member 310 with the tines 520 pointed substantially distally.

The carrier member 310 can be formed as a substantially rigid, semi-rigid, or flexible tubular member. Additionally, the carrier member 310 can have a proximal end region 310*a* and a distal end region 310*b* and includes a predetermined length 318*a* and a predetermined cross-section 318*b*, both of which can be of any suitable dimension. The carrier member 310 also can define a lumen 314 that extends substantially between the proximal end region 310*a* and the distal end region 310*b* and that is configured to slidably receive at least a portion of the tubular body 210 of the locator assembly 200. Although the cross-section 318*b* of the carrier member 310 generally is substantially uniform, the distal end region 310*b* of the carrier member 310 can have a cross-section that increases distally, as illustrated in FIGS. 3A-3B, for substantially uniformly expanding the substantially tubular closure element 500" beyond the natural cross-section 530 of the closure element 500 when the substantially tubular closure element 500" is deployed. To deploy the closure element 500 without expanding the closure element 500, the distal end region 310*b* can be formed with a cross-section (not shown) that is substantially uniform. Although shown and described as having the cross-section that increases distally for expanding the substantially tubular closure element 500", it will be understood that the distal end region 310*b* of the carrier member 310 can be provided with the substantially-uniform cross-section and that the substantially tubular closure element 500" can be deployed without being expanded.

Being configured to distally deploy the substantially tubular closure element 500", the pusher member 320 has a proximal end region 320*a* and a distal end region 320*b* and is coupled with, and slidable relative to, the carrier member 310. The pusher member 320 includes a predetermined length 328*a* and a predetermined cross-section 328*b*, both of which can be of any suitable dimension and can be configured to slidably receive the carrier member 310 such that the distal end region 320*b* of the pusher member 320 is offset proximally from the distal end region 310*b* of the carrier member 310. As desired, the predetermined length 328*a* of the pusher member 320 can be greater than or substantially equal to the predetermined length 318*a* of the carrier member 310. The predetermined length 328*a* of the pusher member 320, however, can be less than the predetermined length 318*a* of the carrier member 310 such that the carrier member 310 and the pusher member 320 at least partially define a space 360 distal to the distal end region 320*b* of the pusher member 320 and along the periphery 312*b* of the carrier member 310.

Being formed from a substantially rigid, semi-rigid, or flexible material, the pusher member 320 can be substantially tubular and can define a lumen 324 that extends substantially between the proximal end region 320*a* and the distal end region 320*b* and that is configured to slidably receive at least a portion of the carrier member 310. The cross-section 328*b* of the pusher member 320 can be substantially uniform, and the distal end region 320*b* of the pusher member 320 can include one or more longitudinal extensions 325, which extend distally from the pusher member 320 and along the periphery 312*b* of the carrier member 310 as shown in FIG. 3C. The longitudinal extensions 325 can be biased such that the longitudinal extensions 325 extend generally in parallel with common longitudinal axis 350. The longitudinal extensions 325 are sufficiently flexible to expand radially, and yet sufficiently rigid to inhibit buckling, as the distal end region 320*b* is directed distally along the carrier member 310, and to engage the distally-increasing cross-section of the distal end region 310*b* of the carrier member 310 to deploy the substantially tubular closure element 500".

A cover member 330 is configured to retain the substantially tubular closure element 500" substantially within the carrier assembly 300 prior to deployment as shown in FIG. 3D. Being coupled with, and slidable relative to, the pusher member 320, the cover member 330 has a proximal end region 330*a* and a distal end region 330*b* and includes a predetermined length 338*a* and a predetermined cross-section 338*b*, both of which can be of any suitable dimension. The cover member 330 can be formed as a substantially rigid, semi-rigid, or flexible tubular member. Additionally, the cover member 330 can have an inner periphery 332*a* and an outer periphery 332*b* and can define a lumen 334. The lumen 334 can extend substantially between the proximal and distal end regions 330*a*, 330*b* of the cover member 330 and can be configured to slidably receive at least a portion of the pusher member 320. When the cover member 330 is properly positioned within the carrier assembly 300, the distal end region 330*b* can be configured to extend over the space 360, thereby defining an annular cavity 370 for receiving and retaining the substantially tubular closure element 500".

The cross-section 338b of the cover member 330 can be substantially uniform, and the distal end region 330b of the cover member 330 can include one or more longitudinal extensions 335, which extends distally from the cover member 330 and along an outer periphery 322b of the pusher member 320 as shown in FIG. 3D. Although the longitudinal extensions 335 can extend generally in parallel with common longitudinal axis 350, the longitudinal extensions 335 can be biased such that the plurality of longitudinal extensions 335 extends substantially radially inwardly as illustrated in FIGS. 3A and 3D. Thereby, the longitudinal extensions 335 can at least partially close the lumen 334 substantially adjacent to the distal end region 330b of the cover member 330. To permit the substantially tubular closure element 500" to be deployed from the annular cavity 370, the longitudinal extensions 335 can be sufficiently flexible to expand radially to permit the distal end region 310b of the carrier member 310 to move distally past the cover member 330 to open the annular cavity 370 such that the distal end region 330b no longer extends over the space 360.

If the carrier assembly 300 is assembled as the plurality of nested, telescoping members as shown in FIG. 3A, the carrier member 310 can be at least partially disposed within, and slidable relative to, the lumen 324 of the pusher member 320 as shown in FIG. 3C. The pusher member 320, in turn, can be at least partially disposed within, and slidable relative to, the lumen 334 of the cover member 330. To couple the carrier assembly 300 with the locator assembly 200, the tubular body 210 of the locator assembly 200 can be at least partially disposed within, and slidable relative to, the lumen 314 of the carrier member 310. The longitudinal axis of the locator assembly 200 can be substantially in axial alignment with the common longitudinal axis 350 of the carrier member 310, the pusher member 320, the cover member 330, and the support tube 340.

It will be appreciated that the tube set 305 can also include a support member 340 as shown in FIGS. 3A and 3E. The support member 340 is configured to slidably receive the tubular body 210 of the locator assembly 200 and to provide radial support for the distal end region 210b of the tubular body 210 when the locator assembly 200 is coupled with the carrier assembly 300. The carrier assembly 300 can advantageously include the support member 340, for example, if the tubular body 210 is not sufficiently rigid or under other circumstances in which support for the tubular body 210 might be desirable. It also will be appreciated that the support member 340 also can be configured to inhibit the plurality of longitudinal extensions 335, which extend from the distal end region 330b of the cover member 330, from expanding prematurely prior to the closure element 500 being deployed.

The support member 340 can be formed as a substantially rigid, semi-rigid, or flexible tubular member, having a proximal end region 340a and a distal end region 340b. Wherein an outer periphery 342b of the support member 340 can define a lumen 344 that extends substantially between the proximal end region 340a and the distal end region 340b, the lumen is configured to slidably receive and support at least a portion of the tubular body 210 of the locator assembly 200. The support member 340, in turn, can be at least partially slidably disposed within the lumen 314 of the carrier member 310 such that the tubular body 210 of the locator assembly 200 may be coupled with, and slidable relative to, the carrier member 310 in the manner described in more detail above. The support member 340 can have a predetermined length 348a and a predetermined cross-section 348b, both of which can be of any suitable dimension, and the cross-section 348b can be substantially uniform. Although shown and described as being substantially separate for purposes of illustration, it will be appreciated that the carrier member 310, the pusher member 320, the cover member 330, and/or the support member 340 can be provided, in whole or in part, as one or more integrated assemblies.

Figure 4A:
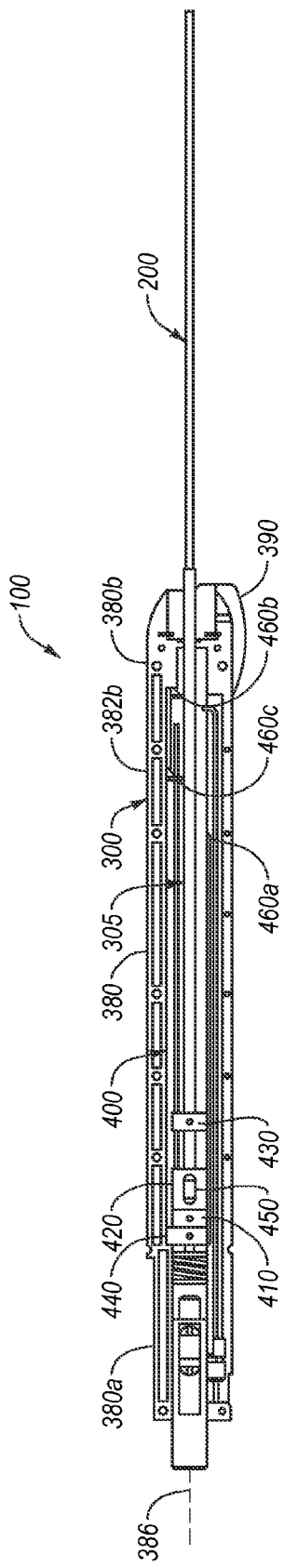
FIG. 4A illustrates a cross-sectional side view of one embodiment of a triggering system for the carrier assembly of FIG. 3A.

The carrier assembly 300 may further include a housing 380 as illustrated in FIG. 4A. The housing 380 can be formed as an elongate member with a longitudinal axis 386. Additionally, the housing 380 can have an outer periphery 382b and includes a proximal end region 380a and a distal end region 380b. Thereby, when the apparatus 100 can be properly assembled, the tubular body 210 of the locator assembly 200 at least partially disposed within the tube set 305 such that the distal end region 210b of the tubular body 210 extends beyond the distal end regions 310b, 320b, 330b, and/or 340b. The tubular body 210, the carrier member 310, the pusher member 320, the cover member 330, and, if provided, the support member 340 can be at least partially disposed within, and slidable relative to, the housing 380, and the respective distal end regions 210b, 310b, 320b, 330b, and 340b extend from the distal end region 380b of the housing 380 such that the common longitudinal axis 350 (shown in FIG. 3A) of the tube set 305 is substantially axially aligned with the longitudinal axis 386 of the housing 380. Being configured to slidably retain the respective proximal end regions 210a, 310a, 320a, 330a, and 340a, the housing 380 supports the tube set 305 and can have one or more handles 390 to facilitate use of the apparatus 100. The handles 390 extend substantially radially from the outer periphery 382b of the housing 380 and can be provided in the manner known in the art.

When the apparatus 100 is properly assembled, the tubular body 210 of the locator assembly 200 can be at least partially disposed within the tube set 305 of the carrier assembly 300 such that the distal end region 210b of the tubular body 210 extends beyond the distal end regions 310b, 320b, 330b, and/or 340b. Further, the proximal end region 210a of the tubular body 210 and the proximal end regions 310a, 320a, 330a, and/or 340a of the tube set 305 are at least partially disposed within, and slidable relative to, the housing 380. The switching system of the locator assembly 200 and a switching system 450 of the triggering system 400 can be accessible external to the housing 380 as shown in FIGS. 4A and 4C.

Figure 4B:
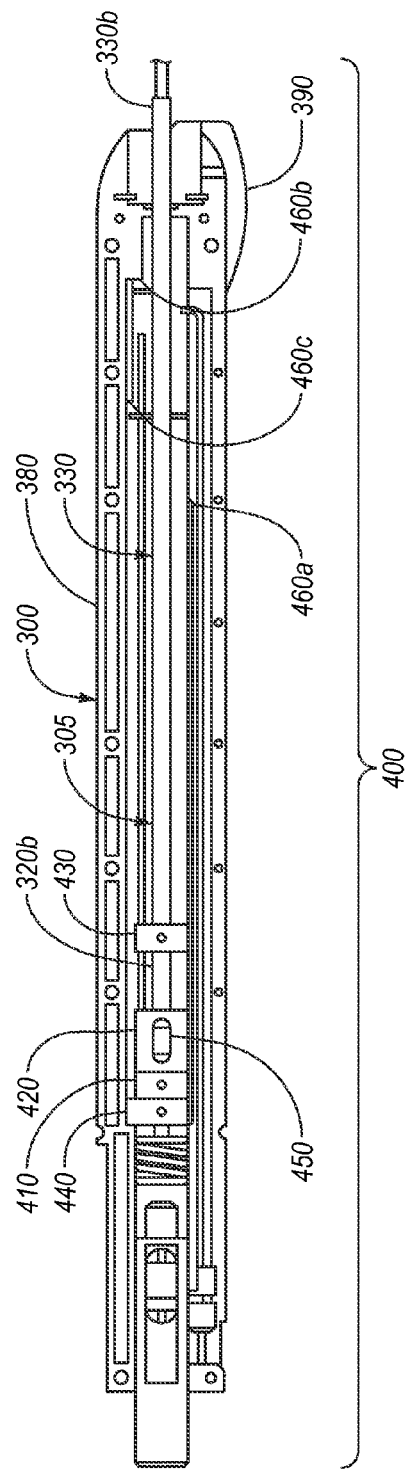
FIG. 4B illustrates a first detailed cross-sectional side view of the triggering system of FIG. 4A.
Figure 4C:
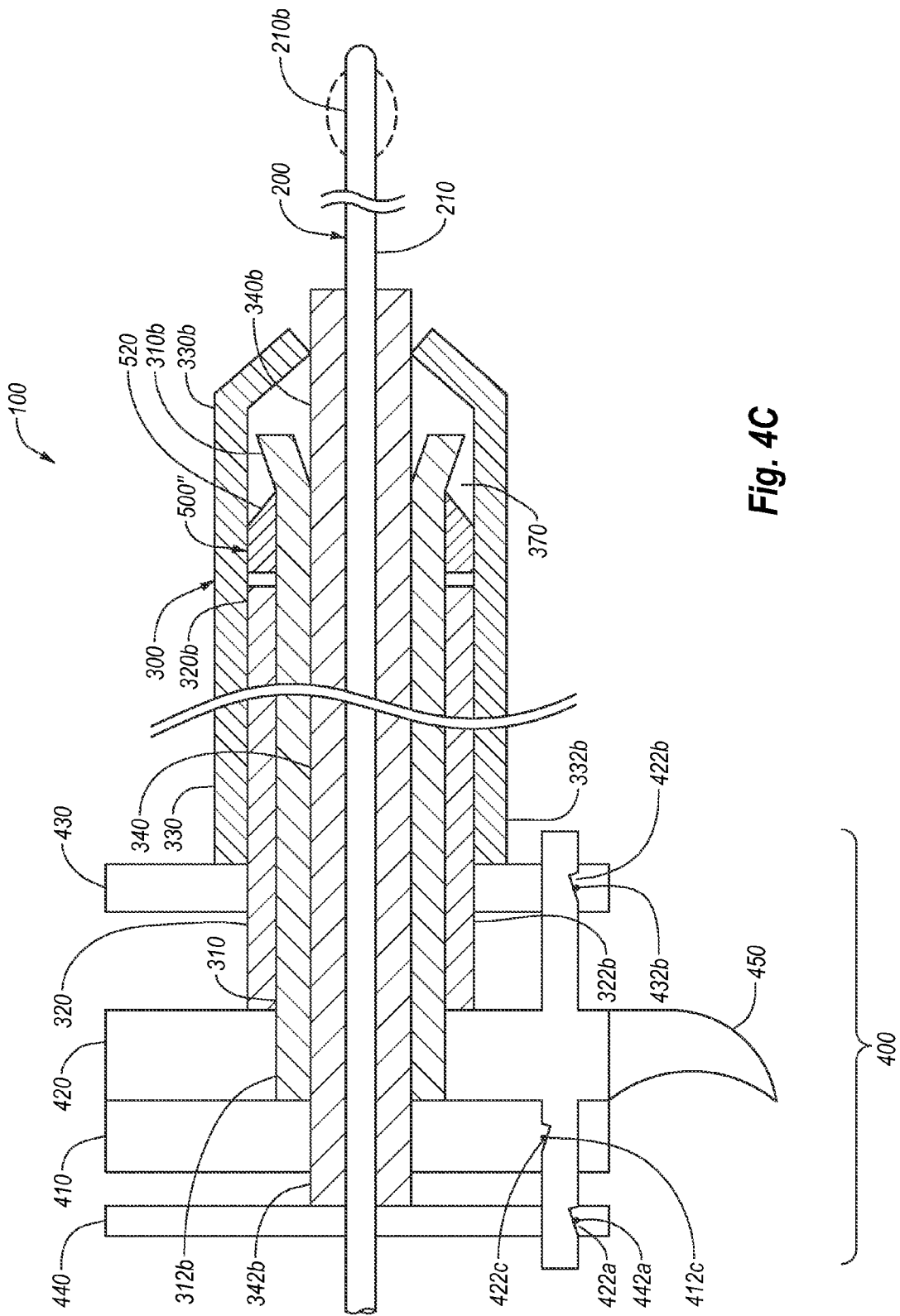
FIG. 4C illustrates a detailed view of the triggering system of FIG. 4B.
Figure 4D:
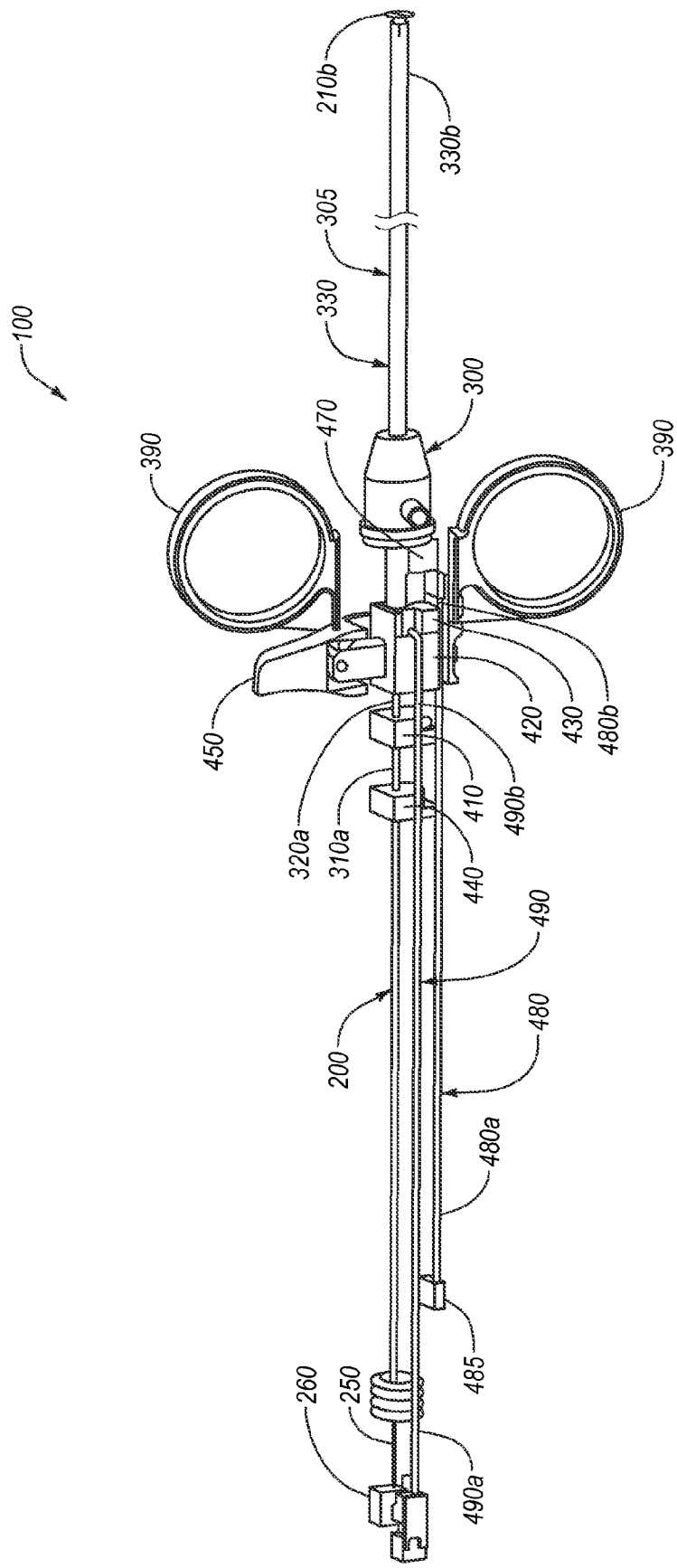
FIG. 4D illustrates a second detailed cross-sectional side view of the triggering system of FIG. 4A.

Turning to FIGS. 4B-4D, a triggering system 400 can be disposed substantially within the housing 380. The triggering system 400 can be configured to control the relative axial movement and/or positioning of the respective distal end regions 310b, 320b, 330b, and 340b of the tube set 305 and/or the distal end region 210b of the locator assembly 200. Being coupled with the proximal end regions 210a, 310a, 320a, 330a, and/or 340a, the triggering system 400 can control the relative axial movement of the distal end regions 210b, 310b, 320b, 330b, and/or 340b in any manner, such as by being activated by the switching system 450. As desired, the triggering system 400 can induce axial motion, such as distal motion, with respect to one or more of the distal end regions 210b, 310b, 320b, 330b, and/or 340b. One or more of the distal end regions 210b, 310b, 320b, 330b, and/or 340b can be axially moved. Axial motion of one or more of the carrier member 310, the pusher member 320, the cover member 330, and the support member 340 and/or the tubular body 210 can be attained, for example, by applying an axial force to the switching system 450. To facilitate monitoring of the positioning of the carrier assembly 300 and/or the substantially tubular closure element 500", one or more of the distal end regions 210b, 310b, 320b, 330b, and/or 340b may include radiopaque markers (not shown) or may be wholly or partially formed from a radiopaque material.

The triggering system 400 can be configured to overcome internal resistance such that the relative axial movement and/or positioning of the respective distal end regions 310b, 320b, 330b, and 340b of the tube set 305 and/or the distal end region 210b of the locator assembly 200 are controlled in accordance with a predetermined manner when the triggering system 400 is activated. Thereby, movement and/or positioning of the distal end regions 310b, 320b, 330b, 340b, and/or 210b can be initiated when at least a predetermined quantity of force is applied to the switching system 450. Stated somewhat differently, a force that is less than the predetermined quantity generally may be insufficient to activate the triggering system 400; whereas, when the force increases to a level that is greater than or substantially equal to the predetermined quantity, the triggering system 400 is configured to activate, move and/or position the distal end regions 310b, 320b, 330b, 340b, and/or 210b in accordance with the predetermined manner. The triggering system 400, once activated, can continue to move and/or position the distal end regions 310b, 320b, 330b, 340b, and/or 210b in accordance with the predetermined manner until the closure element 500 is deployed.

The triggering system 400, for example, can include one or more sets of cooperating detents for coupling the axial motion of the distal end regions 310b, 320b, 330b, and 340b in accordance with a predetermined manner when the triggering system 400 is activated. The term "detents" refers to any combination of mating elements, such as blocks, tabs, pockets, slots, ramps, locking pins, cantilevered members, support pins, and the like, that may be selectively or automatically engaged and/or disengaged to couple or decouple the carrier member 310, the pusher member 320, the cover member 330, and the support member 340 relative to one another. It will be appreciated that the cooperating detents as illustrated and described below are merely exemplary and not exhaustive. For example, the cooperating detents can include a first set of cooperating blocks and pockets for releasably coupling the support member 340, the carrier member 310, the pusher member 320, and the cover member 330. When the carrier assembly 300 reaches a first predetermined distal position, the support member 340 can be decoupled from the carrier member 310, the pusher member 320, and the cover member 330 and can be substantially inhibited from further axial movement. Thereby, the carrier member 310, the pusher member 320, and the cover member 330 may continue to be directed distally as the support member 340 remains substantially stationary.

As shown in FIGS. 4B-4C, the cooperating detents can include a carrier block 410, a pusher block 420, a cover block 430, and a support block 440, which can be configured to couple and decouple in accordance with the predetermined manner. For example, the carrier block 410 can be disposed on the proximal end region 310a of the carrier member 310 and can include a carrier pin 412c that extends from the carrier block 410; whereas, the proximal end region 330a of the cover member 330 and the proximal end region 340a the support member 340 are respectively coupled with the cover block 430 and the support block 440. A cover pin 432b can extend from the cover block 430, and the support block 440 can have a support pin 442a, which extends from the support block 440. The support pin 442a, the cover pin 432b, and the carrier pin 412c each can be formed from a substantially rigid material, such as an alloy of nickel-titanium.

The pusher block 420 can be disposed on the proximal end region 320a of the pusher member 320 and forms a support slot 422a, a cover slot 422b, and a carrier slot 422c. The support slot 422a can be configured to receive and releasably engage the support pin 442a by which the support member 340 can be coupled with, and decoupled from, the pusher member 320. The cover member 330 can be coupled with, and decoupled from, the pusher member 320 via the cover slot 422b, which is configured to receive and releasably engage the cover pin 432b. The carrier slot 422c can be configured to receive and releasably engage the carrier pin 412c such that the carrier member 310 can be coupled with, and decoupled from, the pusher member 320. The carrier block 410, the pusher block 420, the cover block 430, and the support block 440 can be respectively disposed substantially on the outer peripheries 312b, 322b, 332b, and 342b and can be configured to couple and decouple in accordance with the predetermined manner.

The triggering system 400 can further include one or more stops for engaging the pusher block 420, the cover block 430, and/or the support block 440, respectively. As illustrated in FIG. 4B, a support stop 460a, a cover stop 460b, and a carrier stop 460c each can be formed in the housing 380 and are configured to receive, and substantially inhibit further movement of, the support block 440, the cover block 430, and the carrier block 410, respectively, in accordance with the predetermined manner. For example, when an axial force is applied to the tube set 305 via the switching system 450, the cover block 430 can move distally within the housing 380, and the cover block 430 approaches the cover stop 460b. Upon being received by the cover stop 460b, the cover block 430 can be substantially locked in place, substantially preventing any further motion of the cover block 430.

Resisting the axial force, the cover pin 432b can provide a static load while the axial force is less than the predetermined quantity of force. As the axial force increases to a level that is greater than or substantially equal to the predetermined quantity, the cover pin 432b can be displaced from the cover slot 422b, decoupling the cover member 330 from the carrier member 310, the pusher member 320, and the support member 340. Creating the internal resistance to be overcome by the triggering system 400, the static forces provided by the pins 442a, 432b, and 412c is approximately proportional to a composition and cross-section of the respective pins 442a, 432b, and 412c and/or a depth and a slope of the respective slots 422a, 422b, and 422c. As desired, the pins 442a, 432b, and 412c can be configured to provide static loads that are differing and/or substantially uniform.

Turning to FIG. 4D, the triggering system 400 may further include a tube release system 470 for inhibiting inadvertent advancement of the tube set 305. The tube release system 470 is coupled with a tube release member 480, such as a rod, wire, or other elongate member. The tube release member 480 has a proximal end region 480a that is disposed substantially between the pusher block 420 and the housing 380 (shown in FIG. 4A) and a distal end region 480b that is coupled with the tube release system 470. Optionally, a tab 485 is coupled with the proximal end region 480a of the tube release member 480, and a pin (not shown) extends from the pusher block 420 and is disposed substantially between the tab 485 and a groove (not shown) formed in the housing 380. The tube release system 470 is configured to release the tube set 305 when the tube release member 480 is moved proximally, freeing the pusher block 420.

A locator release system 490 for permitting the distal end region 210b, the expansion elements 230, and/or the substantially flexible members 230' of the locator assembly 200 to transition from the expanded state to the unexpanded state can be included with the triggering system 400. The locator release system 490 can include a rod, wire, or other elongate member and has a proximal end region 490a and a distal end region 490b. The proximal end region 490a of the locator release system 490 can be coupled with, and configured to activate, the locator control system 240 (shown in FIG. 2D), and the distal end region 490b extends beyond the pusher block 420. Thereby, when the pusher block 420 is advanced during deployment of the closure element 500, the control block 260 can be disengaged such that the distal end region 210b, the expansion elements 230, and/or the substantially flexible members 230' of the locator assembly 200 to transition from the expanded state to the unexpanded state.

Figure 5A:
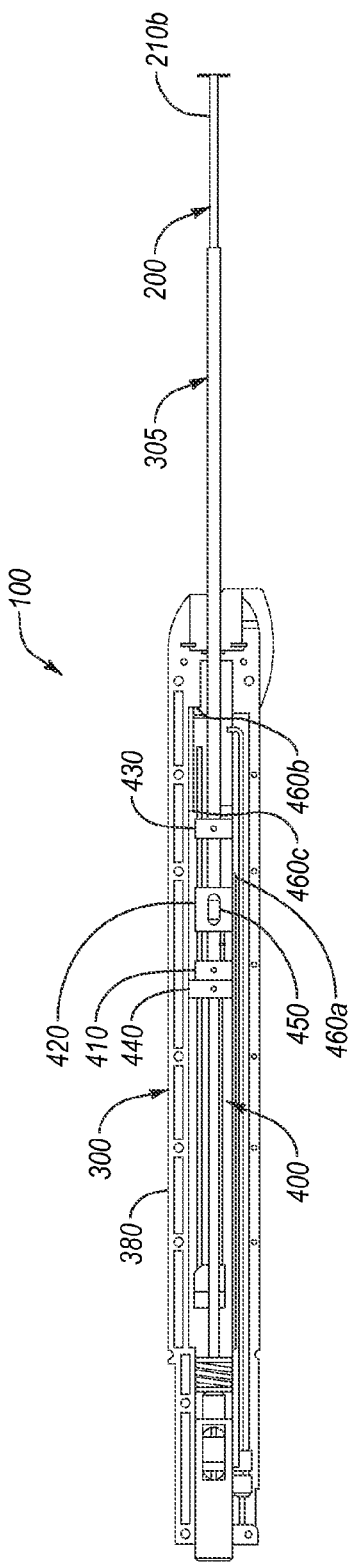
FIG. 5A illustrates the carrier control system of FIGS. 4A-D as the carrier assembly of FIG. 3A moves distally from an initial predetermined position.
Figure 5B:
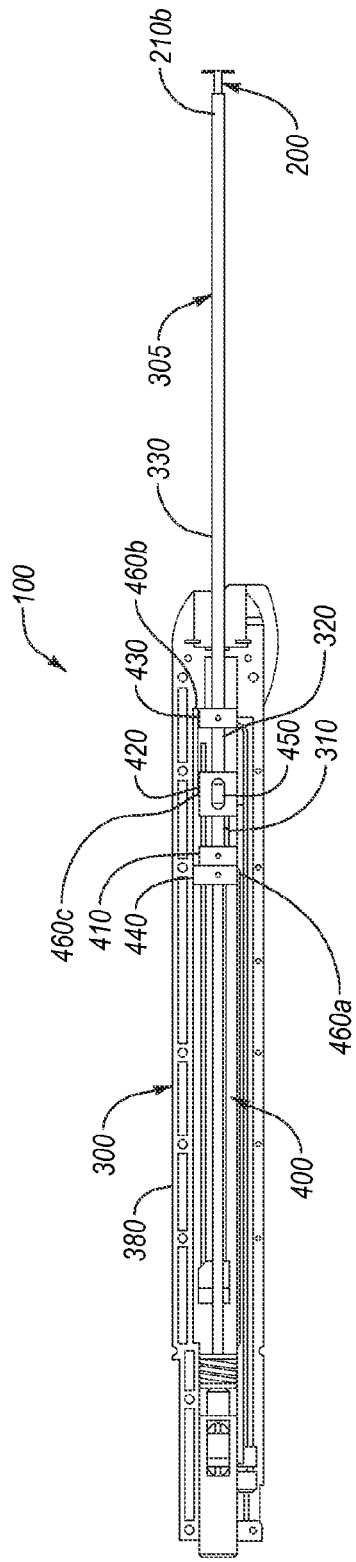
FIG. 5B illustrates the carrier control system of FIGS. 4A-D as the carrier assembly of FIG. 3A reaches a first predetermined position.
Figure 5C:
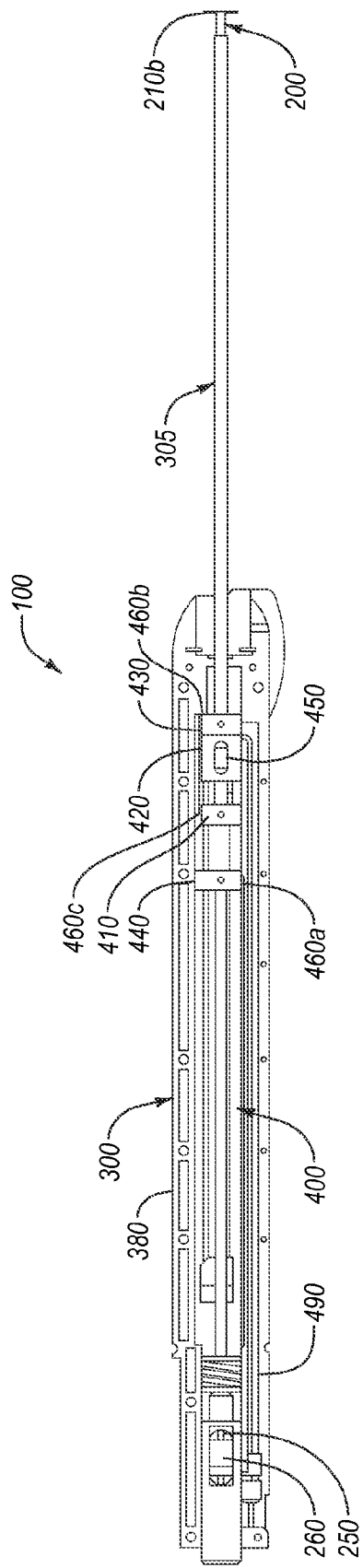
FIG. 5C illustrates the carrier control system of FIGS. 4A-D as the carrier assembly of FIG. 3A reaches a second predetermined position.

The operation of the triggering system 400 in accordance with one predetermined manner is illustrated in FIGS. 5A-5C with the closure element 500 (shown in FIGS. 6A-6B) disposed substantially within the apparatus 100. As shown in FIG. 5A, the distal end region 210b of the locator assembly 200 has been positioned as desired and has transitioned from the unexpanded state to the expanded state. While the locator control system 240 (shown in FIG. 2D) maintains the distal end region 210b in the expanded state, a distally-directed axial force can be applied to the triggering system 400 via the switching system 450. Once the tube release member 480 (shown in FIG. 4D) has been moved proximally to free the pusher block 420, the tube set 305 can be substantially freely slidable within the housing 380 and responds to the axial force by sliding distally from an initial predetermined position to a first predetermined position.

In the initial predetermined position, the carrier member 310, the pusher member 320, the cover member 330, and the support member 340 can be coupled via the slots 422c, 422b, and 422a (shown in FIG. 4C) and the pins 412c, 432b, and 442a (shown in FIG. 4C). Stated somewhat differently, the support pin 442a, the cover pin 432b, and the carrier pin 412c can be respectively disposed within, and engaged by, the support slot 422a, the cover slot 422b, and the carrier slot 422c such that the carrier block 410, the pusher block 420, the cover block 430, and the support block 440 are coupled as illustrated in FIG. 4C. Therefore, the carrier member 310, the pusher member 320, the cover member 330, and the support member 340 each can slide distally from the initial predetermined position to the first predetermined position in response to the axial force.

FIG. 5B illustrates the positions of the carrier member 310, the pusher member 320, the cover member 330, and the support member 340 (FIG. 4C) upon reaching the first predetermined position. In the first predetermined position, the support block 440 and the cover block 430 can respectively engage the support stop 460a and the cover stop 460b. Thereby, the support stop 460a can receive, and substantially inhibit further movement of, the support block 440 and, therefore, the support member 340; whereas, the cover stop 460b receives, and substantially inhibits further movement of, the cover block 430 and, therefore, the cover member 330. Although the support block 440 and the cover block 430 can engage the support stop 460a and the cover stop 460b in the first predetermined position, it will be appreciated that the support block 440 can engage the support stop 460a and the cover block 430 can engage the cover stop 460b in different predetermined positions. In other words, the predetermined manner can include any number of predetermined positions, each predetermined position being associated with any number of the blocks 410, 420, 430, and 440 engaging any number of relevant stops 460a, 460b, and 460c.

To continue distally from the first predetermined position, the carrier member 310 and the pusher member 320 can be decoupled from the cover member 330 and the support member 340 by disengaging the support pin 442a and the cover pin 432b from the support slot 422a and the cover slot 422b, respectively. In the manner described in more detail above with reference to FIGS. 4B-4C, the support pin 442a and the cover pin 432b each resist the axial force. While the axial force is less than the combined static force provided by the support pin 442a and the cover pin 432b, the carrier member 310 and the pusher member 320 remain coupled with the cover member 330 and the support member 340. As the axial force increases to a level that is greater than or substantially equal to the combined static force, the support pin 442a and the cover pin 432b are respectively displaced from the support slot 422a and the cover slot 422b, decoupling the carrier member 310 and the pusher member 320 from the cover member 330 and the support member 340. Thereby, the cover member 330 and the support member 340 can be inhibited from further distal movement and remain substantially stationary; whereas, the carrier member 310 and the pusher member 320 can proceed distally toward a second predetermined position.

The pusher member 320 and the carrier member 310 can continue distally until the second predetermined position is reached as shown in FIG. 5C. In the second predetermined position, the carrier block 410 can engage the carrier stop 460c. Whereby, the carrier stop 460c can receive, and substantially inhibit further movement of, the carrier block 410 and, therefore, the carrier member 310. To continue distally from the second predetermined position, the pusher member 320 can be decoupled from the carrier member 310 by disengaging the carrier pin 412c from the carrier slot 422c. In the manner described in more detail above with reference to FIGS. 4B-C, the carrier pin 412c resists the axial force. While the axial force is less than the static force provided by the carrier pin 412c, the pusher member 320 remains coupled with the carrier member 310.

As the axial force increases to a level that is greater than or substantially equal to the static force, the carrier pin 412c can be displaced from the carrier slot 422c, decoupling the pusher member 320 from the carrier member 310. Thereby, the carrier member 310 can be inhibited from further distal movement and remains substantially stationary; whereas, the pusher member 320 proceeds distally to deploy the closure element 500 and to activate the locator release system 490 (shown in FIG. 4D) such that the distal end region 210b, the expansion elements 230, and/or the substantially flexible members 230' of the locator assembly 200 transition from the expanded state to the unexpanded state. The axial force that is applied to overcome the static force associated with the first predetermined position is sufficient to overcome the static forces associated with the subsequent predetermined positions, to deploy the closure element 500, and to activate the locator release system 490 such that the triggering system 400 operates in one substantially-continuous motion.

It will be appreciated that the triggering system 400 can include an energy storing element (not shown), which can be disposed substantially between the housing 380 and the blocks 410, 420, 430, and 440 and which can be configured to store potential energy for moving the tube set 305 from the initial predetermined position through the other predetermined positions, deploying the closure element 500, and/or activating the locator release system 490. The energy-storing element can be configured store the potential energy when the tube set 305 is in the initial predetermined position and to release the potential energy, when activated, such that the tube set 305 travels through the predetermined positions at a substantially constant and continuous rate. For example, the energy-storing element can include one or more springs (not shown). Each of the springs can be in a compressed state when the tube set 305 is in the initial predetermined position and released from the compressed state when the switching system 450 of the triggering system 400 is activated.

In use, the closure element 500 can be disposed within the carrier assembly and adjacent to the distal end of the pusher tube 320. As shown in FIGS. 7A-7B, for example, the reduced closure element 500' can be slidably received over the distally-increasing cross-section 318b of the distal end region 310b of the carrier member 310 and disposed about the periphery 312 of the carrier member 310 adjacent to the space 360. Since the reduced cross-section 530' of the reduced closure element 500' is less than the cross-section 318b of the distally-increasing cross-section 318b, the reduced closure element 500' must be temporarily radially deformed to be received over the distal end region 310b. Also, as the reduced closure element 500' is received over the distal end region 310b, the opposing tines 520 of the reduced closure element 500' engages the distal end region 310b. The reduced closure element 500' thereby can form the substantially tubular closure element 500" in the manner described in more detail above with reference to FIGS. 6E-6G.

After being received over the distal end region 310b, the substantially tubular closure element 500" can be disposed about the space 360, and the tines 520 are directed substantially distally as shown in FIG. 7B. As desired, one or more of the tines 520 can be disposed proximally of the distally-increasing cross-section 318b of the distal end region 310b, as illustrated in FIG. 7B, and/or can be at least partially disposed upon, and contact, the distally-increasing cross-section 318b of the distal end region 310b. To improve the engagement between the closure element 500 (shown in FIGS. 6A-6B) and the blood vessel wall 620 and/or tissue 630 (collectively shown in FIG. 8A), the substantially tubular closure element 500" can be disposed on the carrier member 310 such that the tines 520 define a first plane that is substantially perpendicular to a second plane defined by the switching system 450 and/or the handles 390 (collectively shown in FIG. 4D).

Once disposed about the space 360, the substantially tubular closure element 500" can be retained on the outer periphery 312b of the carrier member 310 when distal end region 310b of the carrier member 310 and the distal end region 320b of the pusher member 320 are slidably received within the lumen 334 of the cover member 330 as illustrated in FIGS. 7C-7D. When the cover member 330 is properly positioned within the carrier assembly 300, the distal end region 330b of the cover member 330 can extend over the space 360 and define the annular cavity 370 for retaining the substantially tubular closure element 500". As such, the substantially tubular closure element 500" is disposed substantially between the outer periphery 312b of the carrier member 310 and the inner periphery 332a of the cover member 330 such that the substantially tubular closure element 500" maintains the substantially tubular configuration with the tines 520 being directed substantially distally. As desired, the cover member 330 may radially compress the substantially tubular closure element 500" such that the substantially tubular closure element 500" enters and maintains a compressed tubular configuration. The body 510 of the substantially tubular closure element 500" can be disposed distally of the distal end region 320b of the pusher member 320, as illustrated in FIGS. 7C-7D, or can engage the distal end region 320b, as desired.

Figure 8A:
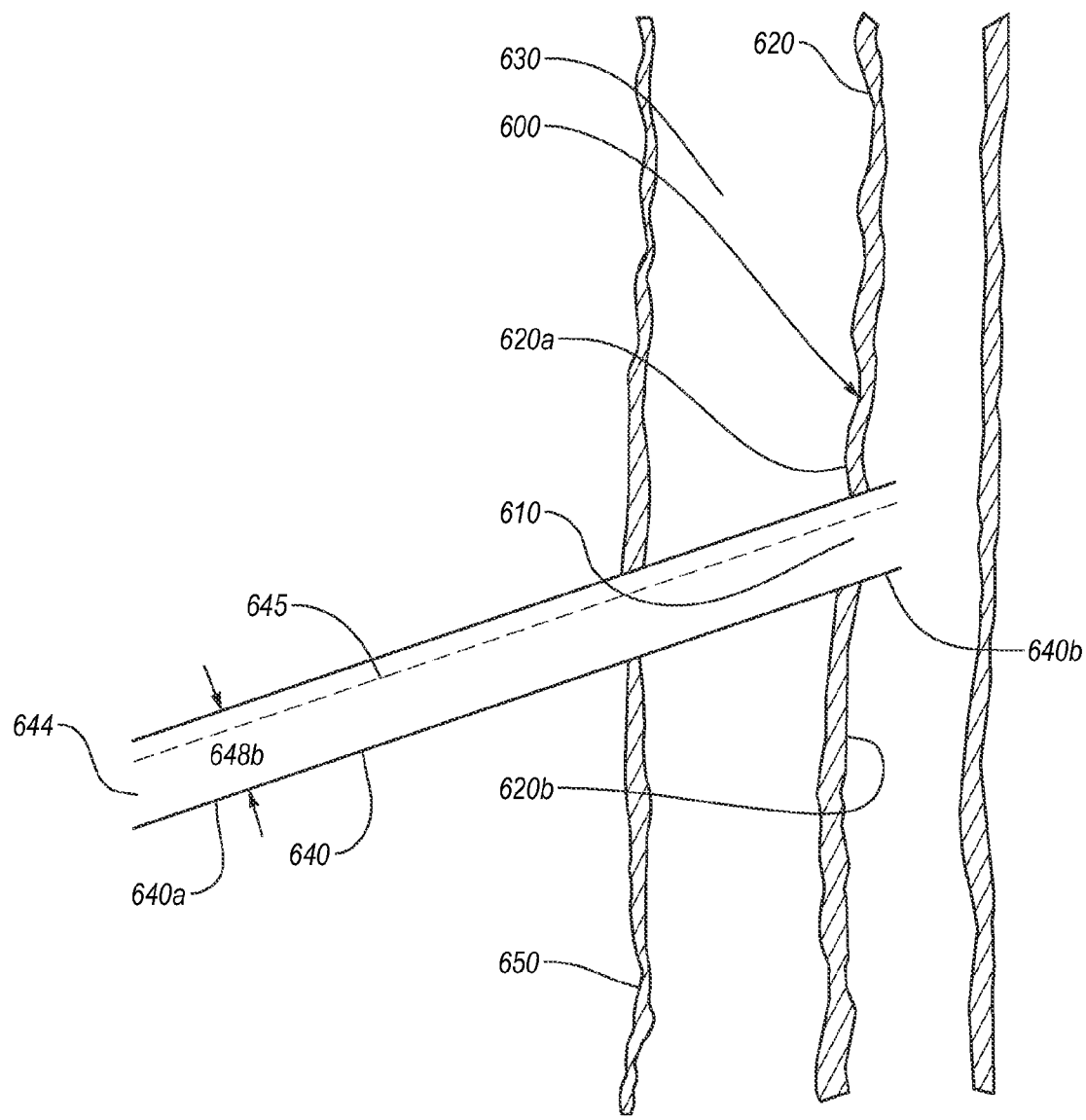
FIG. 8A illustrates a sheath that is positioned through tissue and into an opening formed in a wall of a blood vessel.

Turning to FIG. 8A, a sheath 640 may be inserted or otherwise positioned through skin 650 and tissue 630 and within the blood vessel 600 or other body lumen via the opening 610. While including a substantially flexible or semi-rigid tubular member, the sheath 640 can have a proximal end region 640a and a distal end region 640b and includes a predetermined length and a predetermined cross-section, both of which can be of any suitable dimension. The sheath 640 also can form a lumen 644 that extends along a longitudinal axis of the sheath 640 and substantially between the proximal and distal end regions 640a, 640b. The lumen 644 can have any suitable internal cross-section 648b and is suitable for receiving one or more devices (not shown), such as a catheter, a guide wire, or the like. The lumen 644 can be configured to slidably receive the tubular body 210 of the locator assembly 200 (shown in FIG. 4A) and/or the tube set 305 of the carrier assembly 300 (shown in FIG. 4A).

Since the internal cross-section 648b of the sheath 640 typically can be less than or substantially equal to the predetermined cross-section 338b of the cover member 330, the sheath 640 may be configured to radially expand, such as by stretching, to receive the tube set 305. Alternatively, or in addition, the sheath 640 can be advantageously configured to split as the tube set 305 is received by, and advances within, the lumen 644 of the sheath 640, thereby permitting the apparatus 100 to access the blood vessel wall 620. To facilitate the splitting, the sheath 640 can include one or more splits 645, such as longitudinal splits, each split being provided in the manner known in the art. Each split 645 can be configured to split the sheath 640 in accordance with a predetermined pattern, such as in a spiral pattern. It will be appreciated that, when the internal cross-section 648b of the sheath 640 is greater than the predetermined cross-section 338b of the cover member 330, it may not be necessary for the sheath 640 to be configured to radially expand and/or split. In addition to, or as an alternative to, the apparatus 100 may include a cutting means that initiates a tear line or split in the sheath when the sheath is engaged with the distal end of the apparatus 100.

The sheath 640 may be advanced over a guide wire or other rail (not shown) which has been positioned through the opening 610 and into the blood vessel 600 using conventional procedures such as those described above. The blood vessel 600 is a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, or the like, may be inserted through the sheath 640 and advanced to a preselected location within the patient's body. For example, the devices may be used to perform a therapeutic or diagnostic procedure, such as angioplasty, atherectomy, stent implantation, and the like, within the patent's vasculature.

Figure 8B:
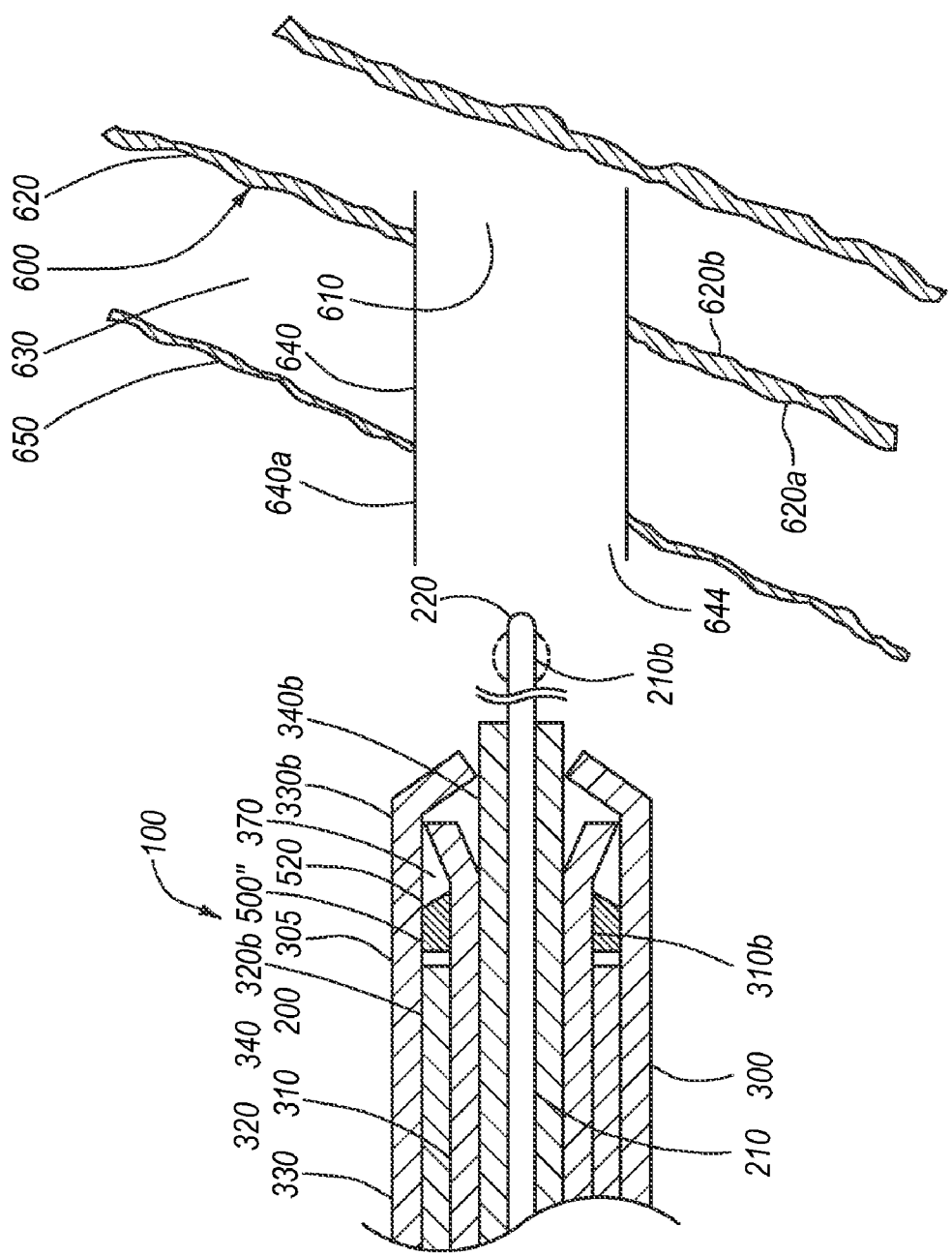
FIG. 8B illustrates the apparatus of FIG. 1 as prepared to be received by the sheath of FIG. 8A.
Figure 8C:
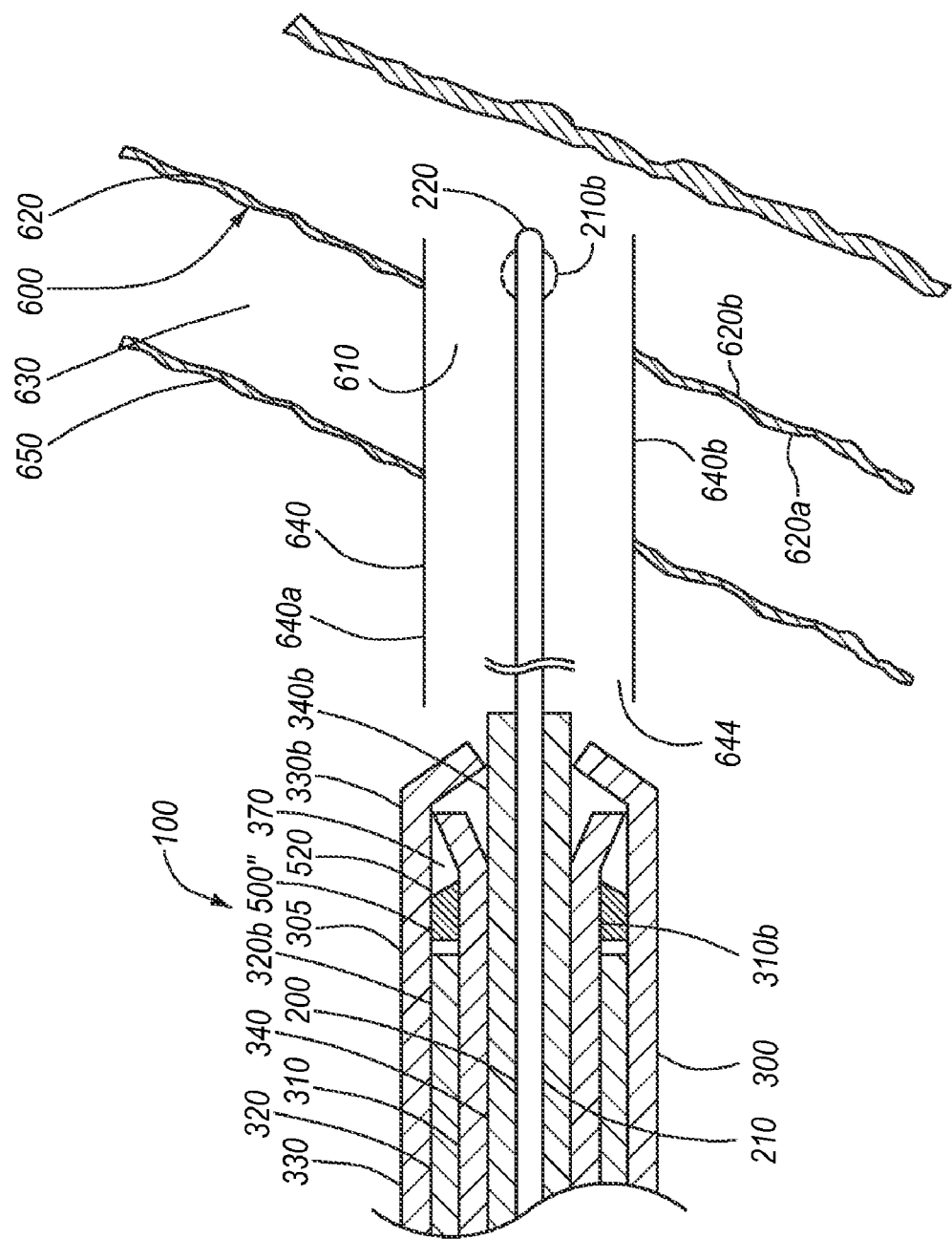
FIG. 8C illustrates a locator assembly of the apparatus of FIG. 8B being advanced distally into the blood vessel.
Figure 8D:
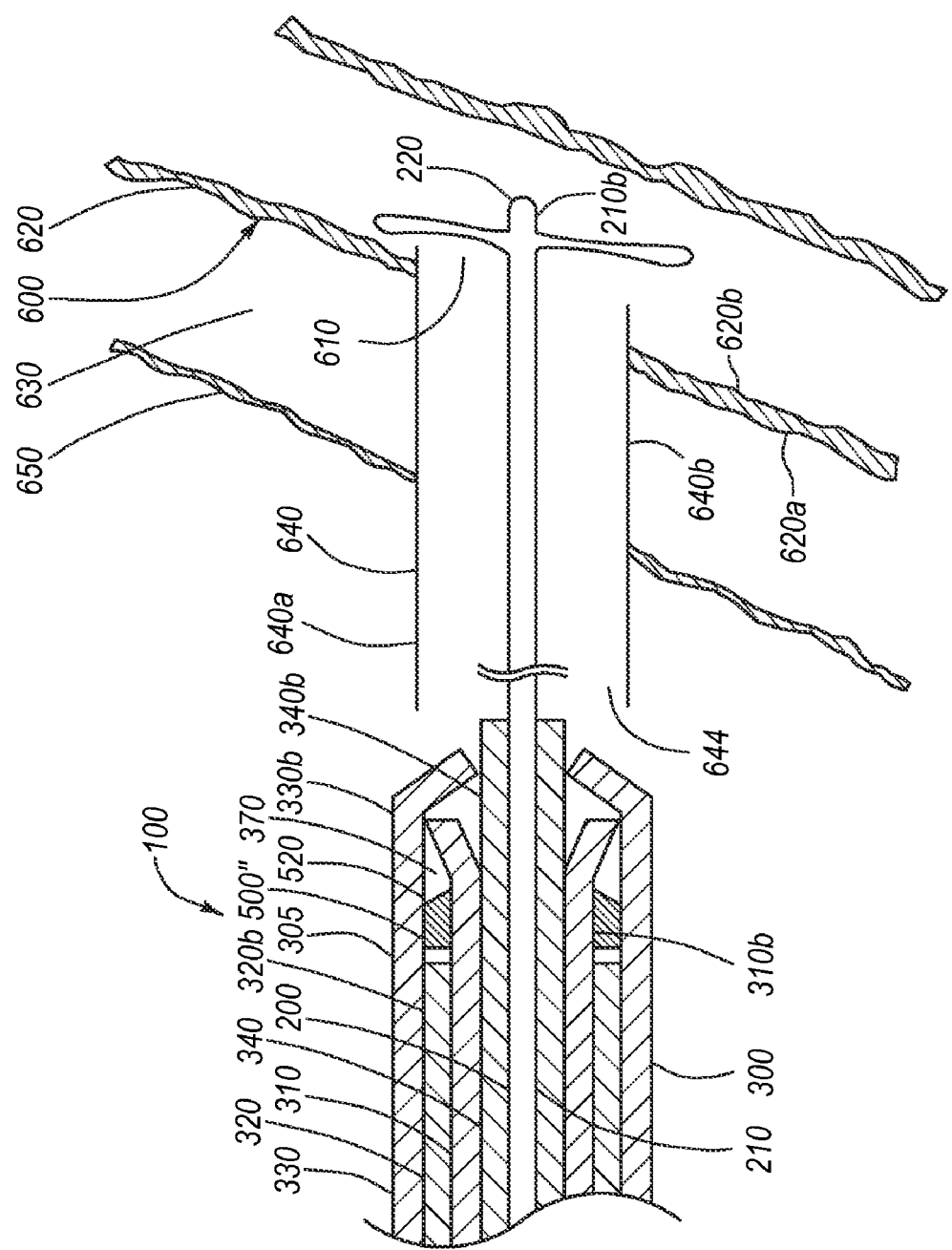
FIG. 8D illustrates a distal end region of the locator assembly of FIG. 8C extending into the blood vessel and being transitioned into an expanded state.

After the procedure is completed, the devices are removed from the sheath 640, and the apparatus 100 is prepared to be received by the lumen 644 of the sheath 640 as shown in FIG. 8B. Being in the unexpanded state, the distal end region 210b of the tubular body 210 of the locator assembly 200 can be slidably received by the lumen 644 and atraumatically advanced distally into the blood vessel 600 as illustrated in FIGS. 8B-C. Once the distal end region 210b of the tubular body 210 extends into the blood vessel 600, the distal end region 210b can transition from the unexpanded state to the expanded state as shown in FIG. 8D by activating the switching system of the locator assembly 200.

Figure 8E:
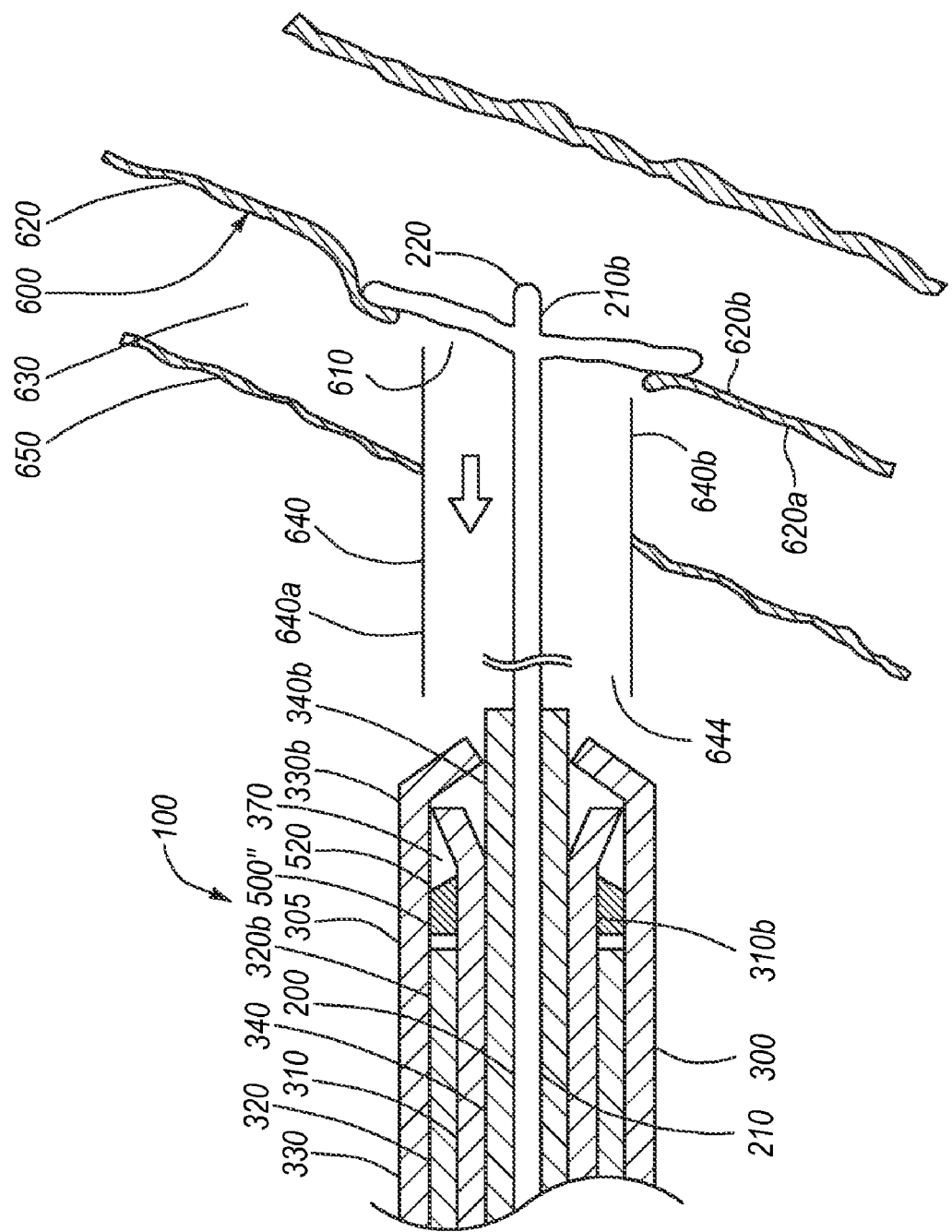
FIG. 8E illustrates the distal end region of FIG. 8D being retracted proximally to engage an inner surface of the blood vessel wall.

Turning to FIG. 8E, the apparatus 100 and the sheath 640 then can be refracted proximally until the distal end region 210b is substantially adjacent to an inner surface 620b of the blood vessel wall 620. The distal end region 210b thereby can draw the blood vessel wall 620 taut and maintains the proper position of the apparatus 100 as the blood vessel 600 pulsates.

Since the expanded cross-section of the distal end region 210b can be greater than or substantially equal to the cross-section of the opening 610 and/or the cross-section of the lumen 644, the distal end region 210b remains in the blood vessel 600 and engages the inner surface 620b of the blood vessel wall 620. The distal end region 210b can frictionally engage the inner surface 620b of the blood vessel wall 620, thereby securing the apparatus 100 to the blood vessel 600. The sheath 640 can be retracted proximally such that the distal end region 640b of the sheath 640 is substantially withdrawn from the blood vessel 600, as shown in FIG. 8E, permitting the apparatus 100 to access the blood vessel wall 620.

As the apparatus 100 is being retracted, the apparatus 100 can be axially rotated such that the first plane defined by the tines 520 of the substantially tubular closure element 500" is substantially parallel with a third plane defined by the blood vessel 600. Thereby, the engagement between the substantially tubular closure element 500" and the blood vessel wall 620 and/or tissue 630 can be improved because the tines 520 are configured to engage the blood vessel wall 620 and/or tissue 630 at opposite sides of the opening 610. If the substantially tubular closure element 500" is disposed on the carrier member 310 such that the first plane defined by the tines 520 is substantially perpendicular to the second plane defined by the switching system 450 and/or the handles 390 (collectively shown in FIG. 5A), for example, the apparatus 100 can be positioned such that the second plane defined by the switching system 450 and/or the handles 390 is substantially perpendicular to the third plane defined by the blood vessel 600.

Figure 8F:
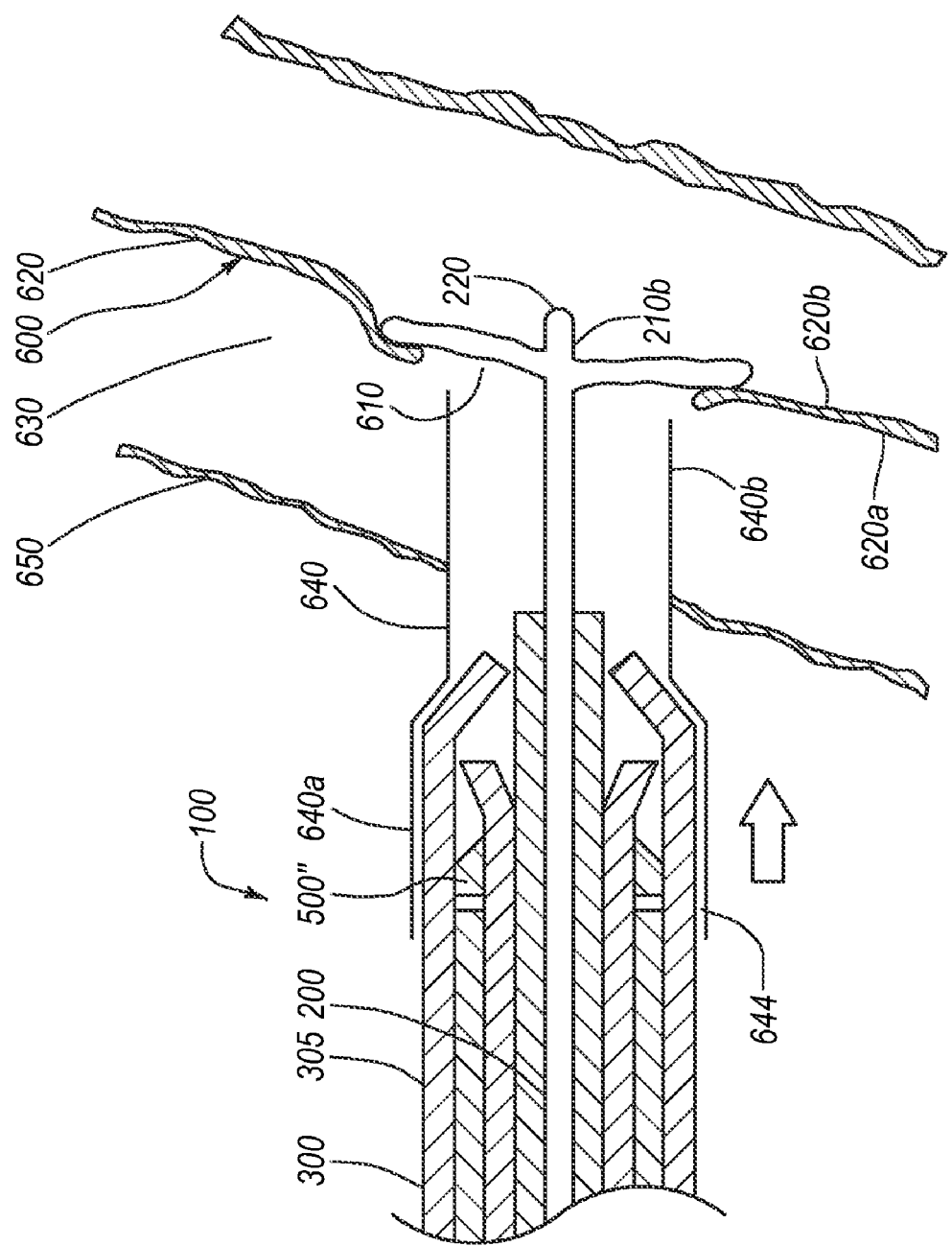
FIG. 8F illustrates a carrier assembly of the apparatus of FIG. 8B being advanced distally into the sheath of FIG. 8A once the distal end region of FIG. 8D has engaged the inner surface of the blood vessel wall.
Figure 8G:
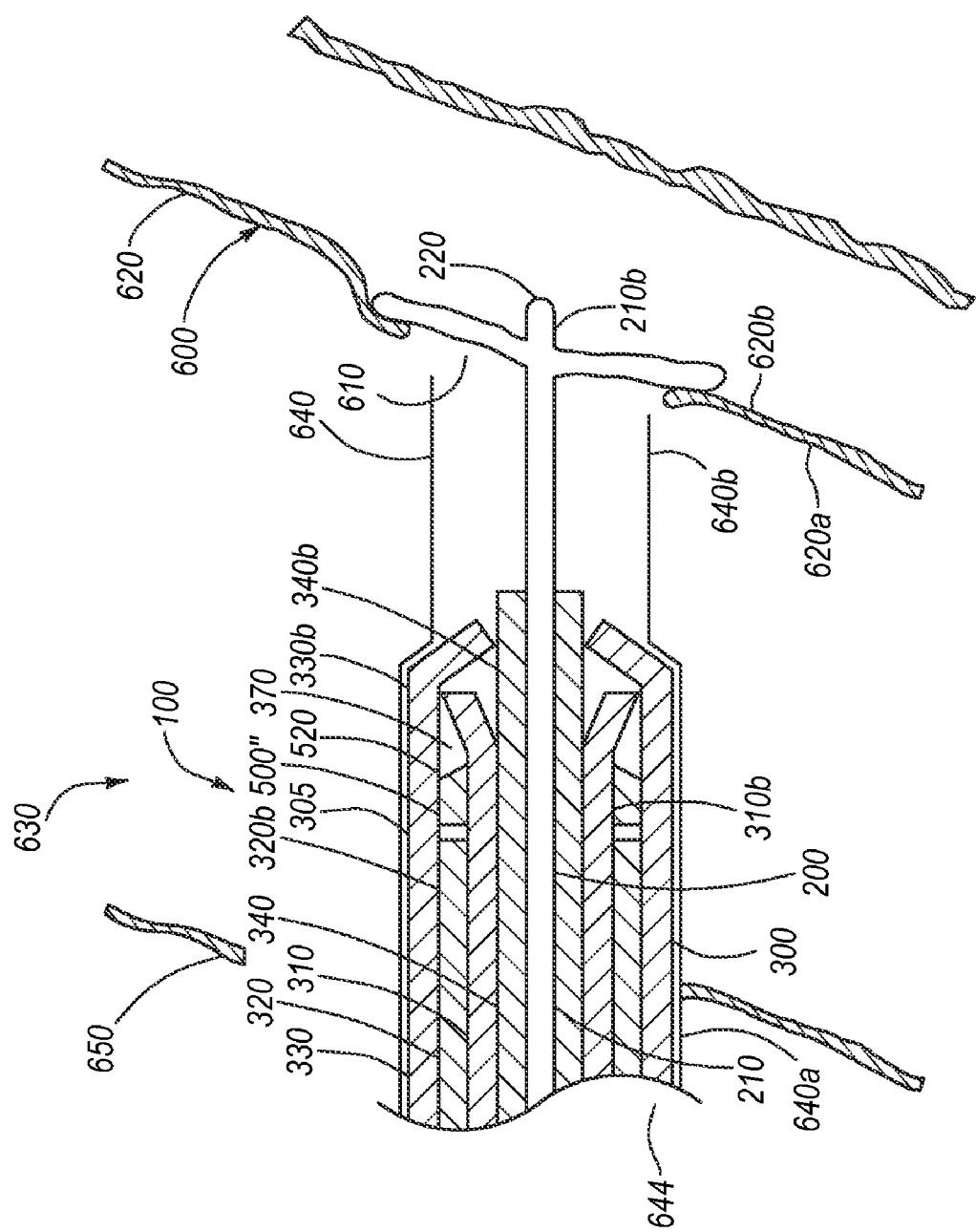
FIG. 8G illustrates relative positions of a tube set of the carrier assembly of FIG. 5F upon reaching a first predetermined position.

Once the distal end region 210b of the locator assembly 200 contacts the inner surface 620b of the blood vessel wall 620, the tube set 305 can then be advanced distally and received within the lumen 644 of the sheath 640 as illustrated in FIG. 8F. In the manner described in more detail above with reference to FIG. 8A, the sheath 640 can radially expand and/or split in accordance with the predetermined pattern as the tube set 305 advances because the internal cross-section 648b of the sheath 640 is less than or substantially equal to the predetermined cross-section 338b of the cover member 330. Being coupled, the carrier member 310, the pusher member 320, the cover member 330, and the support member 340 each advance distally and approach the first predetermined position as illustrated in FIG. 8G.

Upon reaching the first predetermined position, the tube set 305 can be disposed substantially adjacent to the outer surface 620a of the blood vessel wall 620 adjacent to the opening 610 such that the blood vessel wall 620 adjacent to the opening 610 is disposed substantially between the expanded distal region 210b of the locator assembly 200 and the tube set 305. The cover member 330 and the support member 340 can each decouple from the carrier member 310 and the pusher member 320 in the manner described in more detail above with reference to FIGS. 5A-5C when the tube set 305 is in the first predetermined position. Thereby, the cover member 330 and the support member 340 can be inhibited from further axial movement and remain substantially stationary as the carrier member 310 and the pusher member 320 each remain coupled and axially slidable.

Figure 8H:
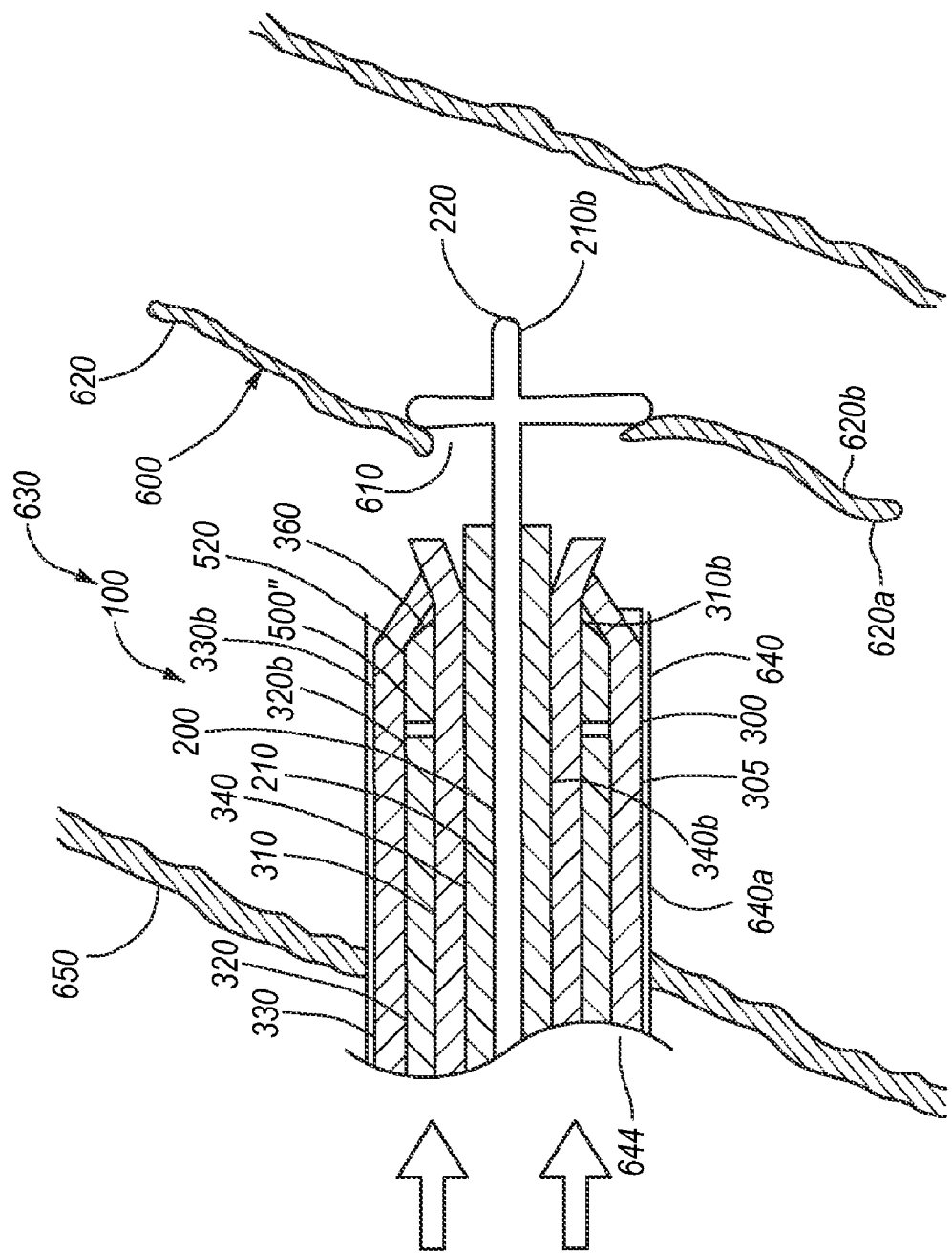
FIG. 8H illustrates the relative positions of the tube set of FIG. 8G upon reaching a second predetermined position.

As shown in FIG. 8H, the cover member 330 and the support member 340 can remain substantially stationary while the carrier member 310 and the pusher member 320 can continue distally and approach the second predetermined position. As the carrier member 310 and the pusher member 320 distally advance toward the second predetermined position, the annular cavity 370 can move distally relative to the substantially-stationary cover member 330 such that the distal end region 330b of the cover member 330 no longer encloses the annular cavity 370.

Thereby, the substantially tubular closure element 500" may not be completely enclosed by the annular cavity 370 formed by the distal end regions 310b, 320b, and 330b of the carrier member 310, the pusher member 320, and the cover member 330.

Although not completely enclosed by the annular cavity 370, the substantially tubular closure element 500" can be advantageously retained on the outer periphery 312b of the carrier member 310 by the distal end region 330b of the cover member 330 as illustrated in FIG. 8H. For example, by retaining the substantially tubular closure element 500" between the distal end region 330b of the cover member 330 and the distal end region 310b the carrier member 310, the apparatus 100 can be configured to provide better tissue penetration. The timing between the deployment of the substantially tubular closure element 500" by the tube set 305 and the retraction and transition to the unexpanded state by the locator assembly 200 likewise is facilitated because the substantially tubular closure element 500" is retained between the distal end region 330b and the distal end region 310b. Further, the carrier member 310 and the cover member 330 can operate to maintain the substantially tubular closure element 500" in the tubular configuration.

Figure 8I:
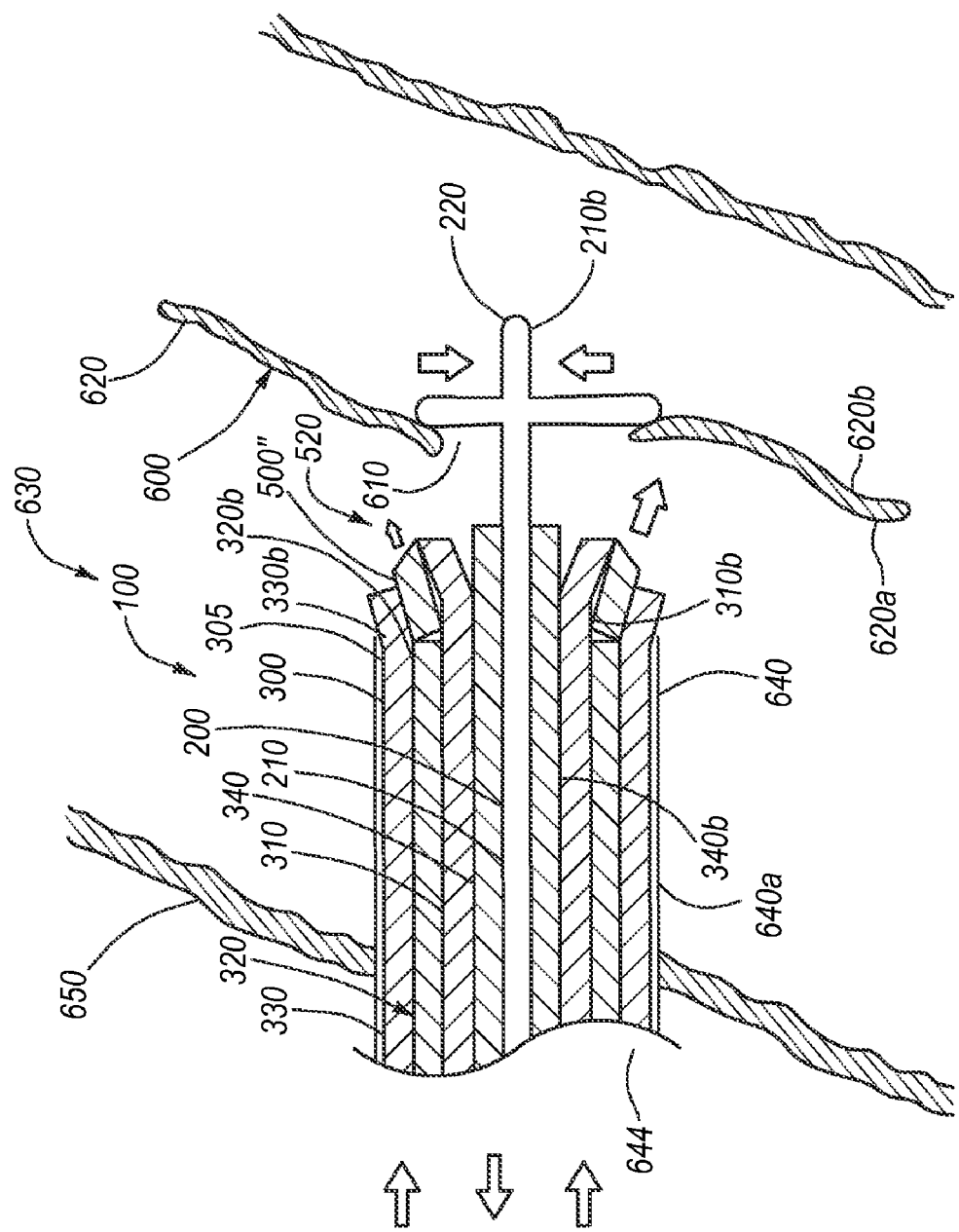
FIG. 8I illustrates a position of a pusher member of the tube set of FIG. 8H moving distally from the second predetermined position and beginning to distally deploy a closure element.

When the tube set 305 is in the second predetermined position, the carrier member 310 can decouple from the pusher member 320 in the manner described in more detail above with reference to FIGS. 5A-5C. Therefore, the carrier member 310, the cover member 330, and the support member 340 can be inhibited from further axial movement and remain substantially stationary; whereas, the pusher member 320 remains axially slidable. As the pusher member 320 continues distally, the distal end region 320b of the pusher member 320 can contact the substantially tubular closure element 500" and displaces the substantially tubular closure element 500" from the space 360 as shown in FIG. 8I. Since the space 360 is substantially radially exposed, the pusher member 320 can direct the substantially tubular closure element 500" over the distally-increasing cross-section of the distal end region 310b of the substantially-stationary carrier member 310 such that the cross-section 530' (shown in FIGS. 6F-6G) of the substantially tubular closure element 500" begins to radially expand in a substantially uniform manner. As the substantially tubular closure element 500" traverses the distally-increasing cross-section of the distal end region 310b, the cross-section 530' of the substantially tubular closure element 500" radially expands beyond the natural cross-section 530 (shown in FIGS. 6A-6B) of the closure element 500.

Figure 8J:
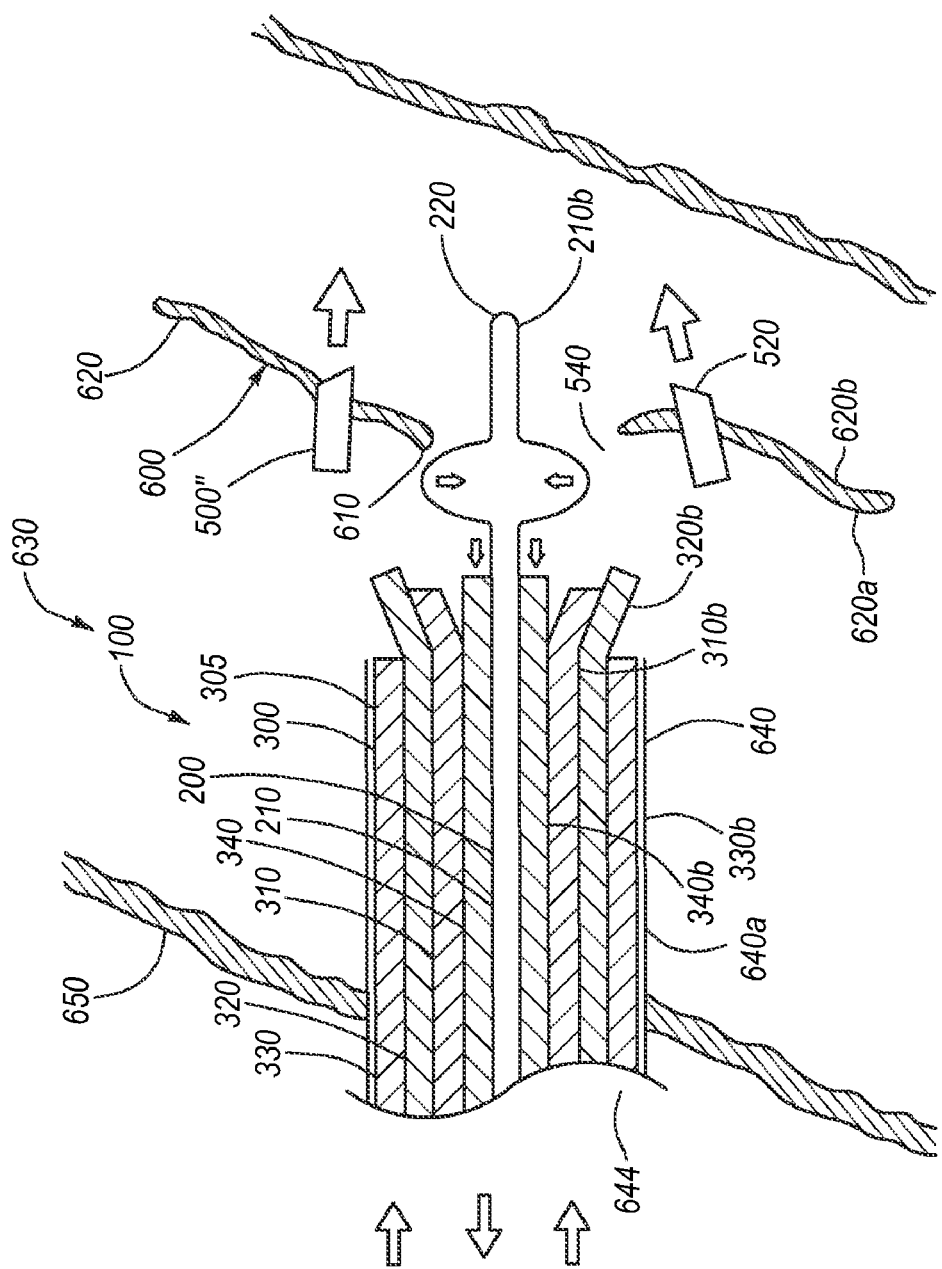
FIG. 8J illustrates the closure element of FIG. 8I upon being deployed and engaging tissue adjacent to the opening in the blood vessel wall.

Upon being directed over the distally-increasing cross-section of the distal end region 310b by the pusher member 320, the substantially tubular closure element 500" can be distally deployed as illustrated in FIG. 8J. When the substantially tubular closure element 500" is deployed, the tines 520 can pierce and otherwise engage a significant amount of the blood vessel wall 620 and/or tissue 630 adjacent to the opening 610. For example, the tines 520 can engage a significant amount of the blood vessel wall 620 and/or tissue 630 because the cross-section 530' of the substantially tubular closure element 500" is expanded beyond the natural cross-section 530 of the closure element 500 during deployment.

As the closure element is being deployed from the space 360, the locator assembly 200 can also begin to retract proximally and the locator release system 490 (shown in FIG. 4D) can be activated to transition from the expanded state to the unexpanded state as the substantially tubular closure element 500" is deployed as shown in FIG. 8J. The distal end region 210b of the locator assembly 200 retracts proximally and transitions from the expanded state to the unexpanded state substantially simultaneously with the deployment of the substantially tubular closure element 500". As desired, the distal end region 210b may be configured to draw the blood vessel wall 620 and/or tissue 630 adjacent to the opening 610 proximally and into the channel 540 defined by the substantially tubular closure element 500". The tines 520 of the substantially tubular closure element 500" thereby can pierce and otherwise engage the drawn blood vessel wall 620 and/or tissue 630. Since the cross-section 530' of the substantially tubular closure element 500" is expanded beyond the natural cross-section 530 of the closure element 500, a significant amount of the blood vessel wall 620 and/or tissue 630 can be drawn into the channel 540 and engaged by the tines 520.

Figure 8K:
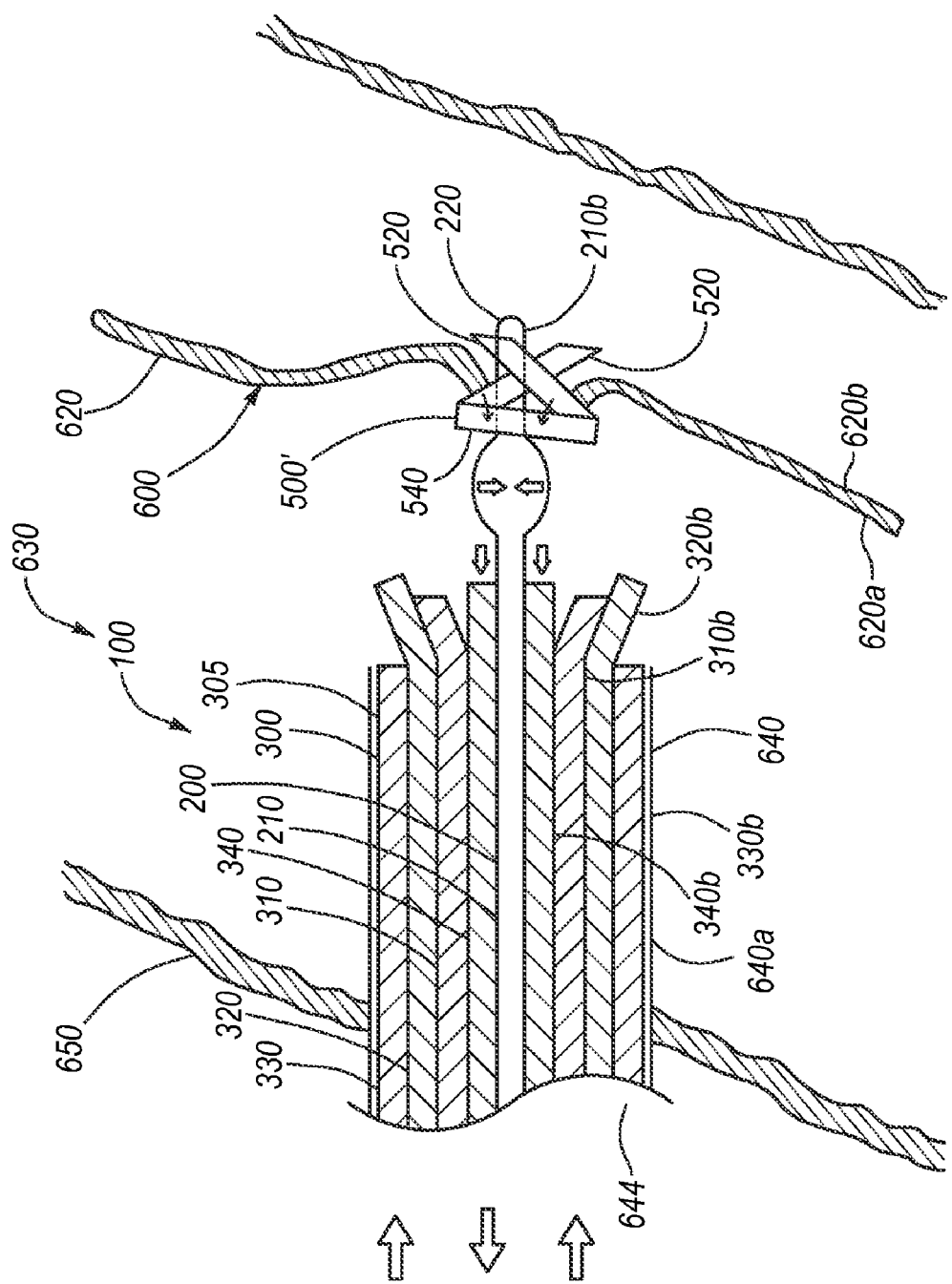
FIG. 8K illustrates the closure element of FIG. 8J transitioning from the substantially tubular configuration to the natural, planar configuration while engaging the engaged tissue.
Figure 8L:
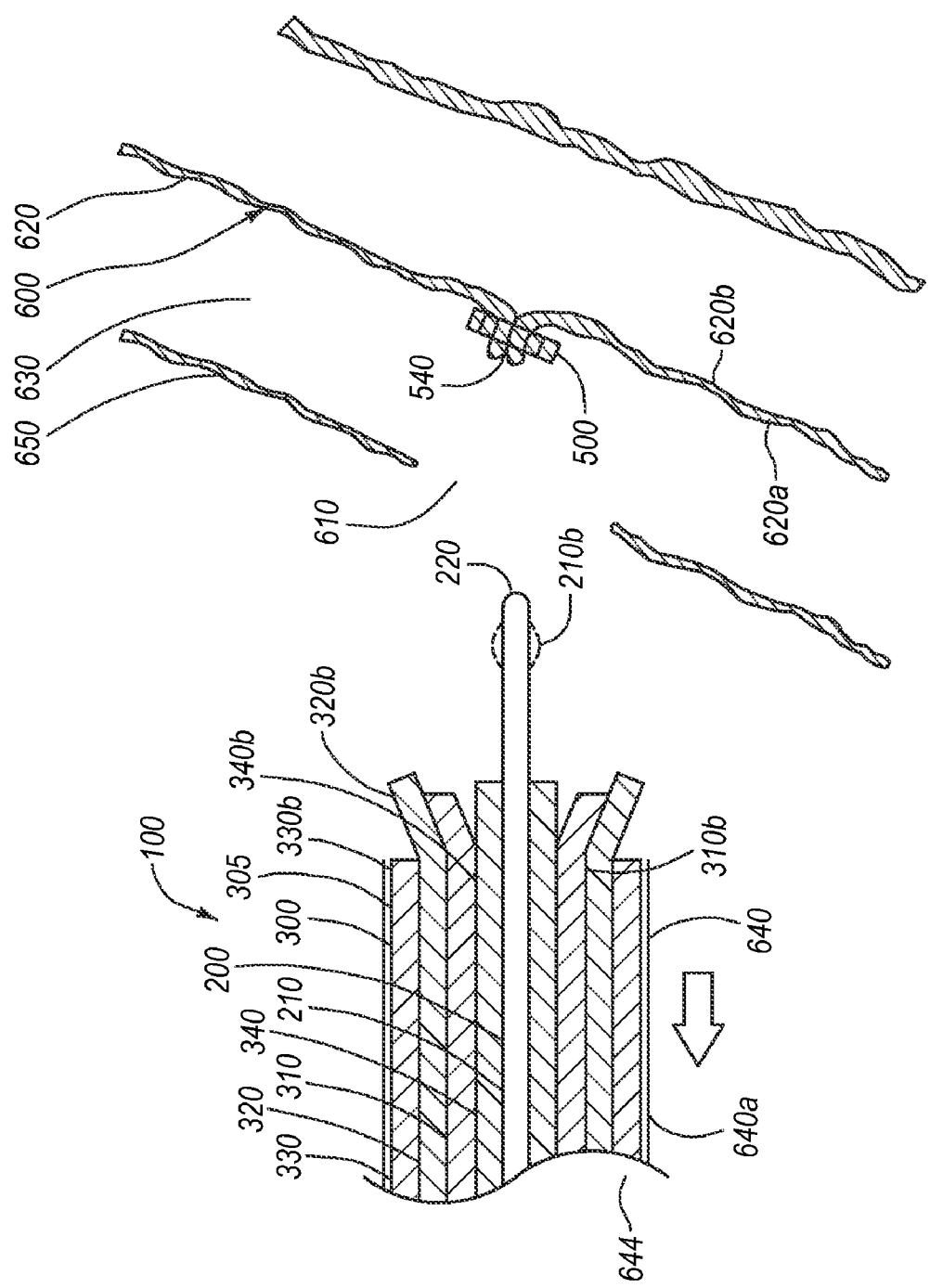
FIG. 8L illustrates the closure element of FIG. 8K drawing the engaged tissue substantially closed and/or sealed.

Turning to FIG. 8K, the substantially tubular closure element 500', once deployed, can begin to transition from the tubular configuration, returning to the natural, planar configuration with opposing tines 520 and a natural cross-section 530 of the closure element 500. The substantially tubular closure element 500' substantially uniformly transitions from the tubular configuration to the natural, planar configuration. Rotating axially inwardly to form the opposing tines 520 of the closure element 500, the tines 520 draw the tissue 630 into the channel 540 as the substantially tubular closure element 500" forms the closure element 500. Also, the tissue 630 can be drawn substantially closed and/or sealed as the cross-section 530' of the substantially tubular closure element 500' contracts to return to the natural cross-section 530 of the closure element 500. Thereby, the opening 610 in the blood vessel wall 620 can be drawn substantially closed and/or sealed via the closure element 500 as illustrated in FIG. 8L.

It will be appreciated that the closure element 500 may be constructed of other materials, that it may include alternative shapes, and that it may adopt alternative methods of operation such that the closure element 500 achieves closure of openings in blood vessel walls or other body tissue. In an additional non-limiting example, the closure element 500 is constructed of materials that use a magnetic force to couple a pair of securing elements in order to close an opening in the lumen wall or tissue. In this alternative embodiment, the closure element 500 may be of a unitary or multi-component construction having a first securing element positionable at a first position adjacent the opening, and a second securing element positionable at a second position adjacent the opening. The first and second securing elements can be provided having a magnetic force biasing the first and second securing elements together, thereby closing the opening, or they are provided having a magnetic force biasing both the first and second securing elements toward a third securing element positioned in a manner to cause closure of the opening. The magnetic closure element 500 may be provided without tines 520, provided the magnetic force coupling the closure elements is sufficient to close the opening. Alternatively, the closure element 500 may be provided with a combination of the magnetic securing elements and tines 520 to provide a combination of coupling forces. Those skilled in the art will recognize that other and further materials, methods, and combinations may be utilized to construct the closure element 500 to achieve the objectives described and implied herein.

Figure 9:
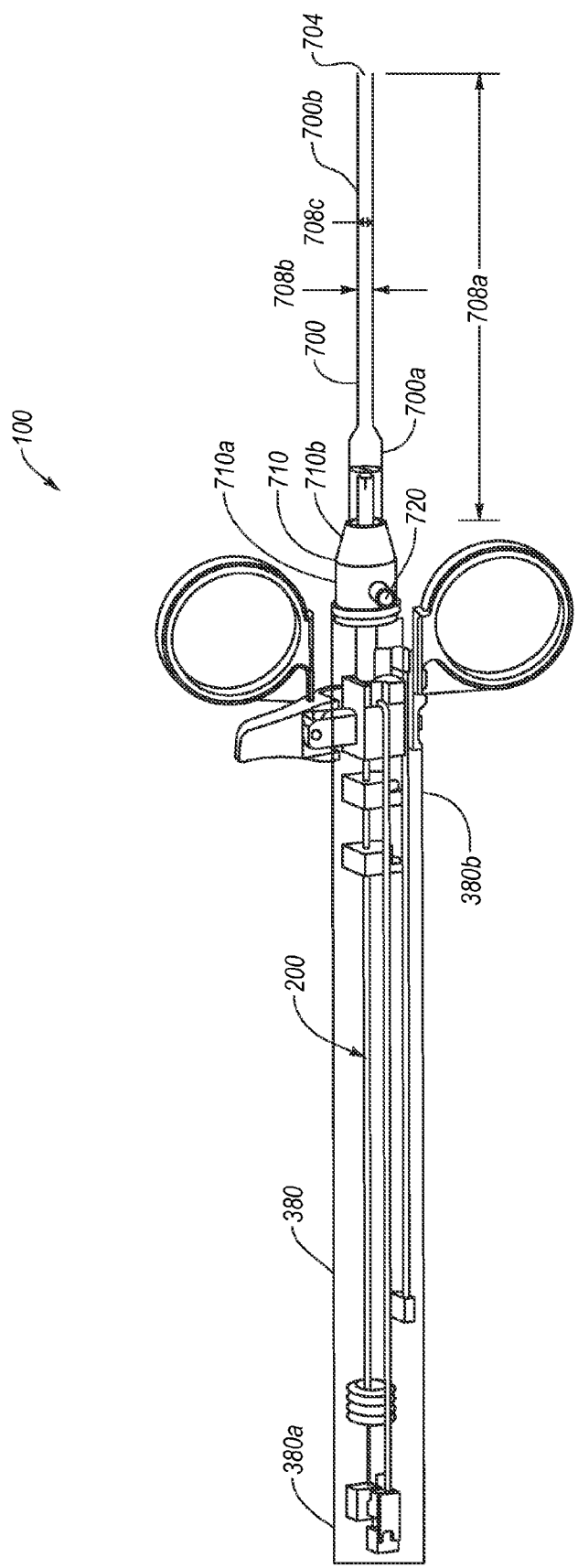
FIG. 9 illustrates one embodiment of an introducer sheath for the apparatus of FIG. 1.

It will be appreciated that the distal end region 380b of the housing 380 can be configured to couple with an introducer sheath 700 as shown in FIG. 9. While being prepared from a substantially flexible or semi-rigid tubular member, the introducer sheath 700 can have a proximal end region 700a and a distal end region 700b and includes a predetermined length and a predetermined cross-section, both of which can be of any suitable dimension. The distal end region 700b can be configured to facilitate insertion of the introducer sheath 700 through tissue and/or into the opening 610 (shown in FIG. 8A) formed in and/or adjacent to the wall 620 (shown in FIG. 8A) of the blood vessel 600 (shown in FIG. 8A) or other body lumen. For example, the distal end region 430b can have a tapered tip (not shown) for facilitating substantially atraumatic introduction of the introducer sheath 700 through a passage formed in the tissue 630 and/or at least partially into the blood vessel wall 620, which is accessible via the passage.

The introducer sheath 700 can also form a lumen 704 that extends along a longitudinal axis of the introducer sheath 700 and substantially between the proximal and distal end regions 700a, 700b. The lumen 704 can have any suitable length 708a and internal cross-section 708b and is configured to slidably receive the tubular body 210 of the locator assembly 200 (shown in FIG. 4A) and/or the tube set 305 of the carrier assembly 300 (shown in FIG. 4A). Since the internal cross-section 708b of the introducer sheath 700 typically can be less than or substantially equal to the predetermined cross-section 338b of the cover member 330, the introducer sheath 700 may be configured to radially expand, such as by stretching, to receive the tube set 305. Alternatively, or in addition, the introducer sheath 700 can be advantageously configured to split as the tube set 305 is received by, and advances within, the lumen 704 of the introducer sheath 700 in the manner described in more detail above with reference to the sheath 640 (shown in FIG. 8A). To facilitate the splitting, the introducer sheath 700 can include one or more splits (not shown), such as longitudinal splits, each split being provided in the manner known in the art. Each split is configured to split the introducer sheath 700 in accordance with a predetermined pattern, such as in a spiral pattern. It will be appreciated that, when the internal cross-section 708b of the introducer sheath 700 is greater than the predetermined cross-section 338b of the cover member 330, it may not be necessary for the introducer sheath 700 to be configured to radially expand and/or split.

The introducer sheath 700 can be coupled with the housing 380 via one or more cooperating connectors (not shown) such that the lumen 704 is substantially axially aligned with the tubular body 210 of the locator assembly 200 and/or the tube set 305 of the carrier assembly 300 and, as desired, may be removably and/or substantially permanently coupled with the housing 380. For example, a hub assembly 710 can be coupled with the proximal end region 700a of the introducer sheath 700. The proximal end region 700a of the introducer sheath 700 can be coupled with, or otherwise provided on, a distal end region 710b of the hub assembly 710, such as via an adhesive, one or more cooperating connectors, and/or a thermo-mechanical joint.

The hub assembly 710 can also include a proximal end region 710a, which provides the one or more mating connectors for coupling the introducer sheath 700 with the housing 380 and forms a lumen (not shown), which extends substantially between the proximal end region 710a and the distal end region 710b. The lumen of the hub assembly 710 can have an internal cross-section or size that is greater than the internal cross-section or size of the lumen 704 of the introducer sheath 700. When the proximal end region 700a of the introducer sheath 700 is properly connected with the hub assembly 710, the lumen of the hub assembly 710 can be configured to communicate with the lumen 704 of the introducer sheath 700. As desired, the proximal end region 700a of the introducer sheath 700 may be flared to facilitate the connection between the introducer sheath 700 and the hub assembly 710.

When properly assembled, the hub assembly 710 can be substantially fluid tight such that the one or more devices can be inserted into the lumen 704 of the introducer sheath 700 without fluid passing proximally through the lumen 704. The hub assembly 710 can be made to be watertight, such as via one or more seals (not shown) and/or valves (not shown) in the manner known in the art. For example, the hub assembly 710 can include a thrust washer and/or valve, a guide for directing the devices into the lumen 704 of the introducer sheath 700, and/or a seal (collectively not shown). The various seals and/or guides can be coupled with the hub assembly 710 via, for example, one or more spacers and/or end caps (also collectively not shown).

As desired, the hub assembly 710 further can include one or more side ports 720. The side ports 720 can communicate with the lumen of the hub assembly 710 and/or the lumen 704 of the introducer sheath 700. At least one of the side ports 720 can be configured to be connected with, and to communicate with, tubing (not shown) to, for example, infuse fluids into the lumen 704 and through the introducer sheath 700. Alternatively, or in addition, at least one of the side ports 720 can provide a "bleed back" indicator, such as in the manner disclosed in the co-pending application Ser. No. 09/680,837. The disclosures of this reference and any others cited therein are expressly incorporated herein by reference.

Another alternative embodiment of a clip applier for sealing openings through tissue is shown in FIGS. 10-15. The embodiment of FIGS. 10-15, as described below, has many identical or similar structures that perform identical or similar functions to the embodiments described above and in reference to the preceding Figures. Accordingly, the description below should be considered in view of the descriptions above of the preceding embodiments. Furthermore, those of ordinary skill in the art will appreciate that one or more of the components and/or features of the embodiment shown in FIGS. 10-15 may also be incorporated in the previously described embodiments, as those components and/or features of the previously described embodiments may optionally be incorporated in the embodiment described below and in reference to FIGS. 10-15. In the description of the alternative embodiment below, and in FIGS. 10-15, components of the apparatus that are identical or substantially correspond to those previously described will bear the same reference numerals identified above with the addition of the prime 0 identifier.

Turning to FIGS. 10 and 11, the locator assembly 200' can be substantially similar to the structure described above in reference to FIGS. 2A-2D, including a flexible or semi-rigid tubular body 210' (such as an elongate rail) with a longitudinal axis. The tubular body 210' can have a proximal end region 210a' and a distal end region 210b' and includes a predetermined length 218a' and a predetermined outer cross-section, both of which can be of any suitable dimension. The distal end region 210b' of the locator assembly 200' can include a substantially rounded, soft, and/or flexible distal end or tip 220' to facilitate atraumatic advancement and/or retraction of the distal end region 210b' into the blood vessel 600. As desired, a pigtail (not shown) may be provided on the distal end 220' to further aid atraumatic advancement of the distal end region 210b'.

The distal end region 210b' of the locator assembly 200' can be selectably controllable between an unexpanded state and an expanded state, in the manner described above in relation to FIGS. 2A-2D. In the alternative embodiment shown in FIGS. 10A-10B, the distal end region is shown in its expanded state, wherein the substantially flexible members 230' of the expansion elements 230 are flexed outward.

A control member 250', such as a rod, wire, or other elongate member, can be moveably disposed within a lumen (not shown) formed by the tubular body 210' and extending substantially between the proximal end region 210a' and the distal end region 210b'. The control member 250' can have a proximal end region 250a' that is coupled with a control block 260', and a distal end region that is coupled with the distal end region 210b' of the locator assembly 200', the expansion elements 230, and/or the movable end regions 230c' of the substantially flexible members 230'. The control block 260' can be a tubular shape and formed of a metal or rigid plastic, and is adapted to be retained in a control block cavity 265' (see FIG. 10B) formed on the internal surface of the housing bottom half 380d', to thereby maintain the control block 260' in a substantially fixed position relative to the housing 380'. The locator control system can selectively transition the distal end region 210b', the expansion elements 230, and/or the substantially flexible members 230' between the unexpanded and expanded states by moving the tubular body 210' axially relative to the control member 250'.

Formed on the proximal end 210a' of the tubular body 210' can have a tubular body block 270' having a proximal groove 271'. The tubular body block 270' can be formed of metal, rigid plastic, or other substantially rigid material and can be formed integrally with or attached securely to the tubular body 210'. The proximal groove 271' and the proximal end of the tubular body block 270' can have a shape adapted to cooperate with a pair of tabs 281a'-b' formed on a locator assembly block 280' whereby the tubular body block 270' is maintained in a fixed axial relationship with the locator assembly block 280'. In this way, the tubular body block 270' and tubular body 210' can be advanced distally by distal advancement of the locator assembly block 280'.

A locator assembly spring 290' can be located coaxially with and substantially surrounds a portion of the tubular body block 270'. The locator assembly spring 290' can be located between and contacts the distal side of two of the tabs 281a'-b' formed on the locator assembly block 280', and the proximal side of a locator assembly spring stop 381' formed on the inner surface of the housing bottom half 380d' (see FIG. 10B). The locator assembly spring 290' so located can provide a force biasing the locator assembly block 280' in the proximal direction relative to the housing 380'.

The locator assembly block 280' can be formed of metal, plastic, or other rigid material. A function of the locator assembly block 280' can allow the user to apply a force causing distal movement of the tubular body 210' relative to the control member 250' to cause the locator assembly 200' to transition from the unexpanded state to the expanded state. The proximal end of the locator assembly block 280' can have a slot 281' formed therein, the slot 281' can have a size sufficient to accommodate the control block 260' and the control block cavity 265', and to allow the locator assembly block 280' to travel axially relative to the housing 380'. The distal end of the locator assembly block 280' can have a pair of distally extending forks 282a-b, with each of the forks 282a-b having a ramp 283a-b on its inward facing surface. Finally, the locator assembly block 280' can have a pair of distally extending release tabs 284a-b, with each of the release tabs 284a-b having a detent 285a-b.

As shown in FIGS. 11A-11B, the locator assembly block 280' can be slidably received and retained within grooves formed in the proximal end of the housing 380', with the proximal end of the locator assembly block extending from the proximal end of the housing. The control block 260' and control block cavity 265' can be located in the slot 281' formed in the proximal end of the locator assembly block 280'.

Figure 10A:
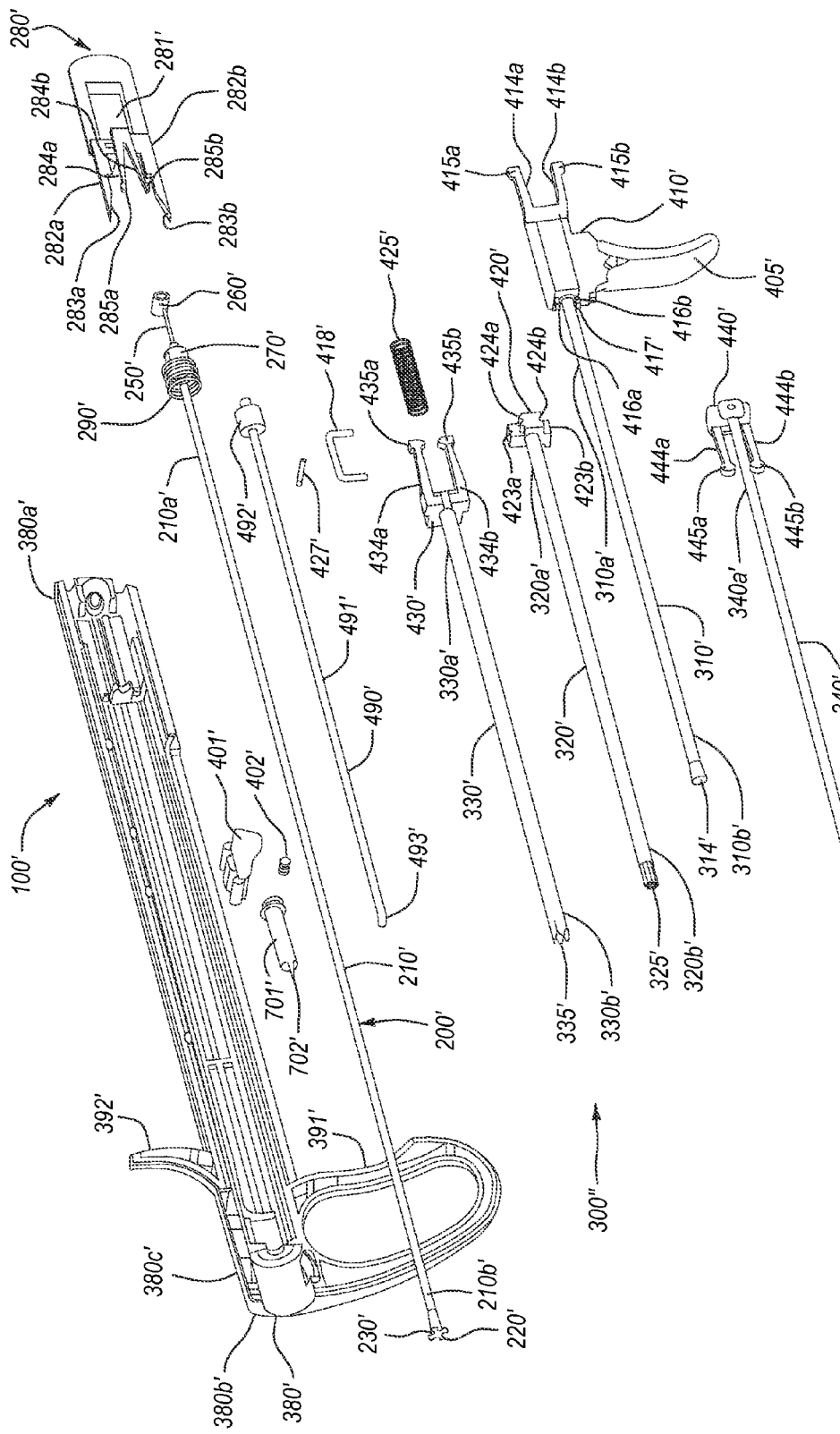
FIG. 10A illustrates an assembly view of the components included in an alternative embodiment of the apparatus for closing openings formed in blood vessel walls.
Figure 10B:
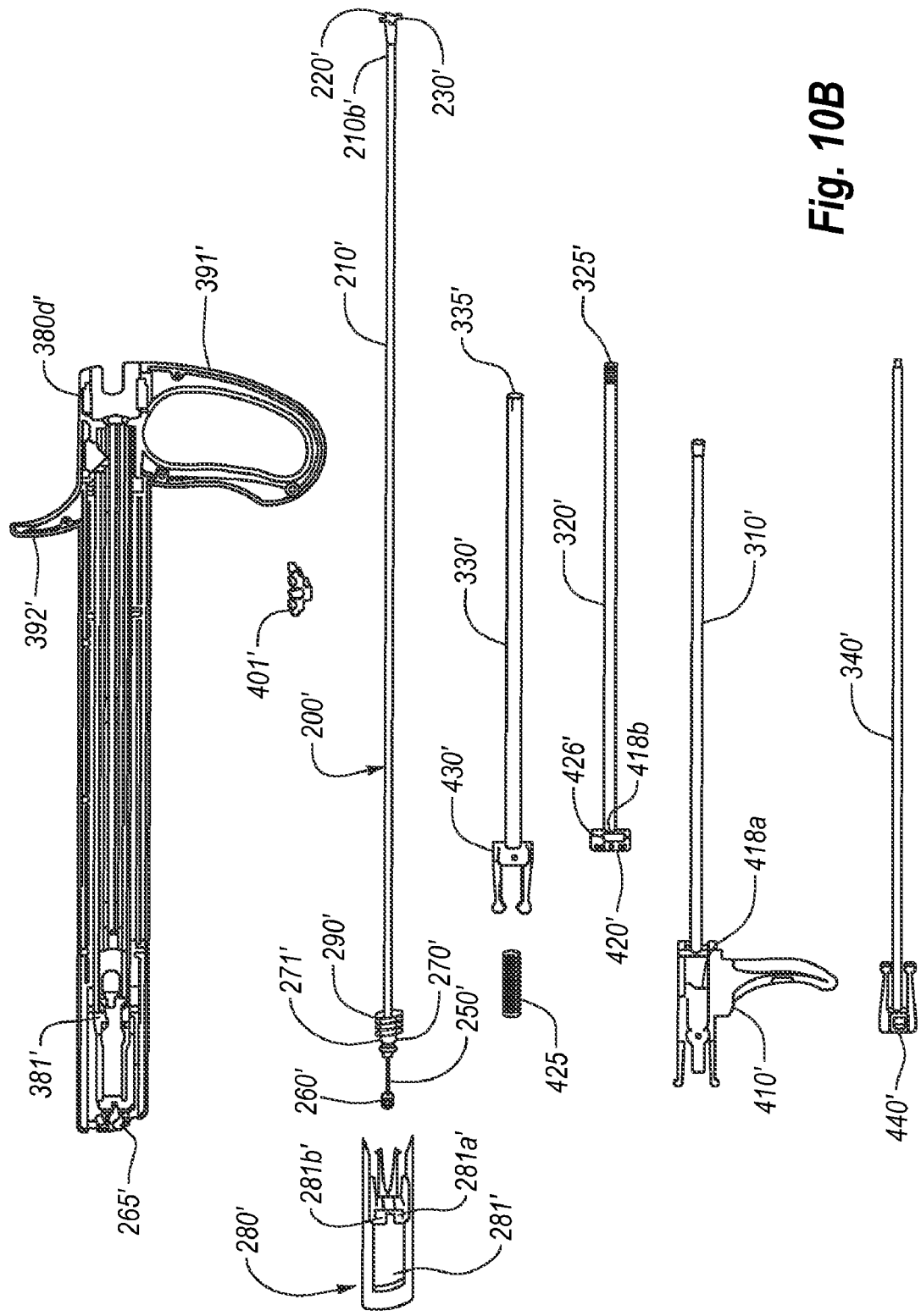
FIG. 10B illustrates an assembly view of the components shown in FIG. 10A, showing the reverse view of that shown in FIG. 10A.
Figure 15:
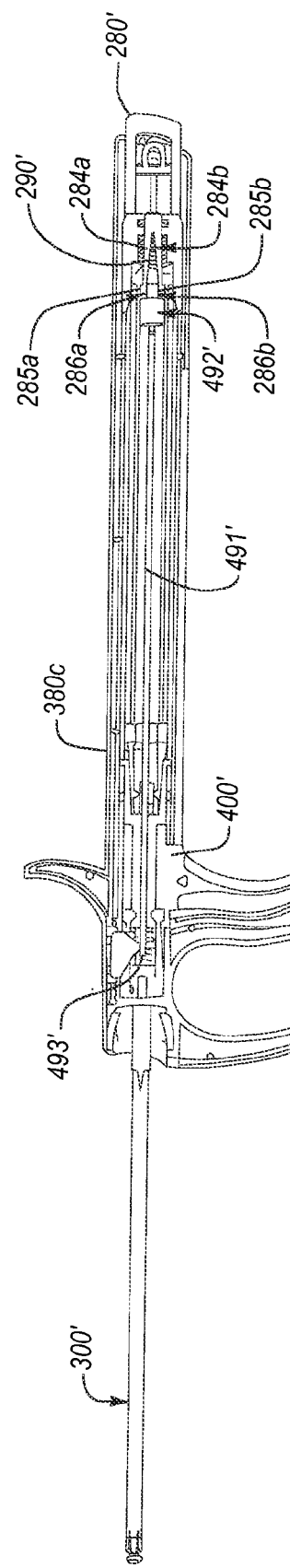
FIG. 15 illustrates a reverse view of the apparatus of FIGS. 11-14D, showing the locator release system.

The locator release system 490' can perform the function of releasing the locator assembly 200', thereby allowing the locator assembly 200' to transition from its expanded state to its unexpanded state. Turning to FIGS. 10A-10B and FIG. 15, the locator release system 490' of the alternative embodiment of the apparatus can include locator release rod 491' having a release tab spacer block 492' formed on its proximal end. The locator release rod 491' and release tab spacer block 492' can be received and retained in a groove formed on the interior surface of the housing bottom half 380d'. The release tab spacer block 492' can be integrally formed with or attached to the proximal end of the locator release rod 491', and is formed of metal, plastic, or other rigid material. As shown in FIG. 15, the release tab spacer block 492' can have a shape and size adapted to fit between the release tabs 284a-b formed on the locator assembly block 280', thereby biasing the release tabs 284a-b outward and causing the outward facing detents 285a-b to engage a pair of retaining grooves 286a-b formed on the interior of the housing 380'. As long as the detents 285a-b are thus engaged with the retaining grooves 286a-b of the housing 380', the locator assembly block 280' can be held in its axial position against the spring force imparted in the proximal direction by the locator assembly spring 290'. The distal end of the locator release rod 491' can have an engagement member 493' that includes an inward bend on the distal end of the locator release rod. As described more fully below, the engagement member 493' on the locator release rod 491' can be positioned within the apparatus such that, when the closure element 500 is delivered, the engagement member 493' is engaged and caused to move axially in the distal direction, thereby disengaging the release tab spacer block 492' from the locator assembly block 280' and causing the locator assembly simultaneously to transition from its expanded state to the unexpanded state.

The alternative embodiment of the apparatus 100' can include a carrier assembly 300' that is coupled with, and slidable relative to, the locator assembly 200'. The carrier assembly 300' can be configured to receive and retain the closure element 500 (shown in FIGS. 6A-6B), which can be disposed substantially within the carrier assembly 300'. When the locator assembly 200' engages the inner surface 620b (shown in FIG. 8A) of the blood vessel wall 620 (shown in FIG. 8A), the carrier assembly 300' can be further configured to position the closure element 500 substantially adjacent to the opening 610 and to deploy the closure element 500, as described elsewhere herein.

Turning to FIGS. 10A-10B, the carrier assembly 300' can include a tube set having a carrier member 310', a pusher member 320', a cover member 330', and a support member 340'. The carrier member 310', pusher member 320', cover member 330', and support member 340' can be provided as a plurality of nested, telescoping members with a common longitudinal axis. The carrier member 310' can be configured to receive and support the closure element 500. While being disposed on the carrier member 310', the closure element 500 can be deformed from the natural, planar configuration to form the substantially tubular closure element 500'' (shown in FIGS. 6F-6G) as described herein.

The carrier member 310' can include a proximal end region 310a' and a distal end region 310b'. The carrier member 310' can also define a lumen 314' that extends substantially between the proximal end region 310a' and the distal end region 310b' and that is configured to slidably receive at least a portion of the tubular body 210' of the locator assembly 200' and/or the support member 340'. Although the exterior cross-section of the carrier member 310' is substantially uniform, the distal end region 310b' of the carrier member 310' can have a cross-section that increases distally, as illustrated in FIGS. 10A-B, for substantially uniformly expanding the substantially tubular closure element 500'' beyond the natural cross-section 530 of the closure element 500 when the substantially tubular closure element 500'' is deployed. Alternatively, the distal end region 310b' may be formed with a uniform cross-section to deploy the closure element 500 without cross-sectional expansion.

The pusher member 320' can have a proximal end region 320a' and a distal end region 320b' and is coupled with, and slidable relative to, the carrier member 310'. The pusher member 320' can include a predetermined length and a predetermined cross-section, both of which can be of any suitable dimension and can be configured to slidably receive the carrier member 310' such that the distal end region 320b' of the pusher member 320' is offset proximally from the distal end region 310b' of the carrier member 310'. As desired, the predetermined length of the pusher member 320' can be greater than or substantially equal to the predetermined length of the carrier member 310'. The predetermined length of the pusher member 320' can be less than the predetermined length of the carrier member 310' such that the carrier member 310' and the pusher member 320' at least partially define a space 360' distal to the distal end region 320b' of the pusher member 320' and along the periphery of the carrier member 310'.

The pusher member 320' can be substantially tubular and can define a lumen (not shown) that extends substantially between the proximal end region 320a' and the distal end region 320b' and that is configured to slidably receive at least a portion of the carrier member 310'. The cross-section of the pusher member 320' can be substantially uniform, and the distal end region 320b' of the pusher member 320' can include one or more longitudinal extensions 325', which extend distally from the pusher member 320' and along the periphery of the carrier member 310'. The longitudinal extensions 325' can be biased such that the longitudinal extensions 325' extend generally in parallel with the common longitudinal axis of the carrier assembly tube set. The longitudinal extensions 325' can be sufficiently flexible to expand radially, and yet sufficiently rigid to inhibit buckling, as the distal end region 320b' is directed distally along the carrier member 310' and engage the distally-increasing cross-section of the distal end region 310b' of the carrier member 310' to deploy the substantially tubular closure element 500''.

The cover member 330' can be configured to retain the substantially tubular closure element 500'' substantially within the carrier assembly 300' prior to deployment. Being coupled with, and slidable relative to, the pusher member 320', the cover member 330' can have a proximal end region 330a' and a distal end region 330b' and includes a predetermined length and a predetermined cross-section, both of which can be of any suitable dimension. The cover member 330' can be formed as a substantially rigid, semi-rigid, or flexible tubular member. Additionally, the cover member 330' can have an inner periphery and an outer periphery and can define a lumen (not shown). The lumen (not shown) can extend substantially between the proximal and distal end regions 330a', 330b' of the cover member 330' and can be configured to slidably receive at least a portion of the pusher member 320'. When the cover member 330' is properly positioned within the carrier assembly 300', the distal end region 330b' can be configured to extend over the space 360', thereby defining an annular cavity (not shown) for receiving and retaining the substantially tubular closure element 500".

The cross-section of the cover member 330' can be substantially uniform, and the distal end region 330b' of the cover member 330' can include one or more longitudinal extensions 335', which extend distally from the cover member 330' and along an outer periphery of the pusher member 320' (see FIG. 3D). Although the longitudinal extensions 335' can extend generally in parallel with common longitudinal axis 350', the longitudinal extensions 335' can be biased such that the plurality of longitudinal extensions 335' extend substantially radially inwardly as illustrated in FIGS. 3A and 3D. Thereby, the longitudinal extensions 335' can at least partially close the lumen (not shown) substantially adjacent to the distal end region 330b' of the cover member 330'. To permit the substantially tubular closure element 500" to be deployed from the annular cavity (not shown), the longitudinal extensions 335' can be sufficiently flexible to expand radially to permit the distal end region 310b' of the carrier member 310' to move distally past the cover member 330' to open the annular cavity (not shown) such that the distal end region 330b' no longer extends over the space 360'.

If the carrier assembly 300' is assembled as the plurality of nested, telescoping members as shown in FIG. 3A, the carrier member 310' can be at least partially disposed within, and slidable relative to, the lumen (not shown) of the pusher member 320'. The support member 340' can be slidable relative to the pusher member 320'. The pusher member 320', in turn, can be at least partially disposed within, and slidable relative to, the lumen (not shown) of the cover member 330'. To couple the carrier assembly 300' with the locator assembly 200', the tubular body 210' of the locator assembly 200' can be at least partially disposed within, and slidable relative to, the lumen 314' of the carrier member 310'. The longitudinal axis of the locator assembly 200' can be substantially in axial alignment with the common longitudinal axis of the carrier member 310', the pusher member 320', and the cover member 330'.

The tube set 305 can also include a support member 340' as shown in FIGS. 10A-B. The support member 340' can be configured to slidably receive the tubular body 210' of the locator assembly 200' and to provide radial support for the distal end region 210b' of the tubular body 210' when the locator assembly 200' is coupled with the carrier assembly 300'. The carrier assembly 300' can advantageously include the support member 340', for example, if the tubular body 210' is not sufficiently rigid or under other circumstances in which support for the tubular body 210' might be desirable. It also will be appreciated that the support member 340' also can be configured to inhibit the plurality of longitudinal extensions 335', which extend from the distal end region 330b' of the cover member 330', from expanding prematurely when the closure element 500 is deployed. If the longitudinal extensions 335' were to expand prematurely, they may become hung up on the introducer sheath 640 or other delivery member (in an introducer sheath or delivery member is used), the tissue 630, or the wall 620 of the blood vessel 600. This may interfere with the proper advancement or other movement of the cover member 330' and the carrier assembly 300'.

The support member 340' can be formed as a substantially rigid, semi-rigid, or flexible tubular member. Additionally, the support member 340' can include a proximal end region 340a' and a distal end region 340b'. Having an outer periphery, the support member 340' can define a lumen 344' that extends substantially between the proximal end region 340a' and the distal end region 340b' and that is configured to slidably receive and support at least a portion of the tubular body 210' of the locator assembly 200'. The support member 340', in turn, can be at least partially slidably disposed within the lumen 314' of the carrier member 310' such that the tubular body 210' of the locator assembly 200' is coupled with, and slidable relative to, the carrier member 310' in the manner described in more detail above. The support member 340' can have a predetermined length and a predetermined cross-section, both of which can be of any suitable dimension, and the cross-section can be substantially uniform. Although shown and described as being substantially separate for purposes of illustration, it will be appreciated that the carrier member 310', the pusher member 320', the cover member 330', and/or the support member 340' can be provided, in whole or in part, as one or more integrated assemblies.

The carrier assembly 300' also can include a housing 380', the top half 380c' of which is illustrated in FIG. 10A, and the bottom half 380d' of which is shown in FIG. 10B. The housing 380' can be formed as an elongate member with a longitudinal axis. Additionally, the housing 380' can have an outer periphery and includes a proximal end region 380a' and a distal end region 380b'. Thereby, when the apparatus 100' is properly assembled, the tubular body 210' of the locator assembly 200' can be at least partially disposed within, and slidable relative to, the tube set 305 such that the distal end region 210b' of the tubular body 210' extends beyond the distal end regions 310b', 320b', 330b', and/or 340b'. The tubular body 210', the carrier member 310', the pusher member 320', the cover member 330', and, if provided, the support member 340' can be at least partially disposed within, and slidable relative to, the housing 380', and the respective distal end regions 210b', 310b', 320b', 330b', and 340b' extend from the distal end region 380b' of the housing 380' such that the common longitudinal axis 350' of the tube set 305 is substantially axially aligned with the longitudinal axis 386' of the housing 380'. Being configured to slidably retain the respective proximal end regions 210a', 310a', 320a', 330a', and 340a', the housing 380' can support the tube set 305 and can have one or more handles 391', 392' to facilitate use of the apparatus 100'. The handles 391', 392' can extend substantially radially from the outer periphery of the housing 380' and can be provided in the manner known in the art.

When the apparatus 100' is properly assembled, the tubular body 210' of the locator assembly 200' can be at least partially disposed within, and slidable relative to, the tube set 305 of the carrier assembly 300' such that the distal end region 210b' of the tubular body 210' extends beyond the distal end regions 310b', 320b', 330b', and/or 340b'. Further, the proximal end region 210a' of the tubular body 210' and the proximal end regions 310a', 320a', 330a', and/or 340a' of the tube set 305 can be at least partially disposed within, and slidable relative to, the housing 380'. The switching system of the locator assembly 200' and a switching system of the triggering system 400' can be accessible external to the housing 380' as shown in FIGS. 11-15.

As shown in FIGS. 11-15, the triggering system 400' of the alternative embodiment of the apparatus 100' can be disposed substantially within the housing 380'. The triggering system 400' can be configured to control the relative axial movement and/or positioning of the respective distal end regions 310b', 320b', 330b', and 340b' of the tube set 305 and/or the distal end region 210b' of the locator assembly 200'. Axial motion of one or more of the carrier member 310', the pusher member 320', the cover member 330', and the support member 340' and/or the tubular body 210' can be attained, for example, by applying an axial force to the switching system 405'.

The triggering system 400' can include a set of block members—a carrier block 410', a pusher block 420', a cover block 430', and a support block 440'—each of which is formed integrally with or securely attached to its respective member of the carrier assembly 300'. The block members can be adapted to selectably couple and decouple the carrier member 310', the pusher member 320', the cover member 330', and the support member 340' relative to one another in order to provide axial movement of those components in a predetermined manner intended to deliver the closure element 500 in the manner described herein. For example, when the carrier assembly 300' reaches a first predetermined distal position, the support member 340' can be decoupled from the carrier member 310', the pusher member 320', and the cover member 330' and is thereafter substantially inhibited from further axial movement. Thereby, the carrier member 310', the pusher member 320', and the cover member 330' may be directed distally as the support member 340' remains substantially stationary. Subsequently, the carrier member 310' and the cover member 330' can be decoupled from the pusher member 320' and thereafter inhibited from further axial movement. Thereby, the pusher member 320' may be directed distally as the support member 340', carrier member 310', and cover member 330' remain substantially stationary, as described more fully herein.

The carrier block 410' can be disposed on the proximal end region 310a' of the carrier member 310' and can include a trigger extension 405' that extends through a slot in the housing 380' to the exterior of the housing 380' to be accessible to the user. The carrier block 410' can include a pair of grooves 413a-b formed on a peripheral surface of the carrier block 410', the grooves 413a-b being adapted to receive and retain a pair of tabs 445a-b formed on a pair of forks 444a-b extending distally from the support block 440', thereby selectably coupling the support block 440' to the carrier block 410'. The carrier block 410' can also include a pair of distal tabs 416a-b extending from the distal end of the carrier block 410', and adapted to engage a pair of slots 423a-b formed on the proximal end of the pusher block 420'.

The carrier block 410' can also include a pair of forks 414a-b extending in the proximal direction from the proximal end of the carrier block, each of the forks having an outward directed tab 415a-b at its proximal end. The tabs 415a-b can be adapted to selectably engage a pair of slots 387a-b (not shown) formed on the interior surface of the housing 380' near its proximal end and, when so engaged, to fix the axial position of the carrier block 410' and, with it, the carrier assembly 300' relative to the housing 380'. The tabs 415a-b can be disengaged from the slots in the housing when the locator assembly block 280' is moved axially in the distal direction in the following manner (see FIG. 11B). As the locator assembly block 280' is advanced distally, the interior surfaces of the ramps 283a-b on the locator assembly block forks 282a-b can engage the exterior surfaces of the tabs 415a-b and cause the carrier block forks 414a-b to flex inward, releasing the tabs 415a-b from the slots in the housing, thereby freeing the carrier block 410' and the carrier assembly 300' to move axially. Thus, axial movement of the carrier block 410' within the apparatus can be inhibited until the locator assembly block 280' is advanced to transition the locator assembly 200' to the expanded condition, simultaneously releasing the tabs 415a-b on the carrier block 410'.

The pusher block 420' can be disposed on the proximal end region 320a' of the pusher member 320'. As described above, the pusher block 420' can include a pair of slots 423a-b formed on its proximal end that are adapted to selectably engage the pair of distal tabs 416a-b extending from the distal end of the carrier block 410'. The pusher block 420' can also include a pair of grooves 424a-b formed on its peripheral surface, the grooves 424a-b being adapted to engage a pair of tabs 435a-b formed on a pair of forks 434a-b extending from the proximal side of the cover block 430' to selectably couple the cover block 430' to the pusher block 420'.

The cover block 430' can be disposed on the proximal end region 330a' of the cover member 330'. As described above, the cover block 430' can include a pair of forks 434a-b extending from the proximal end of the cover block 430', each of the forks having an inward directed tab 435a-b that are adapted to engage the grooves 424a-b on the peripheral surface of the pusher block 420' to selectably couple the cover block 430' to the pusher block 420'.

The support block 440' can be disposed on the proximal end region 340a' of the support member 340'. As described above, the support block 440' can include a pair of forks 444a-b extending from the distal end of the support block 440', each of the forks having an inward directed tab 445a-b that are adapted to engage the grooves 413a-b formed on the surface of the carrier block 410' to selectably couple the support block 440' to the carrier block 410'.

Figure 12:
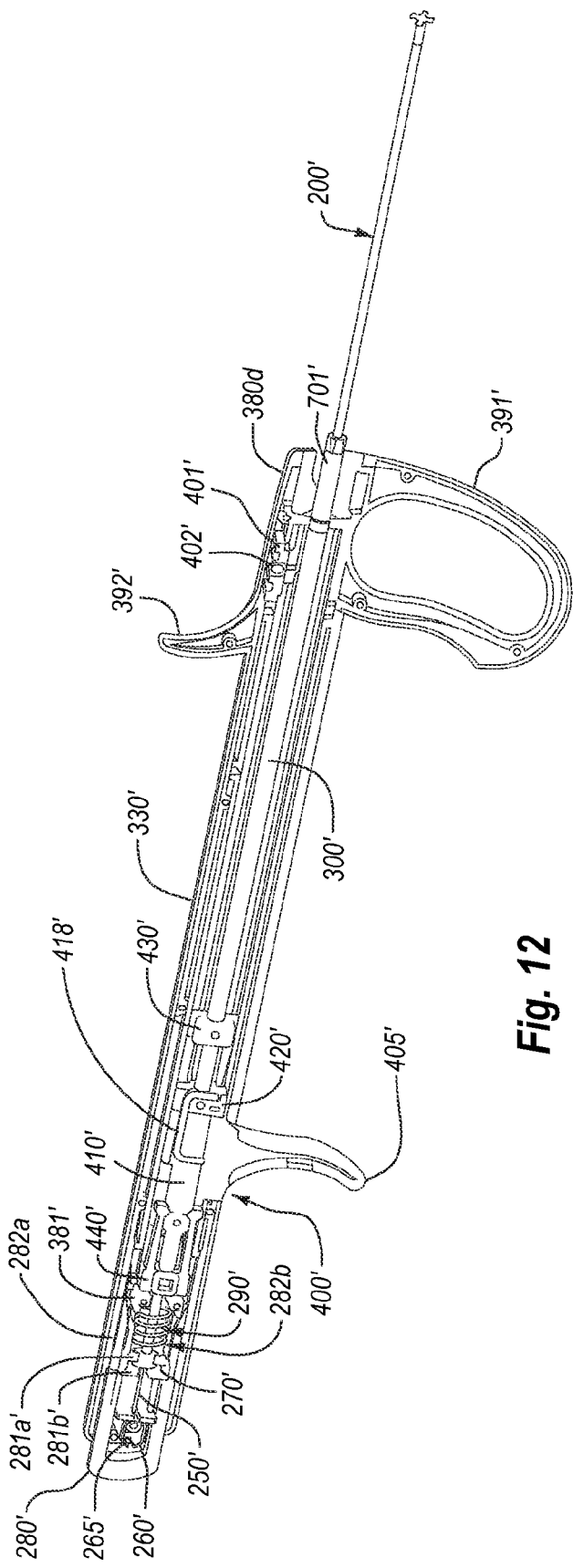
FIG. 12 illustrates the apparatus of FIG. 11A after advancement of the locator assembly block.

The carrier block 410', pusher block 420', cover block 430', and support block 440' are shown in FIGS. 11-13 in their fully coupled state, with the support block 440' coupled to the carrier block 410', the pusher block 420' coupled to the carrier block 410', and the cover block 430' coupled to the pusher block 420'. In this arrangement, the carrier assembly 300' can include a coaxial set of tubes (as shown, for example, in FIG. 3A), with the support member 340' slidably retained substantially within the carrier member 310', which is in turn slidably retained substantially within the pusher member 320', which is in turn slidably retained substantially within the cover member 330'.

The triggering system 400' of the alternative embodiment of the apparatus can include an energy storing element that is used in the final stage of the closure element 500 delivery process. The energy storing element, which can be a spring such as the pusher spring 425' shown in FIGS. 10A-10B, can be substantially retained in a spring cavity 417' formed in the carrier block 410' and coaxially surrounds a proximal portion 310a' of the carrier member 310'. The pusher spring 425' can be capable of expanding and contracting, storing potential energy as it is contracted and releasing energy as it expands. In its fully expanded state, the pusher spring 425' can have a length that is greater than the length of the spring cavity 417'. The cross-sectional dimension of the pusher spring 425' can be such that it backs up against and contacts the proximal end of the pusher block 420'. Thus, when the pusher spring 425' is in place between the carrier block 410' and the pusher block 420', the pusher spring 425' can be capable of imparting a force biasing the carrier block 410' away from the pusher block 420'.

Prior to delivery of the closure element 500, the distal end of the carrier block 410' can be in physical contact with the proximal end of the pusher block 420'. In this pre-delivery condition, the pusher spring 425' can be in a contracted state and can be maintained fully within the spring cavity 417' formed in the carrier block 410'. A catch member 418' can serve the function of maintaining the carrier block 410' and pusher block 420' in the pre-delivery condition against the spring force of the pusher spring 425', the force of which would otherwise force apart the carrier block 410' from the pusher block 420'. The catch member 418' can be a U-shaped piece of metal, plastic, or other rigid material that engages a first groove 418a formed on the surface of the carrier block 410' and a second groove 418b formed on the surface of the pusher block 420'. The pusher block 420' can include a hole 426' extending through a portion thereof, with one end of the hole 426' opening into the groove 418*b*. The hole 426' can be adapted to receive a trip pin 427'. During the closure element deployment process, the trip pin 427' can be advanced through the hole 426', where it can encounter the catch member 418' that is retained in the groove 418*b*. Further advancement of the trip pin 427' can cause the catch member 418' to become disengaged from the groove 418*b*, thereby releasing the restraining force on the pusher spring 425'.

The operation of the triggering system 400' of the alternative embodiment of the apparatus 100' is illustrated in FIGS. 11-14 with the closure element 500 (shown in FIGS. 6A-6B) disposed substantially within the apparatus 100'. As shown in FIGS. 11A-11B, the apparatus can have an initial position in which the locator assembly block 280' is extended proximally and the triggering system 400' is in its most proximal position. Accordingly, the locator control system 200' is in its unexpanded state, as shown. At a point in time that the distal end region 210*b*' of the locator assembly 200' has been positioned as desired (for example, within the blood vessel 600), the locator assembly block 280 is depressed distally, as shown in FIG. 12, thereby transitioning the locator assembly to the expanded state and, simultaneously, releasing the triggering system 400' from the initial position (in the manner described above) such that the triggering system can be advanced distally within the housing 380'.

The triggering system 400' can be advanced distally within the housing 380', thereby advancing the tube set 305 into position adjacent the blood vessel. At a first predetermined position, shown in FIG. 13, the support block 440' can encounter a support stop (not shown) on the interior surface of the housing bottom half 380*d* that inhibits the support block 440' from advancing further distally. As a result, an application of additional distal force to the triggering system 400' can cause the support block 440' to decouple from the carrier block 410', as shown in FIG. 13. More specifically, the tabs 445*a-b* on the forks 444*a-b* of the support block 440' can disengage from the grooves 413*a-b* on the carrier block 410'. Thus, the support block 440' can remain in the position shown in FIG. 13, while the carrier block 410' is able to advance further distally upon application of force to the triggering system 400'.

Figure 14A:
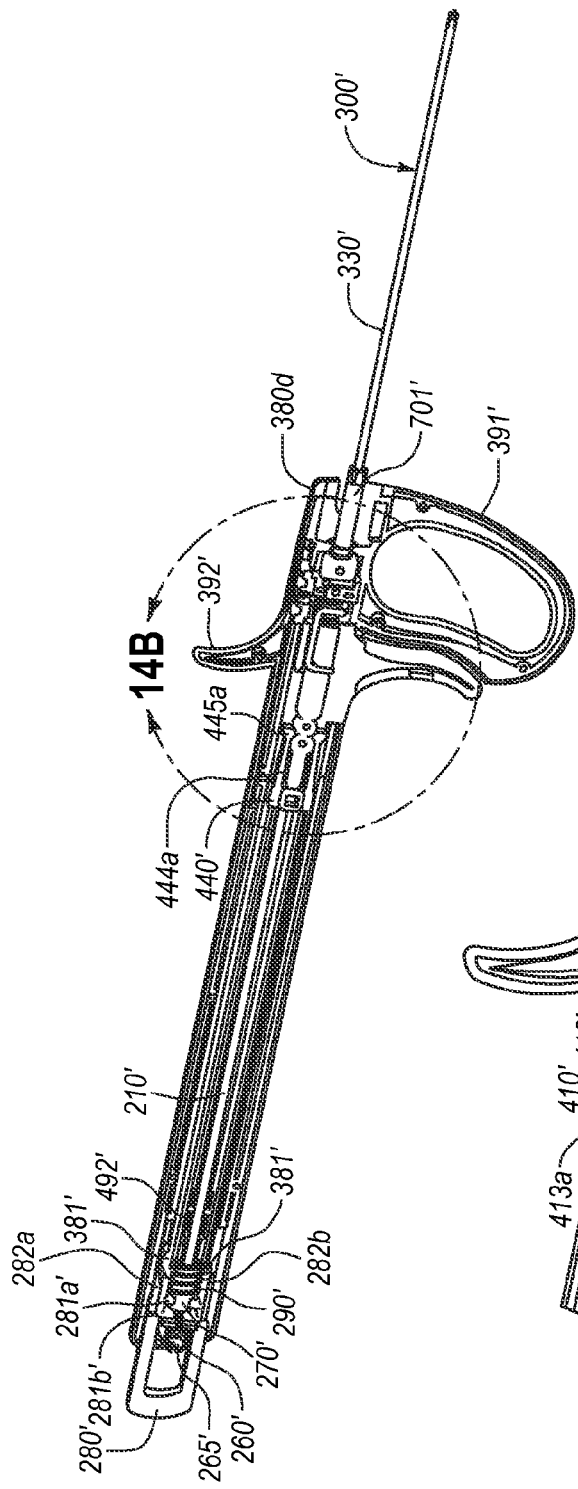
FIG. 14A illustrates the apparatus of FIGS. 13A and 13B after further distal advancement of the triggering system and carrier assembly.
Figure 14B:
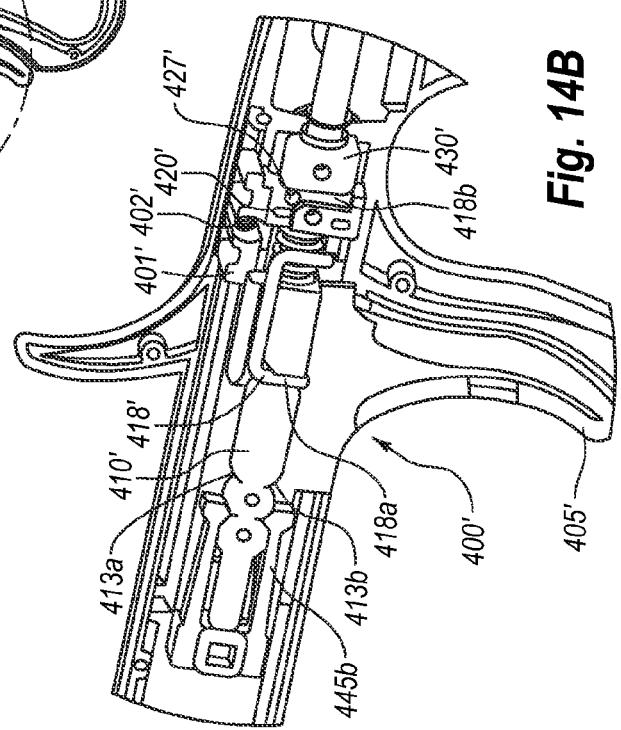
FIG. 14B illustrates a close-up view of the distal end of the housing and internal components of the apparatus shown in FIG. 14A.

Turning to FIGS. 14A-14B, as the triggering system 400' can be advanced further distally, the cover block 430' engages a cover stop on the interior surface near the distal end of the housing 380', thereby inhibiting additional distal advancement of the cover block 430'. In addition, the trigger extension 405' can engage the handle 391' on the exterior of the apparatus, thereby inhibiting additional distal advancement of the carrier block 410'. At this point, the distal end of the tube set corresponds generally to the state illustrated in FIG. 8G, prior to deployment of the closure element 500.

The closure element 500 can be deployed by releasing the pusher spring 425', which causes the pusher block 420' (and, thus, the pusher member 320') to advance distally, deploying the closure element in the manner described above. The pusher spring 425' can be released by disengaging the catch member 418' from the groove 418*b* on the pusher block 420', thereby releasing the pusher spring 425' to force the pusher block 420' and, thus, the pusher member 320'—distally relative to the carrier block 410'. This action can cause the pusher member 320' to deploy the closure element 500, as shown, for example, in FIGS. 8H-8L. The catch member 418' can be disengaged from the groove 418*b* by applying a force to the trigger 401', which, in the deployment position, is aligned with the trip pin 427' retained in the pusher block 420'. A trigger spring 402' can bias the trigger outward relative to the housing 380'. The user can apply an inward directed force to the trigger 401' to counteract the biasing force of the trigger spring 402' and force the trigger 401' against the trip pin 427'.

In addition to deploying the closure element 500, the distal advancement of the pusher block 420' can also cause the locator release system 490' to activate, thereby transitioning the locator control system 200' from the expanded state to the unexpanded state. As the pusher block 420' advances distally to deploy the closure element 500' in the manner described above, the pusher block 420' can also engage the engagement member 493' of the locator release system 490' and advances the locator release rod 491' distally. This action can cause the release tab spacer block 492' to disengage from the release tabs 284*a-b* on the locator assembly block 280' (see FIG. 15), thereby releasing the locator assembly block 280', which returns to its proximal position, causing the locator assembly 200' to return to the unexpanded state.

The closure element 500 deployment and locator release actions can occur nearly simultaneously, as illustrated in FIGS. 8I-8K. As described previously, the apparatus 100 can be brought into contact with the blood vessel 600 by inserting and advancing the distal end of the apparatus through an introducer sheath 640 to the blood vessel location. The use of an introducer sheath 640 is not necessary, as the apparatus can be used to deploy the closure element 500 without the use of an introducer sheath 640. Furthermore, as described above, when an introducer sheath 640 is used, the locator assembly 200, 200' and the carrier assembly 300, 300' may have cross-sectional dimensions that allow them to be received within the introducer sheath 640 either without causing radial expansion or splitting of the sheath, or with causing radial expansion or splitting of the sheath. If the relative cross-sectional dimensions of the introducer sheath 640 and carrier assembly 300, 300' are such that the introducer sheath 640 is intended to be split during advancement of the carrier assembly 300, 200', a sheath cutter 701' having a pointed tip 702' may be utilized to initiate a split at the proximal end of the introducer sheath 640. The sheath cutter 701' can be advantageously placed coaxially over the cover member 330' and can be attached to the distal end of the housing 380' (FIGS. 11A-11B), whereby it will initiate a split in the introducer sheath 640. Distal advancement of the carrier assembly 300, 300' causes the initial split at the proximal end of the sheath to advance as the carrier assembly 300, 300' advances, as will be understood by those skilled in the art.

Another alternative embodiment of a clip applier for sealing openings through tissue is shown in FIGS. 16-19. The embodiment of FIGS. 16-19, as described below, has many identical or similar structures that perform identical or similar functions to the embodiments described above and in reference to the preceding Figures. Accordingly, the description below should be considered in view of the descriptions above of the preceding embodiments. Furthermore, those of ordinary skill in the art will appreciate that one or more of the components and/or features of the embodiment shown in FIGS. 16-19 may also be incorporated in the previously described embodiments, as those components and/or features of the previously described embodiments may optionally be incorporated in the embodiment described below and in reference to FIGS. 16-19.

Turning to FIGS. 16 and 16A, the device 1001 can be adapted for use in conjunction with a guidewire in an over the wire deployment method described below. The device 1001 can have a generally elongated body that includes, beginning at its proximal end, an actuator cap 1280, a generally cylindrical actuator housing 1800, a generally cylindrical release barrel 1810, a generally cylindrical main housing 1380, and a distal extension 1010. Several components of a locator assembly, a carrier assembly, and a triggering system can be contained within the main housing 1380, as described more fully below in relation to FIGS. 18 and 19. The distal extension 1010 of the device can include an external protective sheath 1012 that covers the distal portions of the locator assembly and carrier assembly. The distal end region 1210b of the locator assembly can extend out of the distal end of the protective sheath 1012.

With particular reference to FIG. 16A, the distal end region 1210b of the locator assembly can include expansion elements 1230 that include substantially flexible members 1230'. The substantially flexible members 1230' can be selectively controllable between an unexpanded state (as shown in FIG. 16A) and an expanded state, generally in the manner described above in relation to FIGS. 2A-2D. As shown in FIG. 16A, the locator assembly of the alternative embodiment of the device 1001 can be provided with a central lumen 1003, which can be of a diameter sufficient to accommodate a standard guidewire or other structure, as appropriate. As described below, the central lumen 1003 can extend through the length of the locator assembly and, thus, through the length of the device 1001.

Turning again to FIG. 16, the main housing 1380 can include a pair of grips 1392a-b integrally formed on opposite sides of the main housing 1380. The distal end of the main housing 1380 can be gradually tapered 1382, with the protective sheath 1012 extending out of its distal end. A cylindrical counter spring 1386 can be located coaxially on the external surface of the main housing 1380 and rests, at its distal end, against a shoulder 1384 formed in the main housing just proximal to the section of the main housing upon which the grips 1392 are formed. The proximal end of the counter spring 1386 can rest against the release barrel 1810, biasing the release barrel 1810 proximally in relation to the shoulder 1384 formed on the main housing 1380. The release barrel 1810 is generally cylindrical and coaxially surrounds the main housing 1380. A mechanical linkage 1812 can connect the release barrel 1810 to a release lever 1814 that cooperates with an actuator block 1282, as described more fully below in reference to FIGS. 18 and 19. A longitudinal slot 1388 can be formed on each of the main housing 1380 and the release barrel 1810, through which extends a lever 1405 that, as described below, is used to advance the carrier assembly in the distal direction to operate the device 1001.

A calibration set screw 1818 can be located on the release barrel 1810 near the distal end of the slot 1388. As the user advances the lever 1405 distally to deploy the closure element 500 similar to that described above and shown in FIGS. 6A-6G, the lever 1405 will eventually engage the calibration set screw 1818. As described below, further distal advancement of the lever 1405 can cause the actuator block 1282 to release, thereby causing the locator assembly to release the expansion elements 1230 and 1230' from the expanded state to the unexpanded state. Thus, the setting of the calibration set screw 1818 can allow the user to fine tune the synchronization of the release of the locator assembly with the deployment of the closure element 500, as described below.

Figure 19:
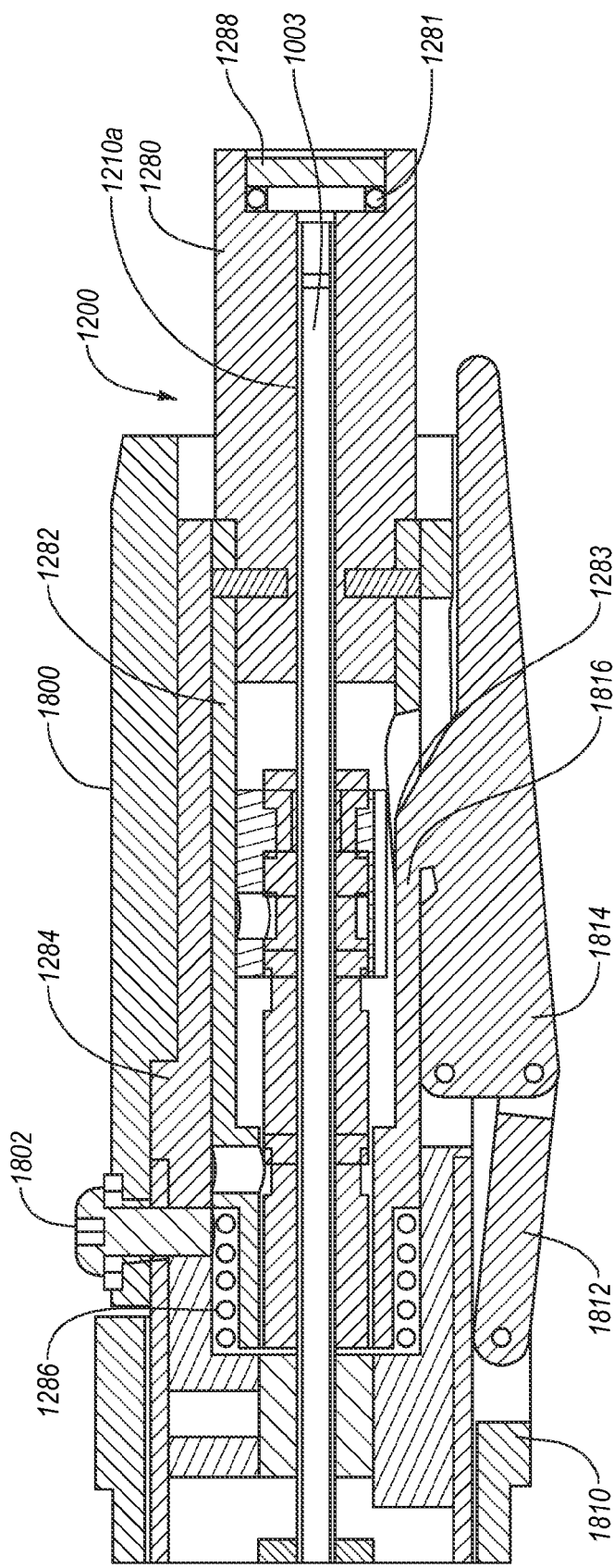
FIG. 19 illustrates a close-up cross-sectional view of the proximal end of the device shown in FIG. 16.

The actuator housing 1800 can be attached by a screw 1802 to the proximal end of the main housing 1380, and extends proximally from the main housing 1380. A longitudinal slot 1804 can be formed in the actuator housing 1800 to accommodate the release lever 1814 and the linkage 1812 (FIGS. 18-19). The actuator cap 1280 can extend out from the proximal end of the actuator housing 1800. The actuator cap 1280 can be a generally cylindrical body that is coaxial with and generally internal of the actuator housing 1800. The actuator cap 1280 can include a slide seal 1288 at its proximal end that is slidable and that provides a fluid-tight seal, as described in more detail below. Additional details concerning the actuator are described below in reference to FIGS. 18 and 19.

Turning to FIGS. 17 and 17A, the proximal end of the device is shown in more detail. As shown, the slide seal 1288 on the actuator cap 1280 has been slid to an open position to expose the interior of the actuator. The slide seal 1288 can be provided with a pair of tabs 1287 that cooperates with a pair of slots 1289 formed on the proximal end of the actuator cap 1280 to allow the slide seal 1288 to slide in relation to the actuator cap 1280. The actuator cap 1280 can include a seal 1281, such as an o-ring, that provides a fluid tight seal with the slide seal 1288.

As described above and as shown in FIGS. 17 and 17A, the central lumen 1003 can extend longitudinally through the center of the device and is accessible at the proximal end of the actuator cap 1280 when the slide seal 1288 is in the open position. Additional details concerning the central lumen 1003 are described below in relation to the additional Figures.

FIG. 17 provides additional detail concerning the shape and orientation of the grips 1392a-b formed on the main housing. As shown, the grips 1392a-b can extend radially outward on opposite sides of a point near the distal end of the main housing 1380, and provide the user with the ability to grip the housing with two fingers while operating the lever 1405 with the user's thumb. Also shown in FIGS. 17 and 17A is the slot 1804 formed in the actuator housing 1800 to accommodate the release lever 1814.

FIGS. 18, 18A, and 18B show a cross-section of the proximal portion of the device 1001, including the previously described main housing 1380, the release barrel 1810 located coaxially in a slidable relation on the external surface of the main housing, the counter spring 1386 that biases the release barrel proximally relative to the shoulder 1384 formed on the main housing, the actuator housing 1800 extending proximally from the proximal end of the main housing, the linkage 1812 and release lever 1814 connected to the release barrel 1810, and the actuator cap 1280 extending proximally from the proximal end of the actuator housing 1800. The actuator cap 1280 can be attached to, or formed integrally with, an actuator block 1282 that is generally cylindrical and that is adapted to slide longitudinally within an actuator base 1284. The actuator base 1284, in turn, can be attached by the screw 1802 to the proximal end of the main housing 1380 and the distal end of the actuator housing 1800, as shown in FIG. 18.

The central lumen 1003 is shown extending through the length of the device along its longitudinal axis. The central lumen 1003 can be defined by the interior diameter of the tubular body 1210 of the locator assembly 1200, which extends from the proximal end region 1210a to a distal end region 1210b (FIG. 16A). The proximal end region 1210a of the tubular body 1210 can be attached or otherwise connected to the actuator block 1282 such that when the actuator block 1282 is advanced distally the tubular body 1210 is also advanced distally, thereby causing the flexible members 1230' to buckle and/or expand transversely outwardly, (in the manner described above, for example, in relation to FIGS. 2A-2D), thereby transitioning the distal end region 1210b of the locator assembly 1200 from the unexpanded state to the expanded state. For example, in FIG. 18, the actuator cap 1280 is shown in the extended position, consistent with the locator assembly 1200 being in the unexpanded state. In FIG. 19, the actuator cap 1280 is shown in the depressed position, consistent with the locator assembly 1200 being in the expanded state. An actuator spring 1286 can be located in a chamber 1285 formed within the interior of the device between the distal end of the actuator block 1282 and the actuator base 1284 attached to the proximal end of the main housing 1380 and the distal end of the actuator housing 1800. The actuator spring 1286 can bias the actuator block 1282 in the proximal direction. Depressing the actuator cap 1280 can cause the actuator spring 1286 to compress within the chamber 1285. Once the actuator cap is fully depressed, the release lever 1814 can be rotated inwardly such that a catch 1816 formed on the release lever engages a slot 1283 formed on the actuator block 1282, thereby holding the actuator block 1282 in place in the depressed position against the spring force of the actuator spring 1286. The release lever 1814 may be disengaged, thus transitioning the locator assembly 1200 from the expanded state to the unexpanded state, either by manually releasing the release lever 1814 from the actuator block 1282 and allowing the actuator block to extend proximally, or by advancing the carrier assembly lever 1405 distally to engage the calibration set screw 1818 on the release barrel 1810 and applying additional distal force to the lever 1405 (and, thus, the release barrel 1810) to cause the release lever 1814 to disengage from the actuator block 1282.

A tube set 1305 can be located within the interior of the main housing 1380, extending distally through the distal extension 1010. The tube set 1305 shown in FIG. 18 includes a carrier tube 1310, a pusher tube 1320, and a cover tube 1330, each located in a coaxial orientation with each other and with the tubular body 1210 of the locator assembly 1200. The tube set 1305 can have a structure otherwise substantially identical to that described above in relation to FIGS. 3A-3E. The cover tube 1330 can be connected or otherwise attached at its proximal end to a cover block 1430. The pusher tube 1320, similarly, can be connected or otherwise attached at its proximal end to a pusher block 1420. Finally, the carrier tube 1310 can be connected or otherwise attached at its proximal end to a carrier block 1410. The lever 1405 can be attached to the pusher block 1420. Thus, any movement of the lever 1405 may cause the pusher block 1420 to move as well.

A leaf spring 1418 can connect the carrier block 1410 to the pusher block 1420, as shown in FIG. 18B. The leaf spring 1418 can be generally flat and can extend longitudinally parallel to the central axis of the device. A lip 1419 can be formed on the distal end of the leaf spring 1418, the lip 1419 oriented such that it engages the distal end of the pusher block 1420, effectively locking the pusher block 1420 to the carrier block 1410 until the leaf spring 1418 is disengaged from the pusher block 1420, as described below. As long as the pusher block 1420 is thereby locked to the carrier block 1410, advancement of the lever 1405 may cause advancement of the combination of the carrier block 1410 and the pusher block 1420.

A guide pin 1900 can be located and fixed on the interior of the main housing 1380, and can extend proximally from the distal wall of the interior of the main housing. The guide pin 1900 can be received within a slot 1902 formed in the pusher block 1420 and cover block 1430, and can prevent the pusher block 1420 and cover block 1430 from rotating inside the main housing 1380.

A grooved pin 1910 can be located and fixed on the interior of the main housing 1380, and can extend proximally from the distal wall of the interior of the main housing 1380. The grooved pin 1910 can be located on an opposite side of the interior of the main housing from the guide pin 1900. The grooved pin 1910 can have a taper 1912 formed on its proximal end and a transverse groove 1914 formed just distally from the beginning of the taper 1912. The location and orientation of the grooved pin 1910 can be such that the taper 1912 formed on the grooved pin 1910 engages and lifts the leaf spring 1418 from its engagement with the pusher block 1420 as the pusher block 1420 and carrier block 1410 are advanced distally within the device. As the pusher block 1420 and carrier block 1410 are advanced still further, the lip 1419 formed on the leaf spring 1418 can engage and lock in place in the transverse groove 1914 formed on the grooved pin 1910, thereby preventing the carrier block 1410 (and, thus, the carrier tube 1310) from advancing any further distally. This position of the device also corresponds to the engagement of the lever 1405 with the calibration set screw 1818 (FIG. 16). Any additional distal movement of the lever 1405 may cause the pusher block 1420 to move further distally while the carrier block 1410 remains stationary, thus causing the pusher tube 1320 to deploy the closure element 1500, in the manner described above in relation to FIGS. 8A-8L. This additional distal movement of the lever 1405 may simultaneously cause the release barrel 1810 to move distally and to disengage the release lever 1814 from the actuator block 1282, thereby releasing the actuator block 1282 and causing the locator assembly 1200 to transition from the expanded state to the unexpanded state.

Referring now to FIGS. 20A-20G, methods of use of the device 1001 in accordance with the present invention will be described. As previously described above and shown in FIGS. 16-19, the device 1001 can be configured to deploy a closure element 500 over a wire, wherein the over the wire deployment method utilizing the device 1001 described herein may for example include the following steps, though methods of use associated with the apparatus should not be limited to those described herein or shown in the appended drawings.

Figure 20A:
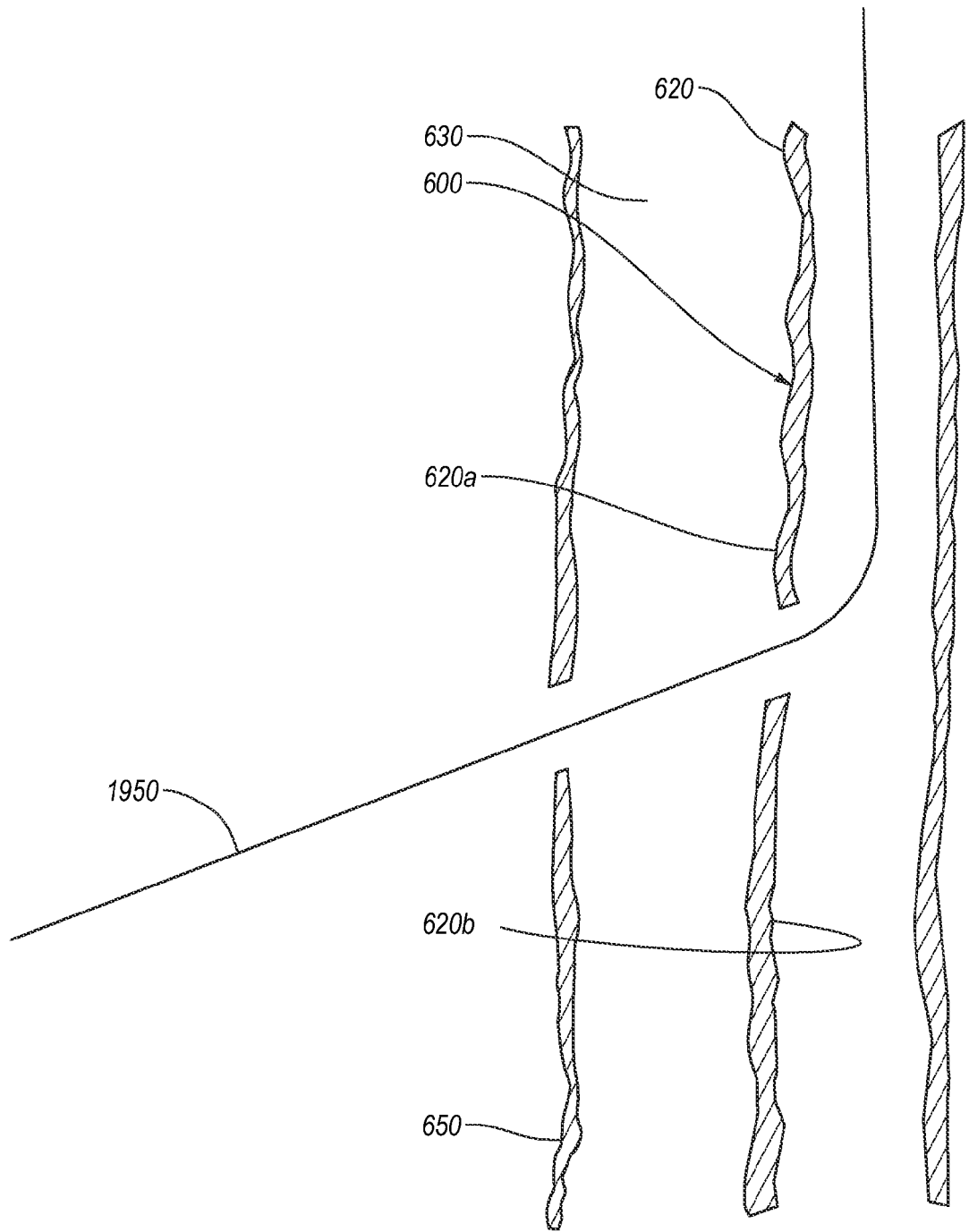
FIG. 20A is a cross-sectional side view illustrating an opening formed in a vessel, wherein a guidewire is shown disposed within the opening.

Referring now to FIG. 20A, there is shown a vessel wall 620 disposed below a patient's tissue 630 and skin 650, wherein a guidewire 1950 is shown disposed through an opening formed in the vessel and tissue as described above. The guidewire 1950 may be introduced into the blood vessel for the sole purpose of using the device 1001 to deploy the closure element 500", or the guidewire may have already been present from a previously completed interventional procedure. If an introducer sheath is in place, it should be removed prior to use of the apparatus 1001, thereby leaving the guidewire 1950 in place extending into the blood vessel.

Figure 20B:
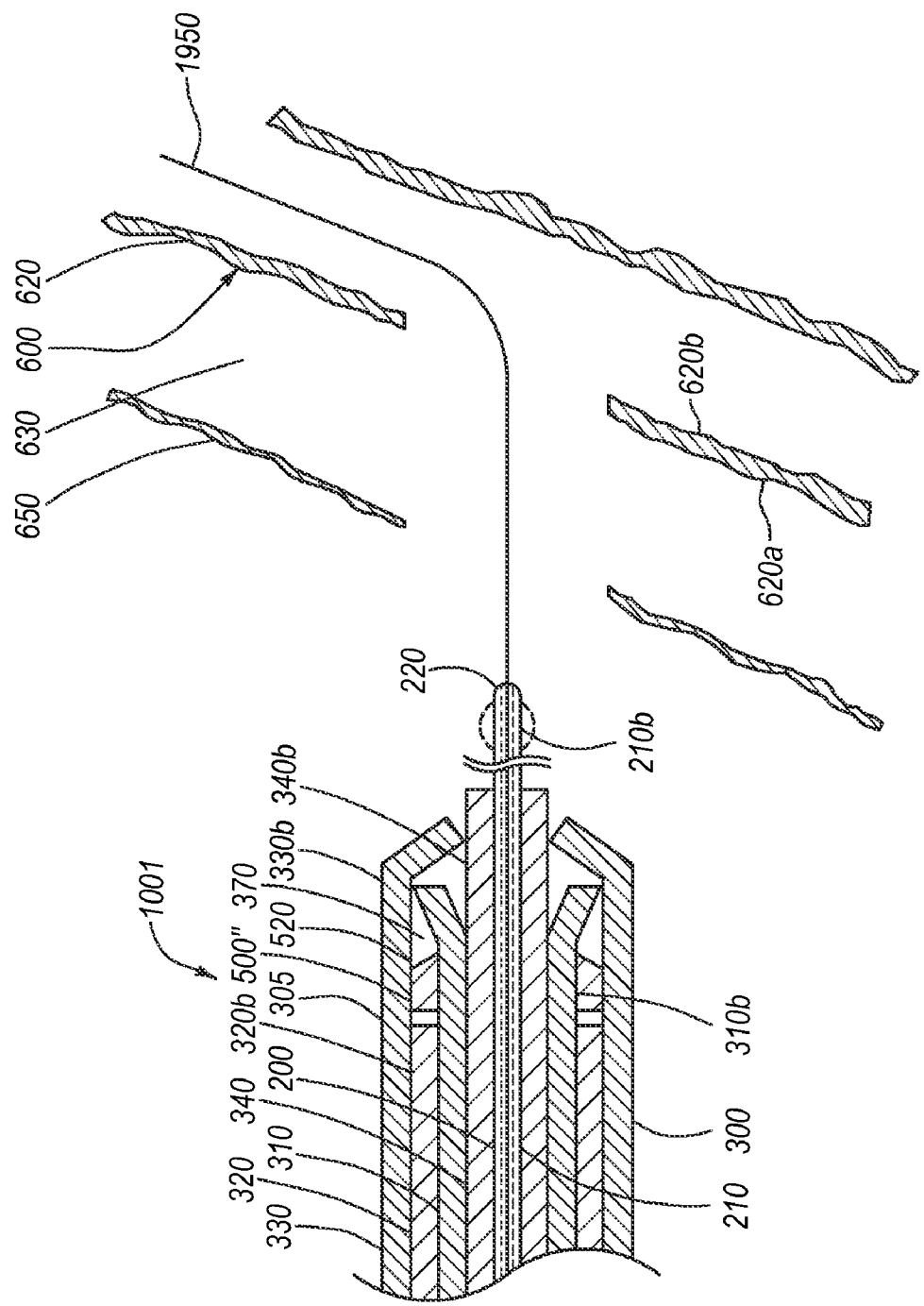
FIGS. 20B-20F are partial cross-sectional views illustrating the alternative embodiment of the closure device in accordance with the present invention wherein the device is illustrated being disposed over a guidewire.
Figure 20C:
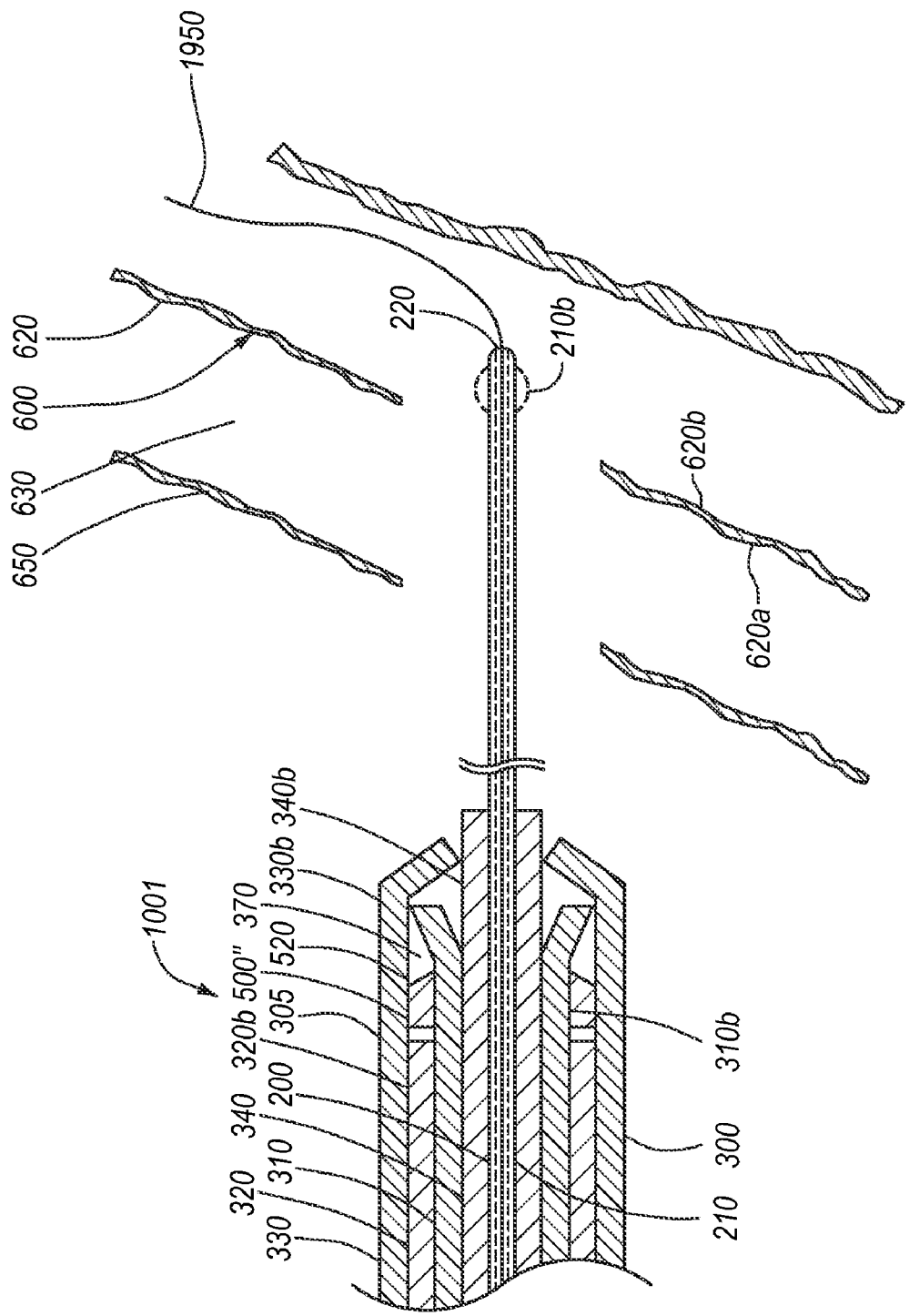

As shown in FIG. 20B, the device 1001 can be threaded over the guidewire 1950 by inserting the proximal end of the guidewire 1950 into the central lumen of the device 1001 at the distal end of the device, the guidewire is disposed through the device and exits at the proximal end of the device. The device 1001 can be advanced along the guidewire until the distal end 210*b* of the locator assembly is disposed through the opening formed in the blood vessel as shown in FIG. 20C, whereby the correct position of the device is confirmed by observing a slight flow of blood out of the proximal end of the device, through the open slide seal 1288 on the actuator cap 1280 (FIG. 18).

Figure 20D:
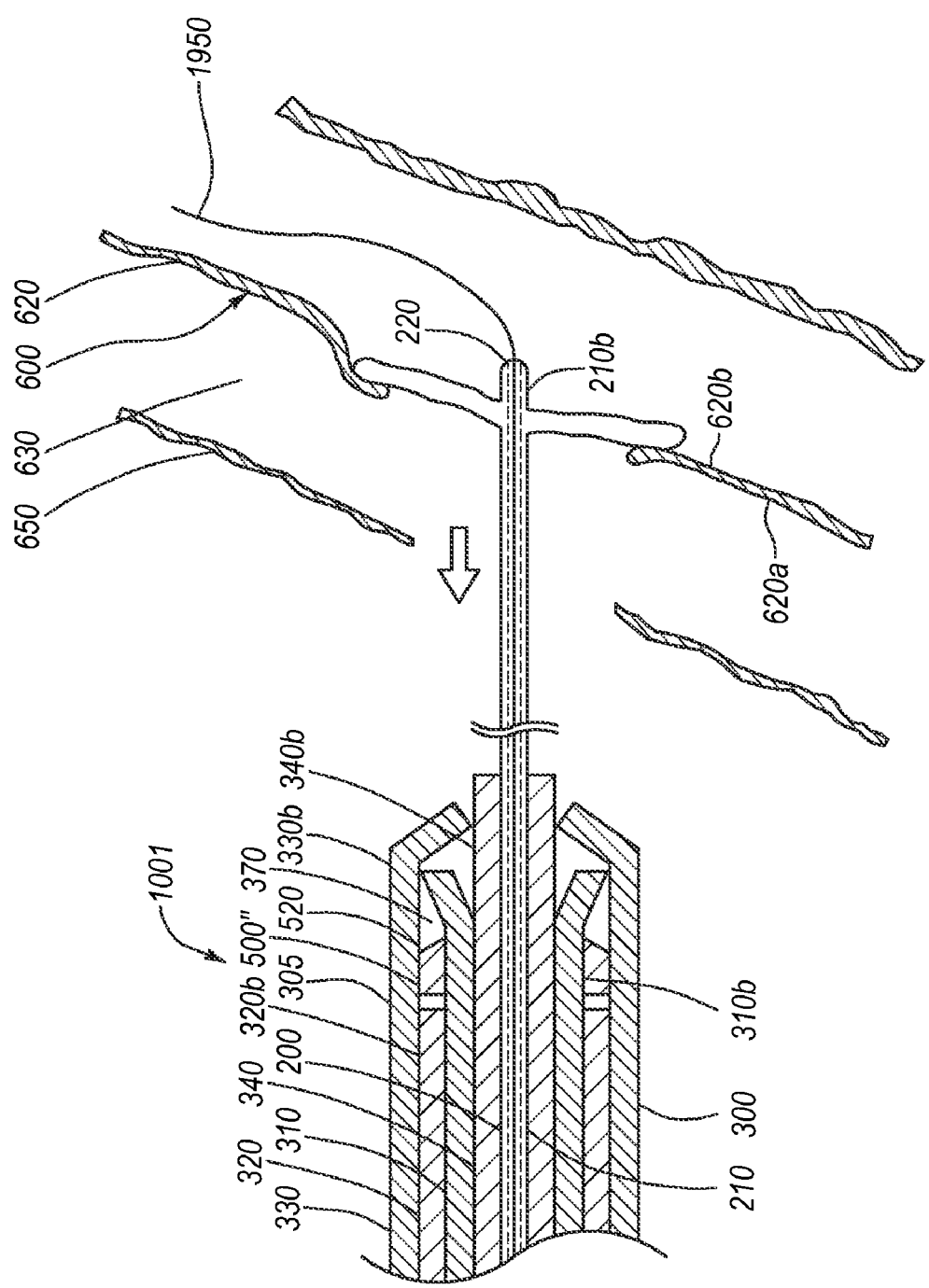
Figure 20E:
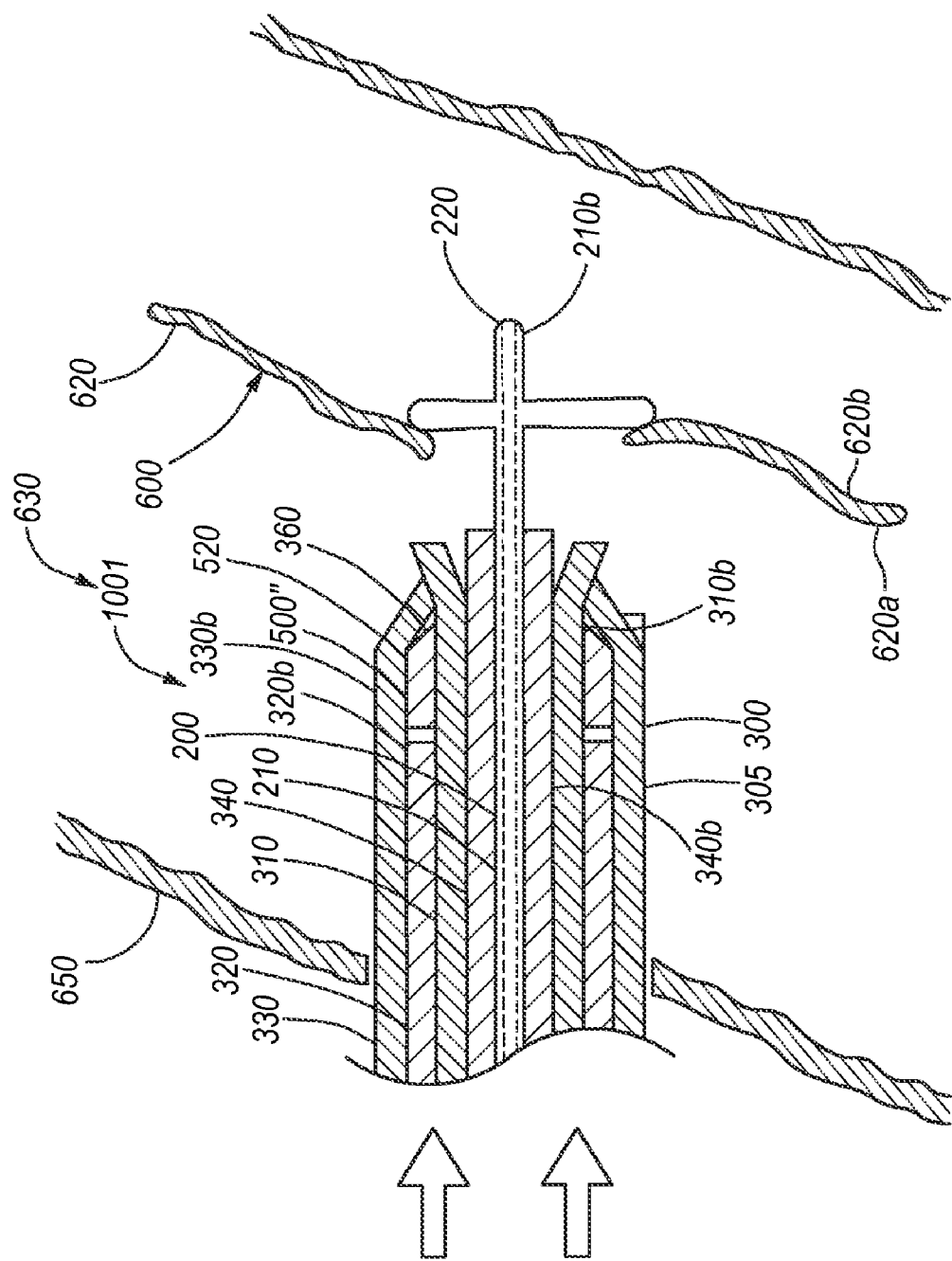

Once the correct position of the device is confirmed, the actuator cap 1280 can be depressed (i.e., the actuator block 1282 is advanced distally) to deploy the flexible members on the distal end 210*b* of the locator assembly, i.e., to transition the locator assembly from the unexpanded state to the expanded state. In the expanded state, the flexible members can engage the inside of the vessel wall at the location of the opening in the blood vessel as shown in FIG. 20D. The correct position of the device at this point may be confirmed by gently pulling on the device to feel the resistance of the vessel wall against the flexible members in the expanded state as shown in FIG. 20E. After verifying the correct position in this manner, the guidewire may be removed from the vessel and from the device by withdrawing the guidewire through the proximal end of the device. Once the guidewire is removed, the slide seal 1288 on the actuator cap 1280 may be closed to prevent further flow of blood through the device.

Figure 20F:
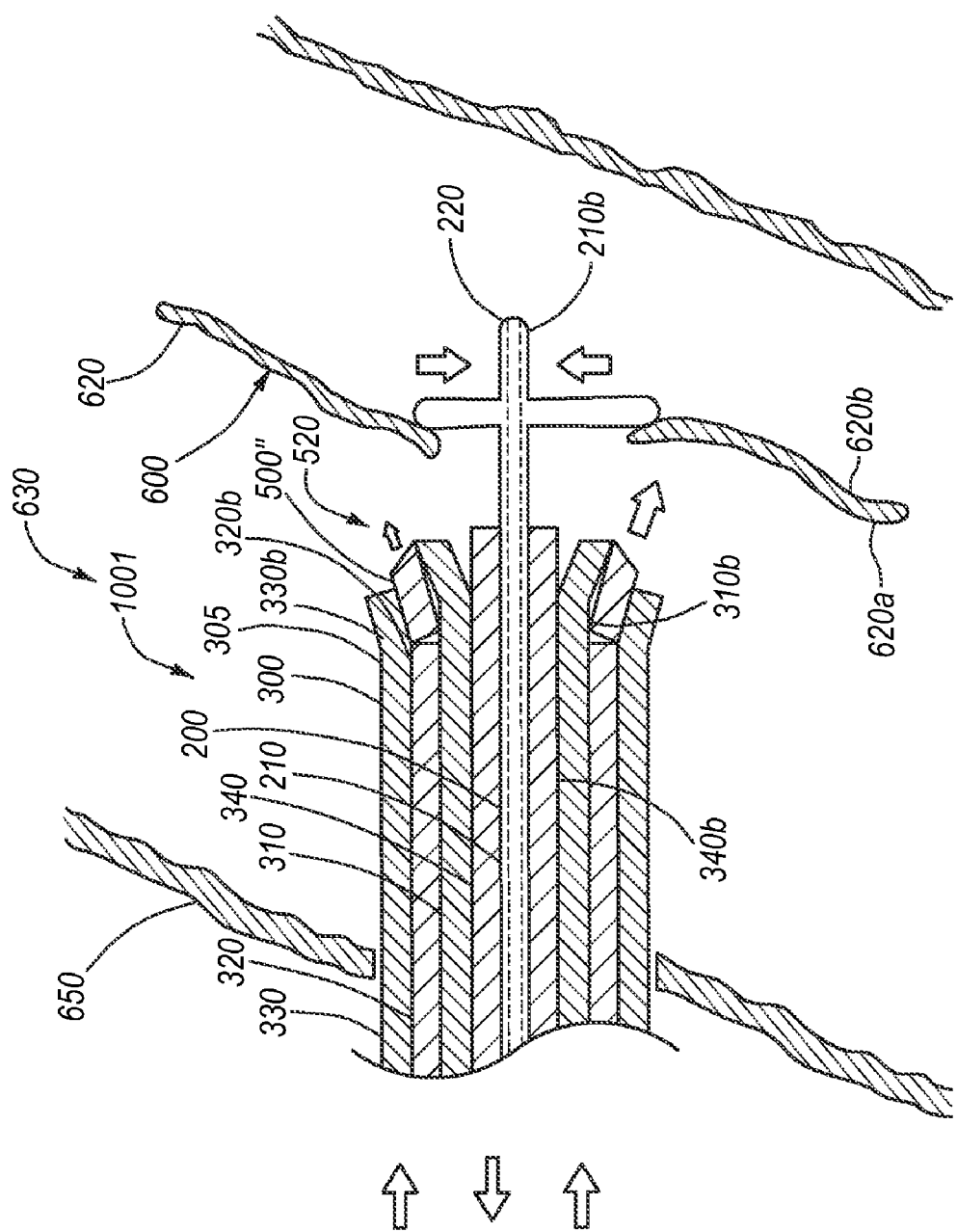
Figure 20G:
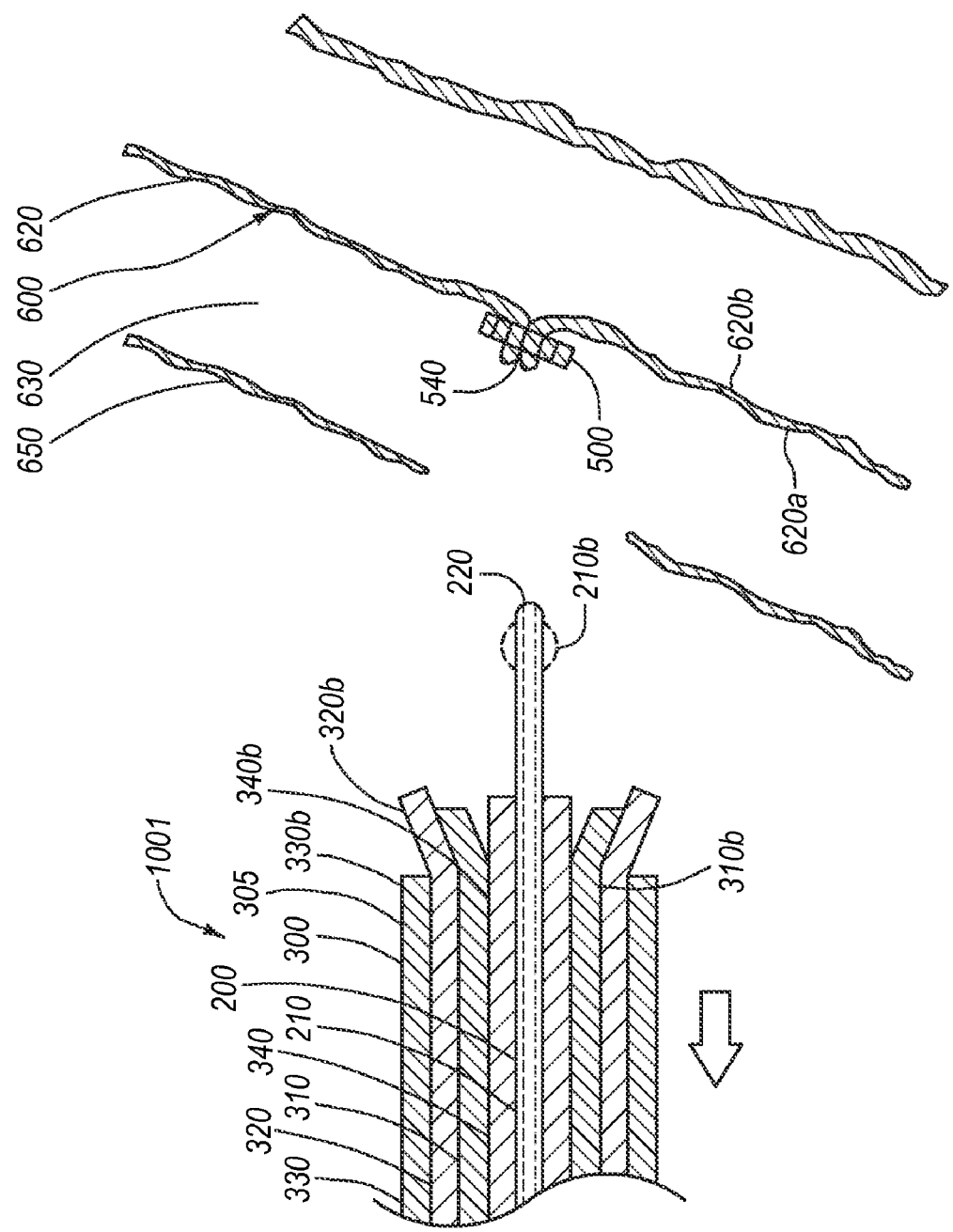
FIG. 20G is a partial cross-sectional view illustrating the placement of a closure element in accordance with the device illustrated in FIGS. 20B-20F.

Referring now to FIGS. 20F and 20G, the device 1001 is in the proper position to deploy the closure element 500″. The closure element 500″ can be deployed by advancing the lever 1405, which advances the carrier block 1410, pusher block 1420, and cover block 1430 until further distal advancement of the carrier block 1410 and cover block 1430 are prevented by the interaction of the leaf spring 1418 engaging and locking in place in the transverse groove 1914 formed on the grooved pin 1910, thereby preventing the carrier block 1410 (and, thus, the carrier tube 1310) from advancing any further distally. Further distal advancement of the lever 1405 thereafter can cause advancement only of the pusher block 1420, which causes deployment of the closure element 500 in the identical manner described above, for example, in relation to FIGS. 8H-L. In addition, further distal advancement of the lever 1405 can cause the lever 1405 simultaneously to engage the release barrel 1810, which in turn pulls the release lever 1814 and frees the actuator block 1282 to spring back proximally, transitioning the locator assembly 1200 from the expanded state to the unexpanded state. The closure element deployment and locator release actions can occur nearly simultaneously, as illustrated, for example, in FIGS. 8I-8K.

As shown in FIG. 20G, the closure element 500 is shown in a deployed position, wherein the closure element has been engaged with the vessel wall to effectively close the opening formed therein. As previously described and shown in FIGS. 20F and 20G, the closure element 500 can be expanded as it is deployed from the device 1001, wherein by increasing the diameter of the closure element 500, the closure element may engage tissue adjacent the opening in the tissue. It is contemplated that the closure element may be configured to penetrate the vessel wall to effect a closure, or partially penetrate the vessel wall to effect closure.

Another alternative embodiment of a clip applier for sealing openings through tissue is shown in FIGS. 21A-21E. The embodiment of FIGS. 21A-21E, as described below, has many identical or similar structures that perform identical or similar functions to the embodiments described above and in reference to the preceding figures. Accordingly, the description below should be considered in view of the descriptions above of the preceding embodiments. Furthermore, those of ordinary skill in the art will appreciate that one or more of the components and/or features of the embodiment shown in FIGS. 21A-21E may also be incorporated in the previously described embodiments, as those components and/or features of the previously described embodiments may optionally be incorporated in the embodiment described below and in reference to FIGS. 21A-21E.

Figure 21A:
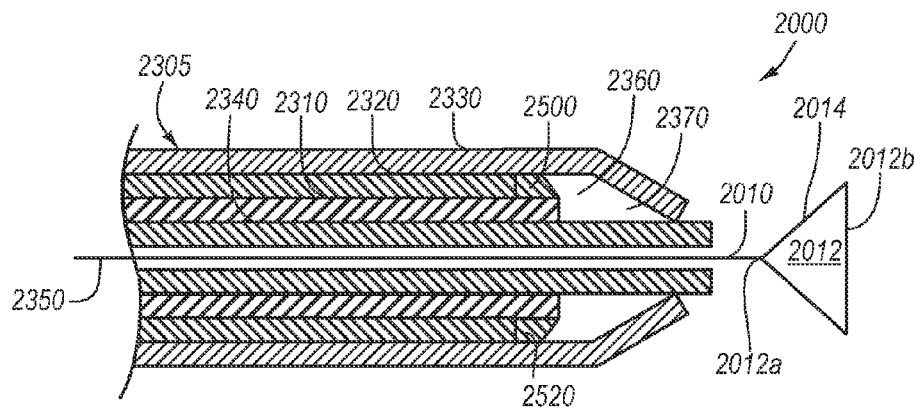
FIG. 21A illustrates one embodiment of a carrier assembly having a splitter and tubular members for delivering a closure element.

Turning to FIGS. 21A-21E, the carrier assembly 2000 can include a tube set 2305 having a carrier tube 2310, a pusher tube 2320, a support tube 2340, and a cover tube 2330. The carrier tube 2310, the pusher tube 2320, the support tube 2340, and the cover tube 2330 can be provided as a plurality of nested, telescoping tubes with a common longitudinal axis 2350 as illustrated in FIG. 21A. While the carrier assembly 2000 is described as having a tube set 2305, such tubes can be exchanged with other members with substantially similar functionalities as described herein.

As shown, the carrier tube 2310 can be configured to receive and support the closure element 2500. While being disposed on the carrier tube 2310, the closure element 2500 can be deformed from the natural, planar orientation to form the substantially tubular orientation (shown in FIGS. 6F-6G). Being disposed substantially about and supported by an outer periphery 2312 of the carrier tube 2310, the substantially tubular closure element 2500 can be substantially in axial alignment with the carrier tube 2310 with the tines 2520 pointed substantially distally and parallel with the tube set 2305.

Additionally, the carrier assembly 2000 can be operable with a splitter 2012. The splitter 2012 can be configured to include at least one splitting face 2014 that can split various members of the tube set 2305. Also, the splitter 2012 can be configured to radially dilate or outwardly expand the tines 2520 or body of the substantially tubular closure element 2500 by having a splitter body that increases in cross-section from the proximal end 2012a to the distal end 2012b. Also, the splitter 2012 can be moved axially with respect to the tubes of the tube set 2305 by being coupled via a coupling to a wire 2010, such as a guide wire, in order to facilitate placement of the closure element 2500. However, the wire 2010 can be substituted with a tube, rod, elongate member, or the like. Moreover, the splitter 2012 can cooperate with tubes of the tube set 2305 that are configured to split so that the tubes can expand around the splitter 2012 and increase in outer diameter as they move distally with respect to the splitter 2012, which can be useful for directing the tines 2520 in an outward-radial direction.

Figure 21B:
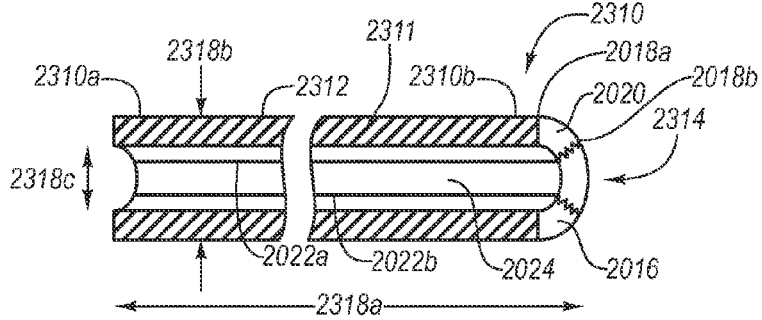
FIG. 21B illustrates one embodiment of a carrier member for the carrier assembly of FIG. 21A.

As shown in FIG. 21B, the carrier tube 2310 can have a proximal end region 2310a and a distal end region 2310b. Also, the carrier tube 2310 can include a predetermined length 2318a, a predetermined outer diameter 2318b, and a predetermined inner diameter 2318c, any of which can be of any suitable dimension. The carrier tube 2310 can be formed as a substantially rigid, semi-rigid, or flexible tubular member; however, other suitable configurations can also be employed. The carrier tube 2310 can define a lumen 2314 that extends substantially between the proximal end region 2310a and the distal end region 2310b, and can be configured to slide relative to the other tubes in the tube set 2305 disposed in the lumen 2314.

Figure 23A:
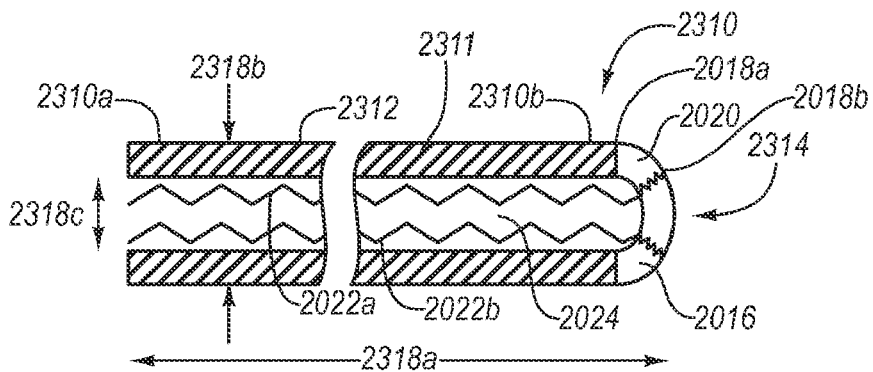
FIG. 23A illustrates one embodiment of a carrier member.

As illustrated, the carrier tube 2310 can include a body 2311 that is configured to radially expand either by stretching or by including slits 2022 in the body 2311 that provide the carrier tube 2310 with regions along which the carrier tube 2310 can split or separate into multiple portions. As shown, the slits 2022 are generally longitudinally oriented along the lumen; however, other orientations can be used, such as spirals, zigzags (shown in FIG. 23A), or the like. As such, the carrier tube 2310 can have a splitting end 2016 at the distal end region 2310b configured to split and separate by movement of the splitter 2012 and/or the carrier tube 2310. The splitting end 2016 can include a plurality of slit openings 2018a-b that provide a splitting region or portion along which the carrier tube 2310 can separate when receiving a force, such as when the splitter 2012 moves from the distal end 2310b toward the proximal end 2310a of the carrier tube 2310. The slit openings 2018 can be spaced apart by portions of the splitting end 2016 that become carrier flap ends 2020 after the distal end region 2310b becomes split. Additionally, the body 2311 can include slits 2022 that extend partially or completely along the length 2318a of the carrier tube 2310. The slits 2022 can be continuous, intermittent, or composed of perforations. The slits 2022 can (i) extend radially from the lumen to the outer periphery 2312 of the carrier tube 2310, (ii) partially extend radially from the lumen toward the outer periphery 2312 of the carrier tube 2310, or (iii) partially extend radially from the outer periphery 2312 of the carrier tube 2310 toward the lumen. For example, when the splitter 2012 interacts with the carrier tube 2310, the slits 2022a and 2022b can split and separate so as to form carrier flaps 2024.

The carrier flaps 2024 can bend or deform outwardly, and carry the closure element 2500 during deployment.

In an alternative to other embodiments, the outer diameter 2318b of the carrier tube 2310 can be substantially uniform such that the distal end region 2310b of the carrier tube 2310 has a cross-section similar to the proximal end region 2310a. However, it may be beneficial for the distal end region 2310b to be expandable or configured in such a way that the outer diameter 2318b can selectively expand or bend outwardly so that the closure element 2500 and/or tines 2520 can be expanded during deployment. This can include expanding at least the distal end of the substantially tubular closure element 2500 beyond the natural cross-section when being deployed; however, the entire closure element 2500 can be expanded with the distal end being expanded before the proximal end. The carrier flaps 2024 separate and radially expand or bend outwardly so as to expand the closure element 2500.

Figure 21C:
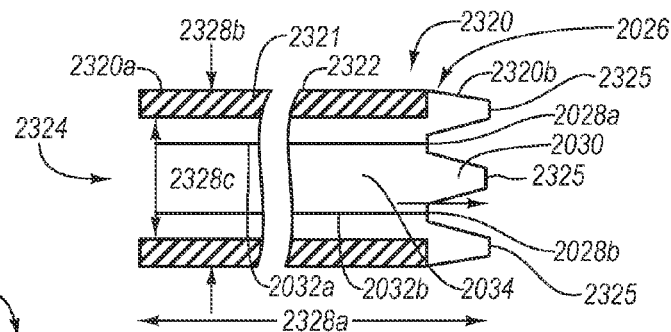
FIG. 21C illustrates one embodiment of a pusher member for the carrier assembly of FIG. 21A.

As shown in FIG. 21C, the pusher tube 2320 can be configured to distally push and/or deploy the substantially tubular closure element 2500. As such, the pusher tube 2320 can have a proximal end region 2320a and a distal end region 2320b and can be coupled with, and slidable relative to, the carrier tube 2310. The pusher tube 2320 can include a predetermined length 2328a, a predetermined outer diameter 2328b, and a predetermined inner diameter 2328c, any of which can be of any suitable dimension. The pusher tube 2320 can be configured to slidably receive the carrier member 2310 in the lumen 2324 of the pusher tube 2320 such that the distal end region 2320b of the pusher tube 2320 can be offset proximally from the distal end region 2310b of the carrier tube 2310. As desired, the predetermined length 2328a of the pusher tube 2320 can be greater than or substantially equal to the predetermined length 2318a of the carrier tube 2310. The predetermined length 2328a of the pusher tube 2320, however, can be less than the predetermined length 2318a of the carrier tube 2310 such that the carrier tube 2310 and the pusher tube 2320 at least partially define a space 2360 distal to the distal end region 2320b of the pusher tube 2320 and along the periphery 2312 of the carrier tube 2310. The space 2360 can be configured for housing or containing the closure element 2500.

The pusher tube 2320 can be formed from a substantially rigid, semi-rigid, or flexible material. Also, the pusher tube 2320 can be substantially tubular and can define a lumen 2324 that extends substantially between the proximal end region 2320a and the distal end region 2320b. The pusher tube 2320 can be configured to slidably receive at least a portion of the carrier tube 2310 so that the inner diameter 2328c of the pusher tube 2320 is equal to or larger than the outer diameter 2318b of the carrier tube 2310. The outer diameter 2328b and/or inner chamber 2328c of the pusher tube 2320 can be substantially uniform. Also, the distal end region 2320b of the pusher tube 2320 can have one or more longitudinal extensions 2325, which extend distally from the pusher tube 2320 and along the periphery 2312 of the carrier tube 2310. Optionally, the longitudinal extensions 2325 can be biased such that the longitudinal extensions 2325 extend generally in parallel with a common longitudinal axis 2350, which can be at the guidewire 2010. The longitudinal extensions 2325 can be sufficiently flexible to expand radially or bend outwardly, and yet sufficiently rigid to inhibit buckling, as the distal end region 2320b is directed distally along the carrier tube 2310 and engages the substantially tubular closure element 2500 for deployment.

Figure 23B:
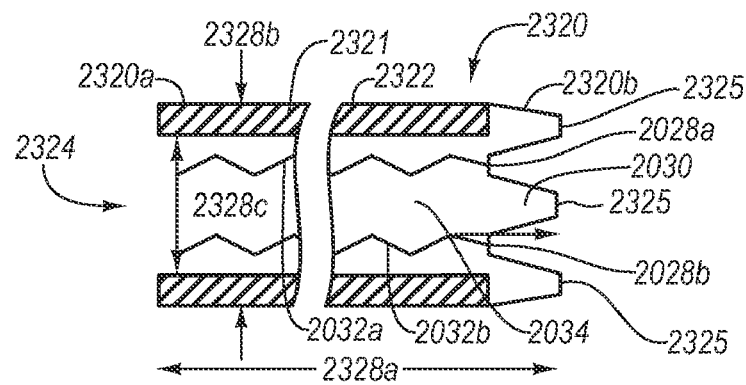
FIG. 23B illustrates one embodiment of a pusher member.

Additionally, the pusher tube 2320 can include a body 2321 that is configured to radially expand either by stretching or by including slits 2032 in the body 2321 that can separate along the lumen 2324. As shown, the slits 2032 are generally longitudinally oriented; however, other orientations can be used, such as spirals, zigzags (shown in FIG. 23B), or the like. As such, the pusher tube 2320 can have a splitting end 2026 at the distal end region 2320b configured to split and separate, which can be induced by the splitter 2012. The splitting end 2026 can include a plurality of slit openings 2028a-b that can separate when receiving a force, such as when the splitter 2012 moves from the distal end 2320b toward the proximal end 2320a of the pusher tube 2320. The slit openings 2028a-b can be spaced apart by portions of the splitting end 2026 that become pushing flap ends 2030 after being split. Additionally, the body 2321 can include slits 2032 that extend partially or completely along the length 2328a of the pusher tube 2320, and can be continuous or intermittent, or composed of perforations. The slits 2032 can (i) extend radially from the lumen 2324 to the outer periphery 2322, (ii) partially extend radially from the lumen 2324 toward the outer periphery 2322, or (iii) partially extend radially from the outer periphery 2322 toward the lumen 2324. For example, when the splitter 2012 interacts with the pusher tube 2320, the slits 2032a and 2032b can split and separate so as to form pusher flaps 2034. The pusher flaps 2034 can then retain the pushing capability so as to push the closure element 2500 during deployment.

Figure 21D:
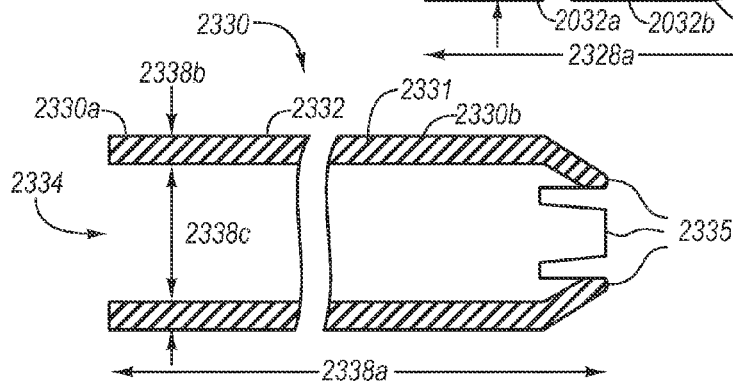
FIG. 21D illustrates one embodiment of a cover member for the carrier assembly of FIG. 21A.

As shown in FIGS. 21A and 21D, a cover tube 2330 can be configured to retain the substantially tubular closure element 2500 substantially within the carrier assembly 2000 prior to deployment. Being coupled with, and slidable relative to, the pusher tube 2320, the cover tube 2330 can have a proximal end region 2330a and a distal end region 2330b. Also, the cover tube 2330 can include a predetermined length 2338a, a predetermined outer diameter 2338b, and a predetermined inner diameter 2338c, any of which can be of any suitable dimension.

The cover tube 2330 can be formed as a substantially rigid, semi-rigid, or flexible tubular member. Also, the cover tube 2330 can have an outer periphery 2332 and have a body 2331 that defines a lumen 2334. The lumen 2334 can extend substantially between the proximal and distal end regions 2330a, 2330b of the cover tube 2330, and it can be configured to slidably receive at least a portion of the pusher tube 2320 or any member of the tube set 2305. When the cover tube 2330 is positioned within the carrier assembly 2000, the distal end region 2330b can be configured to extend over the space 2360, thereby defining an annular cavity 2370 for receiving, retaining, and deploying the substantially tubular closure element 2500.

The outer diameter 2338b and/or inner diameter 2338c of the cover tube 2330 can be substantially uniform along the length 2338a, or vary in dimensions as desired. Additionally, the distal end region 2330b of the cover tube 2330 can include one or more longitudinal extensions 2335, which extend distally from the cover tube 2330 and along an outer periphery 2322 of the pusher tube 2320. Although the longitudinal extensions 2335 can extend generally in parallel with a common longitudinal axis 2350, the longitudinal extensions 2335 can also be biased such that the plurality of longitudinal extensions 2335 extend substantially radially inwardly. Thereby, the longitudinal extensions 2335 can at least partially close the lumen 2334 substantially adjacent to the distal end region 2330b of the cover tube 2330. To permit the substantially tubular closure element 2500 to be deployed from the annular cavity 2370, the longitudinal extensions 2335 can be sufficiently flexible to expand or bend radially outward so as to permit the distal end region 2310b of the carrier tube 2310 to move distally past the cover tube 2330 to open the annular cavity 2370 such that the distal end region 2330b no longer extends over the space 2360.

Figure 21E:
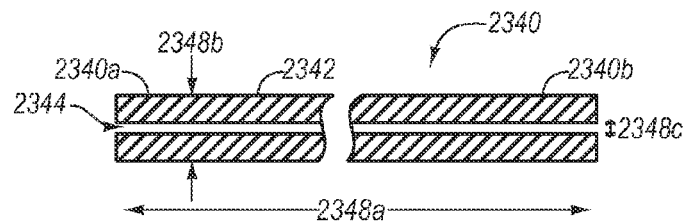
FIG. 21E illustrates one embodiment of a support member for the carrier assembly of FIG. 21A.

As shown in FIGS. 21A and 21E, the tube set 2305 can include a support tube 2340. The support tube 2340 can be configured to slidably receive the wire 2010 that is coupled to the splitter 2012. The support tube 2340 can also provide radial support for the other tubes within the tube set 2305. The carrier assembly 2000 can advantageously include the support tube 2340, for example, to provide sufficient support to the carrier tube 2310 in the instance it is not sufficiently rigid or under other circumstances in which support for the carrier tube 2310 or other tubes in the tube set 2305 might be desirable. Also, the support tube 2340 can include slits (not shown) that can provide a region of separation similar to those described with respect to the carrier tube 2310 and/or pusher tube 2320.

The support tube 2340 can be formed as a substantially rigid, semi-rigid, or flexible tubular member, and have a proximal end region 2340a and a distal end region 2340b. A body 2342 of the support tube 2340 can define a lumen 2344 that extends substantially between the proximal end region 2340a and the distal end region 2340b. The lumen 2344 can be configured to slidably receive and support at least a portion of the wire 2010 or other type of movable member coupled to the splitter 2012. The support tube 2340, in turn, can be at least partially slidably disposed within the lumen 2314 of the carrier tube 2310 such that the wire 2010 may be disposed within, and slidable relative to, the carrier member 2310.

The support tube 2340 can have a predetermined length 2348a, a predetermined outer diameter 2348b, and a predetermined inner diameter 2348c, any of which can be of any suitable dimension. Also, the outer diameter 2348b of the support tube 2340 can be substantially uniform and smaller than inner diameter 2318c of the carrier tube 2310, and the inner diameter 2348c of the support tube 2340 can be larger than the size of the wire 2010, a locator tube, or other type of movable member operably coupled to the splitter 2012.

In the instance the carrier assembly 2000 is assembled as the plurality of nested, telescoping members as shown in FIG. 21A, the carrier tube 2310 can be at least partially disposed within, and slidable relative to, the lumen 2324 of the pusher tube 2320. The pusher tube 2320, in turn, can be at least partially disposed within, and slidable relative to, the lumen 2334 of the cover tube 2330. To operably couple the carrier assembly 2000 with the splitter 2012, the wire 2010 can be at least partially disposed within, and slidable relative to, the lumen 2314 of the carrier tube 2310. In the instance the carrier assembly 2000 includes a support tube 2340 as depicted, the wire 2010 can be disposed within, and slidable relative to, the lumen 2344 of the support tube 2340. The longitudinal axis of the wire 2010 can be substantially in axial alignment with the common longitudinal axis 2350 of the carrier tube 2310, the pusher tube 2320, the cover tube 2330, and/or the support tube 2340. Although shown and described as being substantially separate for purposes of illustration, it will be appreciated that the carrier tube 2310, the pusher tube 2320, the cover tube 2330, and/or the support tub 2340 can be provided, in whole or in part, as one or more integrated assemblies, and the various tubes may be combined.

Another alternative embodiment of a closure element carrier system having a tube splitter for sealing openings through tissue is shown in FIGS. 22A-22E. The embodiment of FIGS. 22A-22E, as described below, has many identical or similar structures that perform identical or similar functions to the embodiments described above and in reference to the preceding figures. Accordingly, the description below should be considered in view of the descriptions above of the preceding embodiments. Furthermore, those of ordinary skill in the art will appreciate that one or more of the components and/or features of the embodiment shown in FIGS. 22A-22E may also be incorporated in the previously described embodiments, and those components and/or features of the previously described embodiments may optionally be incorporated in the embodiment described below and in reference to FIGS. 22A-22E.

Turning to FIGS. 22A-22E, the carrier assembly 2002 can include a tube set 2605 having a carrier tube 2610, a pusher tube 2620, a splitter tube 2680, and a cover tube 2630. The carrier tube 2610, the pusher tube 2620, the splitter tube 2680, and the cover tube 2630 can be provided as a plurality of nested, telescoping tubes with a common longitudinal axis 2650 as illustrated in FIG. 22A. While the carrier assembly 2002 is described by including a tube set 2605, such tubes can be exchanged with other members with substantially similar functionalities as described herein.

As shown, the carrier tube 2610 can be configured to receive and support the closure element 2500. While being disposed on the carrier tube 2610, the closure element 2500 can be deformed from the natural, planar orientation to form the substantially tubular orientation (shown in FIGS. 6F-6G). Being disposed substantially about, and supported by, an outer periphery 2612 of the carrier tube 2610, the substantially tubular closure element 2500 can be substantially in axial alignment with the carrier tube 2610 with the tines 2520 pointed substantially distally and parallel with the tube set 2605.

Additionally, the carrier assembly 2002 can be operable with a splitter tube 2680, which includes a support tube 2640 coupled to a splitter 2070. The splitter 2070 can be configured to include at least one splitting face 2074 that can split various members of the tube set 2605. Also, the splitter 2070 can be configured to radially-dilate or outwardly expand the tines 2520 or body of the substantially tubular closure element 2500. In part, this is because the splitter 2070 can have a body that increases in dimension from the proximal end 2070a to the distal end 2070b. Also, the splitter 2070 can be moved axially by moving the splitter tube 2680 with respect to the other tubes of the tube set 2605 in order to facilitate placement of the closure element 2500. Moreover, the splitter tube 2680 can cooperate with the other tubes of the tube set 2605 that are configured to split so that the tubes can expand around the splitter and increase in outer diameter or bend outwardly as they move distally with respect to the splitter 2070, which can be useful for expanding the closure element 2500 and/or directing the tines 2520 in an outward-radial direction.

As shown in FIG. 22B, the carrier tube 2610 can have a proximal end region 2610a and a distal end region 2610b. Also, the carrier tube 2610 can include a predetermined length 2618a, a predetermined outer diameter 2618b, and a predetermined inner diameter 2618c, any of which can be of any suitable dimension. The carrier tube 2610 can be formed as a substantially rigid, semi-rigid, or flexible tubular member; however, other suitable configurations can also be employed. The carrier tube 2610 can include a body 2611 that defines a lumen 2614 that extends substantially between the proximal end region 2610a and the distal end region 2610b.

Figure 24A:
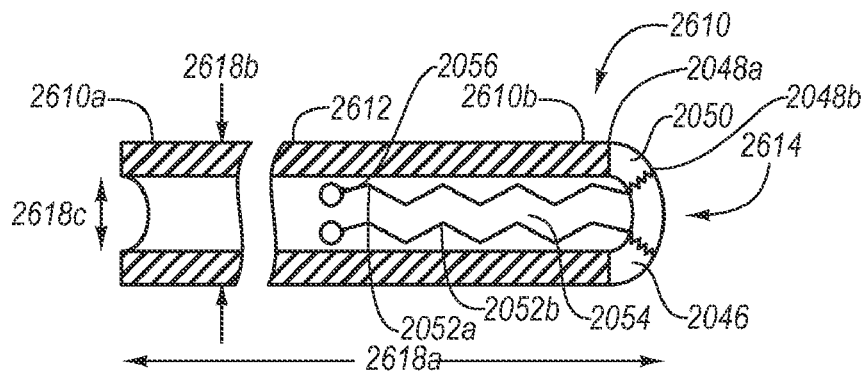
FIG. 24A illustrates one embodiment of a carrier member.

The carrier tube 2610 can include a portion 2613 of the body 2611 that is configured to radially expand either by stretching or by including slits 2052 in the portion 2613 that can separate along the lumen 2614. As shown, the slits 2052 are generally longitudinally oriented; however, other orientations can be used, such as spirals, zigzags (shown in FIG. 24A), or the like. As such, the carrier tube 2610 can have a splitting end 2046 at the distal end region 2610b configured to split and separate when interacting with the splitter 2070. The splitting end 2046 can include a plurality of slit openings 2048a-b that provide a region along which the carrier tube 2610 can separate when receiving a force, such as when the splitter 2070 moves from the distal end 2610b toward the proximal end 2610a of the carrier tube 2610. The slit openings 2048 can be spaced apart by portions of the splitting end 2046 that become carrier flap ends 2050 after being split. Additionally, the portion 2613 can include slits 2052 that extend partially down the length 2618a of the carrier tube 2610. The slits 2052 can be continuous, intermittent, or composed of perforations. The slits 2052 can (i) extend radially from the lumen 2614 to the outer periphery 2612, (ii) partially extend radially from the lumen 2614 toward the outer periphery 2612, or (iii) partially extend radially from the outer periphery 2612 toward the lumen 2614.

As shown, each of the slits 2052 can terminate at a slit end 2056. A slit end 2056 can be a member that inhibits the propagation of cracks or splitting, which can be exemplified by an aperture, hole, recess, reinforcement, dead end, or the like. For example, when the splitter 2070 interacts with the carrier tube 2610, the carrier tube 2610 splits along the slits 2052a and 2052b to form the carrier flap 2054. The carrier flap 2054 can expand radially or bend outwardly to carry the closure element 2500 during deployment.

In an alternative to other embodiments, the outer diameter 2618b of the carrier tube 2610 can be substantially uniform such that the distal end region 2610b of the carrier tube 2610 can have a cross-section similar to the proximal end region 2610a. However, it may be beneficial for the distal end region 2610b to be expandable or configured in such a way that the outer diameter 2618b can selectively expand so that the closure element 2500 and/or tines 2520 can be expanded during deployment. This can include expanding at least the distal end of the substantially tubular closure element 2500 beyond the natural cross-section when being deployed; however, the entire closure element 2500 can be expanded. The carrier flaps 2054 separate and radially expand or bend outwardly so as to expand the closure element 2500 during deployment.

As shown in FIG. 22C, the pusher tube 2620 can be configured to distally push and/or deploy the substantially tubular closure element 2500 over the carrier tube 2610. As such, the pusher tube 2620 can have a proximal end region 2620a and a distal end region 2620b and can be coupled with, and slidable relative to, the carrier tube 2610. The pusher tube 2620 can include a predetermined length 2628a, a predetermined outer diameter 2628b, and a predetermined inner diameter 2628c, any of which can be of any suitable dimension. The pusher tube 2620 can be configured to slidably receive the carrier member 2610 in a lumen 2624 such that the distal end region 2620b of the pusher tube 2620 can be offset proximally from the distal end region 2610b of the carrier tube 2610. As desired, the predetermined length 2628a of the pusher tube 2620 can be greater than or substantially equal to the predetermined length 2618a of the carrier tube 2610. The predetermined length 2628a of the pusher tube 2620, however, can be less than the predetermined length 2618a of the carrier tube 2610 such that the carrier tube 2610 and the pusher tube 2620 at least partially define a space 2660 distal to the distal end region 2620b of the pusher tube 2620 and along the periphery 2612 of the carrier tube 2610. The space 2660 can be configured for housing or containing the closure element 2500.

The pusher tube 2620 can be formed from a substantially rigid, semi-rigid, or flexible material. Also, the pusher tube 2620 can be substantially tubular and can define the lumen 2624 that extends substantially between the proximal end region 2620a and the distal end region 2620b. The lumen 2624 can be configured to slidably receive at least a portion of the carrier tube 2610 so that the inner diameter 2628c of the pusher tube 2620 is equal to or larger than the outer diameter 2618b of the carrier tube 2610. The inner diameter 2628c and the outer diameter 2628b of the pusher tube 2620 are substantially uniform.

Also, the distal end region 2620b of the pusher tube 2620 can include one or more longitudinal extensions 2625, which extend distally from the pusher tube 2620 and along the periphery 2612 of the carrier tube 2610. The longitudinal extensions 2625 can be biased such that the longitudinal extensions 2625 extend generally in parallel with a common longitudinal axis 2650. The longitudinal extensions 2625 can be sufficiently flexible to expand radially or bend outwardly and yet sufficiently rigid to inhibit buckling. Thus, the longitudinal extensions 2625 can be configured so as to engage and push the substantially tubular closure element 2500 over the carrier tube 2610 for deployment.

Figure 24B:
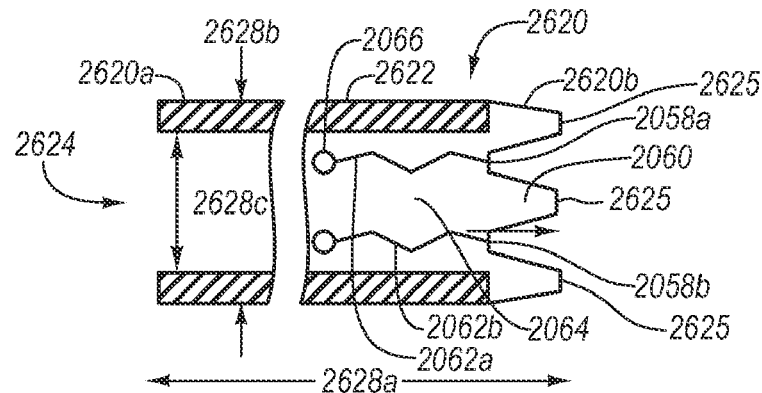
FIG. 24B illustrates one embodiment of a pusher member.

Additionally, the pusher tube 2620 can include a portion 2623 of a body 2621 that is configured to radially expand or bend outwardly either by stretching or by including slits 2062 in the portion 2623 along which the pusher tube 2620 can separate along the lumen 2624. As shown, the slits 2062 are generally longitudinally oriented; however, other orientations can be used, such as spirals, zigzags (shown in FIG. 24B), or the like. As such, the pusher tube 2620 can have a splitting end 2068 at the distal end region 2620b configured to split and separate, which can be induced by the splitter 2070. The splitting end 2068 can include a plurality of slit openings 2058a-b that provide a splitting region or portion along which the pusher tube 2620 can separate when receiving a force, such as when the splitter 2070 moves from the distal end 2620b to the proximal end 2620a. The slit openings 2058a-b can be spaced apart by portions of the splitting end 2068 that become pushing flap ends 2060 after being split. Additionally, the portion 2623 can include slits 2062 that extend partially down the length 2628a of the pusher tube 2620. The slits 2062 and can be continuous, intermittent, or composed of perforations. The slits 2062 can (i) extend radially from the lumen to the outer periphery 2622 of, (ii) partially extend radially from the lumen toward the outer periphery 2622, or (iii) partially extend radially from the outer periphery 2622 toward the lumen.

As shown, the slits 2062 can terminate at a slit end 2066. A slit end 2066 can be a member that inhibits the propagation of cracks or splitting, which can be exemplified by an aperture, hole, recess, reinforcement, dead end, or the like. For example, when the splitter 2070 interacts with the pusher tube 2620, the slits 2062a and 2062b can split and separate so as to form pusher flaps 2064. The pusher flaps 2064 can then retain the pushing capability so as to push the closure element 2500 over the carrier tube 2610 during deployment.

As shown in FIGS. 22A and 22D, a cover tube 2630 can be configured to retain the substantially tubular closure element 2500 substantially within the carrier assembly 2002 prior to deployment. The cover tube 2630 can be coupled with, and slidable relative to, the pusher tube 2620. The cover tube 2630 can have a proximal end region 2630a and a distal end region 2630b. Also, the cover tube 2630 can include a predetermined length 2638a, a predetermined outer diameter 2638b, and a predetermined inner diameter 2638c, any of which can be of any suitable dimension. The cover tube 2630 can be configured substantially similarly as described in connection with FIG. 21D.

Additionally, the distal end region 2630b of the cover tube 2630 can include one or more longitudinal extensions 2635, which extend distally from the cover tube 2630 and along an outer periphery 2622 of the pusher tube 2620. Although the longitudinal extensions 2635 can extend generally in parallel with common longitudinal axis 2650, the longitudinal extensions 2635 can be biased such that the plurality of longitudinal extensions 2635 extend substantially radially inwardly. Thereby, the longitudinal extensions 2635 can at least partially close the lumen 2634 substantially adjacent to the distal end region 2630b of the cover tube 2630. To permit the substantially tubular closure element 2500 to be deployed from the annular cavity 2670, the longitudinal extensions 2635 can be sufficiently flexible to expand radially or bend outwardly so as to permit the distal end region 2610b of the carrier tube 2610 to move distally past the cover tube 2630 to open the annular cavity 2670 such that the distal end region 2630b no longer extends over the space 2660. Also, the longitudinal extensions 2635 can be sufficiently expandable so that they can expand around the splitter 2070 when moved into or out of the cover tube 2630. The splitter 2070 can also split the cover tube 2630 as described herein.

As shown in FIGS. 22A and 22E, the tube set 2605 can include a splitter tube 2680 having a support tube 2640 coupled to a splitter 2070. Also, the splitter tube 2680 can provide radial support for the other tubes within the tube set 2605. The carrier assembly 2002 can advantageously include the splitter tube 2680, for example, to provide sufficient support to the carrier tube 2610 in the instance it is not sufficiently rigid or under other circumstances in which support for the carrier tube 2610 or other tubes in the tube set 2605 might be desirable. It also will be appreciated that the splitter tube 2680 can move the splitter 2070 with respect to the other tubes in the tube set 2605. This can include moving the splitter 2070 so that it can split the carrier tube 2610, pusher tube 2620, and/or cover tube 2630.

The splitter tube 2680 can be formed as a substantially rigid, semi-rigid, or flexible tubular member. As such, the splitter tube 2680 can include a support tube 2640 having a proximal end region 2640a and a distal end region 2640b that it is coupled to the splitter 2070. The body 2642 of the support tube 2640 can define a lumen 2644 that extends substantially between the proximal end region 2640a and the distal end region 2640b. Additionally, the splitter 2070 can also include a lumen 2072 that communicates with the lumen 2644 of the support tube 2640, wherein the lumen 2072 of the splitter 2070 can be the same or different sizes. The lumens 2644 and 2072 can be configured to slidably receive and support at least a portion of a wire, a locator tube, or other type of movable member disposed therein. The support tube 2640 portion of the splitter tube 2680 can be at least partially slidably disposed within the lumen 2614 of the carrier tube 2610 such that the wire may be disposed within, and slidable relative to, the carrier tube 2610 in the manner described in more detail above. However, the splitter 2070 can be disposed distally from the splitting end 2046 of the carrier tube 2610 such that moving the splitter 2070 in a proximal direction relative to the splitting end 2046 can cause splitting of the carrier tube 2610 at the slit openings 2048 and along the slits 2052 to form carrier flaps 2054. The splitter 2070 can then be moved proximally with respect to and under the carrier flaps 2054, which can deform and bend outwardly from the splitter face 2074.

Additionally, the support tube 2640 and/or splitter tube 2680 can have a predetermined length 2648a, a predetermined outer diameter 2648b, and a predetermined inner diameter 2648c, any of which can be of any suitable dimension. Also, the outer diameter 2648b of the support tube 2640 can be substantially uniform and smaller than inner diameter 2618c of the carrier tube 2610. The inner diameter 2648c of the support tube 2640 can be larger than the size of the wire, locator tube, or other type of member that can be disposed therein.

In the instance the carrier assembly 2002 is assembled as the plurality of nested, telescoping members as shown in FIG. 22A, the support tube 2640 portion of the splitter tube 2680 can be at least partially disposed within, and slidable relative to, the lumen 2614 of the carrier tube 2610. However, unless during or after splitting the carrier tube 2610, the splitter 2070 is usually disposed distally adjacent to the carrier tube 2610. Additionally, the carrier tube 2610 can be at least partially disposed within, and slidable relative to, the lumen 2624 of the pusher tube 2620. The pusher tube 2620, in turn, can be at least partially disposed within, and slidable relative to, the lumen 2634 of the cover tube 2630. Also, the splitter 2070 can be disposed within the lumen 2634 of the cover tube 2630. In the instance a guidewire and/or locator tube to be disposed and/or slidable within the lumen 2644 of the splitter tube 2680 the longitudinal axis thereof can be substantially in axial alignment with the common longitudinal axis 2650 of the carrier tube 2610, the pusher tube 2620, the cover tube 2630, and/or the support tube 2640. Although shown and described as being substantially separate for purposes of illustration, it will be appreciated that the carrier tube 2610, the pusher tube 2620, the cover tube 2630, and/or the splitter tub 2680 can be provided, in whole or in part, as one or more integrated assemblies.

Additionally, various embodiments of tube splitters that can be used with a clip applier for sealing openings through tissue are shown in FIGS. 25A-30B. The embodiments of splitters of FIGS. 25A-30B can have various configurations to cooperate and split various tubes of the clip appliers described herein. As such, the splitters can have many identical or similar structures that perform identical or similar functions to the embodiments described above and in reference to the preceding figures. Accordingly, the description below should be considered in view of the descriptions above of the preceding embodiments of clip appliers and/or splitters. Furthermore, those of ordinary skill in the art will appreciate that one or more of the components and/or features of the embodiments shown in FIGS. 25A-30B may also be incorporated in the previously described embodiments, such as FIGS. 21A-22E, and those components and/or features of the previously described embodiments may optionally be incorporated in the various splitter embodiments described below and in reference to FIGS. 25A-30B. Moreover, FIGS. 25A-28 can be characterized as sliding splitters because they slid into the lumen of a carrier tube in order to effect splitting. On the other hand, FIGS. 29A-30B can be characterized as expandable splitters because they expand within the lumen of the carrier tube in order to effect splitting.

FIGS. 25A-25D are schematic illustrations of different shapes of sliding splitters. While various shapes are shown, such shapes can be modified, altered, or manipulated between planar and volumetric configurations as long as the described functionality is retained (e.g., split one or more tubes of a tube set and/or expand the tines of a closure element). FIG. 25A is a representation of a polygonal splitter 2402 having a representative trapezoidal cross-sectional profile. The polygonal splitter 2402 can include a feature common with other embodiments, e.g., having a tapered cross-sectional profile. As such, the splitter 2402 can increase in cross-sectional profile from the proximal end 2402a to the distal end 2402b. The tapered cross-sectional profile allows the proximal end 2402a of the splitter 2402 to enter into the lumen of a carrier tube or other tube of a tube set. As the splitter 2402 moves proximally with respect to the tube of the tube set, the cross-sectional profile of the splitter 2402 positioned in the lumen of the tube begins to increase until it is larger than the lumen. At this point, the tube can split into separate flaps, as described above. Another common feature is the splitter being coupled to a movable member, such as a wire, tube, rod, elongate member, or the like that can move the splitter 2402 into or through a lumen of a tube of the tube set. As depicted, the splitter 2402 can be coupled at the proximal end 2402a to a wire 2414.

Alternate configurations of the splitter are illustrated in FIGS. 25B-25D. FIG. 25B shows a conical-shaped splitter 2404, FIG. 25C shows a hemispherical splitter 2406, and FIG. 25D shows a spherical splitter 2408; however, other shapes can be used.

Referring now to FIG. 26, a schematic representation of another embodiment of a splitter 2410 is illustrated. The splitter 2410 can include a passage 2411 extending therethrough. While the passage 2411 is depicted to be substantially at the longitudinal axis, it can be disposed at any location and in any orientation of the splitter 2410 that retains functionality. The passage 2411 can be configured and sized so that a wire 2414 can be passed therethrough. The wire 2414 can be used for moving the splitter 2410 proximally and/or distally with respect to any of the tubes in the tube set. In order to facilitate movement of the splitter 2410, a recess 2412 can be disposed therein that can retain a retention member 2416 coupled to the wire 2414. The retention member 2416 can be any member that is attached to the wire 2414 having a dimension that is too large to pass through the passage 2411. As such, the retention member 2416 can be trapped within the recess. Alternatively, the recess 2412 can be a substantially closed compartment, container, cavity, or other configuration configured to house the retention member 2416. The retention member 2416 can be a crimp, clamp, brace, fastener, or the like that has a diameter larger than the wire 2414 and/or the passage 2411.

Referring now to FIGS. 27A-27C, schematic diagrams of embodiments of splitters configured to take hold of or grab a portion of tissue to the splitter. With tissue held by the splitter, or the splitter selectively receiving or securing tissue, the tissue around the opening in the vessel to be closed by the closure element can be pulled. The splitter can optionally function as a locator to aid with positioning the device.

Turing to FIG. 27A, depicted is a toothed splitter 2420. The toothed splitter 2420 can include one or more teeth 2422 extending from a body of the splitter 2420. The teeth 2422 can have various orientations and can be pointed toward the proximal end 2420a, normal, or toward the distal end 2420b of the toothed splitter 2420. Any number of teeth 2422 can be used in any arrangement.

FIG. 27B depicts another configuration of the splitter that can take hold of or grab a portion of tissue. The barbed splitter 2430 of FIG. 27B can include one or more barbs 2432. The barbs 2432 can be directed toward the proximal end 2430a of the splitter 2430. Additionally, any number of barbs 2432 can be used in any arrangement; however, having barbs at the distal end 2430b is particularly beneficial. In part, barbs 2432 at the distal end 2430b can be particularly advantageous for grabbing and selectively securing tissue from around the opening of the vessel toward the clip applier and the closure element (e.g., clip) that will close the opening.

FIG. 27C depicts yet another configuration of a splitter that can take hold of or grab a portion of tissue. This toothed-barbed splitter 2440 can have both teeth 2422 and barbs 2432. In one configuration, the teeth 2422 can be disposed from the proximal end 2440a toward the distal end 2440b, and the barbs 2432 can be disposed at the most distal end 2440b of the splitter 2440. It will be understood, however, that teeth can be disposed at the ends of the splitter, while the barbs are disposed between the teeth. In still other configurations, the teeth and barbs can be disposed at any location of the splitter and in any number and orientation.

While various embodiments of splitters to take hold of or grab a portion of tissue during a procedure have been depicted and described, modifications can be made thereto that retain the desired functionality.

FIG. 28 is a schematic diagram of an embodiment of a series of splitters 2450 configured to nest or combine together and expand for use with a clip applier. The series of splitters 2450 can include a first splitter 2452, a second splitter 2458, and a third splitter 2466; however, any number of splitters can be used. As depicted, the first splitter 2452 can include a first slit 2454 having a first slit opening 2456 that is configured to receive a proximal end 2460 of the second splitter 2458, and the second splitter 2458 can include a second slit 2462 having a second slit opening 2464 configured to receive the proximal end 2468 of the third splitter 2466. As the proximal end 2460 of the of the second splitter 2458 contacts the first slit opening 2456, the first slit 2454 opens to receive the second splitter 2458 therein. As such, the first slit 2454 can be configured as a hole, recess, aperture, cavity, or the like. When the second splitter 2458 enters the first slit 2454, the first splitter radially expands so as to increase in size. Additionally, the second splitter 2458 and third splitter cooperate so that the second splitter 2458 expands. Moreover, as the second splitter 2458 expands, the first splitter 2452 can further expand for a larger size. Thus, the splitter 2474 can include the following: the first splitter 2452 opened so as to have a cavity 2470 receiving the second splitter 2458; and the second splitter 2458 opened so as to have a cavity 2472 receiving the third splitter 2466.

While only one embodiment of a series of splitters 2450 configured to combine and expand is illustrated, various other configurations can be used that include more than one splitter combining so as to expand or further expand the proximally disposed splitters. The splitters can be configured to be moved independently or in combination with each other by being coupled to a guidewire, tube, rod, elongate element, or the like that can be slidably disposed within a lumen or aperture of other splitters in the series.

A clip applier apparatus in accordance with the present invention can include an expandable element. An expandable element can be used in place of any of the slidable tube splitters described herein or in addition thereto. Also, an expandable element can be selectively expanded in order to split the tubes described herein. An expandable element can be selectively expanded so that a clip is expanded prior or during deployment, which can be beneficial for expanding the clip from a retaining orientation that has a narrow orthogonal cross-sectional profile. As such, an expandable element can be located at a distal end of the clip applier apparatus, which may be within the lumen of a distal end portion of a carrier tube and/or support tube, and can be selectively expanded when the clip is disposed thereon and/or being deployed therefrom.

Figure 29A:
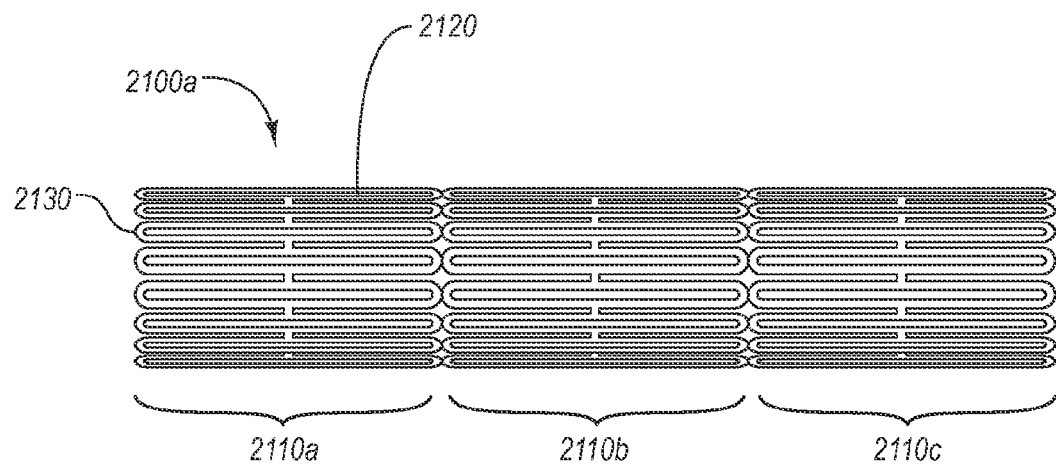
FIG. 29A illustrates an embodiment of a selectively expandable splitter in a collapsed orientation.
Figure 29B:
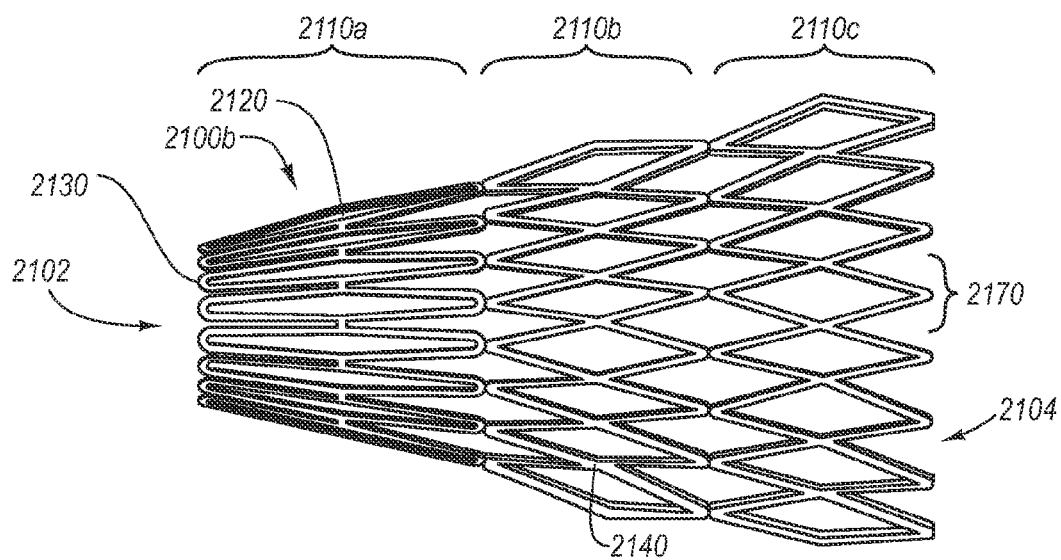
FIG. 29B illustrates the selectively expandable splitter of FIG. 29A in an expanded orientation.

FIGS. 29A-29B illustrate an embodiment of an expandable member 2100 that can be selectively expanded so that the entire expandable member or a portion thereof can be expanded. Accordingly, the expandable member 2100 can be configured to be substantially tubular in shape. The expandable member 2100 can include a plurality of annular elements 2110a-2110c that can have a plurality of crossbars 2120 that are connected together by elbows 2130 and intersections 2140. More particularly, circumferentially-adjacent crossbars 2120 can be coupled at an elbow 2130 and four or more circumferentially-adjacent crossbars 2120 can be coupled together at an intersection 2140. With this configuration, crossbars 2120, intersections 2140, and elbows 2130 can cooperate so as to form a structure 2170 that allows for flexibility as each structure 2170 can expand or collapse in order for the expandable member to be selectively expanded and/or collapsed. In the illustrated configuration, the structure 2170 has a generally diamond shape that can provide the identified flexibility to the expandable member 2100. Thus, each annular element 2110 can have a series of circumferentially-interconnected flexible structures 2170, such as, but not limited to, diamond structures, that can expand or collapse under the influence of a balloon or change of temperature.

It will be understood that structure 2170 can have other configurations while providing flexibility to the endoprosthesis 2100. For instance, structure 2170 could be replaced with a repeating "V", a repeating "U", or other structures well known in the art of stents. As such, the expandable element 2100 can be substantially similar to a stent and can have the various components and functionalities well known to be used in stents, which can allow for selective expansion from a collapsed orientation.

FIG. 29A shows the expandable element 2100a in a collapsed orientation so that the annular elements 2110a-2110c are contracted toward each other, which can be beneficial for use within a tube set of a clip applier. In the contracted position, the structure 2170 enables each of the annular elements 2110a-2110c to flex in the longitudinal, and cross directions. Also, the structure 2170 can allow for each of the first annular element 2110a, second annular element 2110b, and/or third annular element 2110c to be selectively expanded.

FIG. 29B shows the expandable member 2100b in a selectively expanded orientation so that the annular elements 2110a-c are outwardly expanded. As shown, the first annular element 2110a is partially expanded with a first end 2102 not expanding or being expanded less than a second end 2104 so as to have a substantially conical shape. Similarly, the second annular element 2110b and third annular element 2110c are selectively expanded with conical shapes. As such, the expandable member 2100b in a selectively expanded orientation can have a substantially conical shape with the proximal end 2102 (i.e., first end) being less expanded compared to the distal end 2104 (i.e., second end). In the instance the first end 2102 of the first annular element 2110a does not expand, the crossbars 2120 or elbows 2130 at the first end 2102 can be coupled together or integrally formed into a continuous annular end.

Additionally, an expandable member can be used as a tube in a tube set. This can include the entire tube being selectively expandable as described herein, or a portion of the tube having the expandable member. For example, a support tube and/or a carrier tube can have a distal portion configured as an expandable member, which can be exemplified by either of the tubes being coupled to an end of the expandable member.

Figure 30A:
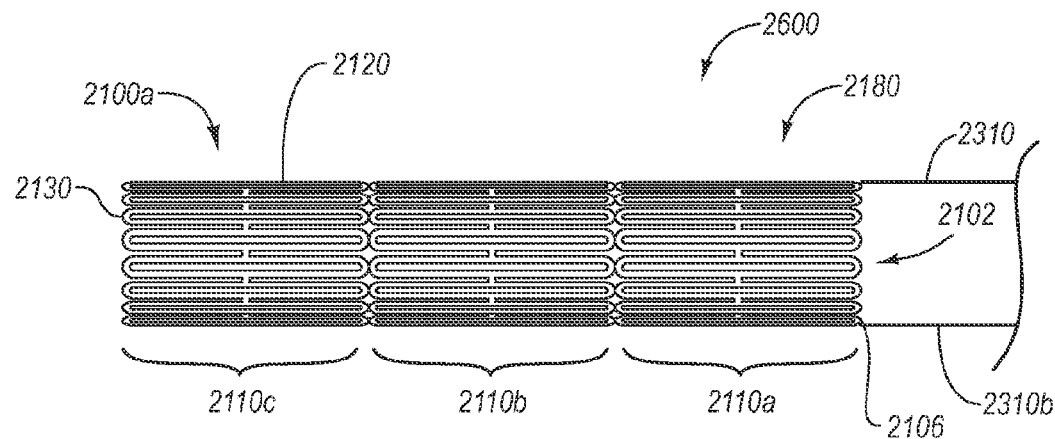
FIG. 30A illustrates an embodiment of a selectively expandable splitter member in a collapsed orientation.
Figure 30B:
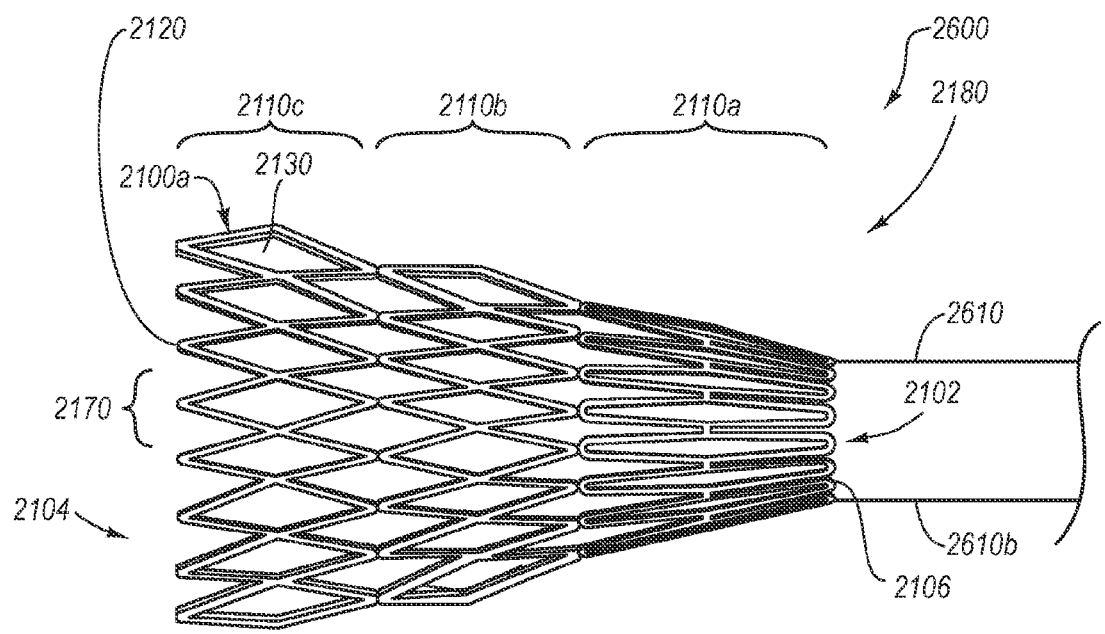
FIG. 30B illustrates the selectively expandable splitter member of FIG. 30A in an expanded orientation.

FIGS. 30A-30B show an embodiment of a selectively expandable carrier tube 2600 having a carrier tube 2310 coupled to an expandable member 2100. As such, the selectively expandable carrier tube 2180 can have any of the characteristics and elements described herein with respect to a carrier tube 2310, and can have any of the characteristics and elements described herein with respect to an expandable member 2100 (see FIGS. 29A-29B). FIG. 30A shows the selectively expandable carrier tube 2180 in a collapsed orientation, and FIG. 30B shows the selectively expandable carrier tube 2180 in a selectively expanded orientation. The selectively expandable carrier tube 2180 can be characterized by a proximal end 2102 of the expandable member 2100 being coupled to a distal portion 2610b of the carrier tube 2610 through a coupling 2106. The coupling 2106 can hold the proximal end 2102 of the expandable member 2100 so that it does not expand. This can allow for the expandable element to expand into a conical shape.

Additionally, various methods of using a clip applier having a splittable tube and splitter for delivering closure elements into tissue openings are shown in FIGS. 31A-32D. The methods can utilize embodiments of clip appliers and splitters shown in the previous figures. As such, the use of splitters in delivering a clip can be used as shown, and can have many identical or similar structures that perform identical or similar functions to the embodiments described above and in reference to the preceding figures. For example, the splitter can be configured to move proximally with respect to the carrier tube carrying the closure element by being coupled with a wire, a tube, or another element that can manipulate the orientation of the splitter with respect to the clip appliers. Accordingly, the description below should be considered in view of the descriptions above of the preceding embodiments of clip appliers and splitters and methods of using the same. Furthermore, those of ordinary skill in the art will appreciate that one or more of the uses, components, and/or features of the embodiment shown in FIGS. 31A-32D may also be incorporated in the previously described embodiments, and those components and/or features of the previously described embodiments may optionally be incorporated in the various splitter embodiments described below and in reference to FIGS. 31A-32D. While slidable splitters are depicted and described in connection with FIGS. 31A-32B, expandable splitters may be similarly used where modifications in using such expandable splitters are well within the capabilities of one of ordinary skill in the art.

Figure 31A:
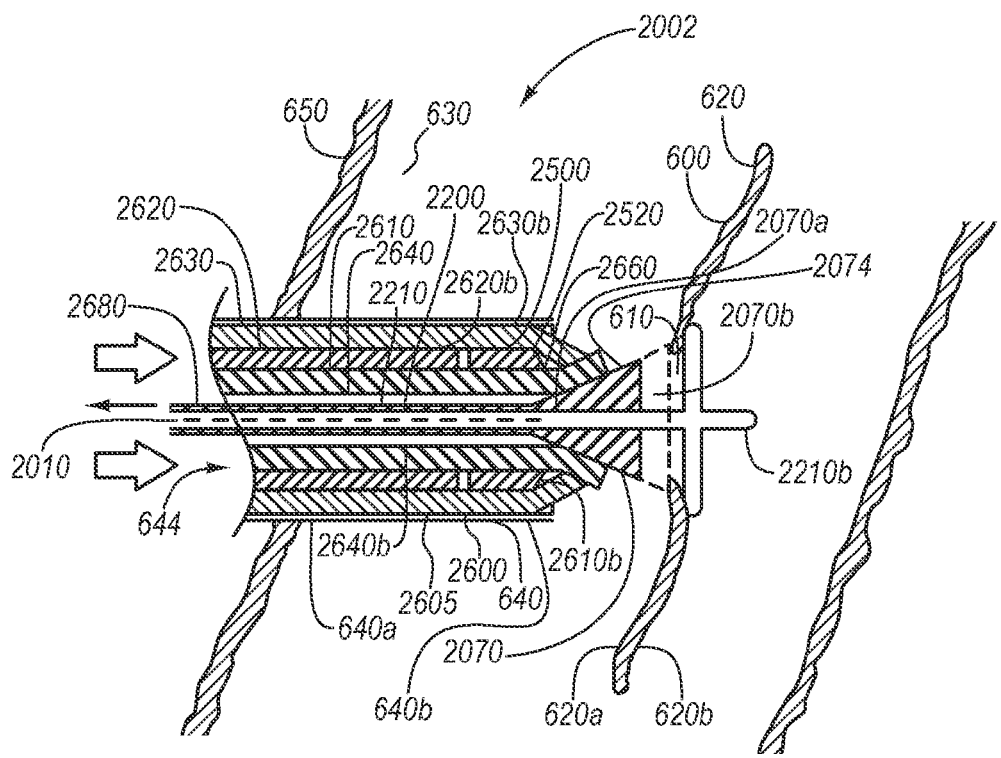
FIG. 31A illustrates one embodiment of a carrier assembly having a slidable splitter that is splitting tubular members for delivering a closure element into an opening formed in a wall of a blood vessel.

Turning to FIG. 31A, a sheath 640 may be inserted or otherwise positioned through skin 650 and tissue 630 and within the blood vessel 600 or other body lumen via the opening 610. The sheath 640 can be formed from a substantially flexible or semi-rigid tubular member. Additionally, the sheath 640 has a proximal end region 640a and a distal end region 640b and includes a predetermined length and a predetermined cross-section, both of which can be of any suitable dimension. The sheath 640 can form a lumen 644 that extends along a longitudinal axis of the sheath 640 and substantially between the proximal and distal end regions 640a, 640b. The lumen 644 can have any suitable internal cross-section and is suitable for receiving one or more devices (not shown), such as a catheter, a guide wire, locator, or the like. The lumen 644 can be configured to slidably receive the tubular body 210 of the locator assembly 200 (shown in FIG. 4A) and/or the tube set 2605 of the carrier assembly 2002 (shown in FIGS. 22A-22E).

Since the internal cross-section of the sheath 640 typically is less than or substantially equal to the predetermined outer diameter of the cover member 2630, the sheath 640 may be configured to radially expand, such as by stretching, to receive the tube set 2605. Alternatively, or in addition, the sheath 640 can be advantageously configured to split, as described in connection to the carrier tube 2610 and/or pusher tube 2620. The tube set 2605 can be received by, and advanced within, the lumen 644 of the sheath 640, thereby permitting the apparatus 2002 to access the blood vessel wall 620. To facilitate the splitting, the sheath 640 can include one or more splits (not shown), such as longitudinal splits, each split being provided in the manner known in the art. Each split can be configured to split the sheath 640 in accordance with a predetermined pattern, such as in a longitudinal, zigzag, spiral, or like pattern. It will be appreciated that, when the internal cross-section of the sheath 640 is greater than the predetermined cross-section of the cover member 2630, it may not be necessary for the sheath 640 to be configured to radially expand and/or split. In addition to, or as an alternative to, the apparatus 2002 may include a splitting means, such as a splitter 2070, which initiates a tear line or split in the sheath when the sheath is engaged with the distal end of the apparatus. The sheath 640 can be placed, deployed, and used as described herein or well known in the art.

After the sheath 640 is placed proximate to the blood vessel 600, the locator assembly 2200 can be received by the lumen 644 of the sheath 640. Being in the unexpanded state, the distal end region 2210b of the tubular body 2210 of the locator assembly 2200 can be slidably received by the lumen 644 and atraumatically advanced distally into the blood vessel 600. Once the distal end region 2210b of the tubular body 2210 can extend into the blood vessel 600, the distal end region 2210b can transition from the unexpanded state to the expanded state by activating the switching system of the locator assembly 2200.

The locator assembly 2200 and the sheath 640 can be retracted proximally until the distal end region 2210b is substantially adjacent to an inner surface 620b of the blood vessel wall 620. The distal end region 2210b can thereby draw the blood vessel wall 620 taut and maintains the proper position as the blood vessel 600 pulsates. Since the expanded cross-section of the distal end region 2210b is greater than or substantially equal to the cross-section of the opening 610 and/or the cross-section of the lumen 644, the distal end region 2210b remains in the blood vessel 600 and engages the inner surface 620b of the blood vessel wall 620. The distal end region 2210b can frictionally engage the inner surface 620b of the blood vessel wall 620, thereby securing the locator assembly 2200 to the blood vessel 600. The sheath 640 can be retracted proximally such that the distal end region 640b of the sheath 640 is substantially withdrawn from the blood vessel 600 permitting the tube set 2605 to access the blood vessel wall 620.

Once the distal end region 2210b of the locator assembly 2200 contacts the inner surface 620b of the blood vessel wall 620, the splitter tube 2680 can be advanced distally toward the outer surface 620a of the blood vessel wall 620. The splitter tube 2680 can be moved relative to the other tubes in the tube set 2605 by the support tube 2640 that is coupled to the splitter 2070. As illustrated by the dashed lines in FIGS. 31A-31B, the splitter 2070 can abut against the outer surface 620a of the vessel 620 such that the locator assembly 2200 and splitter 2070 can cooperate to hold the vessel wall 620. After the splitter 2070 is at a distal position, the other tubes in the tube set 2605 can then be advanced distally and received within the lumen 644 of the sheath.

Alternatively, the splitter tube 2680 can be coupled to the other tubes in the tube set 2605. Being coupled, the carrier tube 2610, the pusher tube 2620, the cover tube 2630, and the splitter tube 2680 each advance distally and approach the first predetermined position. The tubes in the tube set 2605 can be decoupled at any time so that any of which can be moved and positioned independently.

Upon reaching the first predetermined position, the tube set 2605 can be disposed substantially adjacent to the outer surface 620a of the blood vessel wall 620 and adjacent to the opening 610 such that the splitter 2070 and blood vessel wall 620 are disposed substantially between the expanded distal region 2210b of the locator assembly 2200 and the tube set 2605. The cover member 2630 and the splitter tube 2680 can each decouple from the carrier tube 2610 and the pusher tube 2620. Thereby, the cover tube 2630 can be inhibited from further axial movement and remain substantially stationary as the carrier tube 2610 and the pusher tube 2620 each remain coupled and axially slidable. Additionally, the splitter tube 2680 can be moved independently or with the carrier tube 2610 until placement adjacent to the vessel wall 620.

When the tube set 2605 is in the second predetermined position, the carrier tube 2610 can decouple from the pusher tube 2620. As such, the carrier tube 2610 can be advanced toward the splitter 2070 so that the proximal end 2070a of the splitter enters the lumen 2614 (FIG. 22B) of the carrier tube 2610. After the carrier tube 2610 engages with the splitter 2070, opposing movement by either element can cause the carrier tube 2610 to split. For example, moving the splitter tube 2680 or splitter 2070 proximally with respect to the carrier tube 2610 can cause the distal end 2610b of the carrier tube 2610 to move up a splitting face 2074 of the splitter 2070. Alternatively, moving the carrier tube 2610 distally towards the splitter tube 2680 or splitter 2070 can also cause the distal end 2610b of the carrier tube 2610 to move up the splitting face 2074. In some instances, such as when the splitter 2070 cooperates with the locator assembly 2200 to hold the vessel wall 620, the carrier tube 2610 can be configured to move distally with respect to the splitter tube 2680 or splitter 2070. In other instances, such as when the carrier tube 2610 is at a maximum distal location, the splitter tube 2680 can be moved proximally with respect to the carrier tube 2610.

Accordingly, the carrier tube 2610 can be split by the splitter 2070 so that the split distal end 2610b of the carrier tube 2610 expands radially or bends outwardly around the splitter 2070. This can be by the carrier tube 2610 having slits 2052 (FIG. 22B) that can separate along the lumen 2614 as the carrier tube 2610 is advanced over the splitter 2070. For example, when the carrier tube 2610 is advanced over the splitter 2070, the carrier tube 2610 can split and separate so as to form carrier flaps 2054. The carrier flaps 2054 can then carry the closure element 2500 for delivery to the blood vessel wall 620.

Figure 31B:
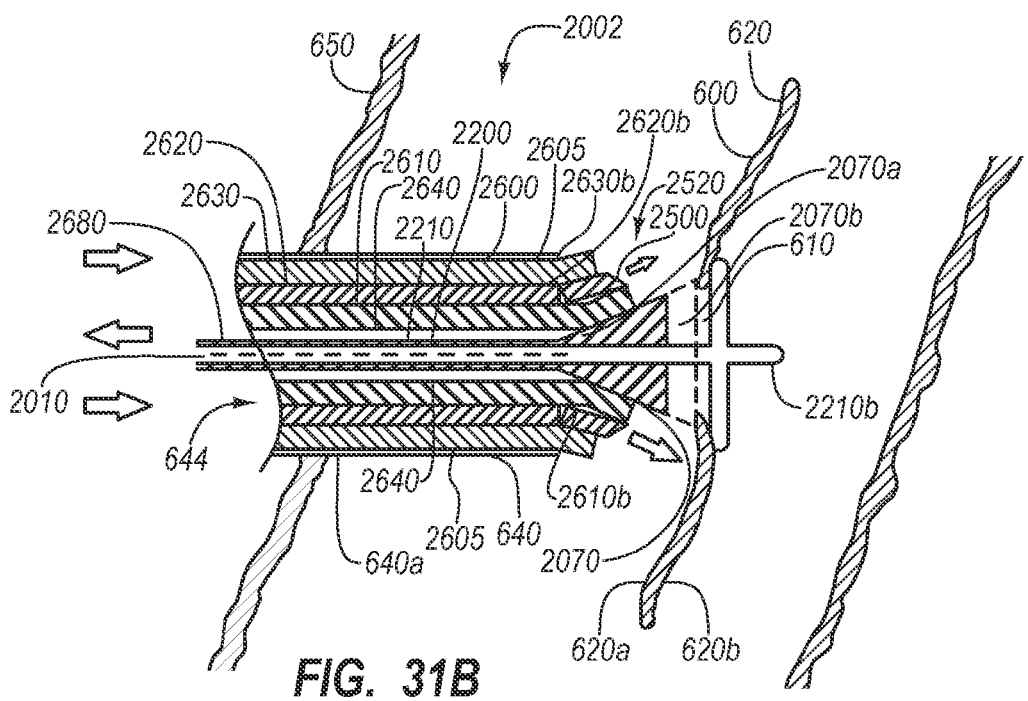
FIG. 31B illustrates the closure element of FIG. 31A being deployed over the splitter so as to be capable of engaging tissue adjacent to the opening in the blood vessel wall.

As shown in FIG. 31B, the pusher tube 2620 can engage with the closure element 2500 for delivery. After the carrier tube 2610 is split around the splitter 2070, the pusher tube 2620 can be pushed distally so that the distal end region 2620b contacts and pushes the substantially tubular closure element 2500. As such, the pusher tube 2620 can displace the substantially tubular closure element 2500 from the space 2660 and toward the blood vessel wall 620. The pusher tube 2620 can direct the substantially tubular closure element 2500 over the distally-increasing cross-section of the split distal end region 2610b of the substantially-stationary carrier member 2610 and over the splitter 2070 such that the cross-section (shown in FIGS. 6A-6G) of the substantially tubular closure element 2500 begins to radially expand in a substantially uniform manner. As the substantially tubular closure element 2500 traverses the distally-increasing cross-section of the distal end region 2610b and the splitter 2070, the cross-section of the substantially tubular closure element 2500 radially expands beyond the natural cross-section (shown in FIGS. 6A-6G) of the closure element 2500. This allows the tines 2520 to project in a more outward direction while being advanced past the splitter 2070. After passing the splitter 2070 and moving distal with respect thereto, the tines 2520 can then penetrate the blood vessel wall 620 and contract inwards, as described above in connection to other embodiments. Optionally, the pusher tube 2620 can split as shown in FIG. 22C so as to expand around the splitter 2070 and facilitate deployment of the closure element 2500.

Referring now to FIGS. 32A-32D, methods of using a guidewire splitter 2004 in accordance with the present invention will be described. The guidewire splitter 2004 can be used in conjunction with the carrier assembly 2000 depicted and described in connection with FIGS. 21A-21E.

Figures 32A, 32B:
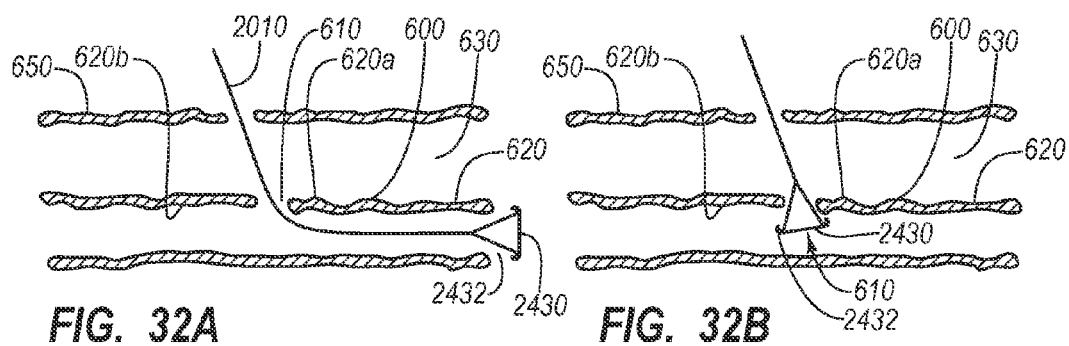
FIG. 32A is a cross-sectional side view illustrating an opening formed in a vessel, wherein a guidewire coupled with an embodiment of a tissue-grabbing splitter is shown disposed within the opening.
FIG. 32B illustrates the guidewire coupled with the tissue-grabbing splitter of FIG. 32A, wherein the splitter is shown to be grabbing tissue disposed around the opening.

Referring now to FIG. 32A, there is shown a vessel 600 disposed below a patient's tissue 630 and skin 650, wherein a guidewire 2010 is disposed through an opening 610 formed in the vessel 620 and tissue 630 as described above such that a splitter 2430 coupled to the guidewire 2010 is located within the vessel 600. The guidewire 2010 having a splitter 2430 may be introduced into the blood vessel for the sole purpose of using a splitter 2430 with the carrier assembly 2000 to deploy the closure element 2500. Alternatively, the guidewire 2010 having the splitter 2430 may have already been present from a previously completed interventional procedure. That is, the guidewire splitter 2004 can be adapted to be used in place of a standard guidewire.

Referring now to FIG. 32B, the guidewire 2010 is shown to be refracted from the vessel 600 so that the splitter 2430 interacts with the inner wall 620b of the vessel 600. As such, the splitter 2430 can be configured as a tissue-grabbing splitter by having a plurality of barbs 2432 disposed thereon (see, FIG. 27B). Accordingly, as the splitter 2430 is advanced toward the opening 610 in the vessel 600, the barbs 2432 can gather tissue from the inner wall 620b of the vessel 600, and pull such tissue toward the opening 610. After the splitter 2430 has grabbed and pulled some tissue toward the opening 610, the splitter 2430 can be used substantially similar as a locator assembly. Briefly, the splitter 2430 can be pulled taut by pulling the guidewire 2010, which can be useful for aiding in deploying the closure element as described herein.

Figure 32C:
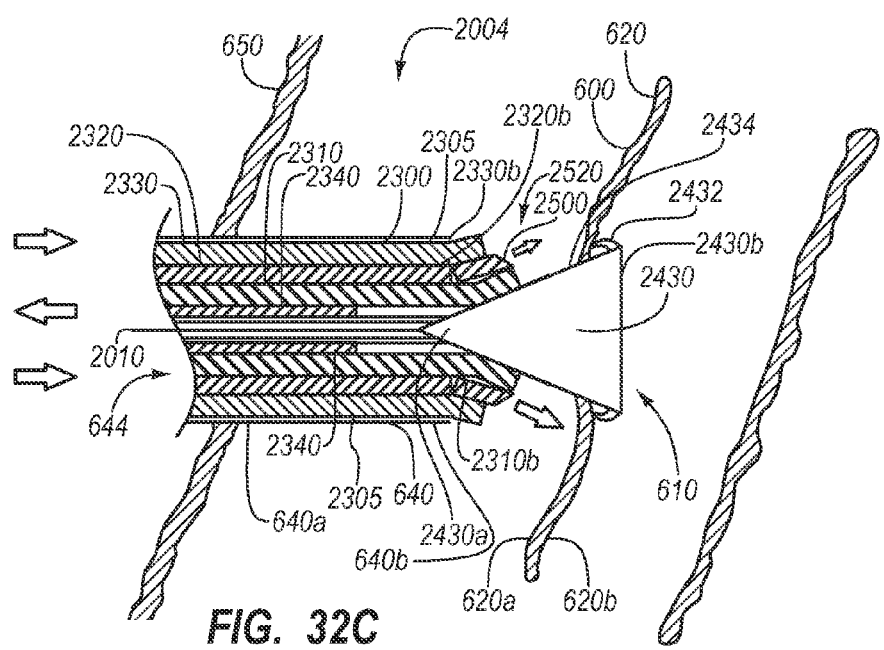
FIG. 32C illustrates an embodiment of a carrier assembly having a guide wire coupled with the tissue-grabbing splitter that is splitting tubular members for delivering a closure element over the splitter so as to be capable of engaging tissue adjacent to the opening in the blood vessel wall.

Referring now to FIG. 32C, the tube set 2305 can be positioned adjacent to the outer wall 620a of the blood vessel 600 as described herein. Briefly, the tube set 2305 can be moved distally down the guidewire 2010 toward the vessel 600. Upon reaching a first predetermined position, the tube set 2305 can be disposed substantially adjacent to the outer surface 620a of the blood vessel wall 620 and adjacent to the opening 610 such that a proximal end 2430a of the splitter 2430 can be disposed between the blood vessel wall 620 and the tube set 2305. The cover member 2330 and the support tube 2340 can each decouple from the carrier tube 2310 and the pusher tube 2320. Thereby, the cover tube 2330 and support tube 2340 can be inhibited from further axial movement and remain substantially stationary as the carrier tube 2310 and the pusher tube 2320 each remain coupled and axially slidable.

When the tube set 2305 is in a second predetermined position, carrier tube 2310 can decouple from the pusher tube 2320. As such, the carrier tube 2310 can be advanced toward the splitter 2430 so that the proximal end 2430a of the splitter 2430 enters the lumen 2314 (FIG. 21B) of the carrier tube 2310. After the carrier tube 2310 engages with the splitter 2430, opposing movement by either element can cause the carrier tube 2310 to split. For example, pulling the splitter 2430 proximally with respect to the carrier tube 2310 can cause the distal end 2310b of the carrier tube 2310 to be split by the barbs 2432 or the splitting face 2434. Alternatively, moving the carrier tube 2310 distally towards the splitter 2430, which is held taut, can also cause the distal end 2310b of the carrier tube 2310 to split and move up the splitting face 2434.

Accordingly, the carrier tube 2310 can be split by the splitter 2430 so that the split distal end 2310b of the carrier tube 2310 expands radially or bends outwardly around the splitter 2430. This can be by slits 2022 (FIG. 21B) that can separate along the lumen 2314 as the carrier tube 2310 is advanced over the splitter 2430. For example, when the carrier tube 2310 is advanced over the splitter 2430, the carrier tube 2310 can split and separate so as to form carrier flaps 2024. The carrier flaps 2024 can then carry the closure element 2500 over the splitter 2430 for delivery to the blood vessel wall 620.

Additionally, the pusher tube 2320 can engage with the closure element 2500 for delivery. After the carrier tube 2310 is split around the splitter 2430, the pusher tube 2320 can be pushed distally so that the distal end region 2320b contacts the tubular closure element 2500. As such, the pusher tube 2320 can displace the tubular closure element 2500 from the space 2360 and toward the blood vessel wall 620. To facilitate delivery of the closure element 2500, the pusher tube 2320 can split while moving over the carrier flaps 2024 of the carrier tube 2310. Since the space 2360 is substantially radially exposed, the pusher tube 2320 can direct the tubular closure element 2500 over the split distally-increasing cross-section of the split distal end region 2310b of the substantially-stationary carrier member 2310 and over the splitter 2430 such that the cross-section (shown in FIGS. 6A-6G) of the tubular closure element 2500 begins to radially expand in a substantially uniform manner. As the tubular closure element 2500 traverses the split distally-increasing cross-section of the distal end region 2310b and the splitter 2430, the cross-section of the tubular closure element 2500 radially expands beyond the natural cross-section (shown in FIGS. 6A-6G) of the closure element 2500. This allows the tines 2520 to project in a more outward direction while being advanced over the splitter 2430. After passing the splitter 2430 and moving distal with respect thereto, the tines 2520 can then penetrate the blood vessel wall 620 and contract inwards, as described above in connection to other embodiments.

Upon being directed over the distally-increasing cross-section of the distal end region 2310b by the pusher member 2320, the tubular closure element 2500 can be distally deployed. When the tubular closure element 2500 is deployed, the tines 2520 can pierce and otherwise engage a significant amount of the blood vessel wall 620 and/or tissue 630 adjacent to the opening 610. For example, the tines 2520 can engage a significant amount of the blood vessel wall 620 and/or tissue 630 because the cross-section of the tubular closure element 2500 is expanded beyond the natural cross-section of the closure element 2500 during deployment.

Figure 32D:
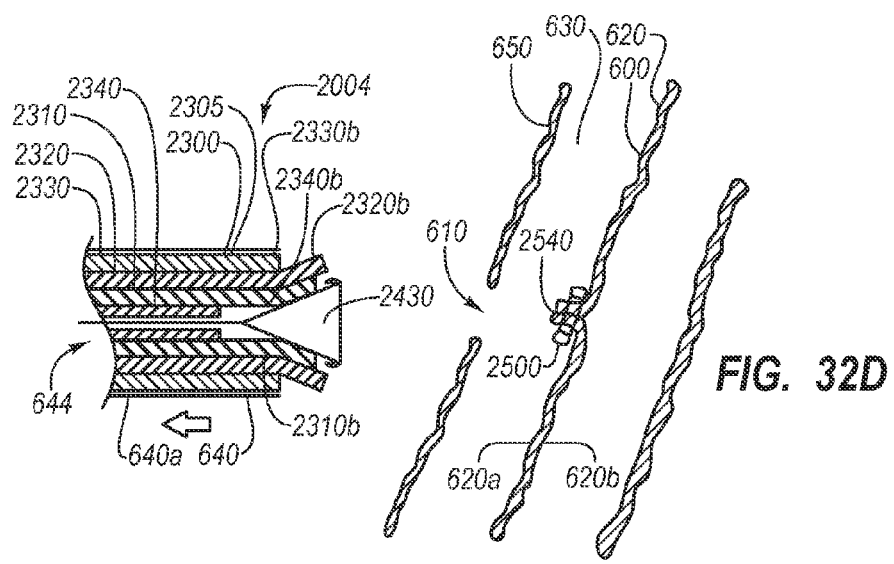
FIG. 32D illustrates the closure element of FIG. 32C drawing the engaged tissue substantially closed and/or sealed.

Turning to FIG. 32D, as the closure element 2500 is being deployed into the tissue of the vessel 600, the splitter 2430 can be pulled through the opening 610 and out of the vessel 600. As this occurs, the tissue held by the barbs 2432 can be pulled inwardly so that the tines 2520 of the closure element can penetrate the tissue further away from the opening 610. Since the cross-section of the tubular closure element 2500 is expanded beyond the natural cross-section of the closure element 2500 and the splitter 2430 has pulled tissue toward the opening, a significant amount of the blood vessel wall 620 and/or tissue can be drawn into the channel 2540 of the closure element 2500 and engaged by the tines 2520. The tines 2520 cause the closure element 2500 to revert to a substantially planar and deployed orientation. This can occur substantially simultaneously, before, or after the splitter 2430 is pulled from the opening 610.

Accordingly, closure element 2500, once deployed, transitions from the tubular orientation, returning to the natural, planar orientation with opposing tines 2520 and a natural cross-section of the closure element 2500. The closure element 2500 substantially uniformly transitions from the tubular configuration to the natural, planar orientation. Rotating axially inwardly, the tines 2520 draw the tissue into the channel 2540 as the closure element 2500 closes the opening 610. Thereby, the opening 610 in the blood vessel wall 620 can be drawn substantially closed and/or sealed via the closure element 2500 as illustrated. Also, after the closure element 2500 has been deployed into the vessel 600, the splitter 2430 can be retracted along with the tube set 2305.

Another alternative embodiment of a clip applier for sealing openings through tissue is shown in FIGS. 33A-43D. The embodiment of FIGS. 33A-43D, as described below, has many identical and/or similar structures that perform identical and/or similar functions to the embodiments described above and in reference to the preceding Figures, and associated configurations of inventions. Accordingly, the description below should be considered in view of the descriptions above of the preceding embodiments. Furthermore, those of ordinary skill in the art will appreciate that one or more of the components, functions and/or features of the embodiment shown in FIGS. 33A-43D may also be incorporated in the previously described embodiments, as those components, functions, and/or features of the previously described embodiments may optionally be incorporated in the embodiment described below and in reference to FIGS. 33A-43D.

Generally, a clip applier in accordance with the present invention can include a clip disposed therein for delivery to a tissue surrounding an opening in the tissue. The clip, which can also be referred to as a closure element, can be any type of clip that can be used to close an opening in a tissue as described herein or well known in the art. In one configuration, the clip can have a relaxed orientation that is substantially annular or a curved variation thereof. Also, the clip can have a retaining and deploying configuration that is substantially tubular and/or offset. The clip can be made of various materials, which can include, but not limited to, metals, plastics, ceramics, biodegradable materials, bioreabsorbable materials, shape memory materials, combinations thereof, and/or other materials that provide the desired characteristics of properties of the described clip. Optionally, the clip can be heat set so as to have any of the configurations described herein, which can include offset or curved configurations so as to conform with the tubular shape of the external wall of a blood vessel when deployed and relaxed. Additionally, examples of clips can be reviewed in the incorporated references.

Figure 33A:
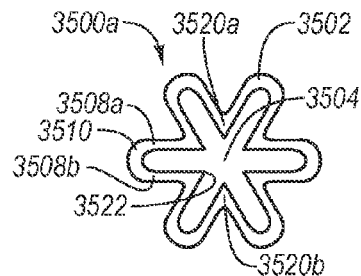
FIG. 33A is an orthogonal cross-sectional profile of a closure element in a relaxed configuration.
Figure 33B:
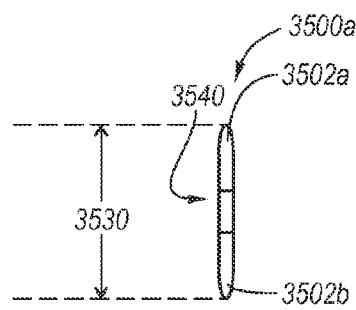
FIG. 33B is a side view of the closure element of FIG. 33A.

FIGS. 33A-33B illustrate an embodiment of a clip 3500*a* in a relaxed configuration in accordance with the present invention. As shown in FIG. 33A, the clip 3500*a* can include a body 3502 that defines central aperture 3504. Additionally, the body 3502 can include tines 3520 that are interconnected by struts 3508 and elbows 3510. The struts 3508*a-b* and elbows 3510 provide structural flexibility that allows the elbow 3510 to bend so that adjacent struts 3508*a-b* can move with respect to each other. Also, each tine 3520 can include a tip 3522 that is configured for penetrating and/or grabbing tissue. As such, oppositely disposed tines 3520*a-b* can be positioned so that tissue on opposite sides of a hole can be grabbed and/or pulled together as tine 3520*a* is drawn inwardly toward tine 3520*b*. It will be understood, however, that tine 3520*b* can move toward tine 3520*a* or a combination of movement of both tines 3520*a-b* can also operate to grab, pull, or otherwise close the opening in the tissue.

As shown in FIG. 33B, the clip 3500*a* in the relaxed configuration has a longitudinal profile 3540 that is substantially planar; however, the profile can be bent or curved so as to conform to a blood vessel as described below. Also, the clip 3500*a* in the relaxed configuration can have a dimension 3530 extending from a first body side 3502*a* to a second body side 3502*b*. The dimension 3530 can be modulated by stretching or compressing the clip 3500*a*; however, the dimension 3530 can be substantially the same when the clip 3500*a* is in the relaxed orientation before being inserted into a clip applier and after being applied to tissue in order to close an opening or hole in the tissue. That is, the clip 3500*a* can revert to having the relaxed dimension 3530 after being applied to close an opening or hole in a tissue. The clip 3500*a* can be heat set into any of a variety of relaxed shapes that the clip can return to after being deployed, such as being substantially planar, bent, curved, or offset.

Figure 34A:
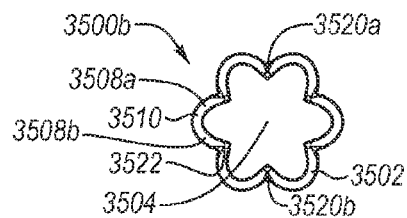
FIG. 34A is an orthogonal cross-sectional profile of the closure element of FIG. 33A in a deploying configuration.
Figure 34B:
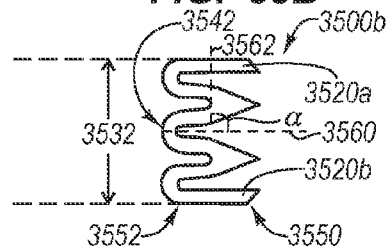
FIG. 34B is a longitudinal cross-sectional profile of the closure element of FIG. 33A in the deploying configuration.

FIGS. 34A-34B illustrate the clip 3500*a* of FIGS. 33A-33B; however, the clip 3500*b* is in a deploying configuration such as when being deployed from a clip applier. As shown in FIG. 34A, the elbows 3510 are bent such that the struts 3508*a-b*, tines 3520, and tips 3522 are substantially aligned with the body 3502. As such, the tines 3520*a-b* are no longer directed inwardly toward the aperture 3504, which opens the aperture 3504 to have a larger orthogonal cross-sectional profile. Accordingly, the clip 3500*b* in the deploying configuration positions the body 3502 to have an orthogonal cross-sectional profile that is substantially more annular or ring-like compared to the relaxed configuration. The clip 3500*a* can be heat set in a relaxed configuration different from the deploying configuration so that the clip passes from the deploying configuration to the relaxed configuration after being deployed into a blood vessel.

As shown in FIG. 34B, the clip 3500*b* in the deploying configuration positions the body 3502 so as to have a longitudinal profile 3542 that is substantially rectangular or tubular, which can be substantially not offset. That is, the clip 3500*b* has a central axis 3560 within the aperture 3504, and the body 3502 forms a tube therearound such that the aperture 3504 is a lumen of the tube that has an even or symmetrical profile. The tubular shape is formed by bending the tines 3520 from pointing inwardly, as in the relaxed configuration, to pointing substantially longitudinally and distally in the deploying configuration. Accordingly, the tines 3520 project from a proximal end 3552 of the clip 3500*b* toward a distal end 3550, which positions the tips 3522 to be at the distal end 3550. Additionally, when the clip 3500*b* is in the deploying configuration, the tines 3520*a-b* and tips 3522 are positioned substantially even with each other so that a line 3562 from any of the tines 3520*a-b* or tips 3522 is orthogonal with respect to the central axis 3560. As such, the line 3562 forms an angle α with the central axis 3560, wherein the angle α is substantially 90 degrees when the clip 3500*b* is in the deploying configuration. This can be seen by tine 3520*a* being substantially even with tine 3520*b*. Although reference is made to the angular orientation of line 3562 and central axis 3560, one skilled in the art would understand that the angular orientation of less than or greater than substantially 90 degrees is possible.

Also, the clip 3500*b* in the deploying configuration has a dimension 3532 extending from a first tine 3520*a* to a second tine 3520*b*. The dimension 3532 can be modulated by stretching or compressing the clip 3500*b*; however, the dimension 3532 can be substantially the same or different compared to instances when the clip 3500*a* is in the relaxed configuration.

Figure 35A:
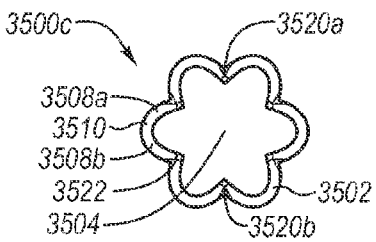
FIG. 35A is an orthogonal cross-sectional profile of the closure element of FIG. 33A in a retaining configuration.
Figure 35B:
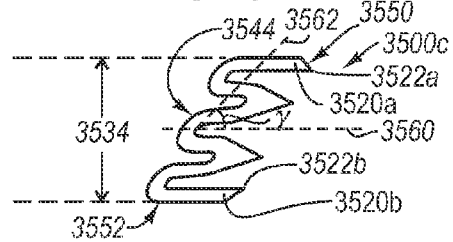
FIG. 35B is a longitudinal cross-sectional profile of the closure element of FIG. 33A in the retaining configuration.

FIGS. 35A-35B illustrate the clip 3500*a* of FIGS. 33A-33B; however, the clip 3500*c* is in a retaining configuration such as when being retained within a clip applier. As shown in FIG. 35A, the elbows 3510 are bent such that the struts 3508*a-b*, tines 3520, and tips 3522 are substantially aligned with the body 3502. As such, the tines 3520*a-b* are no longer directed inwardly toward the aperture 3504, which opens the aperture 3504 to have a larger orthogonal cross-sectional profile compared to the clip 3500a in the relaxed configuration. Accordingly, the clip 3500c in the retaining configuration can position the body 3502 to have an orthogonal cross-sectional profile that is substantially more annular or ring-like compared to the relaxed configuration. The orthogonal cross-sectional profile of the body 3502 in the retaining configuration can be smaller in at least one dimension compared to the deploying configuration.

As shown in FIG. 35B, the clip 3500c in the retaining configuration positions the body 3502 so as to have a longitudinal profile 3544 that is substantially an offset parallelogram or tubular. That is, the clip 3500c has a central axis 3560 within the aperture 3504, and the body 3502 forms an offset tube therearound such that the aperture 3504 is a lumen of the tube. The offset tubular shape (e.g., retaining configuration) can be formed by bending the tines 3520 from pointing inwardly, as in the relaxed configuration, to pointing substantially longitudinally and distally, as in the deploying configuration, and then longitudinally and distally stretching a first tine 3520a compared to a second tine 3520b. Accordingly, the first tine 3520a projects from a proximal end 3552 of the clip 3500c toward a distal end 3550 so as to be more distally located compared to the second tine 3520b. As such, the tip 3522a of the first tine 3520a can be positioned more distally compared to the tip 3522b of the second tine 3520b. Additionally, when the clip 3500c is in the retaining configuration, the tines 3520a-b and tips 3522a-b can be offset from each other. That is, the first tine 3520a and tip 3522a can be positioned more distally, and the second tine 3520b and tip 3522b can be positioned more proximally. As such, a line 3562 from any of the tines 3520a-b or tips 3522 can be offset with respect to the central axis 3560. As such, the line 3562 can form an angle γ with the central axis 3560, wherein the angle γ can be substantially less than 90 degrees when the clip 3500c is in the retaining configuration. This can be seen by tine 3520a being substantially offset with respect to tine 3520b. The clip 3500c in the retaining configuration can have various angular orientations. In this manner, the outside diameter of the clip can be reduced and so the outside diameter of the clip applier used to deploy the clip can also be reduced. In one configuration, the angle γ can be about 20 to about 70 degrees. In another configuration, the angle γ can be about 30 to about 60 degrees. In still another configuration, the angle γ can be about 50 degrees or about 45 degrees.

Optionally, the retaining configuration as described herein can also be the deploying configuration described in connection to FIGS. 33A-33B. That is, a clip 3500c in the retaining configuration can revert to the relaxed configuration without passing through the symmetrical, tubular deploying configuration of FIGS. 33A-33B, and can retain some of the offset character. As such, the clip 3500c can be heat set in a configuration similarly as shown in FIG. 33A with the exception the body 3502 is offset at an angle γ from the axis 3560, which allows the retaining configuration to also be in an offset deploying configuration.

With continued reference to FIG. 35B, the clip 3500c in the retaining configuration can have a dimension 3534 extending from a first tine 3520a to a second tine 3520b. The dimension 3534 can be modulated by stretching or compressing the clip 3500c; however, the dimension 3534 can be smaller compared to when the clip 3500a is in the relaxed configuration or when the clip 3500b is in the deploying configuration. As such, the dimension 3534 can be narrowed when retained within a clip applier so that the dimensions of the clip applier can be similarly reduced. Thus, longitudinally stretching a first tine 3520a away from the opposite second tine 3520b can facilitate the clip 3500c to have a smaller orthogonal cross-sectional profile in at least one dimension.

Figure 36A:
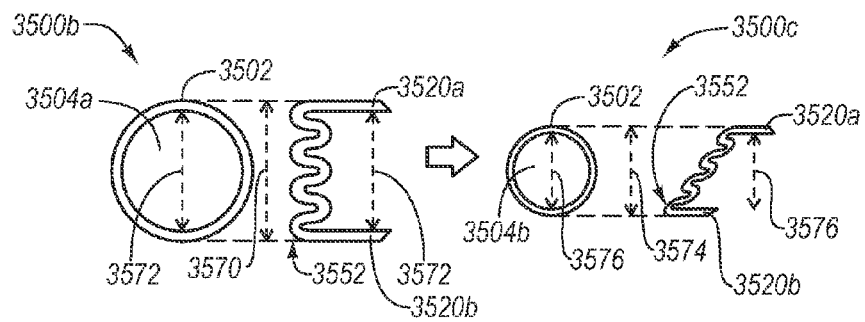
FIG. 36A is a schematic representation of a closure element decreasing when being stretched from the deploying configuration of FIGS. 34A-34B to the retaining configuration of FIGS. 35A-35B.

FIG. 36A is a schematic representation of the change in dimensions when a clip 3500b in the deploying configuration is longitudinally stretched at opposing tines 3520a-b into the clip 3500c in the retaining configuration. While the body 3502 of the clip 3500b is shown to being generally circular, the tines, struts, and elbows can skew portions of the body 3502. As such, the generally circular depiction is merely for convenience and simplicity. The body 3502 of the clip 3500b in the deploying configuration can have an outer dimension 3570, and can define an aperture 3504a that has an orthogonal cross-sectional profile with at least one inner dimension 3572. Additionally, it can be seen that the distance between the first tine 3520a and the second tine 3520b can be substantially the same as the inner dimension 3572 of the aperture 3504a.

After the clip 3500b in the deploying configuration is stretched into the clip 3500c in the retaining configuration, some of the dimensions change. As such, the body 3502 of the clip 3500c in the retaining configuration can have an outer dimension 3574 that is smaller than the outer dimension 3570 when the clip 3500b is in the deploying configuration. Additionally, the aperture 3504b defined by the body 3502 of the clip 3500c in the retaining configuration can have an inner dimension 3576 that is smaller than the dimension 3572 of the aperture 3504a of the clip 3500b in the deploying configuration. The distance between the first tine 3520a and the second tine 3520b can be substantially the same as the inner dimension 3576. The reduced outer dimension 3574 and the inner dimension 3576 of the clip 3500c in the retaining configuration can be achieved by longitudinally and distally stretching the first tine 3520a away from the second tine 3520b and/or longitudinally and proximally stretching the second tine 3520b away from the first tine 3520a. Moreover, the aperture 3504a of the clip 3500b in the deploying configuration and of the clip 3500c in the retaining configuration can be generally circular. This allows a tube in the clip applier assembly to be generally circular so that the clip 3500c can be retained therein and deployed therefrom.

Additionally, the clip 3500c can be heat set in a manner that results in the body having the offset orientation shown in FIG. 36A such that the clip 3500c does not revert to a symmetrical deploying configuration as shown by clip 3500b. That is, the clip 3500b can be stretched to be offset before the tines 3520 are extended (e.g., while still pointing inwardly toward the aperture 3504), which allows the clip 3500b to retract to an offset relaxed configuration.

Figure 36B:
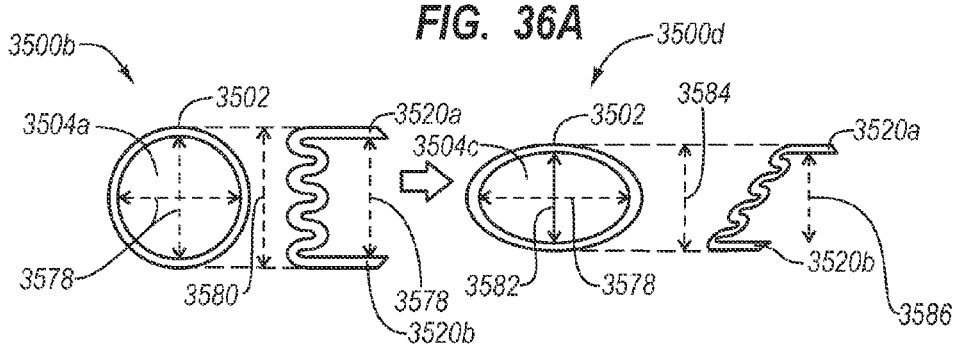
FIG. 36B is a schematic representation of a closure element changing from generally circular to generally oval when being stretched from the deploying configuration of FIGS. 34A-34B to the retaining configuration of FIGS. 35A-35B.

FIG. 36B is another schematic representation of the change in dimensions when a clip 3500b in the deploying configuration is longitudinally stretched at opposing tines 3520a-b into the clip 3500d in a generally oval retaining configuration. As before, while the body 3502 of the clip 3500b is shown to be generally circular, the tines, struts, and elbows can skew portions of the body 3502. The body 3502 of the clip 3500b in the deploying configuration can have an outer dimension 3580, and can define an aperture 3504a that has an orthogonal cross-sectional profile that is generally circular with a first inner dimension 3578 that is substantially the same as an orthogonal second inner dimension 3578. Additionally, it can be seen that the distance between the first tine 3520a and the second tine 3520b can be substantially the same as the inner dimension 3578 of the aperture 3504a.

After the clip 3500b in the deploying configuration is stretched into the clip 3500d in the generally oval retaining configuration, some of the dimensions can change. As such, the body 3502 of the clip 3500d in the generally oval retaining configuration can have an outer dimension 3584 that is smaller than the outer dimension 3580 when the clip 3500b is in the deploying configuration. Additionally, the aperture 3504c defined by the body 3502 of the clip 3500d in the generally oval retaining configuration can have a first inner dimension 3582 that is smaller than the first inner dimension 3578 of the aperture 3504a of the clip 3500b in the deploying configuration. Also, the aperture 3504c defined by the body 3502 of the clip 3500d in the generally oval retaining configuration can have a second inner dimension 3578 substantially the same as the second inner dimension 3578 of the aperture 3504a of the clip 3500b in the deploying configuration. The distance 3586 between the first tine 3520a and the second tine 3520b can be substantially the same as the smaller first inner dimension 3582 of the clip 3500d in the generally oval retaining configuration. The reduced outer dimension 3584 and the reduced inner dimension 3582 of the clip 3500d in the generally oval retaining configuration can be achieved by longitudinally and distally stretching the first tine 3520a from the second tine 3520b and/or longitudinally and proximally stretching the second tine 3520b from the first tine 3520a. Moreover, the aperture 3504c of the clip 3500d in the generally oval retaining configuration can be generally oval and narrower in one dimension compared to an orthogonal second dimension. This allows a tube in the clip applier assembly to be generally oval so that the clip 3500d can be retained therein and deployed therefrom.

Additionally, the clip 3500d can be heat set in a manner that results in the body having an oval and offset orientation shown in FIG. 36B such that the clip 3500d does not revert to a symmetrical deploying configuration as shown by clip 3500b. That is, the clip 3500d can be stretched to be oval and offset before the tines 3520 are extended (e.g., while still pointing inwardly toward the aperture 3504), which allows the clip 3500b to retract to an oval and offset relaxed configuration.

Additionally, a clip in accordance with the present invention can be reduced in size compared to previous clips. In addition to reducing the size of each component of a clip, the number of tines, struts, and elbows can be reduced so that the overall size of the clip can be smaller. For example, the clip can be configured to have two or more tines, and corresponding struts and elbows. Also, the clip can have a reduced number of tines, struts, and/or elbows so that the tines are offset, which can provide a clip having an odd number of tines.

As shown in FIG. 37A, the clip 3500e can be heat set in the relaxed configuration that has a curved longitudinal profile, which can be dimensioned to conform to the shape of an external wall of a blood vessel. Also, the clip 3500e in the curved relaxed configuration can have a dimension 3530e that defines the length of the body 3502e. The dimension 3530e can be modulated by stretching or compressing the clip 3500e or by changing the angle of the curve; however, the dimension 3530e can be substantially the same when the clip 3500e is in the curved relaxed orientation before being inserted into a clip applier and after being applied to tissue in order to close an opening or hole in the tissue. That is, the clip 3500e can revert to having the curved relaxed dimension 3530e after being applied to close an opening or hole in a tissue so that the clip 3500e has a similar shape as the blood vessel. The clip 3500e can be heat set so that the tines 3520e, which are shown by the dashed lines within the body 3502e, follow the contour or curve of the body 3520e.

As shown in FIG. 37B, the clip 3500f can be heat set in the relaxed configuration that has a curved "C" shaped longitudinal profile, which can be dimensioned to conform to the shape of an external wall of a blood vessel. Also, the clip 3500f in the "C" relaxed configuration can have a dimension 3530e that defines the length of the body 3502f. The dimension 3530e can be modulated by stretching or compressing the clip 3500f or by changing the angle of the "C" shaped curve; however, the dimension 3530f can be substantially the same when the clip 3500f is in the curved relaxed orientation before being inserted into a clip applier and after being applied to tissue in order to close an opening or hole in the tissue. That is, the clip 3500f can revert to having the "C" shaped relaxed dimension 3530f after being applied to close an opening or hole in a tissue so that the clip 3500f has a similar shape as the blood vessel. The clip 3500f can be heat set so that the tines 3520f point inwardly so as to aid in forming the "C" shape as shown.

FIG. 37C illustrates an embodiment of a clip 3500g in a retaining and deploying orientation that has been heat set in and reverts to an offset relaxed configuration as shown by 3500h so that the tines 3520 do not point towards each other. As shown, the retaining and deploying configuration of the clip 3500g has the body 3502g in an offset or angled orientation with respect to the tines 3520g such that when released, the tines 3520g return to being inwardly pointing tines 3520h while the body 3502h retains the offset or angled shape. That is, the body 3502h in the relaxed configuration is offset so as to be substantially the same as the body 3502g in the retaining and deploying configuration. Also, the tines 3520h are offset so that they do not point inwardly to the same point, which allows the inwardly pointing tines 3520h to grab different sections of tissue to be pulled toward the body 3502h in different distances so that one tine 3520h is more distal compared to a substantially opposite tine 3520h.

FIG. 37D illustrates an embodiment of a clip 3500i in a retaining and deploying orientation that has been heat set in and reverts to an offset relaxed configuration as shown by 3500j so that the tines 3520j point towards each other. As shown, the retaining and deploying configuration of the clip 3500i has the body 3502i in an offset or angled orientation with respect to the tines 3520i such that when released, the tines 3520i return to being inwardly pointing tines 3520j that point towards each other while the body 3502j retains the offset or angled shape. That is, the body 3502j in the relaxed configuration is offset so as to be substantially the same as the body 3502i in the retaining and deploying configuration.

Also, the outer dimension of a clip in the symmetrical, tubular retaining and/or deploying configuration when the clip is at about 90 degrees with respect to a central axis can be about 0.17 inch. However, the same clip in the offset or angled retaining and/or deploying orientation when the clip is at about 45 degrees with respect to the central axis can have the outer diameter reduced to about 0.12 inch. Accordingly, this can correspond with a clip at about 90 degrees with respect to the central axis having a circumference of about 13.56 mm, which is commonly referred to as 13F, and the clip at about 45 degrees with respect to the central axis can have a circumference of 1.56 mm, which is commonly referred to as 11F. Accordingly, a clip in a retaining configuration can have a smaller dimension as well as a smaller circumference when having a generally circular orthogonal cross-sectional profile or a generally oval orthogonal cross-sectional profile. Also, the orthogonal cross-sectional profile can be fixed, such as by heat setting, as oval, square, rectangular or other shape so that the clip is substantially devoid of reverting to a circular shape when relaxed, and stays in the heat set shape when relaxed. It will be understood that the above-described angular orientations and dimensions are only illustrative of certain configurations of the clip of the presently described invention. It will be understood that other angular orientations and dimensions are possible.

Turning to FIGS. 38A-38F, the carrier assembly 3000 can include a tube set 3305, including a carrier tube 3310, a pusher tube 3320, a support tube 3340, and a cover tube 3330. The carrier tube 3310, the pusher tube 3320, the support tube 3340, and the cover tube 3330 can be provided as a plurality of nested, telescoping tubes with a common longitudinal axis 3350 as illustrated in FIG. 38A. While the carrier assembly 3000 is described as including a tube set 3305, such tubes can be exchanged with other members with substantially similar functionalities as described herein. The carrier tube 3310 can be configured to receive and support the clip 3500 in an offset orientation (e.g., retaining configuration). While being disposed on the carrier tube 3310, the clip 3500 can be deformed from the natural, planar orientation (e.g., relaxed configuration) and selectively stretched to form the substantially offset-tubular shape (e.g., retaining configuration, which is shown in FIGS. 35A-35B). Being disposed substantially about and supported by an outer periphery 3312 of the carrier tube 3310, the substantially offset-tubular clip 3500 can be substantially in axial alignment with the carrier tube 3310 with the tines 3520 pointed substantially distally and parallel with the tube set 3305. Thus, the first tine 3520a being more distally disposed compared to the second tine 3520b.

As shown in FIG. 38B, the carrier tube 3310 can have a proximal end region 3310a and a distal end region 3310b. Also, the carrier tube 3310 can include a predetermined length 3318a, a predetermined outer diameter 3318b, and a predetermined inner diameter 3318c, any of which can be of any suitable dimension. In one configuration, the carrier tube 3310 can be formed as a substantially rigid, semi-rigid, or flexible tubular member; however, other suitable configurations can also be employed. However, the carrier tube 3310 can be a selectively expandable carrier as described in more detail below. The carrier tube 3310 can define a lumen 3314 that extends substantially between the proximal end region 3310a and the distal end region 3310b, and can be configured to slide relative to the other tubes in the tube set 3305. The carrier tube 3310 can have a distal end 3014 that is optionally tapered from a first portion 3014a to a second portion 3014b, which allows for releasing the clip 3500 in the substantially offset-tubular orientation. Alternatively, the distal end 3014 can be blunt as described in connection with other embodiments. Additionally, the carrier tube 3310 can include a body 3311 that is configured to radially expand.

The orthogonal cross-sectional profile of the carrier tube 3310 can be generally circular or generally oval, which can correspond to the orthogonal cross-sectional profile of the clip 3500 in the retaining configuration, but can alternatively have configurations other than generally circular or generally oval while still receiving the clip 3500. Also, the outer diameter 3318b of the carrier tube 3310 can be substantially uniform such that the distal end region 3310b of the carrier tube 3310 has an orthogonal cross-section similar to the proximal end region 3310a. However, it may be beneficial for the distal end region 3310b to be expandable or configured in such a way that the outer diameter 3318b can selectively expand or bend outwardly so that the closure element 3500 and/or tines 3520 can be outwardly oriented. This can include expanding at least the distal end of the offset-tubular closure element 3500 beyond the natural cross-section when being deployed; however, the entire closure element 3500 can be expanded with the distal end being expanded before the proximal end.

As shown in FIG. 38C, the clip 3500 can be disposed on the carrier tube 3310 in an offset tubular orientation (e.g., retaining configuration). As such, the elbows 3510 can be stretched so that the struts 3508 are separated away from each other. This allows for the first tine 3520a and first tip 3522a to be more distally oriented with respect to the second tine 3520b and second tip 3522b.

As shown in FIG. 38D, the pusher tube 3320 can be configured to distally push and/or deploy the substantially offset-tubular clip 3500. As such, the pusher tube 3320 can have a proximal end region 3320a and a distal end region 3320b and can be coupled with, and slidable relative to, the carrier tube 3310. The pusher tube 3320 can include a predetermined length 3328a, a predetermined outer diameter 3328b, and a predetermined inner diameter 3328c, any of which can be of any suitable dimension. The pusher tube 3320 can be configured to slidably receive the carrier tube 3310 such that the distal end region 3320b of the pusher tube 3320 can be offset proximally from the distal end region 3310b of the carrier tube 3310. As desired, the predetermined length 3328a of the pusher tube 3320 can be greater than or substantially equal to the predetermined length 3318a of the carrier tube 3310. The pusher tube 3320 can be positioned in the tube set 3305 with respect to the carrier tube 3310 such that the carrier tube 3310 and the pusher tube 3320 at least partially define a space 3360 distal to the distal end region 3320b of the pusher tube 3320 and along the periphery 3312 of the carrier tube 3310. The space 3360 can be configured for housing or containing the offset-tubular clip 3500.

The pusher tube 3320 can be formed from a substantially rigid, semi-rigid, or flexible material. Also, the pusher tube 3320 can be substantially tubular and have a body 3321 defining a lumen 3324 that extends substantially between the proximal end region 3320a and the distal end region 3320b. The pusher tube 3320 can be configured to slidably receive at least a portion of the carrier tube 3310 so that the inner diameter 3328c of the pusher tube 3320 is equal to or larger than the outer diameter 3318b of the carrier tube 3310. The outer diameter 3328b and/or inner diameter 3328c of the pusher tube 3320 can be substantially uniform, and have a complementary cross-sectional profile to that of the carrier tube 3310 and/or the clip 3500. For example, when the carrier tube 3310 and/or the clip 3500 have orthogonal cross-sectional profiles that are either generally circular or generally oval, the outer diameter 3328b and/or inner diameter 3328c of the pusher tube 3320 can be either generally circular or generally oval.

Also, the distal end region 3320b of the pusher tube 3320 can include one or more longitudinal extensions 3325, which extend distally from the pusher tube 3320 and along the periphery 3312 of the carrier tube. The longitudinal extensions 3325 can be configured to push the clip 3500 during deployment. As such, the longitudinal extensions can include a first extension 3325a, a second extension 3325b, and a third extension 3325c, where the first extension 3325a is more distally disposed compared to the second extension 3325b that is more distally disposed compared to the third extension 3325c. Accordingly, the extensions 3325a-c can be offset so as to facilitate deployment of an offset-tubular clip 3500. Alternatively, the extensions 3325a-c can be blunt as described in connection with other embodiments. The longitudinal extensions 3325a-c can be biased such that the longitudinal extensions 3325a-c extend generally in parallel with a common longitudinal axis 3350. The longitudinal extensions 3325a-c can be sufficiently flexible to expand radially or bend outwardly, and yet sufficiently rigid to inhibit buckling, as the distal end region 3320b is directed distally along the carrier tube 3310 and engages the substantially offset-tubular clip 3500 for deployment.

As shown in FIGS. 38A and 38E, a cover tube 3330 can be configured to retain the substantially offset-tubular clip 3500 substantially within the carrier assembly 3000 prior to deployment. Being coupled with, and slidable relative to, the pusher tube 3320, the cover tube 3330 can have a proximal end region 3330a and a distal end region 3330b. Also, the cover tube 3330 can include a predetermined length 3338a, a predetermined outer diameter 3338b, and a predetermined inner diameter 3338c, any of which can be of any suitable dimension.

The cover tube 3330 can be formed as a substantially rigid, semi-rigid, or flexible tubular member. Also, the cover tube 3330 can have an outer periphery 3332 and have a body 3331 that defines a lumen 3334. The lumen 3334 can extend substantially between the proximal and distal end regions 3330a, 3330b of the cover tube 3330, and it can be configured to slidably receive at least a portion of the pusher tube 3320 or any member of the tube set 3305. When the cover tube 3330 is properly positioned with respect to the other tubes in the tube set 3305, the distal end region 3330b can be configured to extend over the space 3360, thereby defining an annular cavity 3370 for receiving, retaining, and deploying the offset-tubular closure element 3500. The outer diameter 3338b and/or inner diameter 3338c of the cover tube 3330 can be substantially uniform along the length 3338a, or vary in dimensions as desired. Also, the cross-sectional profile of the cover tube 3330 can be complementary to any of the tubes or structures of the tube set 3305 and/or the clip 3500. For example, when tubes or structures of the tube set and/or the clip are generally circular or generally oval, the cross-sectional profile of the cover tube 3330 can be generally circular or generally oval.

Additionally, the distal end region 3330b of the cover tube 3330 can include one or more longitudinal extensions 3335, which extend distally from the cover tube 3330 and along an outer periphery 3322 of the pusher tube 3320. Although the longitudinal extensions 3335 can extend generally in parallel with a common longitudinal axis 3350, the longitudinal extensions 3335 can be biased such that the plurality of longitudinal extensions 3335 extends substantially radially inwardly. Thereby, the longitudinal extensions 3335 can at least partially close the lumen 3334 substantially adjacent to the distal end region 3330b of the cover tube 3330. To permit the substantially offset-tubular clip 3500 to be deployed from the annular cavity 3370, the longitudinal extensions 3335 can be sufficiently flexible to expand or bend radially outward so as to permit the distal end region 3310b of the carrier tube 3310 to move distally past the cover tube 3330 to open the annular cavity 3370 such that the distal end region 3330b no longer extends over the space 3360. Also, the longitudinal extensions 3335 of the cover tube 3330 can be configured substantially similar to the longitudinal extensions 3325 of the pusher tube 3320.

As shown in FIGS. 38A and 38F, the tube set 3305 can include a support tube 3340. The support tube 3340 can be configured to slidably receive a wire (e.g., guidewire), locator, or the like. Also, the support tube 3340 can provide radial support for the other tubes within the tube set 3305. The carrier assembly 3000 can advantageously include the support tube 3340, for example, to provide sufficient support to the carrier tube 3310 in the instance it is not sufficiently rigid or under other circumstances in which support for the carrier tube 3310 or other tubes in the tube set 3305 might be desirable. Also, the support tube 3340 can be configured to be expandable.

The support tube 3340 can be formed as a substantially rigid, semi-rigid, or flexible tubular member, and have a proximal end region 3340a and a distal end region 3340b. An outer periphery 3342 of the support tube 3340 can define a lumen 3344 that extends substantially between the proximal end region 3340a and the distal end region 3340b. The lumen 3344 can be configured to slidably receive and support at least a portion of a guidewire, locator, or other type of movable member disposed therein.

The support tube 3340, in turn, can be at least partially slidably disposed within the lumen 3314 of the carrier tube 3310. The support tube 3340 can have a predetermined length 3348a, a predetermined outer diameter 3348b, and a predetermined inner diameter 3348c, any of which can be of any suitable dimension. Also, the outer diameter 3348b of the support tube 3340 can be substantially uniform and smaller than inner diameter 3318c of the carrier tube 3310, and the inner diameter 3348c of the support tube 3340 can be larger than the size of the guidewire, locator, or other type of movable member disposed therein. Moreover, the support tube 3340 can have a cross-sectional profile that is complementary to other structures of the carrier assembly 3000. For instance, the support tube 3340 can have an orthogonal cross-sectional profile that is generally circular or generally oval to correspond with the orthogonal cross-sectional profile of the carrier tube 3310 and/or the clip 3500.

In the instance the carrier assembly 3000 is assembled as the plurality of nested, telescoping members as shown in FIG. 38A, the carrier tube 3310 can be at least partially disposed within, and slidable relative to, the lumen 3324 of the pusher tube 3320. The pusher tube 3320, in turn, can be at least partially disposed within, and slidable relative to, the lumen 3334 of the cover tube 3330. In the instance the carrier assembly 3000 can include a support tube 3340 as depicted, the guidewire or locator can be disposed within, and slidable relative to, the lumen 3344 of the support tube 3340. Although shown and described as being substantially separate for purposes of illustration, it will be appreciated that the carrier tube 3310, the pusher tube 3320, the cover tube 3330, and/or the support tub 3340 can be provided, in whole or in part, as one or more integrated assemblies. For example, the support tube 3340 can be combined with the carrier tube 3310.

Additionally, any of the tubes in the tube set 3305 can be made of various materials. While polymers or metals can be used, combinations of metals and polymers can also be used. For example, a tube can be prepared with nylon and reinforced with wires that run longitudinally or are spirally wrapped around the tube. Also, the tubes can be prepared from a shape memory material, such as nitinol. In the instance a carrier tube 3310 can be made of nylon and reinforced with wire or made of nitinol, a separate support tube may not be necessary.

A clip applier apparatus in accordance with the present invention can include an expandable member. An expandable member can be used in place of any of the tubes of a tube set or in addition thereto. Also, an expandable member can be selectively expanded so that a clip is expanded prior or during deployment, which can be beneficial for expanding the clip from a retaining configuration that has a narrow orthogonal cross-sectional profile. As such, an expandable member can be located at a distal end of the clip applier apparatus and can be selectively expanded when the clip is disposed thereon and/or being deployed therefrom.

Figure 39A:
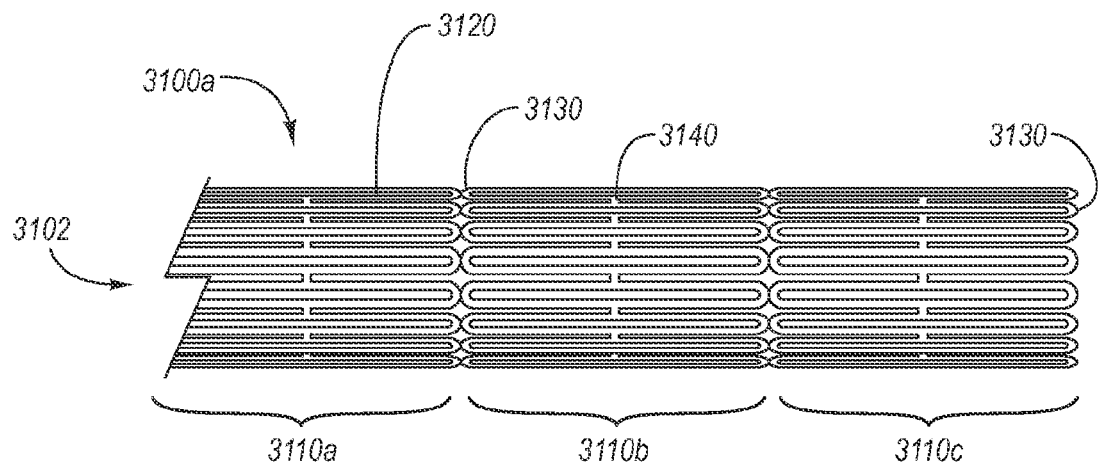
FIG. 39A illustrates one embodiment of a selectively expandable member in a collapsed orientation for retaining a closure element.
Figure 39B:
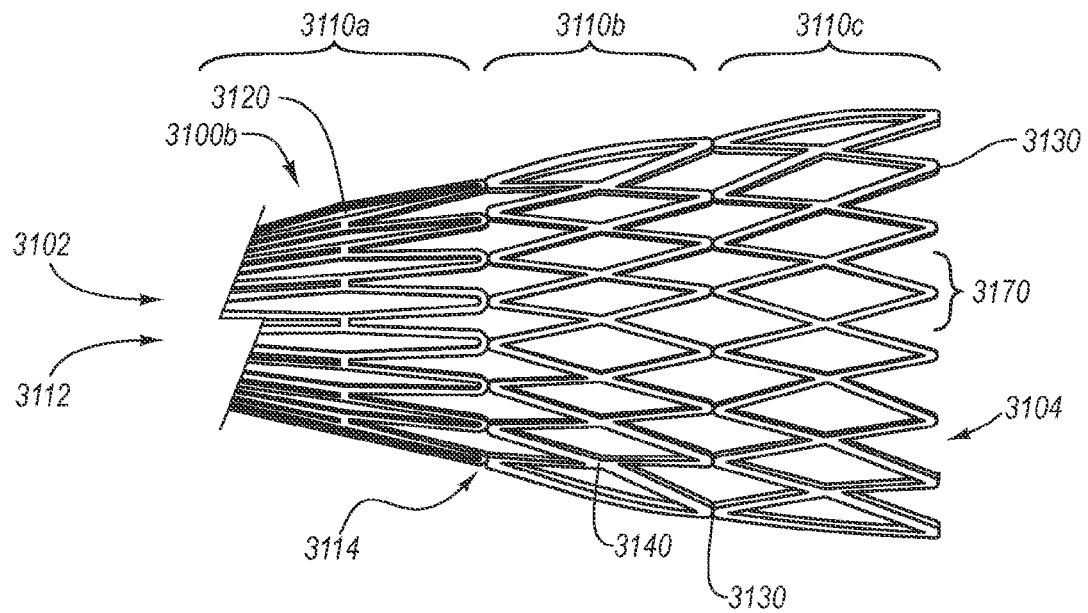
FIG. 39B illustrates one embodiment of a selectively expandable member in a selectively expanded orientation for deploying a closure element.

FIGS. 39A-39B illustrate an embodiment of an expandable member 3100 that can be selectively expanded so that the entire expandable member or a portion thereof can be expanded. Accordingly, the expandable member 3100 can be configured to be substantially tubular in shape. The expandable member 3100 can include a plurality of annular elements 3110*a-c* that can have a plurality of crossbars 3120 that are connected together by elbows 3130 and intersections 3140. More particularly, circumferentially-adjacent crossbars 3120 can be coupled at an elbow 3130 and four or more circumferentially-adjacent crossbars 3120 can be coupled together at an intersection 3140. With this configuration, crossbars 3120, intersections 3140, and elbows 3130 can cooperate so as to form a structure 3170 that allows for flexibility as each structure 3170 can expand or collapse in order for the expandable member to be selectively expanded and/or collapsed. In the illustrated configuration, the structure 3170 has a generally diamond shape that can provide the identified flexibility to the expandable member 3100. Thus, each annular element 3110 can have a series of circumferentially-interconnected flexible structures 3170, such as, but not limited to, diamond structures, that can expand or collapse under the influence of a balloon or change of temperature.

It will be understood that structure 3170 can have other configurations while providing the desired flexibility. For instance, structures 3170 could be replaced with a repeating "V", a repeating "U", or other structures well known in the art of stents. As such, the expandable member 3100 can be substantially similar to a stent and can have the various components and functionalities well known to be used in stents, which can allow for selective expansion from a collapsed orientation. Additionally, it shall be understood that the structures 3170 are sized relative to the clip, such that the clip can be moved relative to the expandable member when the expandable member is in an expanded or contracted configuration.

FIG. 39A shows the expandable member 3100*a* in a collapsed orientation so that the annular elements 3110*a-c* are contracted toward each other, which can be beneficial for use within a tube set of a clip applier.

FIG. 39B shows the expandable member 3100*b* in a selectively expanded orientation so that the annular elements 3110*a-c* are outwardly expanded. As shown, the first annular element 3110*a* is partially expanded with a first end 3112 not expanding or being expanded less than a second end 3114 so as to have a substantially conical shape. Similarly, the second annular element 3110*b* and third annular element 3110*c* are selectively expanded with conical shapes. As such, the expandable member 3100*b* in a selectively expanded orientation can have a substantially conical shape with the proximal end 3102 being less expanded compared to the distal end 3104. In the instance the first end 3112 of the first annular element 3110*a* does not expand, the crossbars 3120 or elbows 3130 at the first end 3112 can be coupled together or integrally formed into a continuous annular end.

Additionally, an expandable member can be used as a tube in a tube set. This can include the entire tube being selectively expandable as described herein, or a portion of the tube having the expandable member. For example, a support tube and/or a carrier tube can have a distal portion configured as an expandable element, which can be exemplified by either of the tubes being coupled to an end of the expandable member.

Figure 40A:
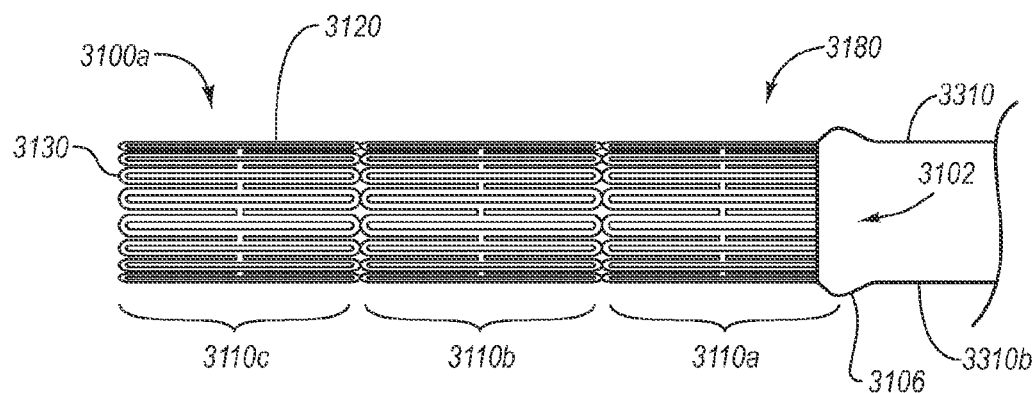
FIG. 40A illustrates one embodiment of a selectively expandable carrier tube in a collapsed orientation for retaining a closure element.
Figure 40B:
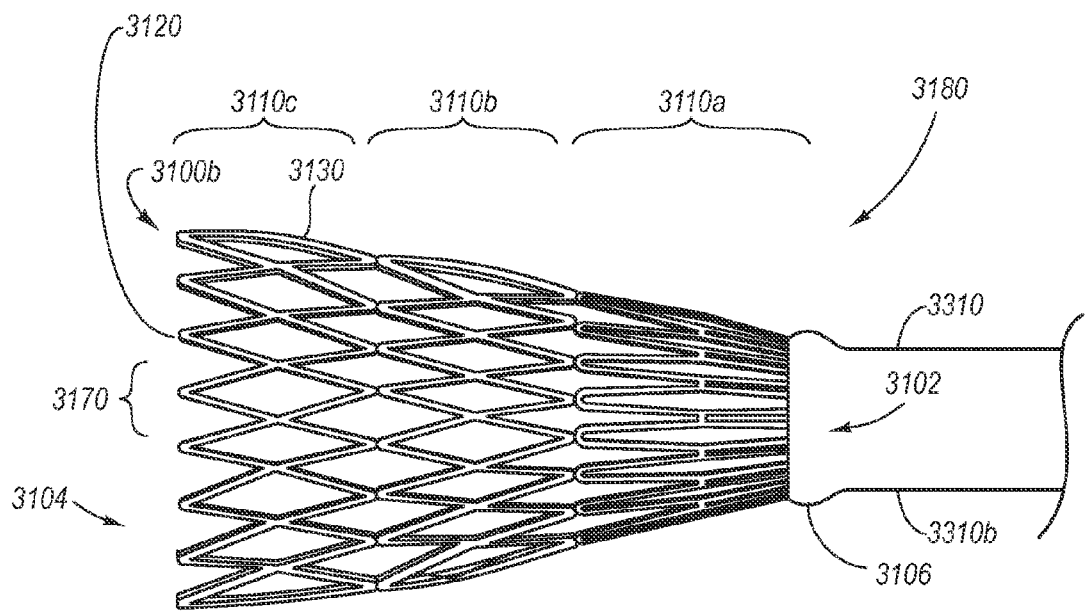
FIG. 40B illustrates one embodiment of a selectively expandable tube in a selectively expanded orientation for deploying a closure element.

FIGS. 40A-40B show an embodiment of a selectively expandable carrier tube 3180 which can include a carrier tube 3310 coupled to an expandable member 3100*a*. As such, the selectively expandable carrier tube 3180 can have any of the characteristics and elements described herein with respect to a carrier tube 3310, and can have any of the characteristics and elements described herein with respect to an expandable member 3100*a*. FIG. 40A shows the selectively expandable carrier tube 3180 in a collapsed orientation, and FIG. 40B shows the selectively expandable carrier tube 3180 having the expandable member 3100*b* in a selectively expanded orientation. The selectively expandable carrier tube 3180 can be characterized by a proximal end 3102 of the expandable member 3100*a* being coupled to a distal portion 3610*b* of the carrier tube 3610 through a coupling 3106. The coupling 3106 can hold the proximal end 3102 of the expandable member 3100*a* so that it does not expand. This can allow for the expandable element to expand into a conical shape. The coupling 3106 can be achieved through a variety of different techniques or structures. For instance and not by way of limitation, the coupling 3106 can be any of the following: (a) a distal portion 3310*b* of the carrier tube 3310 overlapping the proximal end 3102 of the expandable member 3100; (b) adhesives; (c) securing rings; (d) overlapping security sleeve; and (e) the like.

Figure 40C:
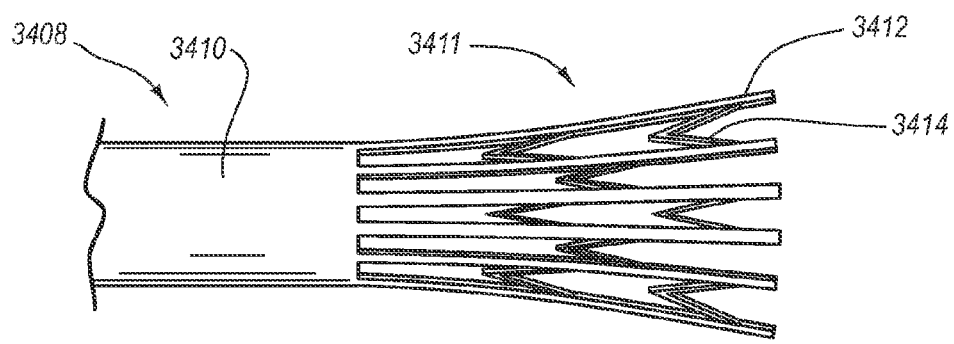
FIG. 40C illustrates one embodiment of a selectively expandable tube in a selectively expanded orientation for deploying a closure element.

FIG. 40C illustrates another embodiment of a selectively expandable carrier tube 3411 which can include a carrier tube 3408 coupled to an expandable member 3412. As such, the selectively expandable carrier tube 3411 can have any of the characteristics and elements described herein with respect to a carrier tube, and can have any of the characteristics and elements described herein with respect to an expandable member. The carrier tube 3408 includes a splittable body 3410 that can split in a predetermined pattern 3414 in order to expand as shown. Accordingly, the predetermined pattern 3414 can include elements similar to those of stents to provide support and allow for expansion of the closure element.

Another alternative embodiment of a clip applier assembly can include an expandable tube and is shown in FIGS. 41A-41F. The embodiment of FIGS. 41A-41F, as described below, can have many identical or similar structures that perform identical or similar functions to the embodiments described above and in reference to the preceding figures. Accordingly, the description below should be considered in view of the descriptions above of the preceding embodiments. Furthermore, those of ordinary skill in the art will appreciate that one or more of the components and/or features of the embodiment shown in FIGS. 41A-41F may also be incorporated in the previously described embodiments, as those components and/or features of the previously described embodiments may optionally be incorporated in the embodiment described below and in reference to FIGS. 41A-41F.

Turning to FIGS. 41A-41F, the carrier assembly 3002 can include a tube set 3605, including a selectively expandable carrier tube 3180, a pusher tube 3620, a support tube 3640, and a cover tube 3630. The expandable carrier tube 3180, the pusher tube 3620, the support tube 3640, and the cover tube 3630 can be provided as a plurality of nested, telescoping tubes with a common longitudinal axis 3650 as illustrated in FIG. 41A. While the carrier assembly 3002 is described as including a tube set 3605, such tubes can be exchanged with other members with substantially similar functionalities as described herein. The expandable carrier tube 3180 can be configured to receive and support the clip 3500 in an offset-tubular orientation (e.g., retaining configuration), and can expand the clip 3500 during deployment. While being disposed on the expandable carrier tube 3180, the clip 3500 can be deformed from the natural, planar orientation (e.g., relaxed configuration) and selectively stretched to form the substantially offset-tubular shape (e.g., retaining configuration, which is shown in FIGS. 35A-35B). Being disposed substantially about and supported by an outer periphery 3612 of the expandable carrier tube 3180, the substantially offset-tubular clip 3500 can be substantially in axial alignment with the expandable carrier tube 3180 with the tines 3520 pointed substantially distally and parallel with the tube set 3605. Thus, the first tine 3520*a* being more distally disposed compared to the second tine 3520*b*.

As shown in FIG. 41B, expandable carrier tube 3180 can include a carrier tube 3610 coupled to an expandable member 3100 through a coupling 3106, in an alternative embodiment, the expandable portion and the carrier tube portion may be formed of a unitary member. As such, the carrier tube 3610 can have a proximal end region 3610a and a distal end region 3610b coupled to a proximal end 3102 of the expandable member 3100. Optionally, the expandable member 3100 can be held in a collapsed and deployable orientation by a sheath 3109, wherein the sheath 3109 can form a part of the coupling. Further still, the expandable member may be expanded by retraction of the support tube 3640, wherein an enlarged diameter portion (not shown) is disposed on the support tube distal to the distal end of the carrier tube. In use, the support tube moves proximal relative to the carrier tube, thereby expanding the expandable portion of the carrier tube to expand the clip. The coupling 3106 can be any of the following: (a) a distal portion 3610b of the carrier tube 3610 overlapping the proximal end 3102 of the expandable member 3100; (b) adhesives; (c) securing rings; (d) overlapping security sleeve; and (e) the like. Also, the sheath can be a part of the body 3611 of the carrier tube 3610.

Additionally, the carrier tube 3610 can include a body 3611 that is configured to radially expand via expansion of the expandable member 3100 as shown by the arrows. Accordingly, the expandable carrier tube 3180 can include the elements of a carrier tube 3610 as described in connection with FIG. 38B or other carrier tube described herein, and can include the elements of an expandable member 3100 as described in connection with FIGS. 39A-39B. Also, the expandable carrier tube 3180 can be substantially as described in connection with FIGS. 40A-40C. Moreover, the cover tube 3630, pusher tube 3620, and support tube 3640 can be substantially as described in connection with FIGS. 38D-38F.

As shown in FIG. 41C, the clip 3500 can be disposed on the expandable carrier tube 3180 in an offset tubular orientation (e.g., retaining configuration). As such, the elbows 3510 can be stretched so that the struts 3508 are separated away from each other. This allows for the first tine 3520a and first tip 3522a to be more distally oriented with respect to the second tine 3520b and second tip 3522b.

As shown in FIG. 41D, the pusher tube 3620 can be configured to distally push and/or deploy the offset-tubular closure element 3500. As such, the pusher tube 3620 can have a proximal end region 3620a and a distal end region 3620b and can be coupled with, and slidable relative to, the expandable carrier tube 3180. The pusher tube 3620 can include a predetermined length 3628a, a predetermined outer diameter 3628b, and a predetermined inner diameter 3628c, any of which can be of any suitable dimension. The pusher tube 3620 can be configured to slidably receive the expandable carrier tube 3180 such that the distal end region 3620b of the pusher tube 3620 can be offset proximally from the distal end region 3610b of the expandable carrier tube 3180. As desired, the predetermined length 3628a of the pusher tube 3620 can be greater than or substantially equal to the predetermined length 3618a of the expandable carrier tube 3180. The pusher tube 3620 can be positioned in the tube set 3605 with respect to the expandable carrier tube 3180 such that the expandable carrier tube 3180 and the pusher tube 3620 at least partially define a space 3660 distal to the distal end region 3620b of the pusher tube 3620 and along the periphery 3612 of the expandable carrier tube 3180. The space 3660 can be configured for housing or containing the offset-tubular clip 3500.

The pusher tube 3620 can be formed from a substantially rigid, semi-rigid, or flexible material. Also, the pusher tube 3620 can be substantially tubular and can define a lumen 3624 that extends substantially between the proximal end region 3620a and the distal end region 3620b and that is configured to slidably receive at least a portion of the expandable carrier tube 3180 so that the inner diameter 3628c of the pusher tube 3620 is equal to or larger than the outer diameter 3618b of the expandable carrier tube 3180. The outer diameter 3628b of the pusher tube 3620 can be substantially uniform, although non-uniform diameters are also possible.

Also, the distal end region 3620b of the pusher tube 3620 can include one or more longitudinal extensions 3625, which extend distally from the pusher tube 3620 and along the periphery 3612 of the expandable carrier tube 3180. The longitudinal extensions 3625 can be configured to push the clip during deployment. As such, the longitudinal extensions can include at least a first extension 3625a, a second extension 3625b, and a third extension 3625c, where the first extension 3625a is more distally disposed compared to the second extension 3625b that is more distally disposed compared to the third extension 3625c. Accordingly, the extensions 3625a-c can be offset so as to facilitate deployment of an offset-tubular clip 3500. Alternatively, the extensions 3625a-c can be blunt as described in connection with other embodiments. The longitudinal extensions 3625a-c can be biased such that the longitudinal extensions 3625a-c extend generally in parallel with a common longitudinal axis 3650. The longitudinal extensions 3625a-c can be sufficiently flexible to expand radially or bend outwardly, and yet sufficiently rigid to inhibit buckling, as the distal end region 3620b is directed distally along the expandable carrier tube 3180 and engages the offset-tubular clip 3500 for deployment.

Additionally, the pusher tube 3620 can include a portion of a body 3621 that is configured to radially expand or bend outwardly either by stretching or by including splittable slits 3623 in the portion that can separate along the lumen 3624. The splittable slits 3623a-b can be spaced apart so as to form pushing flap ends 3626 after being split. Additionally, the splittable slits 3623 can extend at least partially down the length 3628a of the pusher tube 3620, and can be continuous, intermittent, or can include perforations. The splittable slits 3623 can also extend radially from the lumen 3624 to the outer periphery 3622. For example, when the expandable carrier tube 3180 expands so as to interact with the pusher tube 3620, the splittable slits 3623a and 3623b can split and separate so as to form the pusher flaps 3626. The pusher flaps 3626 can then retain the pushing capability so as to push the offset-tubular clip 3500 for delivery.

As shown in FIGS. 41A and 41E, a cover tube 3630 can be configured to retain the offset-tubular clip 3500 substantially within the carrier assembly 3002 prior to deployment. Being coupled with, and slidable relative to, the pusher tube 3620, the cover tube 3630 can have a proximal end region 3630a and a distal end region 3630b. Also, the cover tube 3630 can include a predetermined length 3638a, a predetermined outer diameter 3638b, and a predetermined inner diameter 3638c, any of which can be of any suitable dimension. Additionally, the cover tube 3630 can have an outer periphery 3632 and have a body 3631 that defines a lumen 3634. The cover tube 3630 can be configured substantially similarly as described in connection with FIG. 38E.

Additionally, the distal end region 3630b of the cover tube 3630 can include one or more longitudinal extensions 3635, which extend distally from the cover tube 3630 and along an outer periphery 3622 of the pusher tube 3620. Although the longitudinal extensions 3635 can extend generally in parallel with a common longitudinal axis 3650, the longitudinal extensions 3635 can be biased such that the plurality of longitudinal extensions 3635 extend substantially radially inwardly. Thereby, the longitudinal extensions 3635 can at least partially close the lumen 3634 substantially adjacent to the distal end region 3630b of the cover tube 3630. To permit the offset-tubular clip 3500 to be deployed from the annular cavity 3670, the longitudinal extensions 3635 can be sufficiently flexible to expand radially or bend outwardly so as to permit the distal end region 3610b of the carrier tube 3610 to move distally past the cover tube 3630 to open the annular cavity 3670 such that the distal end region 3630b no longer extends over the space 3660.

As shown in FIGS. 41A and 41F, the tube set 3605 can include a support tube 3640. The support tube 3640 can provide radial support for the other tubes within the tube set 3605. The carrier assembly 3002 can advantageously include the support tube 3640, for example, to provide sufficient support to the expandable carrier tube 3180 in the instance it is not sufficiently rigid or under other circumstances in which support for the expandable carrier tube 3180 or other tubes in the tube set 3605 might be desirable.

The support tube 3640 can be formed as a substantially rigid, semi-rigid, or flexible tubular member. As such, the support tube 3640 can include a proximal end region 3640a and a distal end region 3640b. The outer periphery 3642 of the support tube 3640 can define a lumen 3644 that extends substantially between the proximal end region 3640a and the distal end region 3640b. The lumen 3644 can be configured to slidably receive and support at least a portion of a wire, a locator tube, or other type of movable member disposed therein. The support tube 3640 can be at least partially slidably disposed within the lumen 3614 of the expandable carrier tube 3180.

Additionally, the support tube 3640 can have a predetermined length 3648a, a predetermined outer diameter 3648b, and a predetermined inner diameter 3648c, any of which can be of any suitable dimension. Also, the outer diameter 3648b of the support tube 3640 can be substantially uniform and smaller than inner diameter 3618c of the expandable carrier tube 3180, and the inner diameter 3648c of the support tube 3640 can be larger than the size of the wire, locator tube, or other type of member that can be disposed therein.

In another embodiment, the support tube 3640 can be configured similarly as the expandable carrier tube 3180. As such, the support tube 3640 can include an expandable member 3100. In the instance the support tube 3640 includes an expandable member 3100, the carrier tube 3610 may or may not be configured as a expandable carrier tube 3180.

In the instance the carrier assembly 3002 is assembled as the plurality of nested, telescoping members as shown in FIG. 41A, the support tube 3640 can be at least partially disposed within, and slidable relative to, the lumen 3614 of the expandable carrier tube 3180. Additionally, the expandable carrier tube 3180 can be at least partially disposed within, and slidable relative to, the lumen 3624 of the pusher tube 3620. The pusher tube 3620, in turn, can be at least partially disposed within, and slidable relative to, the lumen 3634 of the cover tube 3630. In the instance a guidewire and/or locator tube to be disposed and/or slidable within the lumen 3644 of the support tube 3640 the longitudinal axis thereof can be substantially in axial alignment with the common longitudinal axis 3650 of the expandable carrier tube 3180, the pusher tube 3620, the cover tube 3630, and/or the support tube 3640. Although shown and described as being substantially separate for purposes of illustration, it will be appreciated that the expandable carrier tube 3180, the pusher tube 3620, the cover tube 3630, and/or the splitter tube 2680 (FIGS. 22A-22E) can be provided, in whole or in part, as one or more integrated assemblies.

Additionally, various methods of using a clip applier having an offset-tubular clip to deliver the clip into tissue openings are shown in FIGS. 42A-43D. The methods can utilize embodiments of clip appliers as shown in the previous figures. As such, the use of a clip applier retaining a clip in an offset-tubular orientation and for delivering the clip can be used as shown, and can have many identical or similar structures that perform identical or similar functions to the embodiments described above and in reference to the preceding figures. For example, the carrier tube carrying the offset-tubular clip can be substantially similar to the foregoing carrier tubes and can be modified to have a shape that corresponds with the clip. Accordingly, the description below should be considered in view of the descriptions above of the preceding embodiments of clip appliers and clips and methods of using the same. Furthermore, those of ordinary skill in the art will appreciate that one or more of the uses, components, and/or features of the embodiment shown in FIGS. 42A-43D may also be incorporated in the previously described embodiments, and those components and/or features of the previously described embodiments may optionally be incorporated in the various embodiments of clip appliers, clips, and methods of use described below and in reference to FIGS. 42A-43D.

Referring now to FIGS. 42A-42E, methods of using a clip applier assembly 3000 will be described. The clip applier assembly 3000 can be substantially similar as depicted and described in connection with FIGS. 38A-38F and/or 41A-41F, and may include various other features of clip appliers as described herein. The use of the clip applier 3000 is depicted and described without the carrier tube 3310 or some other component expanding the clip 3500; however, it should be recognized that a ramped or expandable carrier tube or some other expandable component can be used to expand the clip before being inserted into tissue as described herein.

Figures 42A, 42B:
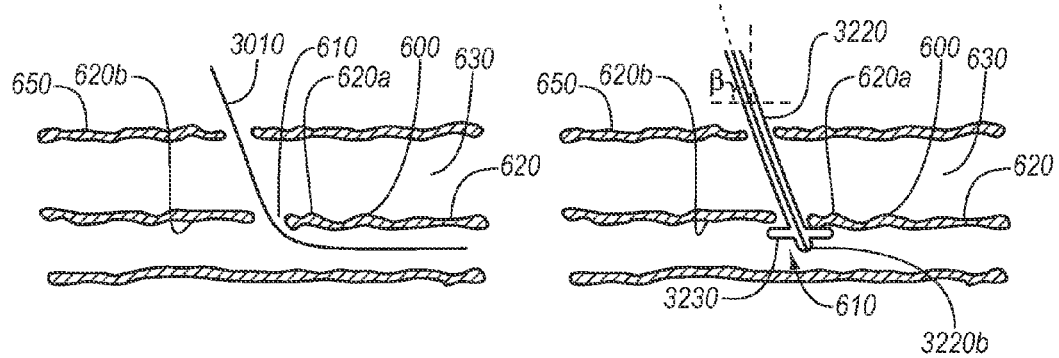

Referring now to FIG. 42A, there is shown a vessel 600 disposed below a patient's tissue 630 and skin 650, wherein a guidewire 3010 is disposed through an opening 610 formed in the vessel wall 620 and tissue 630 so that the guidewire 3010 is located within the vessel 600. The guidewire 3010 may be introduced into the blood vessel for the sole purpose of guiding the positioning of the carrier assembly 3000 to deploy an offset-tubular clip 3500. Alternatively, the guidewire 3010 may have already been present from a previously completed interventional procedure.

As shown in FIG. 42B, a locator tube 3220 can be threaded over the guidewire 3010 by inserting the proximal end of the guidewire 3010 into the central lumen of the locator tube 3220 at the distal end 3220b of the locator tube 3220, the guidewire 3010 is disposed through the device and exits at the proximal end (not shown) of the locator tube 3220. The locator tube 3220 can be advanced along the guidewire 3010 until the distal end 3220b of the locator tube 3220 is disposed through the opening 610 formed in the blood vessel wall 620. The locator tube 3220 can be oriented at an angle beta with respect to the blood vessel 620, and can be retained at about the angle beta throughout the clip deployment procedure.

Previously, such techniques have been performed with the locator being normal to the blood vessel (e.g., 90 degrees or orthogonal) during the clip deployment procedure. However, a clip applier having an offset-tubular clip can allow the locator to be inserted and retained at the angle beta, which can be about 20 to 70 degrees, more likely from about 30 to 60 degrees, even more likely from about 40 to 50 degrees, and most likely about 45 degrees. Alternatively, the device can be orientated at an angle complementary to the angle at which the puncture was made to access the vessel or lumen. Also, the angle beta can correspond with the angle the clip is offset in the carrier assembly. This can be beneficial for delivering the clip into the vessel because the tip of the tines can contact the tissue as substantially the same time. Also, routine medical techniques usually involve introducing instruments, which can include locator tubes and clip appliers, into a blood vessel at an introduction angle, such as 30 degrees. As such, the previous techniques involved orienting the locator from the introduction angle to being normal with respect to the vessel, which can damage the vessel or cause unfavorable tissue compression at the superior side of the locator by displacement of the distal end of the locator. Accordingly, inserting and retaining the locator in the vessel at the angle beta throughout a clip application procedure can minimize the amount of potential damage to the tissue and tissue compression at the superior side.

With continuing reference to FIG. 42B, the flexible and extendable members 3230 on the distal end 3220b of the locator tube 3220 can be expanded so as to transition the locator tube 3220 from the unexpanded state to the expanded state. The expandable portion may be expanded through removal of a sheath as described above, whereby the expandable portion would translate from an unexpanded configuration to an expanded configuration. Alternatively, the expandable portion may be actively expanded by proximal motion of the support tube, wherein the support tube would include an enlarged diameter portion, initially disposed distal the distal end of the expandable portion, proximal motion of the enlarged diameter portion would cause the expandable portion to translate from an unexpanded position to an expanded position. In the expanded state, the extendable members 3230 can engage the inside 620b of the vessel wall 620 at the location of the opening 610 in the blood vessel wall 620. The correct position of the device at this point may be confirmed by gently pulling on the locator tube 3220 to feel the resistance of the vessel wall against the flexible members 3230 in the expanded state. After verifying the correct position in this manner, the guidewire 3010 may be removed from the vessel 600 and from the locator tube 3220 by withdrawing the guidewire 3010 through the proximal end of the locator tube 3220.

Figures 42C, 42D:
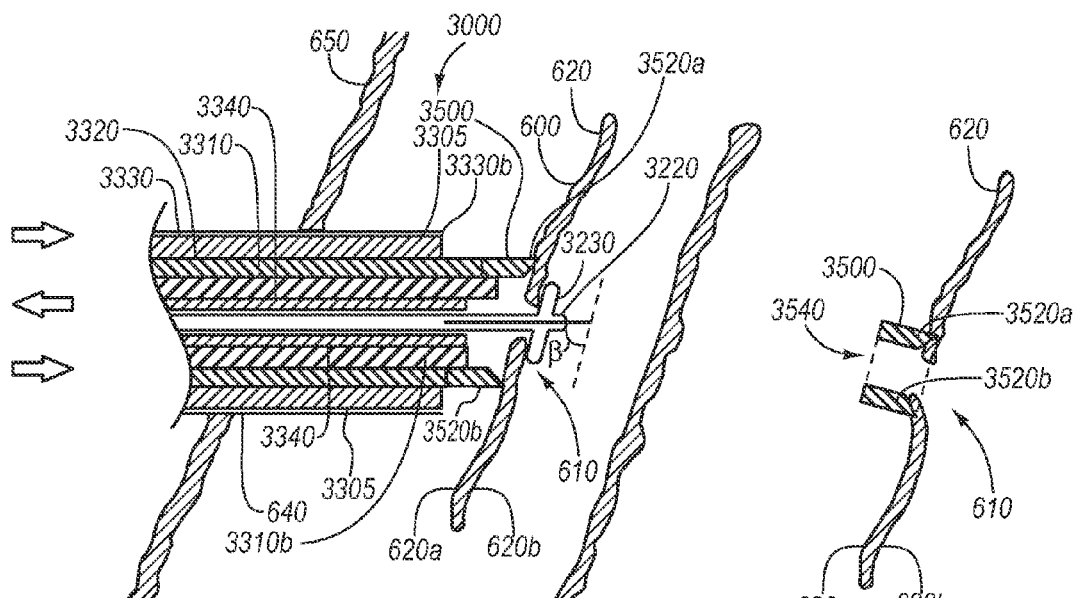

Referring now to FIG. 42C, the tube set 3305 including an expandable carrier tube 3310 can be positioned adjacent to the outer wall 620a of the blood vessel 600 as described herein. Briefly, the tube set 3305 can be moved distally down the locator tube 3220 toward the vessel 600. Upon reaching the first predetermined position, the tube set 3305 can be disposed substantially adjacent to the outer surface 620a of the blood vessel wall 620 adjacent to the opening 610. The cover member 3330 and the support tube 3340 can each decouple from the carrier tube 3310 and the pusher tube 3320. Thereby, the cover tube 3330 and support tube 3340 can be inhibited from further axial movement and remain substantially stationary as the carrier tube 3310 and the pusher tube 3320 each remain coupled and axially slidable.

Accordingly, the cover tube 3330 and the support tube 3340 can remain substantially stationary while the carrier tube 3310 and the pusher tube 3320 can continue distally and approach a second predetermined position. As the carrier tube 3310 and the pusher tube 3320 distally advance toward the second predetermined position, the distal end region 3330b of the cover tube 3330 no longer encloses the carrier tube 3310 and the pusher tube 3320. Thereby, the offset-tubular clip 3500 may not be completely enclosed by the cover tube 3330.

Although not completely enclosed, the offset-tubular clip 3500 can be advantageously retained on the outer periphery 3312 of the carrier tube 3310. For example, by retaining the offset-tubular clip 3500 on the carrier tube 3310, the clip 3500 can be positioned closer to the vessel tissue 620a surrounding the opening 610.

When the tube set 3305 is in the second predetermined position, the carrier tube 3310 can decouple from the pusher tube 3320 in the manner described in more detail above. The carrier tube 3310, the cover tube 3330, and the support tube 3340 can be inhibited from further axial movement and remain substantially stationary; whereas, the pusher tube 3320 remains axially slidable. As the pusher tube 3320 continues distally, the distal end region 3320b of the pusher tube 3320 can contact and push the offset-tubular clip 3500 to the distal end 3310b of the carrier tube 3310. As such, the pusher tube 3320 can displace the clip 3500 from the carrier tube 3310 so that it contacts the tissue 620a around the opening 610 in the vessel (as shown).

While not shown, the carrier tube 3310 can have a distally-increasing cross-section. As such, the pusher tube 3320 can direct the offset-tubular clip 3500 over the distally-increasing cross-section of the distal end region 3310b of the substantially-stationary carrier tube 3310 such that the lumen of the clip 3500 radially expands.

Upon being directed over the distal end region 3310b of the carrier tube 3310 by the pusher tube 3320, the offset-tubular clip 3500 can be distally deployed. When the clip 3500 is deployed, the tines 3520 can pierce and otherwise engage a significant amount of the blood vessel wall 620a and/or tissue 630 adjacent to the opening 610. Accordingly, the clip 3500 can be released from the carrier tube 3310 by being pushed by the pusher tube 3320.

Referring now to FIG. 42D, the clip 3500 is shown to be deployed from the carrier tube 3310. At some point in the deployment process, the clip 3500 can retract from an offset-tubular orientation (e.g., retaining configuration) to a tubular orientation that is substantially even or symmetrical about the central axis of the clip (e.g., deploying configuration). As such, the clip 3500 can retract from being offset to symmetrical so that opposing tines 3520a-b are substantially even or parallel, which is shown by the dashed lines. The clip 3500 can retract from the retaining configuration to the deploying configuration at any time during the deployment process, which can include while being deployed from the carrier tube 3310 through after being released from the carrier tube 3310. In any event, the clip 3500 can retract from the retaining configuration to the deploying configuration before closing the opening.

Figure 42E:
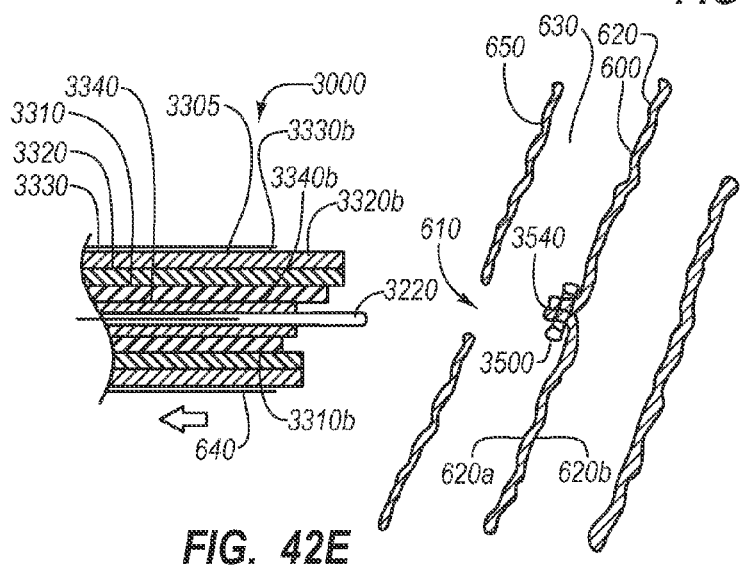

Turning to FIG. 42E, as the clip 3500 is being deployed into the tissue 620a of the vessel 620, the extendable members 3230 can collapse and the locator tube 3220 can be pulled through the opening 610 and out of the vessel 600. As this occurs, the tissue held by the tines 3520 can be pulled inwardly to close the opening 610. In this instance, the cross-section of the clip 3500 is expanded during deployment, more blood vessel wall 620a and/or tissue 630 can be drawn into the channel 3540 of the clip 3500 and engaged by the tines 3520. Also, the clip 3500 can expand when retracting from the retaining configuration to the deploying configuration so that the distance between opposing tines 3520a-b increases during delivery. In any event, the tines 3520 can engage enough of the blood vessel wall 620 and/or tissue 630 to adequately close the opening independent of whether or not the clip 3500 is expanded during delivery.

Accordingly, the clip 3500, once deployed, transitions from the offset-tubular orientation (e.g., retaining configuration; FIGS. 35A-35B) to the symmetrical orientation (e.g., deploying configuration; FIGS. 34A-34B) before returning to the natural, planar orientation (e.g., relaxed configuration; FIGS. 33A-33B) with opposing tines 3520a-b pointing inwardly. In another embodiment, the clip 3500 substantially uniformly transitions from the retaining configuration through the deploying configuration to the relaxed configuration. While rotating axially inwardly, the tines 3520 draw the blood vessel wall 620 and/or tissue 630 into the channel 3540. Thereby, the opening 610 in the blood vessel wall 620 can be drawn substantially closed and/or sealed via the clip 3500 as illustrated. Also, after the clip 3500 has been deployed into the vessel 600, the locator tube 3220 and clip applier 3000 can be refracted.

Referring now to FIGS. 43A-43D, methods of using a clip applier assembly 3002 in accordance with the present invention will be described. The clip applier assembly 3002 can be substantially similar as depicted and described in connection with FIGS. 41A-41F, and may include various other feathers of clip appliers as described herein. The use of the clip applier 3002 is depicted and described with an expandable carrier tube 3180; however, it should be recognized that another expandable element can be used in place of the expandable carrier tube 3180 to expand the clip 3500 before being inserted into tissue as described herein.

Figure 43A:
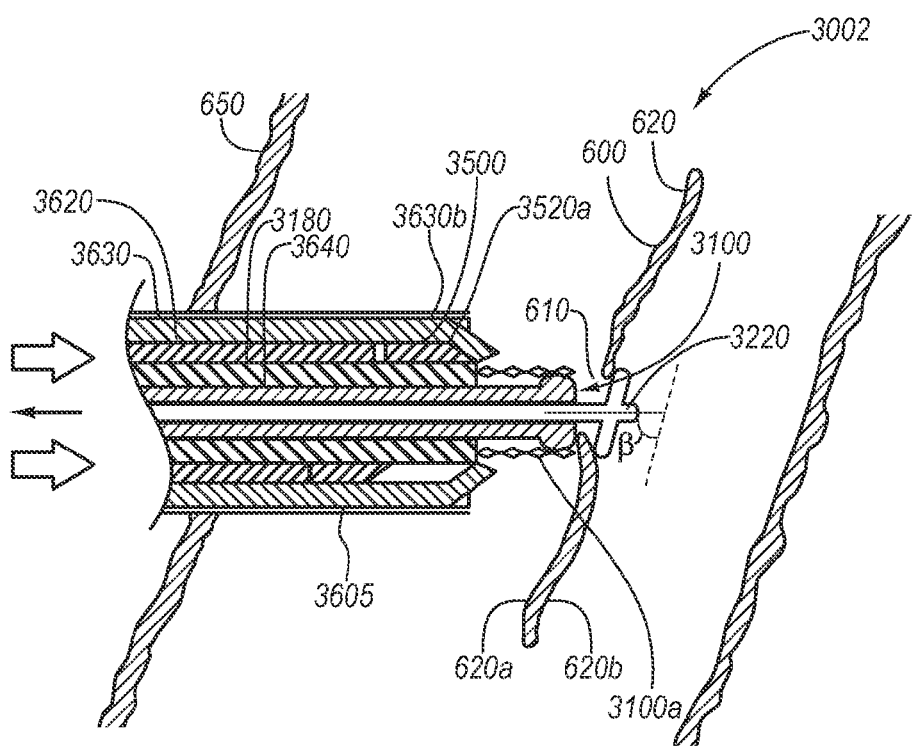
Figure 43B:
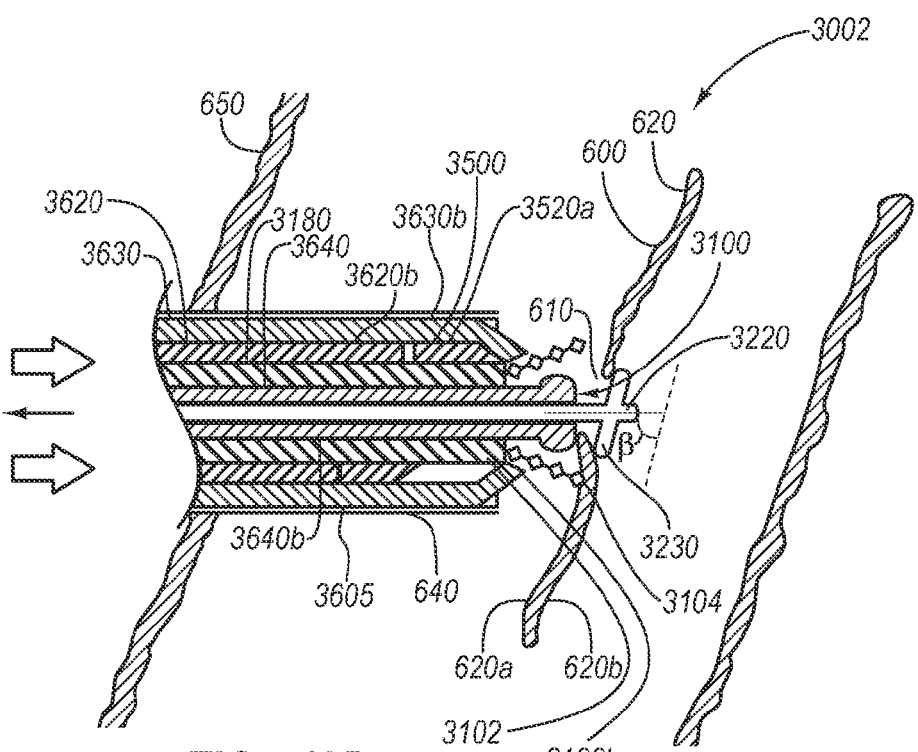
Figure 43C:
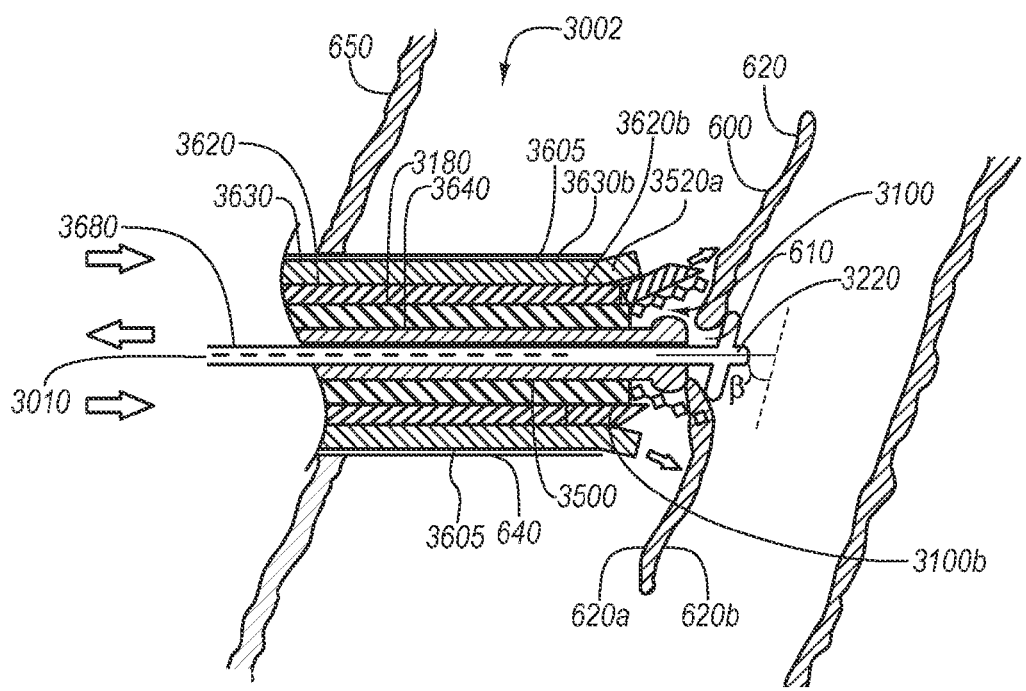
Figure 43D:
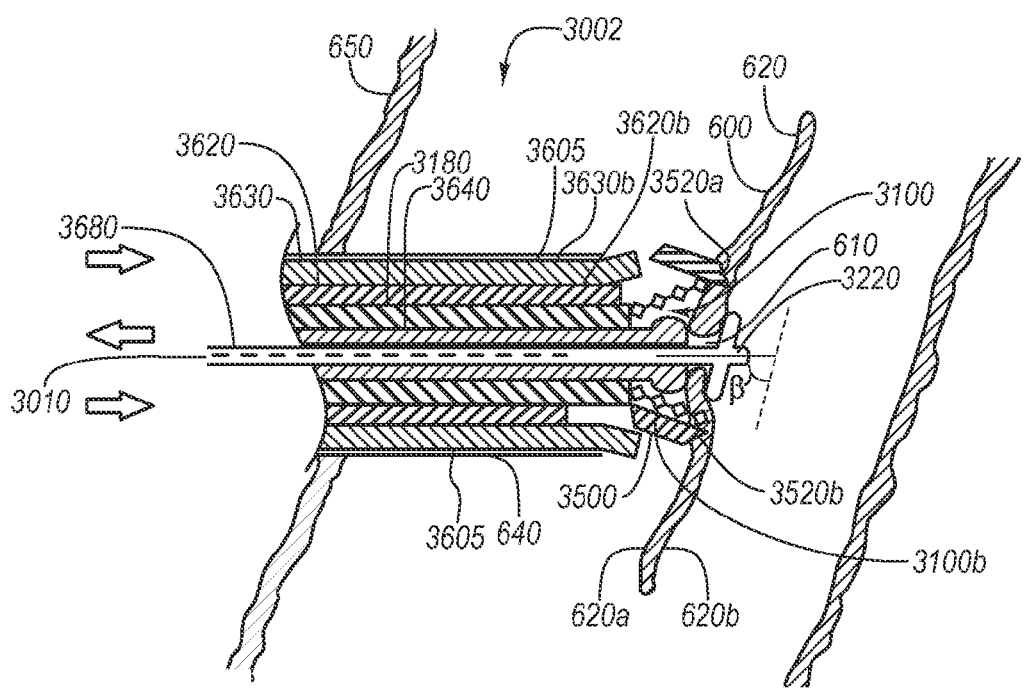

As shown in FIGS. 43C-43D, a guidewire 3010 can be inserted through an opening 610 in a vessel wall 620 so that a locator tube can be disposed therein at an angle beta with respect to the vessel 600. Accordingly, the clip applier 3002 can be placed adjacent to the vessel wall 620 at the opening 610 by being guided over the locator tube as described herein. Advantageously, the clip applier 3002 can be retained at the angle beta with respect to the vessel 600 during deployment of the clip 3500.

Referring now to FIG. 43A, the tube set 3605 including an expandable carrier tube 3180 can be positioned adjacent to the outer wall 620a of the blood vessel 620 as described herein. Briefly, the tube set 3605 can be moved distally down the locator tube 3220 toward the vessel all 620. Upon reaching the first predetermined position, the tube set 3605 can be disposed substantially adjacent to the outer surface 620a of the blood vessel wall 620 adjacent to the opening 610. The cover member 3630 and the support tube 3640 can each decouple from the expandable carrier tube 3180 and the pusher tube 3620. Thereby, the cover tube 3630 and support tube 3640 can be inhibited from further axial movement and remain substantially stationary as the expandable carrier tube 3180 and the pusher tube 3620 each remain coupled and axially slidable.

Accordingly, the cover tube 3630 and the support tube 3640 can remain substantially stationary while the expandable carrier tube 3180 and the pusher tube 3620 can continue distally and approach a second predetermined position. As the expandable carrier tube 3180 and the pusher tube 3620 distally advance toward the second predetermined position, the distal end region 3630b of the cover tube 3630 no longer encloses the expandable member 3100a of the expandable carrier tube 3180. Thereby, the offset-tubular clip 3500 may not be completely enclosed by the cover tube 3630. Although not completely enclosed, the offset-tubular clip 3500 can be advantageously retained on the outer periphery 3612 of the expandable carrier tube 3180 or on the expandable member 3100a. For example, by retaining the offset-tubular clip 3500 on the expandable carrier tube 3180 or the expandable member 3100a, the clip 3500 can be positioned closer to the vessel tissue 620a surrounding the opening 610.

When the tube set 3605 is in the second predetermined position, the expandable carrier tube 3180 can decouple from the pusher tube 3620 in the manner described in more detail above. The expandable carrier tube 3180, the cover tube 3630, and the support tube 3640 can be inhibited from further axial movement and remain substantially stationary; whereas, the pusher tube 3620 can remain axially slidable. As the pusher tube 3620 continues distally, the distal end region 3620b of the pusher tube 3620 can contact and push the offset-tubular clip 3500 to the expandable member 3100a of the expandable carrier tube 3180.

Referring now to FIG. 43B, after the tube set is in the second predetermined position the expandable member 3100 can be expanded from a collapsed orientation (3100a) to an expanded orientation (3100b). As such, the distal portion 3104 can be significantly expanded so that the expandable member 3100b has a distally-increasing orthogonal cross-sectional profile. Also, the proximal portion 3102 of the expandable member 3100b can be substantially not expanded or only minimally expanded so that the expandable member 3100b can expand the clip 3500 when being pushed over the expanded expandable member 3100b. Accordingly, the expandable member 3100b can be expanded as described in connection with FIGS. 39A-40C. Accordingly, the expandable member 3100b can be selectively expanded so that the entire length is expanded or selectively expanded so as to form a substantially conical shape as shown. The expandable member 3100b can be expanded similarly to expanding a stent, which is well known in the art. In part, the expandable member 3100b can be expanded at any time, which includes while being disposed within the cover tube 3630 or after being pushed distally past the cover tube 3630. In some instances, the expandable member 3100b can be expanded by merely being slid distally past the cover tube 3630. In other instances, the expandable member 3100b can be expanded by actuating a mechanism (not shown) that selectively expands the expandable member 3100b. In any event, expansion of the expandable member 3100b can allow the pusher tube 3620 to direct the offset-tubular clip 3500 over the distally-increasing cross-section the substantially-stationary expandable carrier tube 3180 or expandable member 3100b such that the lumen of the clip 3500 radially expands.

Referring now to FIG. 43C, the offset-tubular clip 3500 can be pushed over the expandable member 3100b by the pusher tube 3620 being pushed distally toward the blood vessel wall 620. Upon being directed over the expandable member 3100b of the expandable carrier tube 3180 by the pusher tube 3620, the offset-tubular clip 3500 can be distally deployed. As shown, the first tine 3520a can be pushed over the expandable member 3100b before the second tine 3520b. Alternatively, the offset-tubular clip 3500 can be pushed over the expandable member 3100b in a manner that allows the first tine 3520a to become substantially even or symmetrical with the second tine 3520b so as to retract from the retaining configuration to the deploying configuration. In any event, the clip 3500 can radially expand while being pushed over the expandable member 3100b by the pusher tube 3620.

Referring now to FIG. 43D, when the expanded clip 3500 is deployed from the expandable member 3100b, the tines 3520 can pierce and otherwise engage a significant amount of the blood vessel wall 620a and/or tissue 630 adjacent to the opening 610. Accordingly, the clip 3500 can be released from the expandable member 3100b by being pushed by the pusher tube 3320. As such, the pusher tube 3320 can displace the clip 3500 from the expandable carrier tube 3180 so that it contacts the tissue 620a around the opening 610 in the vessel (as shown).

At some point in the deployment process, the clip 3500 can retract from an offset-tubular orientation (e.g., retaining configuration) to a tubular orientation that is substantially even or symmetrical about the central axis of the clip (e.g., deploying configuration). As such, the clip 3500 can retract from being offset to being symmetrical so that opposing tines 3520*a-b* are substantially even or parallel, which is shown by the first tine 3520*a* and the second tine 3520*b* penetrating the tissue at approximately the same time. The clip 3500 can retract from the retaining configuration to the deploying configuration at any time during the deployment process, which can include while being deployed over the expandable member 3100*b* of the expandable carrier tube 3180 (not shown) through after being released from the expandable member 3100*b* as shown. In any event, the clip 3500 can retract from the retaining configuration to the deploying configuration before closing the opening.

Referring back to FIG. 42E, as the clip 3500 is being deployed into the tissue 620*a* of the vessel 600, the locator tube 3220 can be pulled through the opening 610 and out of the vessel 600. As this occurs, the tissue held by the tines 3520 can be pulled inwardly to close the opening 610. Additionally, the expanded cross-section of the clip 3500 can allow for more blood vessel wall 620*a* and/or tissue 630 can be drawn into the channel 3540 of the clip 3500 and engaged by the tines 3520. Also, the clip 3500 can expand when retracting from the retaining configuration to the deploying configuration so that the distance between opposing tines 3520*a-b* increases during delivery. In any event, the tines 3520 can engage enough of the blood vessel wall 620*a* and/or tissue 630 to adequately close the opening independent of whether or not the clip 3500 is expanded during delivery.

Accordingly, the offset-tubular clip 3500, once deployed, transitions from the offset-tubular orientation (e.g., retaining configuration; FIGS. 35A-35B) to the symmetrical orientation (e.g., deploying configuration; FIGS. 34A-34B) before returning to the natural, planar orientation (e.g., relaxed configuration; FIGS. 33A-33B) with opposing tines 3520*a-b* pointing inwardly. In another embodiment, the offset-tubular clip 3500 substantially uniformly transitions from the retaining configuration through the deploying configuration to the relaxed configuration. While rotating axially inwardly, the tines 3520 draw the blood vessel wall 620*a* and/or tissue 630 into the channel 3540. Thereby, the opening 610 in the blood vessel wall 620 can be drawn substantially closed and/or sealed via the clip 3500 as illustrated.

While not shown, the expandable member 3100 can be collapsed from the expanded orientation (3100*b*; FIG. 40B) to the collapsed orientation (3100*a*; FIG. 40A). However, the expandable member 3100 need not be collapsed after deployment of the clip. In any event, after the clip 3500 has been deployed into the vessel wall 620, the locator tube 3220 and clip applier 3000 can be retracted independent of whether or not the expandable member 3100 is collapsed.

The apparatus is configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus preferably is configured to substantially uniformly expand the closure element beyond a natural cross-section of the closure element such that the closure element, when deployed, is configured to engage a significant amount of the blood vessel wall and/or tissue. Engaging the blood vessel wall and/or tissue, the closure element is further configured to return to the natural cross-section. Thereby, the engaged blood vessel wall and/or tissue are drawn substantially closed and/or sealed, such that, for example, hemostasis within the opening is enhanced.

In one specific embodiment, an apparatus is provided for delivering and deploying a substantially resilient closure element through tissue to an opening in a body lumen perimeterically defined by opposing arterial walls. The closure element is configured to substantially uniformly deform from a natural, substantially resilient planar configuration to a substantially tubular configuration, having a substantially natural transverse cross-sectional dimension. The apparatus includes a delivery assembly positionable through the tissue and into the opening in the body lumen, and having a distal tissue engaging device and a carrier assembly. The carrier assembly is configured to carry and support the closure element in the substantially tubular configuration in a first diameter. The distal tissue engaging device is selectably axially displaceable relative to at least a portion of the carrier assembly between a tissue engaging condition and a tissue closing condition. In the tissue engaging condition, the opposing arterial walls of the body lumen are engaged adjacent to the opening. In contrast, in the tissue closing condition, the engaged opposing arterial walls are urged substantially transversely together such that the closure element may be deployed from the delivery assembly, while substantially maintained in the first diameter, into the opposing arterial walls. The closure element is oriented to engage the engaged opposing arterial walls when deployed and to return to the natural, substantially planar configuration and the natural, transverse cross-sectional dimension such that the engaged opposing arterial walls are drawn substantially closed.

The distal tissue engaging device includes two or more opposed engaging tongs having respective end tips configured to open radially in directions extending beyond the first diameter of the carrier assembly to initially engage the opposing arterial walls, in the engaging condition. These engaging tongs are configured to close radially inward such that the engaged opposing arterial walls are disposed within the first diameter of the closure element, in the substantially tubular configuration, in the closing condition.

In another specific embodiment, the carrier assembly includes a cover member protecting the delivery assembly such that at least the closure element is contained therein. The cover member defines a lumen configured for slidable receipt of the closure element therein. The distal tissue engaging device is integral with a distal end of the cover member to enable movement of the two or more opposing tongs between the engaging condition and the closing condition.

Still another specific arrangement provides a delivery assembly that is formed and dimensioned for sliding axial, reciprocating, receipt in a lumen of an introducer sheath extending through the tissue and terminating proximate the opening. The tissue engaging device is configured to cooperate with the introducer sheath to enable movement between the engaging condition and the closing condition. Further, the two or more tongs are formed and dimensioned for sliding contact with the sheath lumen to effect movement between the engaging condition and the closing condition.

In yet another specific embodiment, the carrier assembly includes a carrier seat configured to seat the closure element, in the substantially tubular configuration, on the delivery assembly prior to deployment. The delivery assembly includes a tubular body supporting the carrier seat, and defines a central receiving lumen extending longitudinally therethrough that is configured for sliding support of the tissue engaging device for axial movement between the engaging condition and the closing condition. Each of the two or more tongs are bowed and biased radially outward, relative one another, from a longitudinal axis of the tubular body such that an end tip of each respective tong is urged outward and toward gripping intravascular engagement with an undersurface of the opposing arterial walls, in the engaging condition, when the tissue engaging device extends distally from the central lumen of the tubular body.

In another aspect of the present invention, a closure system is provided for closing an opening formed in a body lumen perimeterically defined by opposing arterial walls. The system includes a closure element adapted to deform from a natural, substantially resilient planar configuration to a substantially tubular configuration, having a substantially natural transverse cross-sectional dimension. A delivery assembly is positionable through the tissue and into the opening in the body lumen. The delivery assembly includes an elongated body, a carrier assembly and a distal tissue engaging device. The carrier assembly includes a carrier seat configured to carry and peripherally support the closure element in the substantially tubular configuration, in a first diameter. The distal tissue engaging device is selectably axially displaceable relative to the carrier seat between the engaging condition and the closing condition, while substantially maintaining the engaged walls within the first diameter. A pusher member is slidably disposed about the elongated body for relative axial sliding displacement therebetween. The pusher member includes a contact portion disposed proximally adjacent the closure element. The pusher member is applied to selectively distally deploy the closure element from the carrier assembly, in the substantially tubular configuration, to engage the opposing arterial walls and to return to the natural, substantially planar configuration and the natural, transverse cross-sectional dimension such that the engaged opposing arterial walls are drawn substantially closed.

In yet another aspect of the present invention, a method for closing an opening perimeterically defined by edges of the arterial walls of a body lumen is provided including placing a distal end region of a locator portion through tissue into the opening; and engaging the arterial walls adjacent to the opening. The method further includes positioning a distal end region of a carrier assembly through the tissue adjacent to the opening. The carrier assembly is oriented proximal to the locator portion, and the distal end region of the carrier assembly includes a carrier seat configured to seat the closure element thereon in a substantially tubular configuration, having a first diameter. The method includes urging the engaged arterial walls radially inward and toward one another such that at least opposed edges of the arterial walls are drawn with the first diameter of the closure element. The closure element is distally deployed from the carrier assembly without further substantial radial expansion for the closure element, in the substantially tubular configuration, such that the closure element engages the arterial walls, and returns to the natural, planar configuration and the natural cross-section wherein the tissue is drawn substantially closed.

In one specific embodiment, the engaging of the arterial walls is performed by extravascularly engaging the arterial walls with a tissue engaging device. In contrast, the engaging of the arterial walls is performed by intravascularly engaging the arterial walls with a tissue engaging device.

Referring now generally to FIGS. 44-47 and 51A-51H, a clip or closure applier apparatus, generally designated 4100, is provided for delivering and deploying a closure element 4500 to an opening 4610 formed in a body lumen, such as a blood vessel 4600; the opening 4610 of which is perimeterically defined by opposing tissue arterial walls 4620', 4620" (FIG. 51A). Briefly, as shown in FIGS. 46A-46G, the closure element 4500 itself is configured to resiliently deform between a natural, substantially planar configuration (after a curing process (FIG. 46C)) to a substantially tubular configuration (FIGS. 46F and 46G). Further, the closure element can also be resiliently deformed and radially displaced up to an expanded substantially tubular configuration, having a greater cross-sectional dimension, from its natural substantially tubular configuration (FIGS. 51F and 51G), or can be displaced down to a reduced substantially tubular configuration, having a lesser cross-sectional dimension.

Returning to the clip applier apparatus 4100, in accordance with the present invention, a delivery assembly, generally designated 4200, is included that is positionable through the tissue 4630 and into the opening 4610. The delivery assembly 4200 includes a distal tissue engaging device 4400 and a carrier assembly 4300, oriented just proximal to the distal tissue engaging device, that houses and supports the closure element 4500". The carrier assembly 4300 includes a carrier seat portion 4302 configured to carry and support the closure element 4500" in a slightly expanded substantially tubular configuration (FIG. 50A-50C), in a first diameter, that is slightly greater than that in a natural, substantially tubular condition.

The distal tissue engaging device 4400 is selectably axially displaceable relative to the carrier assembly 4300 between a tissue engaging condition (FIG. 51D) and a tissue closing condition (FIG. 51F). In the tissue engaging condition, the tissue engaging device 4400 engages the opposing arterial walls 4620', 4620" (e.g., FIGS. 51D-51E) of the body vessel 4600 adjacent to the opening 4610 so that the engaged walls can be pulled or urged radially inward or transversely toward one another in the closing condition (FIGS. 51F-51G). Hence, in the closing condition, the engaging device 4400 urges the opposing arterial walls 4620', 4620" at the opening 4610, substantially closer together and toward one another radially. By closing the opposing arterial walls within the first diameter of the closure element 4500" (mounted about the carrier seat 4302 in the substantially tubular configuration), the closure element can be deployed directly there from without having to further radially expand the same to sufficiently engage the tissue.

Hence, applying a pusher member 4320 (as will be described), the closure element 4500", which is retained in the substantially tubular configuration, can be deployed into the opposing arterial walls (FIG. 51G). Subsequently, once the closure element engages the opposing arterial walls 4620', 4620" and is released from the delivery assembly, it returns to the natural, substantially planar configuration and the natural cross-section dimension such that the engaged opposing arterial walls are drawn substantially closed (FIG. 51H).

In accordance with the present invention, since the closure element 4500" can be deployed from the closure applier apparatus 4100 without requiring substantial further radial expansion from the substantially tubular configuration atop the carrier assembly, the overall complexity of the closure applier can be significantly reduced. In turn, the diametric footprint can be significantly reduced, as compared to previous designs, which in effect permit the use of a smaller diameter GF introducer sheath. Moreover, a closure applier apparatus is provided that fully encloses the closure element within itself during advancement to the tissue site, prior to deployment and delivery to the targeted vessel walls. Unlike many current designs, the present invention significantly reduces potential tissue snag or contact by the closure element during advancement and positioning. This enclosure approach is similar to those disclosed in co-pending U.S. patent application Ser. No. 11/455,993, filed Jun. 19, 2006, and entitled "APPARATUS AND METHOD FOR DELIVERING A CLOSURE ELEMENT"; and U.S. patent application Ser. No. 10/356,214, filed Jan. 30, 2003, entitled "CLIP APPLIER AND METHODS OF USE" (hereinafter referred to as the '214 patent application), each of which is herein incorporated by reference in their entirely. These designs prove much more desirable and provide a basis for a wide range of medical applications, such as diagnostic and/or therapeutic procedures involving blood vessels or other body lumens of any size.

As will be discussed in more detail below, the clip applier apparatus 4100 can deliver a closure element 4500" (shown in FIGS. 46F-G) through tissue 4630 (shown in FIG. 51A) and into an opening 4610 formed in and/or adjacent to and perimeterically defined perimeterically by the arterial walls 4620 (e.g., the opposed arterial walls 4620', 4620") of a blood vessel 4600 or other body lumen. The closure element (or clip) 4500 preferably has a generally annular-shaped body 4510 (shown in FIGS. 46A-46B) defining a channel 4540 and one or more barbs and/or tines 4520 for receiving and engaging the blood vessel wall 4620 and/or the tissue 4630 around the opening 4610. Although the closure element 4500, when originally fabricated, has a natural shape and size, the closure element 4500 can be deformed into other shapes and sizes, as desired, and is configured to return to the natural shape and size when released. For example, the closure element 4500 can have a natural, planar configuration with opposing tines 4520 and a natural cross-section 4530 as shown in FIGS. 46A-46B. Via a heat-treating process, disclosed in U.S. Pat. No. 6,623,510 to Carley et al., incorporated herein by reference in its entirety, the natural cross-section 4530 of the closure element 4500 will be reduced to form a reduced closure element 4500' that has a natural, planar configuration with opposing tines 4520 and a reduced cross-section 4530' as shown in FIGS. 46C-46D. By rotating the opposing tines 4520 axially as shown in FIG. 46E, the cured closure element 4500' can be further deformed to form a substantially tubular closure element 4500" (shown in FIG. 46F) having a generally annular-shaped body 4510' with an outer diameter 4530' and an inner diameter 4550. In this substantially tubular configuration with the tines 4520 in an axial configuration (FIG. 46G which is the configuration when loaded on the carrier assembly configuration, albeit slightly expanded), the resulting cross-section 4530' when loaded is expanded as well.

Being configured to draw the opposed blood vessel arterial walls 4620', 4620" and/or the tissue 4630 adjacent to the opening 4610 substantially closed and/or to enhance hemostasis within the opening 4610, the closure element 4500 can be formed from any suitable material, including any biodegradable material, any shape memory alloy, such as alloys of nickel-titanium, or any combination thereof. As desired, the closure element 4500 can include radiopaque markers (not shown) or can be wholly or partially formed from a radiopaque material to facilitate observation of the closure element 4500 using fluoroscopy or other imaging systems. Exemplary embodiments of a closure element are disclosed in U.S. Pat. No. 6,197,042, in co-pending application Ser. Nos. 09/546,998; 09/610,238 and 10/081,726. The disclosures of these references and any others cited therein are expressly incorporated herein by reference.

With the exception of the last specific embodiment shown in FIG. 58, the clip applier apparatus 4100 is configured to receive, retain and substantially enclose the closure element 4500" within the apparatus 4100. In the embodiments of FIGS. 44-45 and 47-58, as will be described in greater detail below, the delivery assembly 4200 includes an elongated tubular body 4210 that supports a distal tissue locator portion 4202 and the carrier seat 4302 of the carrier assembly 4300 that is disposed proximal to the locator portion. The carrier assembly 4300 further includes a cylindrical cover member or garage tube 4330 enclosing the pusher member 4320, the tubular body 4210 and the carrier seat 4302 in a nested manner within its receiving lumen 4334 until the closure element is prepared for deployment.

In each embodiment, if the apparatus 4100 is introduced via an introducer sheath 4640 (shown in FIG. 51A), for example, the closure element 4500" can be disposed entirely within the garage tube 4330, and delivered by way of the lumen 4644 (shown in FIG. 51A) of the introducer sheath 4640. Being disposed substantially within the garage tube 4330 of the clip applier apparatus 4100 just prior to deployment of the closure element 4500", the delivery assembly 4200 can deeply penetrate the tissue 4630 adjacent to the opening 4610 without inadvertently contacting or snaring it. The delivery assembly 4200 can thus position the closure element 4500" substantially adjacent to an outer surface 4620a (shown in FIG. 51A) of the blood vessel wall 4620 adjacent to the opening 4610.

Referring to the specific embodiments of FIGS. 44-45 and 47-58, each clip applier apparatus 4100 includes a central distal tissue locator portion 4202 and a carrier assembly 4300 supported on the end of, and integrated with, the tubular body 4210 of the delivery assembly 4200. Briefly, the distal locator portion 4202 is configured to facilitate location of the opening 4610 into the blood vessel 4600, relative to the carrier assembly 4300 and the tissue engaging device 4400 (e.g., FIGS. 51D and 51E).

The carrier assembly 4300, on the other hand, is configured to carry and support the closure element 4500" in the substantially tubular configuration (FIGS. 46F and 46G), albeit in a slightly expanded configuration from its natural tubular configuration. In this manner, the resiliency of the closure element 4500" itself, together with the confinement of the cover member 4330, function to secure it to the carrier seat 4302 of the carrier assembly 4300. When deployed, the closure element 4500" (in the substantially tubular configuration) is oriented with its tines directed distally to engage the blood vessel wall 4620 and/or the tissue 4630 around the opening 4610, and to return to the natural, substantially planar configuration and the natural cross-section such that the engaged tissue is drawn substantially closed (FIG. 51H).

Once strategically oriented, the clip applier apparatus 4100 can be activated to distally deploy the closure element 4500". It will be appreciated that although the closure element 4500" is capable of significantly greater radial expansion from its tubular configuration mounted to the carrier assembly 4300 of the tubular body 4210, the delivery assembly is designed to deploy the closure element 4500" directly from the carrier seat 4302 without requiring any further significant radial expansion.

The apparatus 4100 can be provided as one or more integrated components and/or discrete components. As shown in the embodiment of FIGS. 44-45 and 47-51, for example, the apparatus 4100 can include an elongated delivery assembly 4200 having an integral tissue engaging device 4400, central vessel locator (or obturator) portion 4202 and carrier assembly 4300, that carries the closure element 4500" thereon, on a single subsystem. In contrast, in the embodiments of FIGS. 52-58, the tissue engaging device 4400 is contained on a separate subsystem from the carrier assembly 4300 and the vessel locator portion 4202, all of which cooperate with one another to deploy the closure element.

In fact, in accordance with the present invention, it is the position, implementation and execution of the tissue engaging device 4400 that differentiates each embodiment. In one specific embodiment, for example, the tissue engaging device 4400 is disposed on the distal end to the cover member 4330 (FIGS. 44-45, and 47-51), where it is selectively operated between the tissue engaging condition (FIGS. 51D, 51E) and the closing condition (FIGS. 51F, 51G). In contrast, in the embodiments of FIGS. 52-58, the tissue engaging device 4400 is disposed within a central lumen 4204 of the tissue locator portion 4202, and is selectively operated as it is distally advanced from the lumen. It will be appreciated that these differing implementations of the tissue engaging devices will each be detailed separately below.

In each implementations, however, the tissue engaging device 4400 is capable of gripping, snaring and/or piercing the tissue arterial walls 4620, and urging them together and radially inward, toward one another, such that portions of the arterial walls 4620', 4620" are axially contained within the first diameter of the closure element 4500", in the substantially tubular configuration. As mentioned, this arrangement enables the deployment of the closure element 4500" directly from the carrier seat 4302 of the carrier assembly 4300 without requiring further radial expansion.

Referring back to FIGS. 47-51, the first specific embodiment will be described in detail. In this particular arrangement, the distal tissue locator portion 4202 (obturator) is configured to extend into the opening 4610 and selectably engage an inner surface 4620b of the blood vessel wall 4620 (FIG. 51D). Thereby, the distal locator portion 4202 is configured to draw the blood vessel wall 4620 taut, and maintain the proper position of the clip applier apparatus 4100 as the blood vessel 4600 pulsates. Briefly, in cooperation with the tissue engaging device 4400 oriented at the distal end of the cover member 4330, once the distal locator portion 4202 is properly aligned and positioned, the tissue engaging device can be operated to engage the arterial walls, drawing them radially together as will be described below.

First, the delivery assembly 4200 of this embodiment will be detailed which includes the tubular body 4210, the carrier assembly 4300 and the distal locator portion 4202 integrated on a single subsystem. The tubular body 4210 is preferably provided by a flexible, semi-rigid or rigid, tubular structure, such as an elongate rail, with a longitudinal axis 4216. As illustrated in FIGS. 45 and 47A, the tubular body 4210 has a proximal end region 4210a and a distal end region 4210b that supports the carrier seat 4302 of the carrier assembly 4300 just proximal to the distal locator portion 4202.

The tubular body 4210 is preferably of a predetermined length 4218a and a predetermined outer cross-section 4218b (FIG. 45), both of which can be of any suitable dimension. The distal section of the distal locator portion 4202 preferably includes a substantially rounded, soft, and/or flexible distal end or tip 4220 to facilitate atraumatic advancement and/or retraction of the distal section into the blood vessel 4600. As desired, a pigtail (not shown) may be provided on the distal end 4220 to further aid atraumatic advancement of the delivery assembly 4200.

Turning now to FIGS. 47A and 47B, it will be appreciated that the distal locator portion 4202 functions in a manner similar to those disclosed in co-pending application Ser. Nos. 09/732,835 and 10/081,723, the disclosure of which is expressly incorporated herein by reference. That is, the distal locator portion 4202 is selectably controllable between an unexpanded state (FIG. 47A) and an expanded state (FIG. 47B). In the unexpanded state, the distal locator portion 4202 has an unexpanded size; whereas, in the expanded state, it has an expanded size, which is greater than the unexpanded size in the unexpanded state. The distal locator portion 4202 is configured to expand from the unexpanded size to the expanded size and/or to contract from the expanded size to the unexpanded size, and the expansion and contraction of the distal locator portion 4202 preferably is substantially uniform about the longitudinal axis 4216. For example, one or more expansion elements 4230 can be provided on the distal locator portion 4202 and can be configured to expand substantially transversely with respect to a longitudinal axis 4216 of the locator portion 4202. Preferably being substantially equally distributed about an outer periphery 4212 of the distal locator portion 4202, the expansion elements 4230 may include radiopaque markers (not shown) or may be wholly or partially formed from a radiopaque material to facilitate observation of the expansion elements 4230 and/or the distal locator portion 4202 using fluoroscopy or other imaging systems.

At least one, and preferably all, of the expansion elements 4230 of the distal locator portion 4202 can comprise a substantially flexible member 4230' with a substantially fixed end region 4230a', an intermediate region 4230b', and a movable end region 4230c' as shown in FIGS. 47A-47B. For each substantially flexible member 4230', the proximal fixed end region 4230a' is fixedly coupled, relatively, with an intermediary support region 4211 separating the distal locator portion 4202 from the carrier assembly 4300. In contrast, the movable end region 4230c' is movably coupled, relatively, with the intermediary support region 4211, and configured to be axially movable relative to the fixed end region 4230a'. When each movable end region 4230c' is axially moved toward the relevant fixed end region 4230a', the intermediate regions 4230b' buckle and/or expand transversely outwardly, thereby transitioning the distal locator portion 4202 of the delivery assembly 4200 from the unexpanded state to the expanded state. In contrast, the distal locator portion 4202 transitions from the expanded state to the unexpanded state as each of the movable end regions 4230c' are axially moved away from the relevant fixed end region 4230a'.

Hence, the expansion elements 4230 are relatively resilient, and can buckle without plastic deformation or pure elastic deformation. Further, although the expansion elements 4230 are shown as comprising the flexible members 4230' in FIGS. 47A-47B for purposes of illustration, it is understood that the expansion elements 4230 can comprise any type of expansion elements and are not limited to the illustrated embodiments. For example, inflatable bladder type devices or the like may be employed to cause expansion of the expansion elements, such as a balloon, an expandable mesh or a slit hypotube, etc. In a preferred embodiment, the flexible members are constructed of nitinol.

Referring back to FIGS. 44 and 47-49, the delivery assembly 4200 also includes the carrier assembly 4300 positioned along the distal end of the tubular body 4210, and oriented adjacent and proximate to the distal locator portion 4202. The carrier assembly 4300 is configured to receive and retain the closure element 4500" in the slightly expanded, substantially tubular configuration (shown in FIG. 50B), which preferably is disposed substantially within the cover member 4330 of the carrier assembly 4300. The carrier assembly 4300 includes a substantially cylindrical-shaped carrier seat 4302 configured to seat the closure element 4500" thereagainst. By parking the closure element 4500" within the garage tube 4330 (or cover member) during vessel advancement or positioning, not only is any tissue snaring caused by the closure element reduced, but the closure element itself is protected within the confines of the cover member.

Turning now to FIGS. 48A-48C, the carrier assembly 4300 preferably includes the carrier seat 4302, the pusher member 4320, and the cover member (garage tube) 4330. These components are preferably provided as a plurality of nested, telescoping members with a common longitudinal axis 4350. As mentioned, the substantially cylindrical-shaped seat surface or the carrier seat 4302 is sized and dimensioned to have a transverse cross-sectional dimension slightly greater than that of the closure element 4500", when the closure element is deformed to its natural substantially tubular configuration. Thus, the closure element 4500 preferably is deformed from its natural, planar configuration (FIGS. 46A, 46B) to the natural, substantially tubular closure element 4500" (shown in FIGS. 46F, 46G). When being placed or positioned about an outer periphery of the carrier seat 4302, the closure element must further be slightly radially expanded to fit thereover. In this arrangement, the tines 4520 of the substantially tubular closure element 4500" are pointed substantially distally and ready for tissue engagement. Once seated, the closure element 4500" will primarily be retained in place using its own resiliency toward the natural planar position from the slightly expanded, substantially tubular configuration about the seat surface.

A biocompatible glue or adhesive may further be applied to facilitate retaining the closure element 4500" on the carrier seat 4302 of the carrier assembly 4300. Together with the internal restrictive or confining nature of the cover member 4330, the glue or adhesive must be sufficient to overcome the resilient tendency of the closure element 4500" (FIG. 46G) to return to its natural planar condition (FIGS. 46A and 46B). By way of example, such glues and embedded adhesives include polymer coatings, Loctite, etc. It will further be appreciated that other techniques can be applied to retain the closure element 4500" to the carrier seat 4302.

In accordance with the present invention, the pusher member 4320 is configured to slidably receive at least a portion of the carrier seat 4302, as well as the tubular body 4210, with a receiving lumen 4324 therein and an external surface 4322*b*. The pusher member 4320 is of a predetermined length 4328*a* and a predetermined cross-section 4328*b*, both of which can be of any suitable dimension. The predetermined length 4328*a* of the pusher member 4320 can be greater than or substantially equal to the collective predetermined length 4218*a* and diameter 4218*b* of the tubular body 4210 and the carrier assembly 4300. The predetermined length 4328*a* of the pusher member 4320, however, is preferably less than the collective predetermined length 4218*a* of the tubular body 4210 and the carrier seat 4302, such that a distal end region 4320*b* of the pusher member 4320 is axially offset proximally from the distal end region 4302*b* of the carrier seat 4302. This axial offset, together with the cover member 4330, defines an annular space 4360 designated for receipt of the substantially tubular closure element 4500" about the carrier seat 4302.

Being formed from a substantially rigid, semi-rigid, or flexible material, the pusher member 4320 preferably is substantially tubular and defines receiving lumen 4324 that extends substantially between the proximal end region 4320*a* and the distal end region 4320*b*. This lumen 4324 is configured to slidably receive at least a portion of the tubular body 4210 and the carrier seat 4302 therethrough. The cross-section 4328*b* of the pusher member 4320 preferably is substantially uniform, and the distal end region 4320*b* of the pusher member 4320 can comprise one or more longitudinal extensions 4325, which extend distally from the pusher member 4320 and along the periphery of the carrier seat 4302, as shown in FIG. 48B. The longitudinal extensions 4325 preferably are biased such that the longitudinal extensions 4325 extend generally in parallel with common longitudinal axis 4350. The longitudinal extensions 4325 are sufficiently flexible to expand radially, and yet sufficiently rigid to inhibit buckling.

As best shown in FIGS. 48A and 48C, the cover member 4330 is configured to retain the substantially tubular closure element 4500" and the carrier assembly 4300 substantially within a lumen 4334 thereof prior to deployment. Being coupled with, and slidable relative to, the carrier seat 4302 and the pusher member 4320, the cover member 4330 has a proximal end region 4330*a* and a distal end region 4330*b* and includes a predetermined length 4338*a* and a predetermined cross-section 4338*b*. Preferably being formed as a substantially rigid, semi-rigid, or flexible tubular member formed from a polymer, the cover member 4330 has an outer periphery 4332*b* and an inner periphery 4332*a* that defines lumen 4334. The lumen 4334 extends substantially between the proximal and distal end regions 4330*a*, 4330*b* of the cover member 4330 and can be configured to slidably receive at least a portion of the pusher member 4320. When the cover member 4330 is properly positioned over the pusher member 4320 and the carrier seat 4302, the distal end region 4330*b* is configured to extend over the space 4360, thereby defining an annular cavity for receiving and retaining the closure element 4500" in the substantially tubular configuration.

In one preferred embodiment, as best illustrated in FIGS. 48A, 48C, 50B and 50C, one or more longitudinal extensions 4335 extend distally from the garage tube or cover member 4330. Although the longitudinal extensions 4335 can extend generally in parallel with common longitudinal axis 4350, the longitudinal extensions 4335 preferably are biased such that the plurality of longitudinal extensions 4335 extend substantially radially inwardly as illustrated in FIGS. 48A and 48C. Thereby, the longitudinal extensions 4335 can at least partially close the annular space 4360 slotted for seating of the closure element 4500".

The cross-section 4338*b* of the cover member 4330 preferably is substantially uniform. In the embodiment of FIGS. 44, 45 and 47-51, the distal end region 4330*b* of the cover member 4330 is integrated with the tissue engaging device 4400, as will soon be detailed. To permit the substantially tubular closure element 4500" to be deployed from the annular space 4360, the cover member 4330 can be slidably retracted, relative the carrier seat 4302 to expose the mounted closure element 4500".

If the carrier assembly 4300 is assembled as a plurality of nested, telescoping members as shown in FIG. 48A, the tubular body 4210 of the delivery assembly is at least partially disposed within, and slidable relative to, the lumen 4324 of the pusher member 4320. The pusher member 4320, in turn, is at least partially disposed within, and slidable relative to, the lumen 4334 of the cover member 4330. Hence, the longitudinal axis 4216 of the locator portion 4202, the carrier assembly 4300 and the tubular body 4210 (i.e., of the delivery assembly 4200) are preferably substantially in axial alignment with the common longitudinal axis 4350 of the pusher member 4320 and the cover member 4330.

In accordance with this embodiment of the present invention, the tissue engaging device 4400 is disposed and oriented on the distal end of the cover member 4330 for operation between the tissue engaging condition (FIGS. 51D, 51E) and the tissue closing condition (FIGS. 51F, 51G). As previously indicated, in the tissue engaging condition, the tissue engaging device 4400 engages the opposing arterial walls 4620', 4620" (e.g., FIG. 51E) of the vessel 4600 adjacent to the opening 4610 so that they can be pulled or urged radially inward or transversely toward one another in the closing condition (FIG. 51F). In the closing condition, hence, the engaging device 4400 urges the opposing arterial walls 4620', 4620" at the vessel opening 4610, substantially radially together about axis 4216 and toward one another. By closing the opposing arterial walls within the first diameter of the closure element 4500", the closure element can be deployed directly from the carrier seat 4302 of the carrier assembly 4300 without having to further radially expand to sufficiently engage the tissue.

As best illustrated in FIG. 50B, the engaging device 4400 includes at least two opposing tongs 4402, each of which extends distally from the distal end of the cover member and terminates at a tissue engaging tip 4404. The tips 4404 may be conventionally pointed shaped that facilitate penetration and/or snaring of tissue during operation. These tongs, preferably integral with the cover member or garage tube 4330, are sufficiently flexible to enable control and operation in and by the GF sheath 4640, yet are sufficiently rigid to enable extravascular penetration, snaring and/or grasping of the target arterial wall. In one specific configuration, for example, the distal end of the garage tube may be fabricated from a material having shape memory properties where, in use, the combined subsystem would cooperate the GF sheath 4640 to operate and control the use of the tissue engaging device 4400.

The two or more tongs 4402 of the tissue engaging device 4400 are configured and oriented for sliding reciprocal cooperation with an interior wall 4642 of the sheath 4640 to control movement and operation of the engaging device between the tissue engaging condition (FIGS. 51D, 51E) and the closing condition (FIGS. 51F, 51G). More specifically, the distal tips 4404 of each tong 4402, in the tissue engaging condition, will be manipulated to snare and/or engage the arterial walls 4620', 4620" being held taut by the tissue locator portion 4202, in the expanded condition. Preferably, the engaging device distal tips 4404 will be radially expanded or oriented at least as wide as the first diameter, relative to longitudinal axes 4216, 4350, of the closure element seated about the carrier seat 4302. More preferably, the distal tips 4404 will be radially expanded to a disposition greater than and beyond the first diameter to ensure sufficient snaring and/or engaging of the arterial walls surrounding the vessel opening 4610. Accordingly, the tongs of the tissue engaging device are biased and/or have a disposition extending radially outward. Hence, by retracting the restrictive sheath 4640 proximally relative to the garage tube 4330 (or advancing the delivery assembly distally past the distal end of the sheath), the respective tongs 4402 of the tissue engaging device 4400 will be released and permitted to radially expand to the tissue engaging position (FIG. 51D).

Briefly, as will be described in greater detail below, once the arterial walls 4620', 4620" are snared or pierced by the tissue engaging device 4400, in the tissue engaging condition, the GF sheath can be displaced distally, relative to the garage tube. Sliding contact between the interior wall 4642 of the sheath and the outer facing surfaces 4406 of the tongs 4402 causes the distal tips of the engaging device to draw the tissue radially inward toward one another (FIG. 51F). As the interior wall 4642 of the sheath is advanced distally, the increasing contact along the outer surfaces 4406 of the tongs causes the distal tips to invert inwardly within the first diameter of the closure element in the substantially tubular configuration about the carrier seat 4302, in the closing condition.

FIG. 49 best illustrates that the clip applier apparatus 4100 includes a housing/handle 4380 at a proximal end thereof suitable for gripping and manual support, manipulation and operation of the device and components thereof. Preferably, the housing 4380 is an elongated member having a proximal end 4380*a* and a distal end 4380*b* with a longitudinal axis 4386. When the apparatus 4100 is properly assembled, the tube set 4305 of the delivery assembly 4200 is at least partially disposed within the housing handle such that the pusher member 4320 and the cover member 4330 are slidable relative to the housing 4380, the tubular body 4210, the carrier seat 4302 and the distal locator portion 4202 thereof. Further, respective distal end regions 4210*b*, 4320*b* and 4330*b* extend from the distal end region 4380*b* of the housing 4380 such that the common longitudinal axis 4350 (shown in FIG. 48A) of the tube set 4305 is substantially axially aligned with the longitudinal axis 4386 of the housing 4380. Being configured to slidably retain the respective proximal end regions 4210*a*, 4320*a* and 4330*a*, the housing 4380 supports the tube set 4305 and can have one or more handles 390 to facilitate use of the apparatus 4100. The handles 4390 extend substantially radially from the outer periphery 4382 of the housing 4380 and can be provided in the manner known in the art.

The present invention incorporates various switching systems, triggering systems, locking systems, etc. contained in the handle portion to effect use and operation of the delivery components described herein. While all these subsystems are not shown and described herein in detail, it will be appreciated that they are similar to the design and operation of the analogous subsystems shown and described in our '214 patent application, which as mentioned is incorporated by reference herein for all purposes.

By way of example, however, the locator portion 4202 also can include a locator control system 4240 that is coupled with the proximal end region 4210*a* of the delivery assembly 4200 and that is configured to selectively control the distal locator portion 4202 between the unexpanded and expanded states (FIG. 47C). The locator control system 4240 can selectively control the distal locator portion 4202 between the unexpanded and expanded states, such as by being activated by a switching system (not shown). For example, a control member 4250, such as a rod, wire, or other elongate member, can be moveably disposed within a lumen (not shown) formed by the tubular body 4210 and extending substantially between the proximal end region 4210*a* of the tubular body 4210 and the distal locator portion 4202. The control member 4250 has a proximal end region 4250*a* that is coupled with the locator control system 4240, preferably through a control block (not shown, but operationally similar to the control systems and structures), and a distal end section (not shown) of the control member 4250 that is coupled with the expansion elements 4230, and/or the movable end regions 4230*c*' of the substantially flexible members 4230'. The locator control system 4240 can selectively transition the expansion elements 4230, and/or the substantially flexible members 4230' of the distal locator portion 4202 between the unexpanded and expanded states by moving the control member 4250 axially relative to the tubular body 4210.

The locator control system 4240 preferably includes a locator release system (not shown, but one embodiment which may be similar to that disclosed in the '214 patent application) for maintaining the unexpanded state and/or the expanded state of the distal end region 4210*b*, the expansion elements 4230, and/or the substantially flexible members 4230'. The locator release system is preferably configured to maintain the locator portion in the expanded state. Any type of locking system can be employed, and can be engaged, for instance, by activating the switching system. For example, once the substantially flexible members 4230' have entered the expanded state, the locator release system can secure the control member 4250 to prevent axial movement relative to the tubular body 4210, thereby maintaining the substantially flexible members 4230' in the expanded state.

The locator control system 4240 also can be configured to disengage the locator release system, such that the distal end region 4210b, the expansion elements 4230, and/or the substantially flexible members 4230' can transition between the unexpanded and expanded states. The locator release system can be disengaged, for example, by activating an emergency release system (not shown). As desired, the locator control system 4240 can further include a biasing system (not shown), such as one or more springs, to bias the distal end region 4210b, the expansion elements 4230, and/or the substantially flexible members 4230' to enter and/or maintain the unexpanded state when the locator release system is disengaged.

In use, the closure element 4500" is carried on the carrier seat 4302, in the slightly radially expanded tubular configuration, and is disposed within the cover member 4330. As shown in FIGS. 50A-50C, for example, the closure element 4500" can be slidably received over the distal locator portion 4202 and the distal end region of the carrier assembly 4300. The closure element 4500" is then seated and disposed about the periphery of the carrier seat 4302 adjacent to the space 4360, in the slightly expanded, substantially tubular configuration.

After being received over the distal end region 4302b, the substantially tubular closure element 4500" is disposed in the space 4360, and the tines 4520 are directed substantially distally as shown in FIG. 50B. To improve the engagement between the closure element 4500" (shown in FIGS. 46A-46B) and the blood vessel wall 4620 and/or tissue 4630 (collectively shown in FIG. 51A), the substantially tubular closure element 4500" preferably is disposed on the carrier seat 4302 such that the tines 4520 are contained in a plane.

Once disposed in the space 4360, the resiliency of the slightly expanded closure element 4500" and/or the addition of an adhesive or glue will facilitate retention of the element in place about the carrier seat. Moreover, the sliding receipt of the substantially tubular closure element 4500" and the distal end region 4320b of the pusher member 4320 within the lumen 4334 of the cover member 4330, as illustrated in FIGS. 50B and 50C, also cooperate to retain the closure element 4500" against the carrier seat 4302. When the cover member 4330 is properly positioned over the carrier assembly 4300, the distal end region 4330b (opposite of the proximal end region 4330a) of the cover member 4330 extends over the space 4360 and defines the annular cavity for retaining the substantially tubular closure element 4500". As such, the closure element 4500" is disposed substantially between the outer periphery of the carrier seat 4302 and the inner periphery 4332a of the cover member 4330 such that the substantially tubular closure element 4500" maintains the substantially tubular configuration with the tines 4520 being directed substantially distally. As desired, the tube set 4305 may slightly radially compress the substantially tubular closure element 4500" to facilitate seating against the carrier seat. The body 4510 of the substantially tubular closure element 4500" can be disposed distally of the distal end region 4320b of the pusher member 4320, as illustrated in FIG. 50C, or can engage the distal end region 4320b, as desired.

Turning now to FIGS. 51A-51H, operation of this specific embodiment will now be detailed. Initially, introducer sheath 4640 may be inserted or otherwise positioned through skin 4650 and tissue 4630 and within the blood vessel 4600 or other body lumen via the opening 4610. Comprising a substantially flexible or semi-rigid tubular member, the sheath 4640 has a proximal end region 4640a and a distal end region 4640b and includes a predetermined length and a predetermined cross-section, both of which can be of any suitable dimension. The sheath 4640 also forms a peripheral surface 4645 and a lumen 4644 that extends along a longitudinal axis of the sheath 4640 and substantially between the proximal and distal end regions 4640a, 4640b. The lumen 4644 can have any suitable internal cross-section 4648b and is suitable for receiving one or more devices (not shown), such as a catheter, a guide wire, or the like. The lumen 4644 is configured to slidably receive tube set 4305 and the delivery assembly 4200 of the apparatus 4100, including the nested tubular body 4210, the carrier seat 4302, the distal locator portion 4202, pusher member 4320 and the cover member 4330 as a single unit. Accordingly, one significant advantage of the present invention is that, due to the reduced complexity of the cooperating componentry, the overall diametric footprint can be significantly smaller relative to the current systems. Hence, the entire nested tube set 4305 may be slidably received in the lumen 4644 of the introducer sheath 4640 without requiring a radial expansion or splitting of the sheath 4640. Such a configuration is beneficial in that, when required, the delivery assembly 4200 can be refracted and reinserted unlike the previous designs that irreversibly radially expanded, stretched, split or severed the analogous sheaths.

The introducer sheath 4640 may be advanced over a guide wire or other rail (not shown) that was previously positioned through the opening 4610 and into the blood vessel 4600 using conventional procedures. In one specific use, the blood vessel 4600 is a peripheral blood vessel, such as a femoral or carotid artery, although other body lumens may be accessed using the sheath 4640 as will be appreciated by those skilled in the art. The opening 4610, and consequently the sheath 4640, may be oriented with respect to the blood vessel 4600 such as to facilitate the introduction of devices through the lumen 4644 of the sheath 4640 and into the blood vessel 4600 with minimal risk of damage to the blood vessel 4600. One or more devices (not shown), such as a catheter, a guide wire, or the like, may be inserted through the sheath 4640 and advanced to a predetermined location within the patient's body. For example, the devices may be used to perform a therapeutic or diagnostic procedure, such as angioplasty, atherectomy, stent implantation, and the like, within the patent's vasculature.

After the procedure is completed, the devices are removed from the sheath 4640, and the apparatus 4100 is prepared to be slidably received by the lumen 4644 of the sheath 4640 as shown in FIG. 51B. Being in the unexpanded state, the distal end region of the distal locator portion 4202, via tubular body 4210, is slidably received by the lumen 4644 and atraumatically advanced distally into the blood vessel 4600 (FIG. 51B). Briefly, it will be appreciated that, due to the fixed configuration between the distal end region of the carrier assembly 4300 and the proximal end region of the distal locator portion 4202, in a support configuration, that the carrier seat 4302, the pusher member 4320 and the cover member 4330, together with the closure element in the slightly expanded, substantially tubular configuration, are also advanced distally near the blood vessel 4600 as a unit. Moreover, since the pusher member 4320 and the cover member 4330 are also coupled to the tubular body 4210, those components are likewise advanced distally together with the locator portion 4202. Once the distal end region of the distal locator portion 4202 extends into the blood vessel 4600, the distal locator portion 4202 can transition from the unexpanded state (FIG. 51B) to the expanded state (FIG. 51C) by activating the switching system of the locator portion 4202.

Turning now to FIG. 51D, the apparatus 4100 and the sheath 4640 then are retracted proximally until the distal end region of the locator portion 4202 is substantially adjacent to an inner surface 4620b of the blood vessel wall 4620. The distal end region of the locator portion 4202 thereby draws the opposing blood vessel walls 4620', 4620" taut and maintains the proper position of the apparatus 4100 as the blood vessel 4600 pulsates. Since the expanded cross-section of the expansion elements 4230 is collectively greater than or substantially equal to the cross-section of the opening 4610 and/or the cross-section of the lumen 4644, the expansion elements remain in the blood vessel 4600 and engage the inner surface 4620b of the blood vessel wall 4620. The expansion elements 4230 can frictionally engage the inner surface 4620b of the blood vessel wall 4620, thereby securing the apparatus 4100 to the blood vessel 4600. The sheath 4640 is then retracted proximally such that the distal end region 4640b of the sheath 4640 is substantially withdrawn from the blood vessel 4600, as shown in FIG. 51D, permitting the apparatus 4100 to access the blood vessel wall 4620.

While the relative distance between the distal end region of the carrier assembly 4300 (i.e., the carrier seat 4302) and the proximal end region of the distal locator portion 4202 is preferably substantially fixed, it will be appreciated that such relative distances can be non-fixed as well. More particularly, upon establishing a first position of FIG. 51D, the carrier seat 4302 and the loaded closure element 4500", in the substantially tubular configuration, are disposed proximal and substantially adjacent to the outer surface 4620a of the blood vessel wall 4620. In this manner, the blood vessel wall 4620, adjacent to the opening 4610, is disposed substantially between the expanded distal region of the locator portion 4202 and the distal end region of the carrier assembly 4300.

Hence, once the distal end region of the locator portion 4202 properly engages the inner surface 4620b of the blood vessel wall 4620 as the expansion elements 4230 are selectively positioned and moved to the expanded state, the sheath 4640 is further retracted proximally, exposing the tongs 4402 of the tissue engaging device 4400. As mentioned, the interior walls 4642 of the sheath 4640 cooperate with the garage tube 4330 to maintain a substantially cylindrical profile, and to control and operate the use tongs 4402 of the distal tissue engaging device, which are substantially distally facing and flush against the tubular body 4210 when contained in the sheath 4640. Further proximal retraction of the sheath 4640 exposes the tongs 4402 of the tissue engaging device 4400 from inside the sheath lumen 4644, allowing the distal tips 4404 of the tongs to radially expand toward the engaging condition.

Depending upon the particular design of the tissue engaging device 4400, movement of the distal tips 4404 of the tongs may occur in different ways. For instance, if the tissue engaging device 4400 is composed of a shape memory material, exposure of the heat set tissue engaging device 4400 to the tissue environment causes radial expansion of the tongs 4402 toward the engaging condition. In contrast, in a resilient, elbowed-type configuration of the engaging device tongs 4402, as shown in FIGS. 51B-51E, proximal retraction reduces the compressive contact of the exterior facing surfaces of the engaging device tongs 4402 with the interior wall 4642 of the sheath 4640. This allows the distal tips 4404 of the tongs to radially expand toward the engaging condition.

Once the tissue engaging device 4400 has radially expanded to the tissue engaging condition, the garage tube 4330 can be axially advanced distally, relative to the carrier assembly 4300 and the tissue locator portion 4202, maintaining the closure element 4500" seated in the carrier seat 4302 (not shown). It will be appreciated, however, that the tube set 4305, with the exception of the tubular body 4210, can be axially advanced along the tubular body together as a unit, as best viewed in FIG. 51E. Hence, as the cover member is advanced distally, so is the pusher member 4320 that unseats the closure element 4500" from the carrier seat 4302 about the tubular body 4210. Consequently, the distal tips 4404 of the tongs, oriented distally toward arterial walls 4620', 4620" that define the vessel opening 4610, are extravascularly advanced into piercing or snaring contact therewith. In cooperation with the expansion elements 4230 of the distal locator portion 4202, in the expanded condition, the arterial walls are maintained taut to facilitate engagement by the tongs.

Referring now to FIG. 51F, the tissue engaging device 4400 at the distal end of the garage tube 4330 is collapsed together in the closing condition. This is performed by sliding the sheath 4640 distally, relative to the carrier assembly 4300 and the tissue locator portion 4202 (or retracting the garage tube 4330 into the sheath 4640), increasing contact and engagement of the tongs 4402 with the lumen interior wall 4642 of the sheath. In effect, the sliding contact pinches the distal tips 4404 of the tissue engaging device tongs 4402 together, pulling the opposed arterial walls 4620', 4620" radially inward toward the closing condition (i.e., within the first diameter of the closure element).

During operation of the tissue engaging device from the tissue engaging condition to the closing condition, the substantially tubular closure element 4500" is advantageously retained on the outer periphery of the carrier seat 4302 by the cover member 4330 as illustrated in FIG. 51E. By retaining at least the proximal portion of the substantially tubular closure element 4500" between the distal end region (e.g., the radially, inwardly directed longitudinal extensions 4335) of the cover member 4330 and the distal end region of the carrier seat 4302, the apparatus 4100 is configured to provide better tissue penetration for the seated closure element 4500".

As mentioned, in one specific embodiment, the carrier seat 4302 and the cover member 4330 of the carrier assembly 4300 cooperate to maintain the substantially tubular closure element 4500" in the tubular configuration, and fixed relative to the distal tissue engaging device 4400. After the tissue engaging device 4400 engages the opposed arterial walls 4620', 4620" in the closing condition (FIG. 51F), the locator release system (not shown) can be activated to transition the expansion elements 4230 of the tissue locator portion or obturator 4202 from the expanded state to the unexpanded state, as shown in FIG. 51G.

The proximal end region of the locator portion 4202 can be retracted proximally, effectively retracting the tubular body 4210 and the distal locator portion 4202 into the lumen 4324 of the pusher member 4320, and relative to the garage tube 4330, closure element 4500" and sheath 4640 (FIG. 51G). Simultaneously, the distal end of the pusher member 4320 can be advanced distally, contacting the closure element 4500" and advancing it distally and axially along the tubular body 4210 of the delivery assembly 4100 and toward the tissue locator portion 4202. Once the distal end region of the tissue locator portion 4202 is axially proximate to the closure element 4500" (e.g., seated about the expansion elements 4230 of the tissue locator portion), the closure element is nearly ready to be deployed. The tissue locator portion 4202 and the cover member 4330 preferably are inhibited from further relative axial movement and remain substantially stationary, relative the handle portion; whereas, the pusher member 4320 remains axially slidable. As the pusher member 4320 selectively continues distally, the distal end region 4320b of the pusher member 4320 further engages the substantially tubular closure element 4500" and displaces it from its seating about the expansion elements 4230 of the obturator (FIG. 51G).

In accordance with the present invention, the closure element 4500", seated about the delivery assembly 4200 in the slightly expanded, substantially tubular condition, is delivered into engagement with the opposed blood vessel arterial walls 4620', 4620" and/or tissue 4630 adjacent to the opening 4610 without further radial expansion thereof. As previously indicated, this benefit is due to the fact that the tissue engaging device 4400 is simultaneously engaged with the vessel wall 4620, and draws the opposed engaged side walls 4620', 4620" radially inward relative to one another and within the first diameter of the closure element.

Upon being advanced over the distal locator portion 4202, in the unexpanded state, by the pusher member 4320, the substantially tubular closure element 4500" is distally deployed as illustrated in FIG. 51G. Continued distal advancement of the pusher member 4320 past the distal end of the obturator delivers the tongs 4402 of the closure element 4500" into piercing engagement with the arterial walls 4620', 4620" surrounding the vessel opening. When the substantially tubular closure element 4500" is deployed, the tines 4520 can pierce and otherwise engage a significant amount of the blood vessel wall 4620 and/or tissue 4630 adjacent to the opening 4610 without requiring significant further radio expansion in order to sufficiently engage the walls. Due to the simultaneous engagement of the tissue engaging device 4400 with the vessel walls, the tines 4520 can engage a significant amount of the opposed blood vessel arterial walls 4620', 4620" and/or tissue 4630 because the vessel walls 4620', 4620" are pulled together by the engaging device, in the closing condition. In particular, the tongs 4402 of the tissue engaging device 4400 engage the opposed vessel walls 4620', 4620", and urge them radially inwardly, within the first diameter (and hence within the cross-section 4530) of the substantially tubular closure element 4500" simultaneously while the pusher member 4320 is deploying the closure element.

Once the substantially tubular closure element 4500" is deployed (FIG. 51H), it begins to transition from the tubular configuration to the natural, planar configuration with opposing tines 4520 and a natural cross-section 4530 of the closure element 4500". Preferably, the substantially tubular closure element 4500" substantially uniformly transitions from the tubular configuration to the natural, planar configuration. Rotating axially inwardly to form the opposing tines 4520 of the closure element 4500", the tines 4520 draw the tissue 4630 and/or opposing vessel walls 4620', 4620" into the channel 4540 of the transitioning closure element 4500". In addition, the tissue 4630 is drawn substantially closed and/or sealed as the cross-section 4530' of the substantially tubular closure element 4500" contracts to return to the natural cross-section 4530 of the closure element 4500. Thereby, the opening 4610 in the blood vessel wall 4620 can be drawn substantially closed and/or sealed via the closure element 4500 as illustrated in FIG. 51H. Subsequently, the sheath 4640 and the tube set 4305 of the delivery assembly 4200 can be withdrawn from the tissue 4630.

To reduce interference of the closure element tines 4520 with the tissue engaging tongs, while the tongs are engaged with the vessel walls 4620', 4620" in the closing condition, the tips 4404 and the tongs 4402 can be configured so as to be angularly off-set (at virtually any angle resulting in non-interference) from one another (not shown) about the common longitudinal axis 4350. For example, as little as about a 5 degrees angular off-set between the engaging device tongs 4402 and the closure element tines 4520, about the common longitudinal axis 4350, will significantly reduce contact of the tines with the tongs during delivery of the closure element.

Turning now to FIGS. 52 and 53, an alternative embodiment delivery assembly 4200 is illustrated wherein the tissue engaging device 4400 is disposed within and deployed from a central lumen 4204 of the tubular body 4210. As indicated above, the primary difference between the various embodiments of the present invention is the location, implementation and execution of the tissue engaging device 4400. For example, in this embodiment, the tissue engaging device 4400 is configured to intravascularly engage the opposing arterial walls 4620', 4620", while in the previous embodiment, the tissue engaging device extravascularly engages the arterial walls.

The primary orientation and operation of the remaining components of the delivery assembly 4200, however, are similar to the previously discussed embodiments. That is, the delivery assembly 4200 contains a similar tube set 4305 consisting of the locator portion 4202 and the carrier assembly 4300, the carrier assembly of which is located at the distal end of the tubular body 4210, just proximal to the locator portion 4202. Briefly, the carrier assembly 4300 similarly consists of the carrier seat 4302, the tubular pusher member 4320 and a nested garage tube 4330; the latter of which surrounds the former two, and all of which are coaxial with longitudinal axis 4216 of the tubular body 4210.

The tissue locator portion 4202 includes a tubular bleed back shaft 4260 distally extending from a distal end of the carrier seat 4302. Preferably, both the carrier seat and the bleed back shaft 4260 are integrally formed with one another on the end of the delivery assembly tubular body 4210. The bleed back shaft 4260 includes a bleed back port 4262 that functions to locate the vessel opening 4610 at puncture site in the vessel 4600. This port 4262 is oriented a predetermined distance from the distal end from the bleed back shaft 4260. The bleed back port 4262 communicates with a bleed back lumen (not shown) that longitudinally extends from the locator portion and through the tubular body 4210 of the delivery assembly, although it will be appreciated that the port could also share a lumen with the tissue engaging device.

In accordance with this specific embodiment, the cover member or garage tube 4330 similarly covers the pusher member 4320, the carrier seat 4302 of the carrier assembly 4300, and the tubular body 4210 (i.e., tube set 4305). Since the tissue engaging device is not disposed at the distal end of the garage tube, the annular distal end preferably terminates just distal to the carrier seat 4302, defining the annular space 4360 that seats the closure element 4500" in the substantially tubular configuration. In one preferred embodiment, one or more longitudinal extensions extend distally from the garage tube or cover member 4330, similar to extensions 4355 of FIG. 50B. Although these longitudinal extensions can extend generally in parallel with common longitudinal axis 4350, the longitudinal extensions preferably are biased such that they extend substantially radially inwardly. Thereby, the longitudinal extensions can at least partially close the central lumen 4334 substantially adjacent to the distal end region of the cover member 4330.

Referring back to FIG. 52, in operation, the tube set 4305 of the delivery assembly 4200 of the clip applier apparatus 4100 is advanced through the sheath lumen 4644 of the sheath 4640 using similar techniques to those shown and described in FIGS. 51A and 51B. When the tissue locator portion 4202 locates the vessel opening 4610 and the bleed back shaft 4260 is inserted into the body vessel 4600 to the predefined depth, the bleed back port 4262 communicates with fluid flow, hence locating the vessel opening 4610.

Once tissue locator portion 4202 is properly oriented, the tissue engaging device 4400 can be distally deployed from a distal end of the tubular body 4210. As shown in FIGS. 53 and 54, the tissue engaging device 4400 is slidably disposed within a lumen 4204 of the tubular body 4210. This lumen 4204 further extends through the carrier assembly 4300 and the locator portion 4202, terminating at an end port 4264 at the distal end thereof. The tissue engaging device 4400 includes one or more tongs 4410 having proximal end regions associated with a common control shaft (not shown) operated at the handle portion 4380 of the clip applier apparatus 4100. Each resilient tong 4410 is naturally bowed in a U-shaped manner such that when continually distally advanced from the tubular body end port 4264, each tong resiliently bows radially outwardly from common axis 4216, and bows upwardly toward the interior surface 4620b of the opposing arterial walls 4620', 4620". As the tongs 4410 of the tissue engaging device are further deployed, the tips 4412 (e.g., barbed tips) of the tongs 4410 are configured to intravascularly pierce, snare or grab the arterial walls 4620', 4620" from the underside surface 4620b surrounding the puncture site (i.e., in a tissue engaging condition of FIG. 52). The snaring, piercing and/or grabbing of the arterial walls could be accomplished by hooks, barbs, or similar on the ends of the tongs 4410. The piercing from the underside surface, furthermore, may be accomplished by the curved shape of the tongs 4410 as they exit the distal end of the bleed back shaft 4260.

Accordingly, the resilient tongs 4410 are sufficiently flexible for sliding reciprocal receipt in the receiving lumen 4204 of the tubular body 4210 of the delivery assembly 4200, yet sufficiently rigid to enable piercing, snaring or grabbing of the arterial walls when engaged therewith. Such materials exhibiting these characteristics, for example, include Nitinol and stainless steel.

Once the opposing arterial walls 4620', 4620" are sufficiently grasped, snared or penetrated, the tubular body 4210 of the delivery assembly 4200 is retracted extravascularly through the receiving lumen 4204 of the pusher member 4320. This operation is performed while the garage tube 4330, the closure element 4500" and the pusher member 4320 are substantially axially maintained at their position relative to the vessel opening 4610 of the body vessel 4600. Accordingly, the relative movement between the tubular body 4210 and the pusher member 4320, in turn, unseats the closure element 4500" from the carrier seat 4302 and advances it toward the distal end of the tubular body 4210. Alone or in combination with the above tubular body refraction, the tongs 4410 of the tissue engaging device 4400 may also be retracted into the receiving lumen 4204 of the tubular body 4210. As the tubular body 4210 and/or the tongs 4410 are being retracted, the arterial walls 4620', 4620" are pulled together radially inward until they are disposed within the first diameter of the closure element 4500", in a closing condition (FIG. 53). Continued refraction further urges the engaged opposing arterial walls 4620', 4620" radially together under the bleed back shaft and into the channel 4540 defined by the substantially tubular closure element 4500".

To permit the substantially tubular closure element 4500" to be deployed from the annular cavity 4360, the cover member 4330 can also be slidably retracted, relative the tubular body 4210. The longitudinal extensions 4335 of the cover member 4330 preferably are sufficiently flexible to expand radially to permit retroactive movement of the distal end region of the cover member 4330 peripherally over the mounted closure element 4500". This opens the annular cavity 4360 such that the distal end region of the cover member 4330 no longer fully encloses the closure element.

Turning now to FIG. 54, the pusher member 4320 is then advanced distally to deploy the closure element 4500". Similar to the technique applied above, the tines 4520 of the closure element 4500" pierce the opposing arterial walls 4620', 4620" that are radially pulled together, via the tissue engaging device 4400 in the closing condition, within the first diameter. Once the substantially tubular closure element 4500" is deployed, it begins to transition from the tubular configuration to the natural, planar configuration with opposing tines 4520 and a natural cross-section 4530 of the closure element 4500 (substantially similar to the deployment of the closure element detailed and shown in FIGS. 51G and 51H). The arterial walls 4620', 4620" are drawn substantially closed and/or sealed as the cross-section 4530' of the substantially tubular closure element 4500" contracts to return to the natural cross-section 4530 of the closure element 4500. Thereby, the opening 4610 in the blood vessel wall 4620 can be drawn substantially closed and/or sealed via the closure element 4500, as illustrated in FIG. 51H. Subsequently, the tongs 4410 of the tissue engaging device 4400 are retracted in the bleed back shaft 4260, and the delivery assembly 4200 and sheath 4640 can be removed.

It will be appreciated that the bleed back shaft 4260 is composed of a material that reduces sticking of the tines 4520 of the closure element during deployment, should any contact ensue. This would be detrimental, of course to the proper clip deployment. Essentially, the composition should be at least as hard as the tines of the closure element so as not to stick into the bleed back shaft itself. Beneficial shaft compositions include any hard material that can be formed into a tube and is also biocompatible, such as stainless steel and Nitinol to name a few. Further, similar to the embodiments above-mentioned, the seating of the closure element 4500" about the carrier seat 4302 is in a manner angularly off-setting the closure element tines 4520 (relative to the longitudinal axis 4216) from the angular position of the tissue engaging tongs 4410, to reduce interference during deployment of the closure element.

FIGS. 55 and 56 represent another specific embodiment clip applier apparatus 4100 incorporating a tissue engaging device 4400 that intravascularly engages the opposing arterial walls 4620', 4620". In accordance with this specific embodiment, however, the analogous tongs 4410 cooperate to radially push the engaged opposing arterial walls together as opposed to radially pulling them together, as does the embodiment disclosed in FIGS. 52-54. As best illustrated in FIG. 55, the tongs 4410 of the tissue engaging device 4400, in their natural configuration, are substantially C-shaped. For each tong 4410, the respective distal tip 4412 is configured to loop nearly all the way around onto itself. That is, in their respective own plane substantially intersecting the longitudinal axis 4216 of the bleed back shaft 4260, the distal tip of each tong loops back around from the end port 4264 of the bleed back shaft 4260. Briefly, it will be appreciated that natural loop shape of each tong neither needs to be exactly circular, nor be curvilinear for that matter, as long as the tip 4412 extends back around in a direction toward the longitudinal axis 4216 of the shaft 4260.

Again, using similar placement and advancement techniques through the sheath lumen 4644 of the sheath 4640, as shown and described in FIGS. 51A and 51B, the tube set 4305 of the delivery assembly 4200 can be positioned near the vessel opening 4610. Once the tissue locator portion 4202, via bleed back port 4262, has determined the location and proper depth of insertion of the bleed back shaft 4260 into the vessel opening 4610 of the vessel body 4600, the two or more tongs 4410 are advanced distally out of the shaft end port 4264, via controls at the handle member 4380 (FIG. 49). As the advancement of the tongs 4410 of the tissue engaging device 4400 distally continue, the tips 4412 of the tongs 4410 continue to loop back around until they grip, snag and/or partially pierce the underside surface 4620b of the opposing arterial walls 4620', 4620" (in a manner similarly described in the operation of the embodiment of FIGS. 52 and 53.

Once the arterial walls 4620', 4620" are sufficiently initially engaged, further advancement of the tongs from the distal end port 4264 of the bleed back shaft 4260 causes the tong tips 4412 to return to their natural state, in their respective plane (i.e., directed back toward longitudinal axis 4216 of the bleed back shaft 4260). In effect, the engaged opposed arterial walls 4620', 4620" are pushed together by the advancing tong tips 4412, which return to their natural state, until the edges 4622', 4622" of the opposing arterial walls 4620', 4620" contact the exterior surface of the bleed back shaft 4260. Accordingly, unlike the previous embodiment, the engaged opposing arterial walls 4620', 4620" are urged together without retracting the bleed back shaft 4260 and/or retracting the tongs 4410 back into the receiving lumen 4204. This is beneficial in that it allows the user to continue monitoring the proper location of the device. Further, by not retracting the tongs, the chance that the tongs dislodge from the arterial walls decreases prior to deployment of the closure element.

Accordingly, the tips 4412 of the respective tongs 4410 are configured to not fully penetrate the engaged opposing arterial walls 4620', 4620" or each tong may experience difficulty urging and pushing the opposing walls back toward and against the bleed back shaft. For example, the tip configuration can be more blunted, radiused or roughened, so as to partially pierce the tissue, but not fully penetrate it.

Regarding the resilient tongs 4410, they must be capable of sufficient flexibility to unfold from their naturally curved and hooked configuration to a substantially straight configuration when housed or stored within the lumen 4204 of the tubular body 4210. However, the tongs 4410 of the tissue engaging device 4400 must also be sufficiently stiff, strong and resilient to push the engaged arterial walls together, and back against the bleed back shaft 4260 when the tongs are fully deployed from the distal end of the bleed back shaft 4260. Such materials for each tong 4410, for example, may include Nitinol and stainless steel.

Since the opposed arterial walls 4620', 4620" must be pushed, as opposed to pulled, radially together to an orientation within the first diameter of the seated closure element 4500", the diameter of the bleed back shaft 4260 at the region of contact by the edge 4622', 4622" of the arterial walls 4620', 4620" is reduced from that of the carrier seat 4302. Such a diameter reduction, relative to the carrier seat, increases the width of tissue engagement about by the tines 4520 of the closure element 4500", about the vessel opening 4610, by enabling the opposed arterial walls to be pushed closer together.

Referring now to FIG. 57, the pusher member 4320 may be distally advanced to engage the seated closure element 4500", in the substantially tubular condition, during deployment. The delivery assembly 4200, and hence the bleed back shaft 4260, are axially maintained in position during the deployment of the closure element 4500". Once the substantially tubular closure element 4500" is deployed, it begins to transition from the tubular configuration to the natural, planar configuration with opposing tines 4520 and a natural cross-section 4530 of the closure element 4500 (substantially similar to the deployment of the closure element detailed and shown in FIGS. 51G and 51H). Again, the opening 4610 in the blood vessel wall 4620 can be drawn substantially closed and/or sealed via the closure element 4500" as illustrated in FIG. 51H. Subsequently, the tongs 4410 of the tissue engaging device 4400 are the refracted in the bleed back shaft 4260, and then the bleed back shaft 4260 is refracted from the "closed" opening 4610 of the puncture site.

It will again be appreciated that the bleed back shaft 4260 is composed of a material that reduces sticking of the tines 4520 of the closure element therewith during deployment and withdrawal of the shaft from the opening, should any contact ensue. As mentioned above, beneficial shaft compositions include any hard material that can be formed into a tube and is also biocompatible, such as Nitinol and Stainless steel. Furthermore, the seating of the closure element 4500" about the carrier seat 4302 is in a manner angularly off-setting the closure element tines 4520 (relative to the longitudinal axis 4216) from the angular position of the tissue engaging tongs 4410, to reduce interference during deployment of the closure element.

Referring now to FIG. 58, another specific embodiment of the clip applier apparatus 4100 is illustrated that is structurally and functionally similar to the clip applier apparatus embodiment detailed in FIGS. 52-54. In this specific embodiment, however, the cover member or garage tube 4330 shown in the embodiment of FIG. 52 is removed, providing a significantly reduced diametric footprint for the tube set 4305 of the delivery assembly 4200. Accordingly, during advancement of the delivery assembly to the vessel opening 4610, via the lumen 4644 of the sheath 4640, protection of the seated closure element 4500" is afforded by the sheath itself.

As above-mentioned, the diametric footprint of the clip applier apparatus 4100 in this specific embodiment is further reduced by an amount equivalent to the removal of the garage tube from the tube set 4305. Hence, the tube set 4305 of the delivery assembly only includes the pusher member 4320 of the carrier assembly 4300, and the tubular body 4210. The tubular body 4210, which supports the carrier seat 4302, the tissue locator assembly 4202 and the tissue engaging device 4400 supported within the receiving tubular body lumen 4204, may similarly be capable of axial displacement, relative to the sheath 4640, the pusher member 4320 and the closure element 4500", in the substantially tubular configuration.

Furthermore, the introducer sheath 4640 will be selected to cooperate with the tube set 4305 of the delivery assembly 4200 in a manner similar to the cooperation between the garage tube 4330 and the pusher member 4302 and closure element 4500" of the previous embodiments. That is, the interior diameter of the sheath lumen 4644 should be sized to cooperate with the exterior diameter of the pusher member 4320 and the seated closure element 4500" to permit sliding axial displacement therebetween, yet be sufficiently snug at the distal tip to retain the closure element in the substantially tubular configuration until it is released out of its distal end thereof.

Referring back to FIG. 58, the tissue engaging device 4400 of this embodiment is illustrated incorporating a similar device to that described in the embodiment of FIGS. 52-54 (i.e., centrally deployed resilient tongs 4410). It will be appreciated, however, that any tissue engaging device could be incorporated that is functionally capable of engaging and urging the opposed arterial walls 4620', 4620" together and radially within the first diameter of the closure element 4500" (about longitudinal axis 4216).

Again, similar to the operation of the embodiment of FIGS. 52-54, once the tissue locator portion 4202 is properly oriented, the tissue engaging device 4400 can be distally deployed from a distal end of the tubular body 4210. The tissue engaging device 4400 includes one or more tongs 4410 having proximal end regions associated with a common control shaft (not shown) operated at the handle portion of the clip applier apparatus 4100. Each resilient tong 4410 is naturally bowed in a U-shaped manner such that when continually distally advanced from the tubular body end port 4264, each tong resiliently bows radially outwardly from common axis 4216, and bows upwardly toward the interior surface 4620b of the opposing arterial walls 4620', 4620". Once the tongs 4410 of the tissue engaging device are sufficiently anchored to the corresponding arterial walls 4620', 4620" (in the tissue engaging condition similar to that shown in FIG. 52), the tubular body 4210 and/or the tongs 4410 are retracted, while the pusher member 4320 and the closure element 4500" are substantially maintained, axially. Similar to the closing condition of FIG. 53 and as shown in FIG. 58, the engaged opposing arterial walls 4620', 4620" are drawn and urged together, radially inward toward one another until they are disposed within the first diameter of the closure element 4500". Continued retraction further urges the engaged opposing arterial walls 4620', 4620" radially together under the bleed back shaft and into the channel 4540 defined by the substantially tubular closure element 4500".

The pusher member 4320 is then advanced distally to deploy the closure element 4500" off of the end of the obturator or tissue locator device 4202, and out of the lumen 4644 of the introducer sheath 4640. The distally directed tines 4520 of the closure element 4500" pierce the opposing arterial walls 4620', 4620" that are radially pulled together, via the tissue engaging device 4400 in the closing condition, within the first diameter. Once the substantially tubular closure element 4500" is deployed, it begins to transition from the tubular configuration to the natural, planar configuration with opposing tines 4520 and a natural cross-section 4530 of the closure element 4500 (substantially similar to the deployment of the closure element detailed and shown in FIGS. 51G and 51H). The arterial walls 4620', 4620" are thus drawn substantially closed and/or sealed. Subsequently, the tongs 4410 of the tissue engaging device 4400 are retracted in the bleed back shaft 4260, and the delivery assembly 4200 and sheath 4640 can be removed.

Generally, the present invention is directed toward a medical device and method for maintaining hemostasis while delivering a closure element through tissue and into an opening formed in, or adjacent to, a wall of a blood vessel or other body lumen of any size. As such, the present invention provides a medical device and method for use that maintains or improves hemostasis during a medical procedure for closing and/or sealing openings through tissues and/or blood vessels. The present invention also includes an implantable locator that can be used to facilitate hemostasis as well as a locator that includes hemostatic components.

The apparatus can be configured to receive and retain the closure element such that the closure element is disposed substantially within the apparatus. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening. The apparatus can include a locator element that locates the blood vessel to improve placement of the closure element, where the locator can optionally be implantable or hemostatic.

Additionally, the apparatus is configured to maintain hemostasis throughout the medical procedure so as to inhibit blood from oozing or flowing from the blood vessel. Further, the apparatus includes an expandable hemostatic element that expands so as to contact the blood vessel at the opening and/or around the opening on the external surface of the blood vessel so as to maintain or improve hemostasis after the apparatus is retracted and the locator element is adjacent to the opening. This can include the expandable hemostatic element being selectively expandable such that the expandable element is retracted while the apparatus is being placed adjacent to the opening and the locator element is locating the blood vessel wall. The expandable hemostatic element is selectively expanded during or after the procedure for locating the blood vessel wall so as to maintain hemostasis, and then refracted during placement of the closure element so that the closure element can engage tissue around the expandable element. After placement of the closure element, the apparatus can be withdrawn.

When properly positioned, the apparatus can be activated to distally deploy the closure element. During deployment, the apparatus can be configured to substantially uniformly expand the closure element beyond a natural cross-section of the closure element such that the closure element, when deployed, is configured to engage a significant amount of the blood vessel wall and/or tissue. Engaging the blood vessel wall and/or tissue, the closure element can be further configured to return to the natural cross-section. Thereby, the engaged blood vessel wall and/or tissue are drawn substantially closed and/or sealed, such that, for example, hemostasis within the opening is enhanced. Also, the implantable locator can be held against the inner wall of the blood vessel by the closure element, and thereby implanted, to enhance hemostasis.

During the deployment of the closure element, the expandable hemostatic element expands at or around the opening in the blood vessel so as to provide improved hemostasis. The expandable hemostatic element can be expandable by various means which are described in more detail herein. In one example, the expandable hemostatic element can be selectively expanded as shown herein with relation to the expandable locator, and the expandable hemostatic element can include the features of the expandable locator.

Since current apparatuses for sealing openings formed in blood vessel walls can snag tissue adjacent to the openings during positioning and may not provide an adequate seal, an apparatus that is configured to prevent inadvertent tissue contact during positioning and to engage a substantial of amount of tissue adjacent to the opening can prove much more desirable and provide a basis for a wide range of medical applications, such as diagnostic and/or therapeutic procedures involving blood vessels or other body lumens of any size. This result can be achieved by employing a clip applier and associated methods of use in accordance with the present invention.

Additionally, methods of using the improved hemostasis system described herein are shown in FIGS. 59A-59E. The methods can utilize embodiments of the hemostasis systems as shown in the various figures. As such, the use of a hemostasis member during the process of delivering a closure element to close an opening in a body lumen can be used as shown, and can have many identical or similar structures that perform identical or similar functions to the embodiments of the invention described herein in reference to the figures.

Accordingly, the description below should be considered in view of the descriptions herein of the different embodiments of hemostasis systems and methods of using the same. Furthermore, those of ordinary skill in the art will appreciate that one or more of the uses, components, and/or features of the embodiment shown in FIGS. 59A-59E may also be incorporated in the other embodiments described herein, and vice versa.

Referring now to FIGS. 59A-59E, methods of using a hemostasis system 52201 will be described. The hemostasis system 52201 can be used with closure element applying devices described herein, and may include various features of such closure element applying devices as described herein. However, FIGS. 59A-59E only show the hemostasis system 52201 for purposes of clarity, and it should be understood that the hemostasis system 52201 is employed so as to provide improved hemostasis during the process of applying a closure element to seal a blood vessel 52600.

Figure 59A:
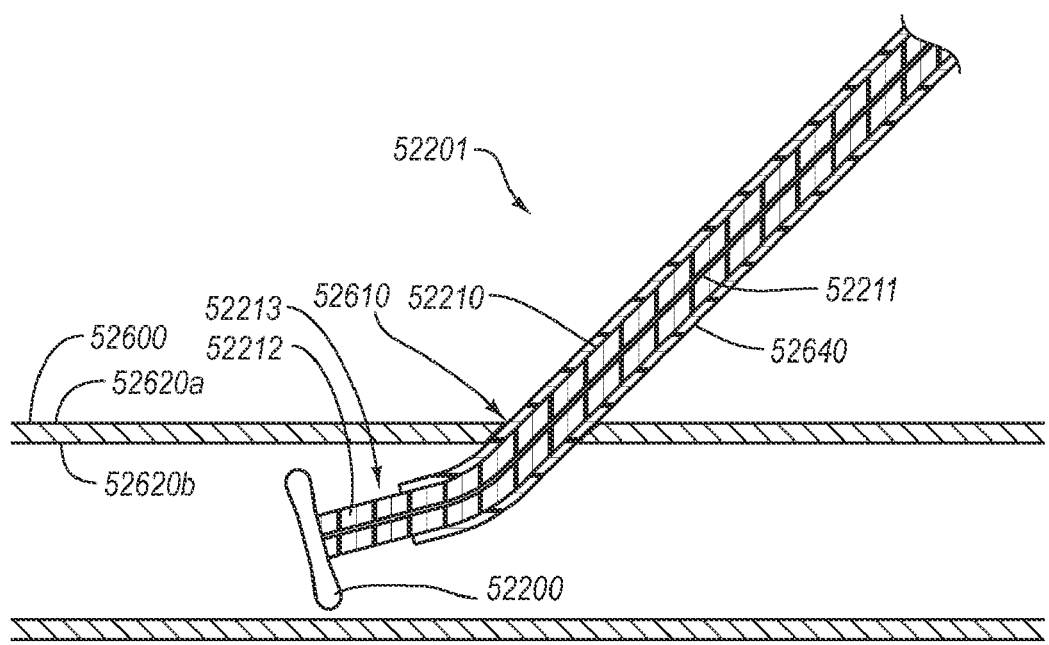

Referring now to FIG. 59A, there is shown a vessel 525600 having an external surface 52620a and an internal surface 52620b. The vessel 52620 includes an opening 52610 disposed therein where a medical device, such as a catheter, can be inserted for performing a medical procedure. As described above, a guidewire (not shown) can be inserted through the opening 52610 of the vessel 52620 such that the hemostasis system 52201 can be inserted into the opening 52610 by being traversed over the guidewire.

The hemostasis system 52201 is illustrated to include a sheath 52640 through which the components of the locator assembly, hemostasis components, and tube set, described herein, can be deployed into and/or adjacent to the opening 52610 in the vessel 52620. As illustrated in FIG. 59A, the sheath 52640 is disposed through the opening 52610 such that locator 52200 extends therefrom and into the vessel 52620. The hemostasis tube 52212 is also shown to extend from the sheath 52640 so as to form a gap 52213 between the sheath 52640 and the locator 52200. A wire 52211, or other suitable mechanism for operation of the locator 52200 and/or hemostasis system 52201 is disposed within a lumen in the hemostasis system 52201, such as within the hemostasis tube 52212.

Figure 59B:
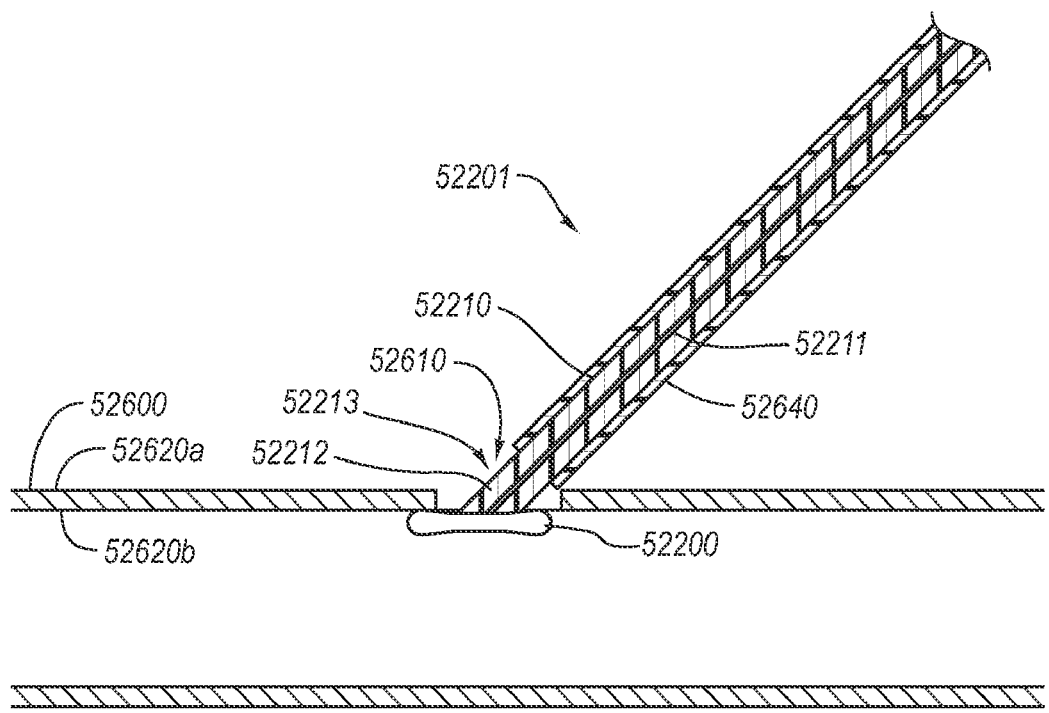

As shown in FIG. 59B, when the locator 52200 is withdrawn so as to locate the vessel 52620 by contacting the internal surface 52620b of the vessel, the gap 52213 is positioned at the opening 52610 of the vessel 52620. This provides incomplete hemostasis because blood is able to ooze, seep, and/or flow through the opening 52610 at the gap 52213. As such, the process of locating the vessel 52620 can cause incomplete hemostasis, which is undesirable.

Figure 59C:
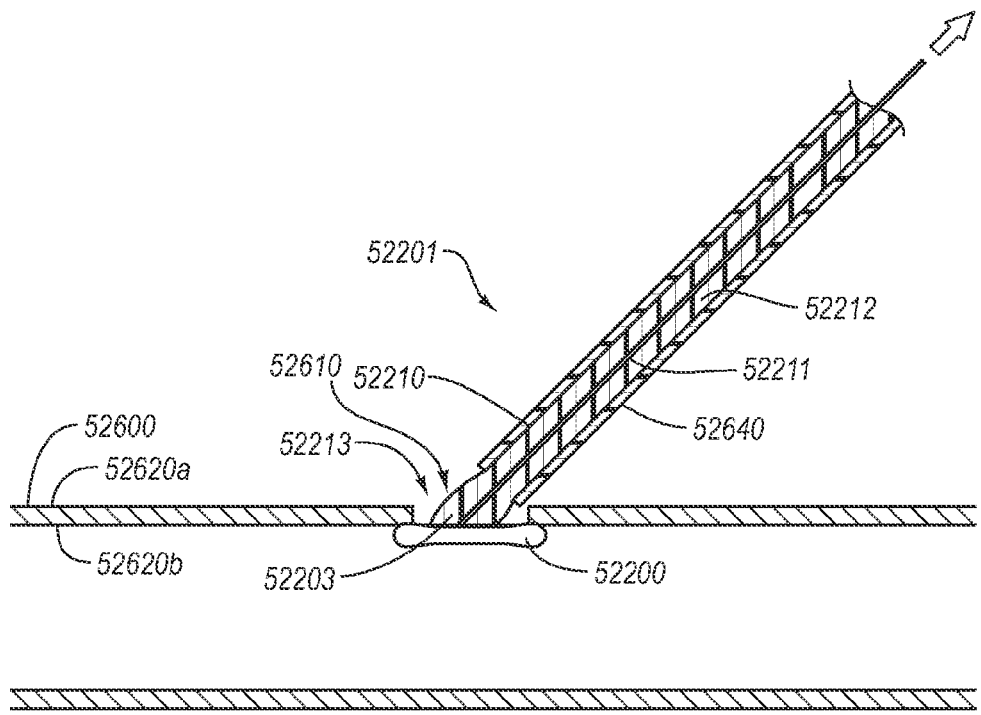

As shown in FIG. 59C, the hemostasis system 52201 can be manipulated so that an expandable member 52203 can be expanded so as to fill the gap 52213 and plug the opening 52610 in the vessel 52620. For example, the wire 52211 can be manipulated in a manner that causes the expandable member 52203 to begin to expand so as to fill the gap 52213 and plug the opening 52610 of the vessel 52620. In another example, the first manipulation of the wire 52211 can expand the locator 52200, and the second manipulation of the wire 52211 can expand the expandable member 52203. The order of which expandable members 52203 and/or the locator 52200 expand may be selected depending on the characteristics of improved hemostasis.

Figure 59D:
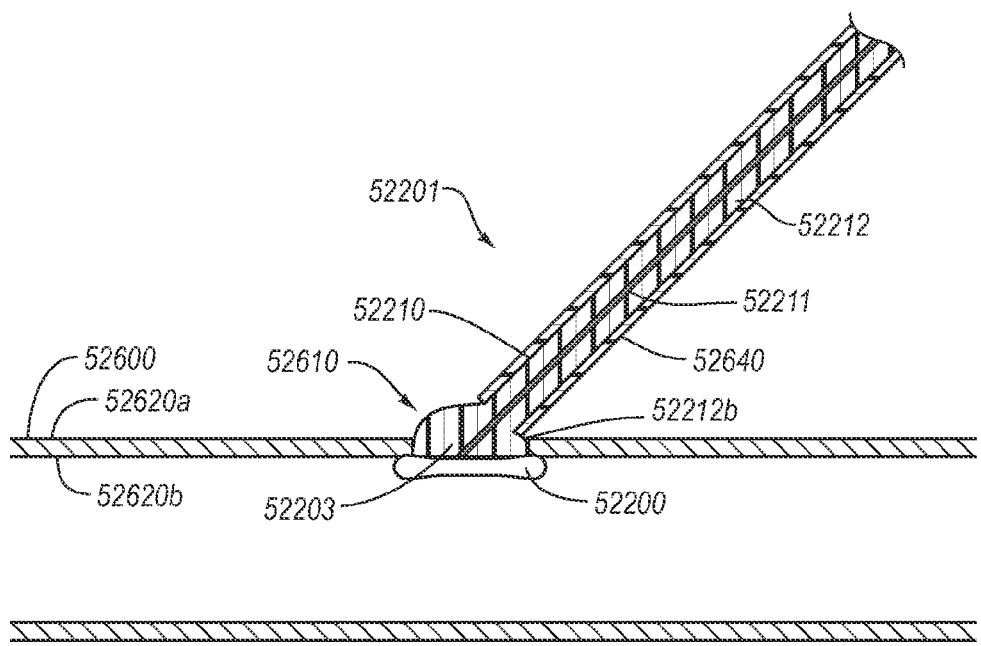

As shown in FIG. 59D, the fully expanded expandable member 52203 has a sufficient size to plug the opening 52610 in the vessel 52620. Also, the expanded expandable member 52203 provides hemostasis so that blood is inhibited from passing through the opening 52610. The expanded expandable member 52203 can extend from the locator 52200 to the sheath 52640 or any distance therebetween. The hemostasis can be maintained throughout the process of delivering the closure element into the vessel 52620 so as to close the opening 52610.

While not shown, the expandable member 52203 and locator 52200 can be collapsed as the closure element is deployed into the vessel 52620. The collapse of the expandable member 52203 and locator 52200 can be facilitated as described herein. For example, the wire 52211 can be manipulated in a manner that automatically causes the collapse as the closure element is delivered into the vessel 52620. Otherwise, the mechanism described herein that collapses the locator and hemostatic member as the closure element is deployed can be used.

Figure 59E:
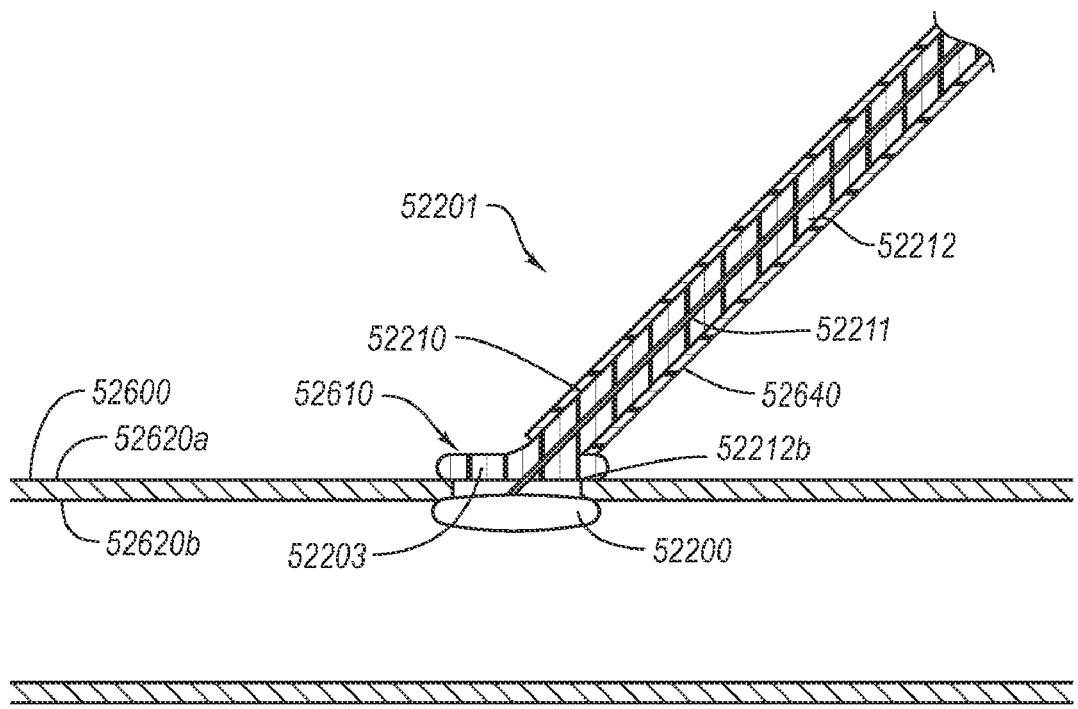

FIG. 59E shows the hemostasis system 52201 can include an expandable member 52203 that expands radially or laterally in a more disc-like configuration so that it can contact the outer wall 52620a of the vessel 52620 and form a seal to inhibit bleeding. An expandable hemostasis member 52203 can be configured as a cap and/or plug for the hole 52610 and may have an expanded outer diameter that is larger than the diameter of the hole 52610.

Generally, closure systems that are configured to close openings in body vessels can suffer from incomplete hemostasis during the closing procedure. Such incomplete hemostasis allows blood or other body fluids to seep into the medical devices and increase the difficulty in closing and sealing the opening. For example, in an embodiment of a current closure system, the nylon shaft of the locator system is smaller than the arteriotomy or sheath. As the sheath is retracted during the positioning of the locator or split during the advancement of the tube set, blood can ooze out of the opening before the closure element is applied to close the opening. In order to inhibit the oozing of blood through the opening, the hemostasis system of the present invention can be applied to inhibit such oozing and provide improved hemostasis.

In one embodiment, the hemostasis is accomplished by the distal tip of the shaft of the locator selectively expanding. For example, the shaft can be a nylon shaft that is tensioned so as to longitudinally shorten and laterally buckle and expand at the distal end. Such buckling expands the nylon shaft laterally so as to plug or cap the opening in the vessel. Additionally, other embodiments of hemostasis systems can be applied as described herein.

A hemostasis system in accordance with the present invention is configured to substantially plug or cap an opening in a vessel so as to provide improved hemostasis during the deployment of a closure element into the vessel so as to close and seal the opening. Such a hemostasis system can be present in various configurations that have an expandable member that expands so as to plug the opening. Expandable members are well known in the art and can be expanded by a number of mechanisms.

The expandable members of the present invention can be self-expandable so as to automatically expand when subjected to a particular stimulus. Such self-expandable members can include shape-memory materials (e.g., shape memory alloys and shape memory polymers) that expand as is well known in the art. For example, shape memory alloys automatically expand when heated to a certain temperature by the body. Shape memory alloys, such as nitinol, are also known as superelastic metals.

Additionally, a self-expandable member can have an expanded configuration and a contracted configuration, where the member is retained within a device (e.g., sheath) in the contracted configuration and automatically expands when removed from the device. For example, the self-expandable member can have a contracted configuration that fits and is held therein by a sheath as described herein, and automatically expands to the expanded configuration when the sheath is retracted over the expandable member.

In one embodiment, the expandable member is fluid absorbable such that the fluid that oozes through the opening induces the expandable member to expand. An example of this can be a hydroscopic polymer (e.g., hydrogel) that swells and absorbs the body fluid.

In one embodiment, the expandable member is expanded when a mechanism is actuated so as to induce the expansion. This can be similar to a balloon, such as a balloon in a balloon-expandable stent, or an inflatable bladder. The mechanism can be a hydraulic or fluidic mechanism with tubes and pumps that can be automatic and/or selectively controlled.

In one embodiment, the mechanism can be a wire or shaft that changes the configuration of the expandable member from unexpanded to expanded and back to being unexpanded, as desired. Such an expandable member can have expandable elements and components similar to the locator assembly as described herein. This can include the expandable member expanding via the same mechanism that expands the locator assembly or a similarly configured mechanism.

FIGS. 60A-60B are a schematic representation that shows expansion of an expandable hemostasis system 53000, where FIG. 60A shows the hemostasis system 53000 in the unexpanded state and FIG. 60B shows the expanded state. The hemostasis system 53000 includes a hemostasis member 53002 having an internal lumen 53008 that extends from a proximal end 53004 to a distal end 53006. The hemostasis member 53002 is divided into a non-expandable member 53002a at the proximal end 53004 and an expandable member 53002b at the distal end 53006. The non-expandable member 53002a and expandable member 53002b can be two separate materials joined together, or they can be a unitary material with a portion that selectively expands (e.g., expandable member 53002b). The hemostasis member 53002 can be any length 53010, which can be divided in any manner to provide an appropriate non-expandable member 53002a length 53012a and an appropriate expandable member 53002b length 53016a while in the non-expanded state. Also, the non-expandable member 53002a can have a non-expandable diameter 53014a, and the expandable diameter 53018a that is sufficient for providing hemostasis and plugging or capping the opening in the body lumen. After the hemostasis system 53000 is expanded as shown in FIG. 60B, the expandable member 53002b expands to a larger diameter 53018b. Such an expansion in diameter can result in longitudinal shorting in length 53016b.

Figure 61A:
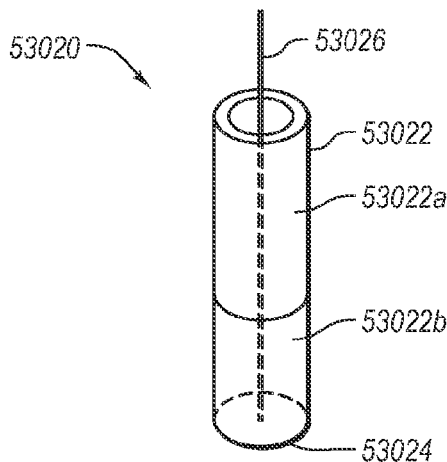

FIGS. 61A-61F are schematic illustrations of various other embodiments of hemostasis systems. FIG. 61A shows an embodiment of a hemostasis system 53020 in a non-expanded state that includes a hemostasis member 53022 that has a non-expanding member 53022A and an expanding member 53022B. Also, the hemostasis system 53020 includes a wire 53026 that is coupled to a rigid base 53024 such that a proximally oriented force applied to the wire 53026 can pull the rigid base 53024 so as to buckle and/or otherwise expand the expanding member 53022B relative to the non-expanding member. Alternatively, the wire 53026 can be configured as a tube, shaft, pin, combinations thereof, or the like that can provide a similar function in expanding the expanding member 53022B. As such, the wire 53026 can have sufficient tensile strength so as to impart a force to the expanding member 53022B so as to induce expansion thereof or activate a mechanism that expands the expanding member 53022B. The non-expanding member 53022A may be a separate material from the expanding member 53022B or a unitary material therewith. The non-expandable member 53022A may similarly expand if desired. However, an external structural member, such as a sheath or tube, can be used to hold the non-expanding member 53022A in place and restrict lateral expansion.

Figure 61B:
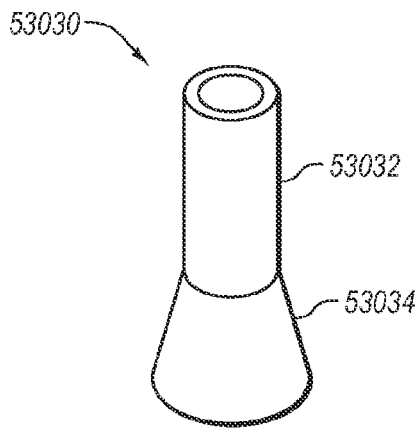

FIG. 61B shows an embodiment of a hemostasis system 53030 having a substantially tubular non-expanding member 53032 and an expanding member 53034 that expands to a substantially conical shape. The tubular non-expanding member 53032 may be capable of expanding; however, it is shown in the non-expanded state so as to be differentiated from the expanding member 53034 that expands within the opening of the vessel so as to form a plug. Also, the taper of the expanding member 53034 can be reversed with the larger end being coupled with the non-expanding member 53032. Insertion of the expanding member 53034 with the smaller end being inserted into a blood vessel can provide a plug/cap with a friction fit.

Figure 61C:
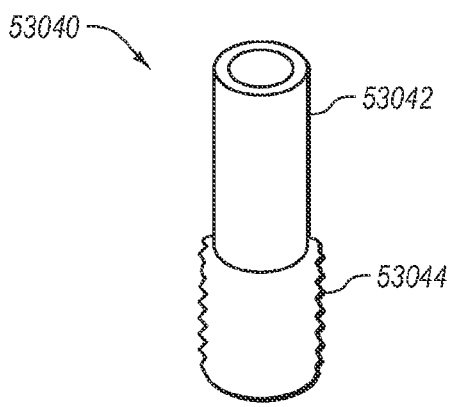

FIG. 61C shows an embodiment of a hemostasis system 53040 having a substantially tubular non-expanding member 53042 and an expanding member 53044 that buckles laterally so as to expand in diameter and shorten in length. The buckling can cause the lateral diameter to vary along the length with wide portions being of sufficient diameter to function as a plug in the opening and provide improved hemostasis. The buckling can also contour with the shape of the blood vessel opening and/or expand greater at the proximal end.

Figure 61D:
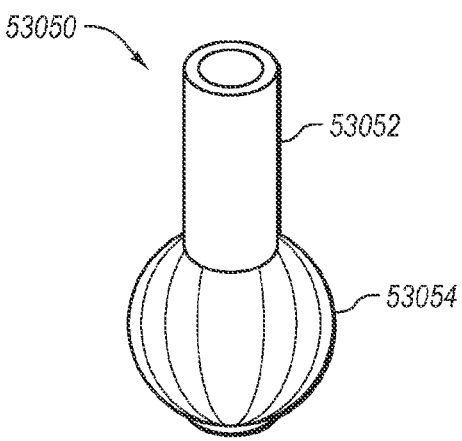

FIG. 61D shows an embodiment of a hemostasis system 53050 having a substantially tubular non-expanding member 53052 and an expanding member 53054 that expands or bows outwardly in the lateral direction. The bowing outwardly can cause the lateral diameter to change or curve along the length with wide portion being of sufficient diameter to function as a plug in the opening and provide improved hemostasis. Usually, the bowing is caused by the material curving outwardly, laterally rather than the material buckling. Alternatively, the bowing can also be similar to the inflation of a balloon or bladder.

Figures 61E, 61F:
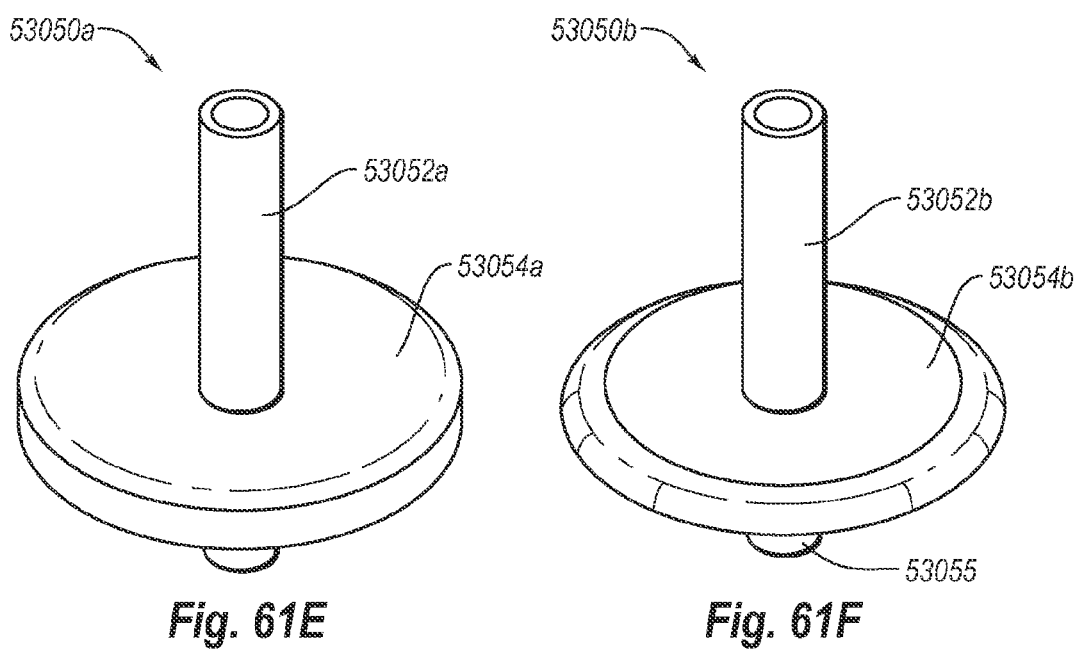

FIG. 61E shows an embodiment of a hemostasis system 53050a having a substantially tubular non-expanding member 53052a and an expanding member 53054a that expands or widens outwardly in the lateral direction to form a plate or discus like shape. The outward expansion can cause the lateral diameter to change to a sufficient diameter to function as a plug, cap, lid or other covering that provides hemostasis to the opening. Usually, the widening is caused by the material expanding outwardly, laterally rather than the material buckling. Alternatively, the widening can also be similar to the inflation of a balloon or bladder.

FIG. 61F shows an embodiment of a hemostasis system 53050b having a substantially tubular non-expanding member 53052b and an expanding member 53054b that expands or widens outwardly in the lateral direction to form a cupped, suction cup, or Frisbee like shape. The outward expansion can cause the lateral diameter to change to a sufficient diameter to function as a plug, cap, lid or other covering that provides hemostasis to the opening. Usually, the widening is caused by the material expanding outwardly, laterally rather than the material buckling. Alternatively, the widening can also be similar to the inflation of a balloon or bladder. Additionally, the distal or vessel side of the expanding member 53054b can include a plug 53055 that inserts into and plugs the vessel hole.

FIGS. 62A-62B illustrate an embodiment of a removable anchor system 54000. The removable anchor system 54000 can include a sheath 54640 that can be configured as any sheath or outer cover or outer tube as described herein. An anchor sheath 54002 can include a pusher member 54004, a removable anchor 54006, and the first anchor wire portion 54008 and second anchor wire portion 54010 positioned opposite of the first anchor wire. The first and second anchor wire portions 54008, 54010 as well as additional anchor wires can have equal or even spacing as well as unequal or uneven spacing with around the lumen 54003 of the anchor sheath 54002. The first anchor wire 54008 and second wire controller 54010 can be formed from the same wire. As such, the same wire forms the first and second anchor wire portions 54008, 54010 and the removable anchor 54006.

The first and second anchor wire portions 54008, 54010 (e.g., of the same wire) can traverse the lumen 54003 until reaching a first wire controller 54014 that couples with and controls the first anchor wire portion 54008 and a second wire controller 54018 that couples with and controls the second anchor wire portion 54010. The first wire controller 54014 can include a first mechanism 54016 that can automatically and/or selectively be pulled to control the distal end of the first anchor wire portion 54008. A similar second mechanism 54020 can control the second wire controller 54018 and second anchor wire portion 54010.

Also, the pusher member 54004 can be operably coupled with a push member controller 4019 for selective axial motion or selective position setting.

Additionally, multiple wires can be used to form additional anchors similarly as formed from the first anchor wire portion 54008, second anchor wire portion 54010, and the anchor 54006. As such, while FIG. 63 shows a two lobe anchor formed from a single wire, multiple wires can be used to form multiple two lobe anchors. Alternatively, a single wire can form multiple-lobed clover shaped anchors that are all controlled by first and second anchor wire portions operated by the wire controllers.

FIG. 63 shows the removable anchor system 54000 after the removable locator 54006 at the distal end has been expanded within a blood vessel 5620. In order to expand, the pusher member 54004 can be held or advanced distally compared to the relative proximal motion of the anchor sheath 54002, which is indicated by the arrows. The locator 54006 automatically expands when passed out of the anchor sheath 54002. The first and second anchor wires 54008, 54010 are shown to be pulled proximally so that the locator 54006 pushes up against the inside of the blood vessel 5620. FIG. 63 also shows a hemostasis tube 54030 and an expandable hemostasis member 53034 that can expand outwardly to provide hemostasis.

The first and second mechanisms 54018, 54020 at the proximal end of the removable anchor system 54000 can be activated to selectively pull the first and second anchor wire portions 54008, 54010. This can include selectively pulling both the first and second anchor wire portions 54008, 54010 so that the locator 54006 is brought tight against the blood vessel 5620.

FIGS. 64A-64B show an anchor being collapsed and withdrawn. As such, the first anchor wire portion 54008 can be pulled while the second anchor wire portion 54010 is not pulled (e.g., stop) so that locator 54006 begins to collapse and be pulled proximally as shown in FIG. 64A. FIG. 64B shows the removable locator 54006 can be deformed and pulled proximally out of the blood vessel 5620 by pulling one or more of the first and second anchor wire portions 54008, 54010. The removal of the removal locator 54006 can occur before or as a closure element is deployed to seal the opening 5610 of the vessel 5620.

FIGS. 65A-65C show an implantable, removable anchor system 54000 being used with a carrier assembly 54300 and tube set 54305 that deploys a blood vessel closure element 4500 into a vessel 5620. The anchor system 54000, carrier assembly 54300 and tube set 54305 can be configured as described herein.

FIG. 65A shows the anchor system 54000 being located within an opening 5610 of the vessel 5620. The locator 54006 is positioned against the internal surface of the vessel 5620 by pulling on the first anchor wire portion 54030 and second anchor wire portion 54032 at the same time to draw the locator 54006 against the vessel 5620 so as to provide the location of the vessel 5620. The anchor 52006 can be opened within a blood vessel 5620 as shown in the figures, and can be held by selectively pulling the first anchor wire portion 54030 and the second anchor wire portion 54032. These anchor wire portions 54030, 54032 are configured to be cut, decoupled, degraded, dissolved, or otherwise decoupled from the locator 54006. This allows for the anchor 54006 to be implanted. Optionally, the anchor 54006 can be formed of an implantable metal or plastic as well as a degradable material, such as a degradable polymer. The anchor wire portions 54030, 54032 can be prepared of materials common to suture materials as well as biocompatible polymers that are biodegradable or biostable.

FIG. 65B shows the carrier assembly 54300 and tube set 54305 being located adjacent to the opening 5610 in the vessel 5620, and can be positioned as described herein. As shown, the closure element 4500 penetrates through the vessel 5620 at a diameter wider or circumference larger than the locator 54006 after being deployed by the tube set 54305 and carrier assembly 54300. The closure element 4500 can be inserted into the blood vessel 5620 before, during or after the expandable hemostasis member 52213 is retracted or unexpanded as shown by the dashed lines. Accordingly, the dashed lines show the hemostasis member 52213 in the deployed and expanded orientation. The hemostasis member 52213 can be collapsed upon deployment of the closure element 4500.

FIG. 65C shows the closure element 4500 collapsed and returned to its natural and substantially planar shape. While the closure element 4500 is collapsing, it grabs the implantable anchor 54006 and draws it against the blood vessel 5620 to close the opening 5610. The anchor 54006 is decoupled from the first and second anchor wires 54030, 54032.

Optionally, the closure element and/or anchor 54006 can include portions that are hemostatic, such as having a hemostatic agent coated on selected surfaces, such as non-blood flow facing surfaces or tissue facing surfaces.

FIGS. 66A-66B show another embodiment of an anchor 54006a, which can be removable or implantable, in the form of a tight coil. The coiled anchor 54006a can function much as the looped anchor 54006 of FIGS. 62-66. FIG. 67A shows that the closure element 4500 can reach around the edges of the coiled anchor 54006a so that it is pulled against the vessel. FIG. 66B also shows the first and second anchor wires 54030a, 54032a that are dissolvable.

FIG. 67A shows an anchor 54050 that is integrally formed with or coupled to one or more anchor wire portions 54040 via a coupler 54020. The coupler 54020 can be selectively undone or dissolved to decouple an implantable anchor 54050 from the anchor wire portion 54040. Alternatively, the coupler 54020 can couple to different materials of a removable anchor 54050 and the anchor wire portion 54040. The shape of the anchor 54050 is a spiral, and which can be delivered into a vessel and expanded as described herein. The spiral anchor 54050 can also be extracted from the blood vessel by pulling on the anchor wire 54040 so that the anchor 54050 unwinds into a lumen 54042 of a locator assembly 54044.

FIG. 67B shows an anchor 54052 and anchor wire portion 54040 and coupler 54020 substantially as FIG. 67A. However, the anchor 54052 has a continuous looped shape with one or more loops (shown with 2 loops). The looped anchor 54052 can be deployed and withdrawn or implanted as described herein.

FIGS. 68A-68B show an anchor system 54000 that is operated with an expandable hemostasis member 52213. The expandable hemostasis member 52213 and anchor system 54000 (removable or implantable) can be deployed and expanded as described herein. As shown, the expandable hemostasis member 52213 expands and causes the first and second anchor wire portions 54008, 54010 to be tightened and drawn against the vessel 5620 so that the anchor 54006 locates and anchors against the inside of the vessel 5620 while the expandable hemostasis member 52213 is pushed against the outside of the vessel 5620 to provide hemostasis.

FIG. 68A shows a dashed line 54025 marking the outer diameter of the expandable hemostasis member 52213. As such, the closure element (not shown) can have a diameter larger than 54025 when deployed with the hemostasis member 52213 after being expanded. Accordingly, dashed line 54025 shows the diameter of closure element when deployed around an expanded hemostasis member 52213. The closure element can then pierce the blood vessel outside or wider than the dashed line 54025. This can ensure the expandable hemostasis member 52213 can be unexpanded and withdrawn. As shown, the diameter of dashed line 54025 is also wider than the diameter of the anchor 54006 so that the closure element wraps around and encompasses the anchor 54006 upon deployment and implantation.

FIG. 68B shows an instance where the expandable hemostasis member 52213 is unexpanded before or as the closure element pierces the vessel to an unexpanded outer diameter 54026 shown by the dashed line. The dashed line 54026 shows a diameter larger than the diameter of the unexpanded hemostasis member 52213, and the closure element can have a diameter that is larger than the dashed line 54026. As such, the closure element (not shown) can have a diameter upon deployment that is larger than the diameter of the unexpanded diameter 54026 of the hemostasis member 52213. The closure element can also have a diameter that is smaller than the expanded diameter 54025 of the expanded hemostasis member 52213 and/or anchor 54006.

The anchors described herein can function as locators and can be configured with components described herein in connection to locators and locator assemblies. Also, the anchors can be prepared from shape-memory materials that are alloys or polymers, as well as metals or polymers that are implantable as well as degradable. Examples of the closure element materials can be used as the anchor materials.

The embodiments of hemostasis systems and the components for providing improved hemostasis described herein are representative of the different types of hemostasis providing elements that can be included in a device and/or system for delivering a closure element into a vessel for closing and sealing an opening therein. The hemostasis elements can be varied from that which has been illustrated and described; however, the function remains to provide improved hemostasis during the closure element delivery process. As such, the skilled artisan could make various modifications to the hemostasis elements and still provide improved hemostasis. Accordingly, some of the variations that may be employed will be discussed in more detail below.

The hemostasis system has been illustrated and described as having non-expanding portions and expanding portions. This can include a single material with portions configured to function different in the non-expanding portion compared to the expanding portion. For example, the material at the expanding portion can be narrower or less resistant to forces so as to preferentially expand compared to the non-expanding portion. The non-expanding portion could also have a non-expanding shape or solid composition without an internal lumen, such as a rod, shaft, wire, pin, and the like. Alternatively, the non-expanding portion can be configured identically with the expanding portion, and the hemostasis system includes a member that confines the non-expanding portion so as to inhibit expansion. For example, the sheath can be retracted enough to only expose the expanding portion, and thereby allow the expanding portion to expand while retaining the non-expanding portion within the sheath such that contact between the sheath and the non-expanding portion inhibits expansion. A similar configuration can be applied with different materials for the non-expanding portion and the expanding portion, where the material of the non-expanding portion is coupled to the material of the expanding portion. Additionally, the non-expanding portion can have a material or plurality of materials that are different from the material or plurality of materials of the expanding portion. For example, the non-expanding portion can have a structurally reinforcing member, such as rod, ribs, braces, or the like that inhibit expansion. On the other hand, the expandable portion can have expandable members (e.g., shape memory materials) disposed in a polymeric member that is capable of expanding, whereby the expandable members cause the polymeric member to correspondingly expand.

In the instance the non-expanding portion and the expanding portion are different materials coupled together, such coupling can be accomplished by well known methods for attaching a material to another material. The type of coupling employed can depend on the type of the first material and the second material. For example, the coupling can be achieved by adhesive, melt-bonding, sintering, welding, brazing, threading, friction resistance, and the like.

In one example, the expandable member can include a laminate structure having structural elements that can be expanded, and thereby expand the laminate structure. The structural elements that can expand can be configured similarly to a stent that expands when deployed. Thus, the hemostasis system can include the components of a stent delivery system that are used to expand a stent, which can include self-expanding systems, balloon/bladder expanding systems, and the like.

The materials of the hemostasis system can be varied and still retain the same function. Generally, the hemostasis materials are biocompatible so that adverse physiological reactions do not occur when the expandable member expands to contact and plug the opening in the vessel. Such biocompatible materials can include metals, alloys, superelastic alloys (e.g., shape memory alloys) polymers, plastics, foams, elastomers, natural or synthetic rubbers, ceramics, and combinations thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An apparatus comprising:
   a housing;
   a shaft slidably extending from the housing;
   a tissue locating structure selectably deployable distal a distal end of the shaft;
   an actuator operatively coupled to the housing and the tissue locating structure and being configured to selectively move distally into the housing to radially expand the tissue locating structure and move proximally to radially retract the tissue locating structure, the actuator including two spaced apart portions configured to receive a tissue locating shaft, operatively coupled to the tissue locating structure, therebetween;
   a closure structure disposed within the shaft and selectably deployable from the shaft;
   an elongate member operatively associated with the closure structure, the elongate member and the shaft cooperating to deploy the closure structure.

2. The apparatus of claim 1, further comprising a trigger assembly operatively associated with the elongate member and extending from the housing.

3. The apparatus of claim 1, further comprising another shaft disposed within the shaft, the another shaft receiving the tissue locating shaft associated with the tissue locating structure.

4. The apparatus of claim 1, wherein the elongate member and the shaft slide relative to one another.

5. The apparatus of claim 1, wherein the tissue locating structure has a substantially rounded distal tip.

6. An apparatus for deploying a closure structure, the apparatus comprising:
   a housing having a distal end with a proximally facing distal wall portion;
   a tissue locating structure selectably deployable distal to the distal end of the housing;
   a first block disposed within the housing and selectively contacting the proximally facing distal wall portion of the housing, the first block having a first lumen and cooperating with a shaft extending distally from the first block and the housing;
   a second block movable within the housing, the second block having a second lumen aligned with the first lumen, the second block cooperating with an elongate member extending distally through at least a portion of the shaft to distally advance a closure structure within the shaft, the elongate member and the shaft cooperating to deploy the closure structure; and
   a third block movable within the housing, the second block and the third block being movable relative to the first block upon deployment of the closure structure.

7. The apparatus as recited in claim 6, further comprising a tissue locating shaft associated with the tissue locating structure, the tissue locating shaft extending through the first lumen of the first block.

8. The apparatus as recited in claim 6, further comprising an actuator operatively coupled to the housing and the tissue locating structure, the actuator being configured to selectively move into the housing to deploy the tissue locating structure.

9. The apparatus as recited in claim 8, the actuator including two spaced apart portions configured to receive a tissue locating shaft, operatively associated with the tissue locating structure, therebetween.

10. The apparatus as recited in claim 6, wherein the first block and the second block have cooperating engagement structures.

11. The apparatus as recited in claim 10, wherein the cooperating engagement structures include at least one detent.

12. The apparatus as recited in claim 6, wherein the second block and the third block have cooperating engagement structures.

13. The apparatus as recited in claim 6, wherein the housing comprises a plurality of grooves configured to slidably receive a portion of the second block and the third block.

14. A system comprising:
   an introducer sheath including a hub assembly and an introducer sheath portion; and
   a closure delivery device selectively connected to the introducer sheath, the closure delivery device comprising a housing having a distal end with a proximally facing distal wall portion, the closure delivery device including one or more connectors configured to selectively mate with the introducer sheath to selectively secure the housing and the introducer sheath together, the closure delivery device including:
   a tissue locating structure selectably deployable distal to the distal end of the housing;
   a first block disposed within the housing and selectively contacting the proximally facing distal wall portion of the housing, the first block having a first lumen and cooperating with a shaft extending from the first block and the housing;
   a second block movable within the housing, the second block having a second lumen aligned with the first lumen, the second block cooperating with an elongate member extending through the shaft, the elongate member and the shaft cooperating to deploy a closure structure; and
   a third block movable within the housing, the second block and the third block being movable relative to the first block upon deployment of the closure structure.

15. The system as recited in claim 14, further comprising an actuator operatively coupled to the housing and the tissue locating structure, the actuator being configured to selectively move into the housing to deploy the tissue locating structure.

16. The system as recited in claim 15, further comprising a biasing spring operatively coupled to the actuator.

17. The system as recited in claim 15, the actuator including an aperture configured to receive a tissue locating shaft associated with the tissue locating structure.

18. The system as recited in claim 17, the actuator including two spaced apart portions configured to receive the tissue locating shaft.

* * * * *